(12) United States Patent
Davenport et al.

(10) Patent No.: US 8,691,804 B2
(45) Date of Patent: Apr. 8, 2014

(54) AZETIDINES AND CYCLOBUTANES AS HISTAMINE H3 RECEPTOR ANTAGONISTS

(75) Inventors: Adam James Davenport, Abingdon (GB); David James Hallett, Marlow (GB); Massimo Corsi, Florence (IT)

(73) Assignee: Evotec AG, Hamburg (DE)

( * ) Notice: Subject to any disclaimer, the term of this patent is extended or adjusted under 35 U.S.C. 154(b) by 149 days.

(21) Appl. No.: 12/991,225

(22) PCT Filed: May 5, 2009

(86) PCT No.: PCT/EP2009/055418
§ 371 (c)(1),
(2), (4) Date: Dec. 6, 2010

(87) PCT Pub. No.: WO2009/135842
PCT Pub. Date: Nov. 12, 2009

(65) Prior Publication Data
US 2011/0105459 A1 May 5, 2011

Related U.S. Application Data

(60) Provisional application No. 61/139,461, filed on Dec. 19, 2008.

(30) Foreign Application Priority Data

May 8, 2008 (EP) ..................... 08155915

(51) Int. Cl.
*A01N 31/00* (2006.01)
*C07D 243/08* (2006.01)
*C07D 403/00* (2006.01)

(52) U.S. Cl.
USPC ....... 514/210.18; 540/575; 544/364; 544/359

(58) Field of Classification Search
USPC ............... 514/210.18; 540/575; 544/364, 359
See application file for complete search history.

(56) References Cited

U.S. PATENT DOCUMENTS

| 4,956,359 | A | 9/1990 | Taylor et al. |
| 2001/0049367 | A1 | 12/2001 | Bennani et al. |
| 2007/0142369 | A1 | 6/2007 | van Heek et al. |
| 2009/0131415 | A1 | 5/2009 | Letavic et al. |

FOREIGN PATENT DOCUMENTS

| JP | 61-210031 A | 9/1986 |
| JP | 2005-502623 A | 1/2005 |
| JP | 2005-509627 A | 4/2005 |
| WO | WO 03/004480 A2 | 1/2003 |
| WO | WO 03/004480 A3 | 1/2003 |
| WO | WO 2006/040192 A1 | 4/2006 |
| WO | WO 2006/136924 A1 | 12/2006 |
| WO | WO 2007/049123 A1 | 5/2007 |
| WO | WO 2007/080140 A1 | 7/2007 |
| WO | WO 2007/136324 A1 | 11/2007 |
| WO | WO 2007136324 A1 * | 11/2007 |

OTHER PUBLICATIONS

International Preliminary Report of Patentability of Application No. PCT/EP2009/055418 dated Nov. 18, 2010.
Arrang et al., Nature, 302, 1983, pp. 832-837.
Arthur A. Hancock et al., "Assessment of pharmacology and potential anti-obesity properties of H3 receptor antagonists/inverse", Expert opinion on investigational drugs, 14, 2005, pp. 223-241.
Database Beilstein Institute for organic chemistry, XP002498942, 1971.
Database Chemcats, Chemical asbtract service, XP002498938, 2007.
Database Chemcats, Chemical asbtract service, XP002498940, 2008.
Gerold Bongers et al., "Molecular aspects of the histamine H3 receptor", Biochemical Pharmacology 73, 2007, pp. 1195-1204.
Guillaume Drutel et al., "Identification of Rat H3 Receptor Isoforms with Different Brain Expression and Signaling Properties", Molecular Pharmacology, 59, pp. 1-8, published 2001.
J. M. Witkin et al., "Selective histamine H3 receptor antagonists for treatment of cognitive deficiencies and other disorders of the central nervous system", Pharmacology & Therapeutics, 103, (2004), pp. 1-20.
Keri E. Cannon et al., "Immunohistochemical localization of histamine H3 receptors in rodent skin, dorsal root ganglia, superior cervical ganglia, and spinal cord: potential antinociceptive targets", Pain, 129, 2007, pp. 76-92.
M. I. Martinez-Mir et al., "Three histamine receptors X1, H2 and H38 visualized in the brain of human and non-human primates", Brain res, 526, 1990 pp. 322-327.
Severine Morisset et al., "High constitutive activity of native H3 receptors regulates histamine neurons in brain", Nature, vol. 408, 2000, pp. 860-864.

(Continued)

*Primary Examiner* — Yong Chong
*Assistant Examiner* — Jason A Deck
(74) *Attorney, Agent, or Firm* — Birch, Stewart, Kolasch & Birch, LLP

(57) ABSTRACT

The invention relates to compounds of formula (I) wherein R, $R^0$, $R^1$, m, n and $X^1$ to $X^4$ have the meaning as cited in the description and the claims. These compounds are useful as Histamine H3 receptor antagonists. The invention also relates to pharmaceutical compositions, the preparation of such compounds as well as the production and use as medicament.

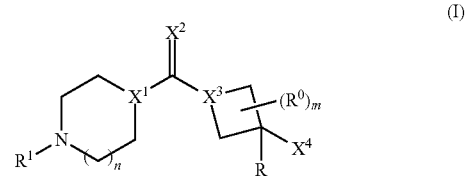

15 Claims, No Drawings

(56) References Cited

OTHER PUBLICATIONS

Timothy A. Esbenshade et al., "Histamine H3 receptor antagonists: preclinical promise for treating obesity and cognitive disorders", Mol Interventions, vol. 6, pp. 77-88, published Apr. 2006.

Zirvi et al., "Infrared Spectral Characteristics of the Cyclobutane Ring System", Journal of the Chemical Society [Section] B: Physical Organic, 1971, (8), pp. 1603-1606.

Zirvi et al., "Synthesis and Neuropharmacology of Cyclobutanecarboxylic Acid Derivatives", Farmaco, Edizione Scientifica, 1976, 31(2), pp. 152-158.

English translation of Japanese Office Action, dated Nov. 19, 2013, for Japanese Application No. 2011-507892.

* cited by examiner

AZETIDINES AND CYCLOBUTANES AS HISTAMINE H3 RECEPTOR ANTAGONISTS

This application is the National Phase of PCT/EP2009/055418 filed on May 5, 2009, which claims priority under 35 U.S.C. 119(a) to EP Patent Application No. 08155915.5 and 35 U.S.C. 119(e) to U.S. Provisional Application No. 61/139,461 filed on Dec. 19, 2008. The entire contents of these applications are hereby incorporated by reference into the present application.

The present invention relates to Histamine H3 receptor antagonists, pharmaceutical compositions thereof, the preparation of such compounds as well as the production and use as medicament.

The histamine H3 receptor is a G protein-coupled receptor (GPCR) and one out of four receptors of the histamine receptor family. Histamine receptors have long been attractive drug targets, mirrored in the development of antihistamines, which were directed at the histamine H1 receptor for the treatment of allergic reactions or at the histamine H2 receptor to ameliorate gastric ulcers by inhibiting gastric acid secretion. The H3 receptor has been identified as a presynaptic autoreceptor, regulating the release of histamine (Arrang et al. (1983) Nature: 302; 832-837), as well as a heteroreceptor that regulates the release of many other important neurotransmitters (acetylcholine, norepinephrine, dopamine, and serotonin). Structurally divergent H3 receptor antagonists/inverse agonists have been developed and shown to comprise activity in a variety of cognition tests in mice and rat (e.g. Esbenshade et al. (2006) Mol Interventions: 6 (2); 77-88) as well as in models for sleeping disorders and energy balance. From these studies it is concluded that such antagonists comprise a potential treatment for a variety of disorders affecting cognition (e.g., Alzheimer's disease, Parkinson's disease, Attention Deficit and Hyperactivity Disorder, Schizophrenia, Foetal Alcohol Syndrome, Mild Cognitive Impairment, Age-related Memory Dysfunction, Down Syndrome and others), as well as sleep (e.g., hypersomnia and narcolepsy), and energy homeostasis (e.g. obesity) (Witkin & Nelson (2004) JPET: 103; 1-20; Hancock & Brune (2005) Exp Opin Inves Drugs: 14 (3), 223-241).

Accordingly, Histamine H3 receptor antagonists are described in the art for the treatment of the above mentioned diseases and disorders.

In WO-A 2007/080140 cyclylhexyl piperazinyl methanone derivatives are disclosed, which are useful as H3 receptor modulators.

In WO-A 2006/136924 cyclobutyl derivatives are disclosed as Histamine-3 receptor antagonists.

U.S. Pat. No. 4,956,359 describes anticonvulsants and antiepileptics having similar chemical structures without referring to H3 receptor antagonism.

However there is a continuing need for new compounds useful as Histamine H3 receptor antagonists.

Thus, an object of the present invention is to provide a new class of compounds as Histamine H3 receptor antagonists which may be effective in the treatment of H3 receptor related diseases and may show improved pharmaceutically relevant properties including activity, ADMET properties and/or reduced side effects.

Accordingly, the present invention provides compounds of formula (I)

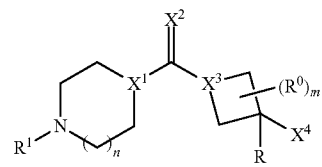

or a pharmaceutically acceptable salt, prodrug or metabolite thereof, wherein $R^1$ is $C_{1-5}$ alkyl; $C_{2-5}$ alkenyl; $C_{2-5}$ alkynyl; or $T^0$, wherein $C_{1-5}$ alkyl; $C_{2-5}$ alkenyl; $C_{2-5}$ alkynyl are optionally substituted with one or more substituents, which are the same or different and selected from the group consisting of halogen; OH; $OCH_3$; $OCH_2F$; $OCHF_2$; $OCF_3$; CN; and $T^0$;

$T^0$ is $C_{3-5}$ cycloalkyl; or 4 to 5 membered saturated heterocyclyl, wherein $T^0$ is optionally substituted with one or more substituents, which are the same or different and selected from the group consisting of halogen; $C_{1-5}$ alkyl; $C_{2-5}$ alkenyl; $C_{2-5}$ alkynyl; OH; O—$C_{1-5}$ alkyl; O—$C_{2-5}$ alkenyl; O—$C_{2-5}$ alkynyl; and CN, wherein $C_{1-5}$ alkyl; $C_{2-5}$ alkenyl; $C_{2-5}$ alkynyl; O—$C_{1-5}$ alkyl; O—$C_{2-5}$ alkenyl; and O—$C_{2-5}$ alkynyl are optionally substituted with one or more halogen, which are the same or different;

n is 1 or 2;

$X^1$ is N; or CH;

$X^2$ is O; S; N—CN; N—OH; or N—$OC_{1-4}$ alkyl;

$X^3$ is N; CH; or CF;

$X^4$ is H; F; or $(CH_2)_{n1}X^5(CH_2)_{n2}R^2$;

$R^0$ is F;

m is 0, 1, 2, 3, or 4;

R is H; or F;

Optionally, R, $X^4$ are joined to form oxo (=O);

n1; n2 are independently selected from the group consisting of 0; 1; and 2;

$X^5$ is C(O); C(O)O; OC(O); O; C(O)N($R^{1a}$); N($R^{1a}$)C(O); S(O)$_2$N($R^{1a}$); N($R^{1a}$)S(O)$_2$; S(O)N($R^{1a}$); N($R^{1a}$)S(O); S(O)$_2$; S(O); N($R^{1a}$)S(O)$_2$N($R^{1b}$); S; N($R^{1a}$); N($R^{1a}$)C(O)N($R^{1b}$); N($R^{1a}$)C(O)O; or OC(O)N($R^{1a}$);

$R^{1a}$, $R^{1b}$ are independently selected from the group consisting of H; $C_{1-4}$ alkyl; $C_{2-4}$ alkenyl; and $C_{2-4}$ alkynyl, wherein $C_{1-4}$ alkyl; $C_{2-4}$ alkenyl; and $C_{2-4}$ alkynyl are optionally substituted with one or more halogen, which are the same or different;

$R^2$ is H; T; $C_{1-6}$ alkyl; $C_{2-6}$ alkenyl; or $C_{2-6}$ alkynyl, wherein $C_{1-6}$ alkyl; $C_{2-6}$ alkenyl; and $C_{2-6}$ alkynyl are optionally substituted with one or more $R^3$, which are the same or different;

$R^3$ is halogen; CN; C(O)$R^4$; C(O)O$R^4$; O$R^4$; C(O)N($R^4R^{4a}$); S(O)$_2$N($R^4R^{4a}$); S(O)N($R^4R^{4a}$); S(O)$_2R^4$; S(O)$R^4$; N($R^4$)S(O)$_2$N($R^{4a}R^{4b}$); S$R^4$; N($R^4R^{4a}$); NO$_2$; OC(O)$R^4$; N($R^4$)C(O)$R^{4a}$; N($R^4$)SO$_2R^{4a}$; N($R^4$)S(O)$R^{4a}$; N($R^4$)C(O)N($R^{4a}R^{4b}$); N($R^4$)C(O)O$R^{4a}$; OC(O)N($R^4R^{4a}$); or T;

$R^4$, $R^{4a}$, $R^{4b}$ are independently selected from the group consisting of H; T; $C_{1-6}$ alkyl; $C_{2-6}$ alkenyl; and $C_{2-6}$ alkynyl, wherein $C_{1-6}$ alkyl; $C_{2-6}$ alkenyl; and $C_{2-6}$ alkynyl are optionally substituted with one or more $R^5$, which are the same or different;

$R^5$ is halogen; CN; C(O)$R^6$; C(O)O$R^6$; O$R^6$; C(O)N($R^6R^{6a}$); S(O)$_2$N($R^6R^{6a}$); S(O)N($R^6R^{6a}$); S(O)$_2R^6$; S(O)$R^6$; N($R^6$)S(O)$_2$N($R^{6a}R^{6b}$); S$R^6$; N($R^6R^{6a}$); NO$_2$;

OC(O)R⁶; N(R⁶)C(O)R⁶ᵃ; N(R⁶)SO₂R⁶ᵃ; N(R⁶)S(O)R⁶ᵃ; N(R⁶)C(O)N(R⁶ᵃR⁶ᵇ); N(R⁶)C(O)OR⁶ᵃ; OC(O)N(R⁶R⁶ᵃ); or T;

R⁶, R⁶ᵃ, R⁶ᵇ are independently selected from the group consisting of H; T; C₁₋₆ alkyl; C₂₋₆ alkenyl; and C₂₋₆ alkynyl, wherein C₁₋₆ alkyl; C₂₋₆ alkenyl; and C₂₋₆ alkynyl are optionally substituted with one or more halogen, which are the same or different;

T is phenyl; naphthyl; azulenyl; indenyl; indanyl; C₃₋₇ cycloalkyl; 3 to 7 membered heterocyclyl; or 7 to 11 membered heterobicyclyl, wherein T is optionally substituted with one or more R⁷, which are the same or different;

R⁷ is halogen; CN; C(O)OR⁸; OR⁸; C(O)R⁸; C(O)N(R⁸R⁸ᵃ); S(O)₂N(R⁸R⁸ᵃ); S(O)N(R⁸R⁸ᵃ); S(O)₂R⁸; S(O)R⁸; N(R⁸)S(O)₂N(R⁸ᵃR⁸ᵇ); SR⁸; N(R⁸R⁸ᵃ); NO₂; OC(O)R⁸; N(R⁸)C(O)R⁸ᵃ; N(R⁸)S(O)₂R⁸ᵃ; N(R⁸)S(O)R⁸ᵃ; N(R⁸)C(O)OR⁸ᵃ; N(R⁸)C(O)N(R⁸ᵃR⁸ᵇ); OC(O)N(R⁸R⁸ᵃ); oxo (=O), where the ring is at least partially saturated; T¹; C₁₋₆ alkyl; C₂₋₆ alkenyl; or C₂₋₆ alkynyl, wherein C₁₋₆ alkyl; C₂₋₆ alkenyl; and C₂₋₆ alkynyl are optionally substituted with one or more R⁹, which are the same or different;

R⁸, R⁸ᵃ, R⁸ᵇ are independently selected from the group consisting of H; T¹; C₁₋₆ alkyl; C₂₋₆ alkenyl; and C₂₋₆ alkynyl, wherein C₁₋₆ alkyl; C₂₋₆ alkenyl; and C₂₋₆ alkynyl are optionally substituted with one or more R¹⁰, which are the same or different;

R⁹, R¹⁰ are independently selected from the group consisting of halogen; CN; C(O)R¹¹; C(O)OR¹¹; OR¹¹; C(O)N(R¹¹R¹¹ᵃ); S(O)₂N(R¹¹R¹¹ᵃ); S(O)N(R¹¹R¹¹ᵃ); S(O)₂R¹¹; S(O)R¹¹; N(R¹¹)S(O)₂N(R¹¹ᵃR¹¹ᵇ); SR¹¹; N(R¹¹R¹¹ᵃ); NO₂; OC(O)R¹¹; N(R¹¹)C(O)R¹¹ᵃ; N(R¹¹)SO₂R¹¹ᵃ; N(R¹¹)S(O)R¹¹ᵃ; N(R¹¹)C(O)N(R¹¹ᵃR¹¹ᵇ); N(R¹¹)C(O)OR¹¹ᵃ; OC(O)N(R¹¹R¹¹ᵃ); and T¹;

R¹¹, R¹¹ᵃ, R¹¹ᵇ are independently selected from the group consisting of H; T¹; C₁₋₆ alkyl; C₂₋₆ alkenyl; and C₂₋₆ alkynyl, wherein C₁₋₆ alkyl; C₂₋₆ alkenyl; and C₂₋₆ alkynyl are optionally substituted with one or more halogen, which are the same or different;

T¹ is phenyl; C₃₋₇ cycloalkyl; or 3 to 7 membered heterocyclyl, wherein T¹ is optionally substituted with one or more R¹², which are the same or different;

R¹² is halogen; CN; C(O)OR¹³; OR¹³; C(O)R¹³; C(O)N(R¹³R¹³ᵃ); S(O)₂N(R¹³R¹³ᵃ); S(O)N(R¹³R¹³ᵃ); S(O)₂R¹³; S(O)R¹³; N(R¹³)S(O)₂N(R¹³ᵃR¹³ᵇ); SR¹³; N(R¹³R¹³ᵃ); NO₂; OC(O)R¹³; N(R¹³)C(O)R¹³ᵃ; N(R¹³)S(O)₂R¹³ᵃ; N(R¹³)S(O)R¹³ᵃ; N(R¹³)C(O)OR¹³ᵃ; N(R¹³)C(O)N(R¹³ᵃR¹³ᵇ); OC(O)N(R¹³R¹³ᵃ); oxo (=O), where the ring is at least partially saturated; C₁₋₆ alkyl; C₂₋₆ alkenyl; or C₂₋₆ alkynyl, wherein C₁₋₆ alkyl; C₂₋₆ alkenyl; and C₂₋₆ alkynyl are optionally substituted with one or more halogen, which are the same or different;

R¹³, R¹³ᵃ, R¹³ᵇ are independently selected from the group consisting of H; C₁₋₆ alkyl; C₂₋₆ alkenyl; and C₂₋₆ alkynyl, wherein C₁₋₆ alkyl; C₂₋₆ alkenyl; and C₂₋₆ alkynyl are optionally substituted with one or more halogen, which are the same or different, provided that the following compound salts are excluded:

1-Propyl-4-[3-[3-(trifluoromethyl)phenoxy]-1-azetidinylcarbonyl]piperazine fumarate [1:1];
1-Methyl-4-[3-[3-(trifluoromethyl)phenoxy]-1-azetidinylcarbonyl]piperazine oxalate [1:1.5];
1-Methyl-4-[3-[3-(trifluoromethyl)phenoxy]-1-azetidinylcarbonyl]piperazine fumarate [1:1];
1-[3-(4-Bromophenoxy)-1-azetidinylcarbonyl]-4-methylpiperazine fumarate [1:1];
1-[3-(3-Bromophenoxy)-1-azetidinylcarbonyl]-4-methylpiperazine fumarate [1:1];
1-[3-(4-Fluorophenoxy)-1-azetidinylcarbonyl]-4-methylpiperazine fumarate [1:1];
1-[3-(3,4-Dichlorophenoxy)-1-azetidinylcarbonyl]-4-methylpiperazine fumarate [1:1];
1-[3-[(4-Chlorophenyl)thio]-1-azetidinylcarbonyl]-4-methylpiperazine fumarate [1:1];
Hexahydro-1-methyl-4-[3-[3-(trifluoromethyl)phenoxy]-1-azetidinylcarbonyl]-1H-1,4-diazepine fumarate [1:1].

The individual salts excluded from formula (I) are described in U.S. Pat. No. 4,956,359. Preferably, the underlying compounds as such and pharmaceutical salts thereof are also excluded.

Preferably, the following 4 compounds are excluded from compounds according to formula (I) as far as compounds as such are addressed by the present invention.

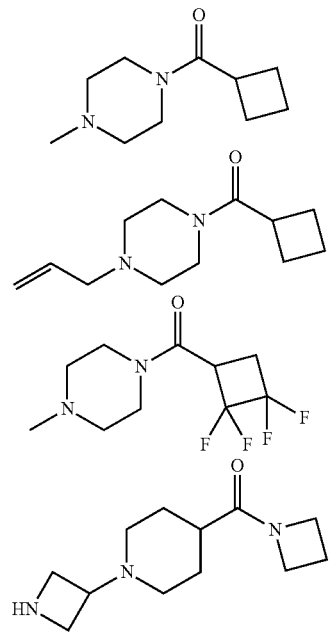

Preferably, the 4 compounds are not excluded as far as pharmaceutical compositions, compounds or pharmaceutical acceptable salts thereof for use as medicament or in a method of treating or preventing disorders, methods of treating or preventing diseases or disorders of the present invention are addressed.

Furthermore it is preferred that the following 5 compounds are also excluded from compounds according to formula (I) as far as compounds as such are addressed by the present invention.

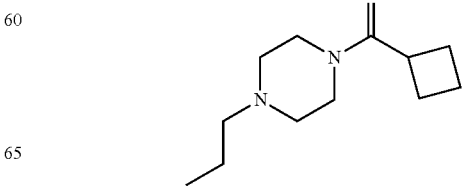

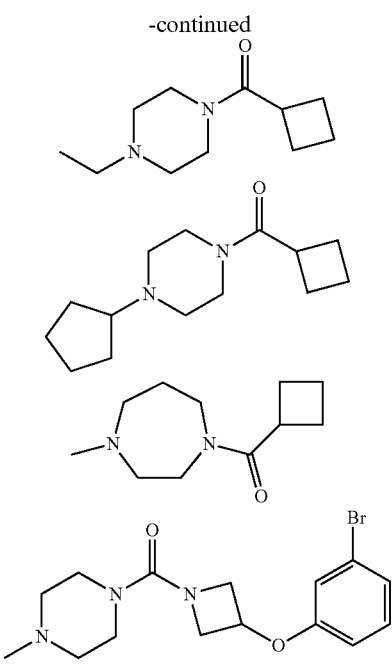

Preferably, the 5 compounds are not excluded as far as pharmaceutical compositions, compounds or pharmaceutical acceptable salts thereof for use as medicament or in a method of treating or preventing disorders, methods of treating or preventing diseases or disorders of the present invention are addressed.

In case a variable or substituent in formula (I) as defined above can be selected from a group of different variants and such variable or substituent occurs more than once the respective variants can be the same or different.

Within the meaning of the present invention the terms are used as follows:

"Alkyl" means a straight-chain or branched saturated hydrocarbon chain. Each hydrogen of an alkyl carbon may be replaced by a substituent as further specified.

"Alkenyl" means a straight-chain or branched hydrocarbon chain that contains at least one carbon-carbon double bond. Each hydrogen of an alkenyl carbon may be replaced by a substituent as further specified.

"Alkynyl" means a straight-chain or branched hydrocarbon chain that contains at least one carbon-carbon triple bond. Each hydrogen of an alkynyl carbon may be replaced by a substituent as further specified.

"$C_{1-4}$ alkyl" means an alkyl chain having 1-4 carbon atoms, e.g. if present at the end of a molecule: methyl, ethyl, n-propyl, isopropyl, n-butyl, isobutyl, sec-butyl, tert-butyl, or e.g. —CH$_2$—, —CH$_2$—CH$_2$—, —CH(CH$_3$)—, —CH$_2$—CH$_2$—CH$_2$—, —CH(C$_2$H$_5$)—, —C(CH$_3$)$_2$—, when two moieties of a molecule are linked by the alkyl group. Each hydrogen of a $C_{1-4}$ alkyl carbon may be replaced by a substituent as further specified.

"$C_{1-6}$ alkyl" means an alkyl chain having 1-6 carbon atoms, e.g. if present at the end of a molecule: $C_{1-4}$ alkyl, methyl, ethyl, n-propyl, isopropyl, n-butyl, isobutyl, sec-butyl, tert-butyl, n-pentyl, n-hexyl, or e.g. —CH$_2$—, —CH$_2$—CH$_2$—, —CH(CH$_3$)—, —CH$_2$—CH$_2$—CH$_2$—, —CH(C$_2$H$_5$)—, —C(CH$_3$)$_2$—, when two moieties of a molecule are linked by the alkyl group. Each hydrogen of a $C_{1-6}$ alkyl carbon may be replaced by a substituent as further specified. The term "$C_{1-5}$ alkyl" is defined accordingly.

"$C_{2-6}$ alkenyl" means an alkenyl chain having 2 to 6 carbon atoms, e.g. if present at the end of a molecule: —CH═CH$_2$, —CH═CH—CH$_3$, —CH$_2$—CH═CH$_2$, —CH═CH—CH$_2$—CH$_3$, —CH═CH—CH═CH$_2$, or e.g. —CH═CH—, when two moieties of a molecule are linked by the alkenyl group. Each hydrogen of a $C_{2-6}$ alkenyl carbon may be replaced by a substituent as further specified. The terms "$C_{2-4}$ alkenyl" and "$C_{2-5}$ alkenyl" are defined accordingly.

"$C_{2-6}$ alkynyl" means an alkynyl chain having 2 to 6 carbon atoms, e.g. if present at the end of a molecule: —C≡CH, —CH$_2$—C≡CH, CH$_2$—CH$_2$—C≡CH, CH$_2$—C≡C—CH$_3$, or e.g. —C≡C— when two moieties of a molecule are linked by the alkynyl group. Each hydrogen of a $C_{2-6}$ alkynyl carbon may be replaced by a substituent as further specified. The terms "$C_{2-4}$ alkynyl" and "$C_{2-5}$ alkynyl" are defined accordingly.

"$C_{3-7}$ cycloalkyl" or "$C_{3-7}$ cycloalkyl ring" means a cyclic alkyl chain having 3 to 7 carbon atoms, e.g. cyclopropyl, cyclobutyl, cyclopentyl, cyclohexyl, cycloheptyl. Each hydrogen of a cycloalkyl carbon may be replaced by a substituent as further specified. The term "$C_{3-5}$ cycloalkyl" is defined accordingly.

"Halogen" means fluoro, chloro, bromo or iodo. It is generally preferred that halogen is fluoro or chloro.

"3 to 7 membered heterocyclyl" or "3 to 7 membered heterocycle" means a ring with 3, 4, 5, 6 or 7 ring atoms that may contain up to the maximum number of double bonds (aromatic or non-aromatic ring which is fully, partially or un-saturated) wherein at least one ring atom up to 4 ring atoms are replaced by a heteroatom selected from the group consisting of sulfur (including —S(O)—, —S(O)$_2$—), oxygen and nitrogen (including N-oxide: ═N(O)—) and wherein the ring is linked to the rest of the molecule via a carbon or nitrogen atom. Examples for 3 to 7 membered heterocycles are azeridine, azetidine, oxetane, thietane, furan, thiophene, pyrrole, pyrroline, imidazole, imidazoline, pyrazole, pyrazoline, oxazole, oxazoline, isoxazole, isoxazoline, thiazole, thiazoline, isothiazole, isothiazoline, thiadiazole, thiadiazoline, tetrahydrofuran, tetrahydrothiophene, pyrrolidine, imidazolidine, pyrazolidine, oxazolidine, isoxazolidine, thiazolidine, isothiazolidine, thiadiazolidine, sulfo lane, pyran, dihydropyran, tetrahydropyran, imidazolidine, pyridine, pyridine-N-oxide, pyridazine, pyrazine, pyrimidine, piperazine, piperidine, morpholine, tetrazole, triazole, triazolidine, tetrazolidine, diazepane, azepine or homopiperazine. The term "4 to 5 membered heterocyclyl" or "4 to 5 membered heterocycle" is defined accordingly. The term "5 to 6 membered heterocyclyl" or "5 to 6 membered heterocycle" is defined accordingly.

"4 to 5 membered saturated heterocyclyl" or "4 to 5 membered saturated heterocycle" means a "4 to 5 membered heterocyclyl" or "4 to 5 membered heterocycle" without double bonds in the ring.

"7 to 11 membered heterobicyclyl" or "7 to 11 membered heterobicycle" means a heterocyclic system of two rings with 7 to 11 ring atoms, where at least one ring atom is shared by both rings and that may contain up to the maximum number of double bonds (aromatic or non-aromatic ring which is fully, partially or un-saturated) wherein at least one ring atom up to 6 ring atoms are replaced by a heteroatom selected from the group consisting of sulfur (including —S(O)—, —S(O)$_2$—), oxygen and nitrogen (including N-oxide: ═N(O)—) and wherein the ring is linked to the rest of the molecule via a carbon or nitrogen atom. Examples for 7 to 11 membered heterobicycles are imidazo[1,5-a]pyridine, imidazo[2,1-b][1,3]oxazole, imidazo[2,1-b][1,3]thiazole, 5,6,7,8-tetrahydro-1,6-naphthyridine, indole, indo line, benzo furan, benzothiophene, benzoxazole, benzisoxazole, benzothiazole, benzisothiazole, benzimidazole, benzimidazoline, quinoline, quinazoline, dihydroquinazoline, quinoline, dihydroquinoline, tetrahydroquino line, decahydroquinoline, isoquino line, decahydroisoquino line, tetrahydroisoquino line, dihydroisoquinoline, benzazepine, purine or pteridine. The term 7 to 11 membered heterobicycle also includes spiro structures of two rings like 1,4-dioxa-8-azaspiro[4.5]decane or bridged heterocycles like 8-aza-bicyclo[3.2.1]octane. The term "8 to 11 membered heterobicyclyl" or "8 to 11 membered heterobicycle" is defined accordingly.

"5 to 6 membered aromatic heterocyclyl" or "5 to 6 membered aromatic heterocycle" means a heterocycle derived from cyclopentadienyl or benzene, where at least one carbon atom is replaced by a heteroatom selected from the group consisting of sulfur (including —S(O)—, —S(O)$_2$—), oxygen and nitrogen (including N-oxide: =N(O)—). Examples for such heterocycles are furan, thiophene, pyrrole, imidazole, pyrazole, oxazole, isoxazole, thiazole, isothiazole, thiadiazole, pyranium, pyridine, pyridine-N-oxide, pyridazine, pyrimidine, triazole, tetrazole.

Preferred compounds of formula (I) are those compounds in which one or more of the residues contained therein have the meanings given below, with all combinations of preferred substituent definitions being a subject of the present invention. With respect to all preferred compounds of the formula (I) the present invention also includes all tautomeric and stereoisomeric forms and mixtures thereof in all ratios, and their pharmaceutically acceptable salts as well as their isotopic derivatives.

In preferred embodiments of the present invention, the substituents R, $R^0$, $R^1$, m, n and $X^1$ to $X^4$ of formula (I) independently have the following meaning. Hence, one or more of the substituents R, $R^0$, $R^1$, m, n and $X^1$ to $X^4$ can have the preferred or more preferred meanings given below.

Preferably, $R^1$ is $C_{1-5}$ alkyl; $C_{2-5}$ alkenyl; $C_{2-5}$ alkynyl; $C_{3-5}$ cycloalkyl; $CH_2$-cyclopropyl; CHF-cyclopropyl; $CF_2$-cyclopropyl; $CH_2$-cyclobutyl; CHF-cyclobutyl; $CF_2$-cyclobutyl; or 4 to 5 membered saturated heterocyclyl, wherein $C_{1-5}$ alkyl; $C_{2-5}$ alkenyl; $C_{2-5}$ alkynyl are optionally substituted with one or more substituents, which are the same or different and selected from the group consisting of halogen; OH; $OCH_3$; $OCH_2F$; $OCHF_2$; $OCF_3$; and CN, and wherein $C_{3-5}$ cycloalkyl; $CH_2$-cyclopropyl; CHF-cyclopropyl; $CF_2$-cyclopropyl; $CH_2$-cyclobutyl; CHF-cyclobutyl; $CF_2$-cyclobutyl; and 4 to 5 membered saturated heterocyclyl are optionally substituted with one or more substituents, which are the same or different and selected from the group consisting of halogen; OH; $OCH_3$; $OCH_2F$; $OCHF_2$; $OCF_3$; CN; $CH_3$; $CH_2F$; $CHF_2$; and $CF_3$.

More preferably, $R^1$ is $C_{1-5}$ alkyl; $C_{3-5}$ cycloalkyl; $CH_2$-cyclopropyl; CHF-cyclopropyl; $CF_2$-cyclopropyl; $CH_2$-cyclobutyl; CHF-cyclobutyl; $CF_2$-cyclobutyl; or 4 to 5 membered saturated heterocyclyl, wherein $C_{1-5}$ alkyl; $C_{3-5}$ cycloalkyl; $CH_2$-cyclopropyl; CHF-cyclopropyl; $CF_2$-cyclopropyl; $CH_2$-cyclobutyl; CHF-cyclobutyl; $CF_2$-cyclobutyl; and 4 to 5 membered saturated heterocyclyl are optionally substituted with one or more substituents, which are the same or different and selected from the group consisting of halogen; OH; $OCH_3$; $OCH_2F$; $OCHF_2$; $OCF_3$; CN; $CH_3$; $CH_2F$; $CHF_2$; and $CF_3$.

More preferably, $R^1$ is $C_{3-5}$ cycloalkyl; $CH_2$-cyclopropyl; CHF-cyclopropyl; $CF_2$-cyclopropyl; $CH_2$-cyclobutyl; CHF-cyclobutyl; $CF_2$-cyclobutyl; or 4 to 5 membered saturated heterocyclyl, wherein $C_{3-5}$ cycloalkyl; $CH_2$-cyclopropyl; CHF-cyclopropyl; $CF_2$-cyclopropyl; $CH_2$-cyclobutyl; CHF-cyclobutyl; $CF_2$-cyclobutyl; and 4 to 5 membered saturated heterocyclyl are optionally substituted with one or more substituents, which are the same or different and selected from the group consisting of halogen; OH; $OCH_3$; $OCH_2F$; $OCHF_2$; $OCF_3$; CN; $CH_3$; $CH_2F$; $CHF_2$; and $CF_3$.

In a more preferred embodiment $R^1$ is substituted or unsubstituted $C_{1-5}$ alkyl; substituted or unsubstituted $C_{3-5}$ cycloalkyl; substituted or unsubstituted $CH_2$-cyclopropyl; or substituted or unsubstituted $CH_2$-cyclobutyl.

In yet another more preferred embodiment $R^1$ is substituted or unsubstituted $C_{3-5}$ cycloalkyl; substituted or unsubstituted $CH_2$-cyclopropyl; or substituted or unsubstituted $CH_2$-cyclobutyl.

In an even more preferred embodiment $R^1$ is isopropyl; cyclobutyl; ethyl; cyclopentyl; cyclopropyl; $CH_2$-cyclopropyl; or $CH_2$-cyclobutyl.

In yet another even more preferred embodiment $R^1$ is isopropyl; cyclobutyl; cyclopentyl; cyclopropyl; $CH_2$-cyclopropyl; or $CH_2$-cyclobutyl.

In an even more preferred embodiment $R^1$ is cyclobutyl; ethyl; isopropyl; or cyclopentyl.

In yet another even more preferred embodiment $R^1$ is cyclobutyl; or cyclopentyl.

Preferably, n is 2.

Preferably, $X^1$ is N. In another preferred embodiment $X^1$ is CH.

Preferably, $X^2$ is S; or O. In a more preferred embodiment $X^2$ is O.

Preferably, at least one of $X^1$, $X^3$ is N. Preferably, $X^3$ is CH. Preferably, $X^3$ is N. Preferably, $X^1$, $X^3$ are N.

Preferably, m is 0.

Preferably, n1; n2 are independently selected from the group consisting of 0; and 1. In a preferred embodiment n1 is 0 or 1 and n2 is 0. In a more preferred embodiment n1 and n2 are 0. In another preferred embodiment is at least one of n1, n2 other than 0.

Preferably, $X^4$ is $(CH_2)_{n1}X^5(CH_2)_{n2}R^2$.

Preferably, $X^5$ is C(O); O; C(O)N($R^{1a}$); N($R^{1a}$)C(O); $S(O)_2$ N($R^{1a}$); N($R^{1a}$)S(O)$_2$; N($R^{1a}$); or N($R^{1a}$)C(O)N($R^{1b}$). Also preferably, $X^5$ is C(O); C(O)N($R^{1a}$); N($R^{1a}$)C(O); $S(O)_2$ N($R^{1a}$); N($R^{1a}$)S(O)$_2$; N($R^{1a}$); or N($R^{1a}$)C(O)N($R^{1b}$). In a more preferred embodiment $X^5$ is C(O); O; C(O)N($R^{1a}$); N($R^{1a}$)C(O); N($R^{1a}$)S(O)$_2$; N($R^{1a}$); or N($R^{1a}$)C(O)N($R^{1b}$). In a further more preferred embodiment $X^5$ is C(O); C(O)N($R^{1a}$); N($R^{1a}$)C(O); N($R^{1a}$)S(O)$_2$; N($R^{1a}$); or N($R^{1a}$)C(O)N($R^{1b}$). In an even more preferred embodiment $X^5$ is C(O); O; C(O)N($R^{1a}$); N($R^{1a}$)C(O); or N($R^{1a}$). In a further even more preferred embodiment $X^5$ is C(O); C(O)N($R^{1a}$); N($R^{1a}$)C(O); or N($R^{1a}$).

Preferably, $R^2$ is H; or T. In a more preferred embodiment $R^2$ is T, especially when T is aromatic. In an even more preferred embodiment T is a 6 membered heterocyclyl, especially when T is aromatic. In a further even more preferred embodiment T is phenyl; or pyridine. In a further even more preferred embodiment T is a phenyl. In a further even more preferred embodiment T is pyridine. T may be unsubstituted or substituted. Preferably, T is unsubstituted or substituted with one, two or three (more preferably, with one or two) $R^7$, which are the same or different.

$R^7$ is preferably selected from the group consisting of halogen; CN; C(O)$R^8$; N($R^8R^{8a}$); O$R^8$; C(O)N($R^8R^{8a}$); S(O)$_2R^8$; $C_{1-6}$ alkyl optionally substituted with one or more $R^9$ (even more preferably substituted or unsubstituted $CH_2$-$T^1$), which are the same or different; or substituted or unsubstituted $T^1$.

Compounds of the formula (I) in which some or all of the above-mentioned groups have the preferred or more preferred meanings are also an object of the present invention.

Preferred individual compounds of the present invention are selected from the group consisting of
1-[(4-cyclobutyl-1,4-diazepan-1-yl)carbonyl]azetidin-3-ol;
1-[(4-cyclobutylpiperazin-1-yl)carbonyl]azetidin-3-ol;
6-({1-[(4-cyclobutyl-1,4-diazepan-1-yl)carbonyl]azetidin-3-yl}oxy)-N-methylpyridine-3-carboxamide;
5-({1-[(4-cyclobutyl-1,4-diazepan-1-yl)carbonyl]azetidin-3-yl}oxy)pyridine-2-carboxamide;
5-({1-[(4-cyclobutyl-1,4-diazepan-1-yl)carbonyl]azetidin-3-yl}oxy)-N-methylpyridine-2-carboxamide;
5-({1-[(4-cyclobutyl-1,4-diazepan-1-yl)carbonyl]azetidin-3-yl}oxy)-N,N-dimethylpyridine-2-carboxamide;
5-({1-[(4-cyclobutyl-1,4-diazepan-1-yl)carbonyl]azetidin-3-yl}oxy)-N,N-diethylpyridine-2-carboxamide;
4-({1-[(4-cyclobutyl-1,4-diazepan-1-yl)carbonyl]azetidin-3-yl}oxy)-N-methylbenzamide;
4-({1-[(4-cyclobutyl-1,4-diazepan-1-yl)carbonyl]azetidin-3-yl}oxy)-N,N-dimethylbenzamide;
1-cyclobutyl-4-({3-[4-(trifluoromethyl)phenoxy]azetidin-1-yl}carbonyl)-1,4-diazepane;
1-cyclobutyl-4-[(3-{[5-(trifluoromethyl)pyridin-2-yl]oxy}azetidin-1-yl)carbonyl]-1,4-diazepane;
4-({1-[(4-cyclobutyl-1,4-diazepan-1-yl)carbonyl]azetidin-3-yl}oxy)benzonitrile;
1-cyclobutyl-4-{[3-(4-fluorophenoxy)azetidin-1-yl]carbonyl}-1,4-diazepane;
1-{[3-(4-chlorophenoxy)azetidin-1-yl]carbonyl}-4-cyclobutyl-1,4-diazepane;
1-cyclobutyl-4-[(3-phenoxyazetidin-1-yl)carbonyl]-1,4-diazepane;
1-cyclobutyl-4-({3-[4-(1H-pyrazol-1-ylmethyl)phenoxy]azetidin-1-yl}carbonyl)-1,4-diazepane;
1-cyclobutyl-4-[(3-{[5-(1H-pyrazol-1-ylmethyl)pyridin-2-yl]oxy}azetidin-1-yl)carbonyl]-1,4-diazepane;
1-[4-({1-[(4-cyclobutyl-1,4-diazepan-1-yl)carbonyl]azetidin-3-yl}oxy)phenyl]pyrrolidin-2-one;
1-cyclobutyl-4-({3-[4-(piperidin-1-ylmethyl)phenoxy]azetidin-1-yl}carbonyl)-1,4-diazepane;
1-cyclobutyl-4-[(3-{4-[(4-methylpiperazin-1-yl)methyl]phenoxy}azetidin-1-yl)carbonyl]-1,4-diazepane;
1-cyclobutyl-4-[(3-{4-[(4,4-difluoropiperidin-1-yl)methyl]phenoxy}azetidin-1-yl)carbonyl]-1,4-diazepane;
1-({3-[(5-bromopyridin-2-yl)oxy]azetidin-1-yl}carbonyl)-4-cyclobutyl-1,4-diazepane;
1-cyclobutyl-4-{[3-(3,4-dichlorophenoxy)azetidin-1-yl]carbonyl}-1,4-diazepane;
1-({3-[(6-bromopyridin-3-yl)oxy]azetidin-1-yl}carbonyl)-4-cyclobutyl-1,4-diazepane;
1-{[3-(4-chloro-2-methylphenoxy)azetidin-1-yl]carbonyl}-4-cyclobutyl-1,4-diazepane;
1-cyclobutyl-4-({3-[4-(1H-imidazol-1-yl)phenoxy]azetidin-1-yl}carbonyl)-1,4-diazepane;
1-cyclobutyl-4-({3-[(2-methylpyridin-4-yl)oxy]azetidin-1-yl}carbonyl)-1,4-diazepane;
1-cyclobutyl-4-({3-[3-(trifluoromethyl)phenoxy]azetidin-1-yl}carbonyl)-1,4-diazepane;
1-cyclobutyl-4-({3-[2-(trifluoromethyl)phenoxy]azetidin-1-yl}carbonyl)-1,4-diazepane;
3-({1-[(4-cyclobutyl-1,4-diazepan-1-yl)carbonyl]azetidin-3-yl}oxy)benzonitrile;
2-({1-[(4-cyclobutyl-1,4-diazepan-1-yl)carbonyl]azetidin-3-yl}oxy)benzonitrile;
1-{[3-(3-chlorophenoxy)azetidin-1-yl]carbonyl}-4-cyclobutyl-1,4-diazepane;
1-{[3-(2-chlorophenoxy)azetidin-1-yl]carbonyl}-4-cyclobutyl-1,4-diazepane;
4-({1-[(4-cyclobutyl-1,4-diazepan-1-yl)carbonyl]azetidin-3-yl}oxy)-N,3-dimethylbenzamide;
5-({1-[(4-cyclobutyl-1,4-diazepan-1-yl)carbonyl]azetidin-3-yl}oxy)-N-(cyclopropylmethyl)pyridine-2-carboxamide;
1-cyclobutyl-4-[(3-{[5-(trifluoromethyl)pyridin-3-yl]oxy}azetidin-1-yl)carbonyl]-1,4-diazepane;
5-({1-[(4-cyclobutylpiperazin-1-yl)carbonyl]azetidin-3-yl}oxy)-N-methylpyridine-2-carboxamide;
1-cyclobutyl-4-[(3-phenoxyazetidin-1-yl)carbonyl]piperazine;
1-cyclobutyl-4-({3-[4-(trifluoromethyl)phenoxy]azetidin-1-yl}carbonyl)piperazine;
4-({1-[(4-cyclobutylpiperazin-1-yl)carbonyl]azetidin-3-yl}oxy)benzonitrile;
1-cyclobutyl-4-{[3-(4-fluorophenoxy)azetidin-1-yl]carbonyl}piperazine;
6-cyclobutyl-2-({1-[(4-cyclobutyl-1,4-diazepan-1-yl)carbonyl]azetidin-3-yl}oxy)-5,6,7,8-tetrahydro-1,6-naphthyridine;
4-({1-[(4-cyclobutyl-1,4-diazepan-1-yl)carbonyl]azetidin-3-yl}oxy)-3-fluoro-N-methylbenzamide;
1-cyclobutyl-4-{[3-(4-iodophenoxy)azetidin-1-yl]carbonyl}-1,4-diazepane;
1-cyclobutyl-4-({3-[(5-fluoropyridin-3-yl)oxy]azetidin-1-yl}carbonyl)-1,4-diazepane;
1-({3-[(6-chloropyridin-3-yl)oxy]azetidin-1-yl}carbonyl)-4-cyclobutyl-1,4-diazepane;
4-({1-[(4-cyclobutyl-1,4-diazepan-1-yl)carbonyl]azetidin-3-yl}oxy)-2-fluoro-N-methylbenzamide;
1-({3-[(3-chloropyridin-2-yl)oxy]azetidin-1-yl}carbonyl)-4-cyclobutyl-1,4-diazepane;
1-cyclobutyl-4-({3-[(3-fluoropyridin-4-yl)oxy]azetidin-1-yl}carbonyl)-1,4-diazepane;
1-({3-[(4-chloro-2-methylpyridin-3-yl)oxy]azetidin-1-yl}carbonyl)-4-cyclobutyl-1,4-diazepane;
5-({1-[(4-cyclobutyl-1,4-diazepan-1-yl)carbonyl]azetidin-3-yl}oxy)imidazo[1,5-a]pyridine;
1-cyclobutyl-4-({3-[(2-methoxypyrimidin-4-yl)oxy]azetidin-1-yl}carbonyl)-1,4-diazepane;
2-[4-({1-[(4-cyclobutyl-1,4-diazepan-1-yl)carbonyl]azetidin-3-yl}oxy)pyridin-2-yl]propan-2-ol;
1-cyclobutyl-4-({3-[(2-ethylpyridin-4-yl)oxy]azetidin-1-yl}carbonyl)-1,4-diazepane;
1-cyclobutyl-4-[(3-{[2-(1-methylethyl)pyridin-4-yl]oxy}azetidin-1-yl)carbonyl]-1,4-diazepane;
1-cyclobutyl-4-({3-[(2-methoxypyridin-4-yl)oxy]azetidin-1-yl}carbonyl)-1,4-diazepane;
4-({1-[(4-cyclobutyl-1,4-diazepan-1-yl)carbonyl]azetidin-3-yl}oxy)pyridin-2-amine;
4-({1-[(4-cyclobutyl-1,4-diazepan-1-yl)carbonyl]azetidin-3-yl}oxy)-N,N-dimethylpyridin-2-amine;
1-cyclobutyl-4-({3-[(6-methylpyridazin-3-yl)oxy]azetidin-1-yl}carbonyl)-1,4-diazepane;
2-[4-({1-[(4-cyclobutyl-1,4-diazepan-1-yl)carbonyl]azetidin-3-yl}oxy)-2-fluorophenyl]propan-2-ol;
1-cyclobutyl-4-({3-[(3,5-dimethylpyrazin-2-yl)oxy]azetidin-1-yl}carbonyl)-1,4-diazepane;
1-cyclobutyl-4-({3-[(2-methoxypyrimidin-4-yl)oxy]azetidin-1-yl}carbonyl)-1,4-diazepane;
1-cyclobutyl-4-({3-[(6-methylpyrazin-2-yl)oxy]azetidin-1-yl}carbonyl)-1,4-diazepane;
1-cyclobutyl-4-({3-[(3,6-dimethylpyrazin-2-yl)oxy]azetidin-1-yl}carbonyl)-1,4-diazepane;
1-cyclobutyl-4-({3-[(2-methylpyrimidin-4-yl)oxy]azetidin-1-yl}carbonyl)-1,4-diazepane;

1-cyclobutyl-4-({3-[(6-methoxypyrazin-2-yl)oxy]azetidin-1-yl}carbonyl)-1,4-diazepane;
1-({3-[(3-chloropyridin-2-yl)oxy]azetidin-1-yl}carbonyl)-4-cyclobutyl-1,4-diazepane;
4-({1-[(4-cyclobutyl-1,4-diazepan-1-yl)carbonyl]azetidin-3-yl}oxy)quino line;
1-cyclobutyl-4-({3-[(2,6-dimethylpyridin-4-yl)oxy]azetidin-1-yl}carbonyl)-1,4-diazepane;
8-({1-[(4-cyclobutyl-1,4-diazepan-1-yl)carbonyl]azetidin-3-yl}oxy)imidazo[1,2-a]pyridine;
7-({1-[(4-cyclobutyl-1,4-diazepan-1-yl)carbonyl]azetidin-3-yl}oxy)imidazo[1,2-a]pyridine;
4-({1-[(4-cyclobutyl-1,4-diazepan-1-yl)carbonyl]azetidin-3-yl}oxy)pyridine-2-carboxamide;
5-({1-[(4-cyclobutyl-1,4-diazepan-1-yl)carbonyl]azetidin-3-yl}oxy)-N-(cyclopropylmethyl)pyridine-2-carboxamide;
1-cyclobutyl-4-[(3-{[6-(piperidin-1-ylcarbonyl)pyridin-3-yl]oxy}azetidin-1-yl)carbonyl]-1,4-diazepane;
3-({1-[(4-cyclobutyl-1,4-diazepan-1-yl)carbonyl]azetidin-3-yl}oxy)-N-methylbenzamide;
1-({3-[(5-chloropyridin-2-yl)oxy]azetidin-1-yl}carbonyl)-4-cyclobutyl-1,4-diazepane;
1-({3-[(5-chloropyridin-2-yl)oxy]azetidin-1-yl}carbonyl)-4-cyclobutyl-1,4-diazepane;
1-cyclobutyl-4-({3-[(3,5-dimethylpyrazin-2-yl)oxy]azetidin-1-yl}carbonyl)-1,4-diazepane;
1-({3-[(3-chloropyridin-4-yl)oxy]azetidin-1-yl}carbonyl)-4-cyclobutyl-1,4-diazepane;
1-({3-[(5-chloropyridin-3-yl)oxy]azetidin-1-yl}carbonyl)-4-cyclobutyl-1,4-diazepane;
1-cyclobutyl-4-{[3-(pyridin-4-yloxy)azetidin-1-yl]carbonyl}-1,4-diazepane;
1-cyclobutyl-4-({3-[(5-methoxypyridin-3-yl)oxy]azetidin-1-yl}carbonyl)-1,4-diazepane;
2-({1-[(4-cyclobutyl-1,4-diazepan-1-yl)carbonyl]azetidin-3-yl}oxy)-6-(cyclopropylcarbonyl)-5,6,7,8-tetrahydro-1,6-naphthyridine;
2-({1-[(4-cyclobutyl-1,4-diazepan-1-yl)carbonyl]azetidin-3-yl}oxy)-6-(cyclopropylacetyl)-5,6,7,8-tetrahydro-1,6-naphthyridine;
4-({1-[(4-cyclobutyl-1,4-diazepan-1-yl)carbonyl]azetidin-3-yl}oxy)-N-methylpyridine-3-carboxamide;
1-cyclobutyl-4-{[3-(4-methoxyphenoxy)azetidin-1-yl]carbonyl}-1,4-diazepane;
1-cyclobutyl-4-({3-[4-(1H-pyrazol-1-yl)phenoxy]azetidin-1-yl}carbonyl)-1,4-diazepane;
1-cyclobutyl-4-({3-[4-(trifluoromethoxy)phenoxy]azetidin-1-yl}carbonyl)-1,4-diazepane;
1-cyclobutyl-4-({3-[4-(difluoromethoxy)phenoxy]azetidin-1-yl}carbonyl)-1,4-diazepane;
1-{[3-(4-chloro-2-fluorophenoxy)azetidin-1-yl]carbonyl}-4-cyclobutyl-1,4-diazepane;
1-cyclobutyl-4-{[3-(3-methoxyphenoxy)azetidin-1-yl]carbonyl}-1,4-diazepane;
1-cyclobutyl-4-{[3-(2-methoxyphenoxy)azetidin-1-yl]carbonyl}-1,4-diazepane;
6-({1-[(4-cyclobutyl-1,4-diazepan-1-yl)carbonyl]azetidin-3-yl}oxy)-2-methylquinoline;
1-cyclobutyl-4-[(3-{[6-(trifluoromethyl)pyridin-3-yl]oxy}azetidin-1-yl)carbonyl]-1,4-diazepane;
1-cyclobutyl-4-({3-[(4-fluorobenzyl)oxy]azetidin-1-yl}carbonyl)-1,4-diazepane;
1-cyclobutyl-4-[(3-methoxyazetidin-1-yl)carbonyl]-1,4-diazepane;
1-({3-[(4-chlorobenzyl)oxy]azetidin-1-yl}carbonyl)-4-cyclobutyl-1,4-diazepane;
4-[({1-[(4-cyclobutyl-1,4-diazepan-1-yl)carbonyl]azetidin-3-yl}oxy)methyl]benzonitrile;
1-cyclobutyl-4-{[3-(prop-2-yn-1-yloxy)azetidin-1-yl]carbonyl}-1,4-diazepane;
3-[(4-cyclobutyl-1,4-diazepan-1-yl)carbonyl]cyclobutanone;
cis-3-[(4-cyclobutyl-1,4-diazepan-1-yl)carbonyl]cyclobutanol;
6-({cis-3-[(4-cyclobutyl-1,4-diazepan-1-yl)carbonyl]cyclobutyl}oxy)-N-methylpyridine-3-carboxamide;
4-({cis-3-[(4-cyclobutyl-1,4-diazepan-1-yl)carbonyl]cyclobutyl}oxy)benzonitrile;
1-cyclobutyl-4-[(cis-3-{[5-(trifluoromethyl)pyridin-2-yl]oxy}cyclobutyl)carbonyl]-1,4-diazepane;
trans-3-[(4-cyclobutyl-1,4-diazepan-1-yl)carbonyl]cyclobutanol;
4-({trans-3-[(4-cyclobutyl-1,4-diazepan-1-yl)carbonyl]cyclobutyl}oxy)benzonitrile;
1-cyclobutyl-4-[(trans-3-{[5-(trifluoromethyl)pyridin-2-yl]oxy}cyclobutyl)carbonyl]-1,4-diazepane;
1-[(4-cyclobutyl-1,4-diazepan-1-yl)carbonyl]azetidin-3-one;
1-[(4-cyclobutyl-1,4-diazepan-1-yl)carbonyl]azetidin-3-amine;
5-({1-[(4-cyclobutyl-1,4-diazepan-1-yl)carbonyl]azetidin-3-yl}amino)-N-methylpyridine-2-carboxamide;
5-[{1-[(4-cyclobutyl-1,4-diazepan-1-yl)carbonyl]azetidin-3-yl}(methyl)amino]-N-methylpyridine-2-carboxamide;
4-[({1-[(4-cyclobutyl-1,4-diazepan-1-yl)carbonyl]azetidin-3-yl}amino)methyl]benzonitrile;
5-({1-[(4-methyl-1,4-diazepan-1-yl)carbonyl]azetidin-3-yl}oxy)-N-methylpyridine-2-carboxamide;
5-({1-[(4-(1-methylethyl)-1,4-diazepan-1-yl)carbonyl]azetidin-3-yl}oxy)-N-methylpyridine-2-carboxamide;
5-({1-[(4-cyclopentyl-1,4-diazepan-1-yl)carbonyl]azetidin-3-yl}oxy)-N-methylpyridine-2-carboxamide;
6-({1-[(4-cyclobutyl-1,4-diazepan-1-yl)carbonyl]azetidin-3-yl}oxy)-3,4-dihydroisoquinolin-1(2H)-one;
6-({1-[(4-cyclobutyl-1,4-diazepan-1-yl)carbonyl]azetidin-3-yl}oxy)-2-methyl-3,4-dihydroisoquinolin-1(2H)-one;
2-[5-({1-[(4-cyclobutyl-1,4-diazepan-1-yl)carbonyl]azetidin-3-yl}oxy)pyridin-2-yl]propan-2-ol;
1-[5-({1-[(4-cyclobutyl-1,4-diazepan-1-yl)carbonyl]azetidin-3-yl}oxy)pyridin-2-yl]ethanone;
1-cyclobutyl-4-({3-[(5-methoxypyrimidin-2-yl)oxy]azetidin-1-yl}carbonyl)-1,4-diazepane;
1-cyclobutyl-4-({3-[(6-methylpyridin-3-yl)oxy]azetidin-1-yl}carbonyl)-1,4-diazepane;
methyl 1-[(4-cyclobutyl-1,4-diazepan-1-yl)carbonyl]azetidine-3-carboxylate;
N-(4-chlorophenyl)-1-[(4-cyclobutyl-1,4-diazepan-1-yl)carbonyl]azetidine-3-carboxamide;
1-cyclobutyl-4-{[3-(piperidin-1-ylcarbonyl)azetidin-1-yl]carbonyl}-1,4-diazepane;
1-cyclobutyl-4-{[3-(morpholin-4-ylcarbonyl)azetidin-1-yl]carbonyl}-1,4-diazepane;
1-{[3-(azetidin-1-ylcarbonyl)azetidin-1-yl]carbonyl}-4-cyclobutyl-1,4-diazepane;
1-cyclobutyl-4-{[3-(pyrrolidin-1-ylcarbonyl)azetidin-1-yl]carbonyl}-1,4-diazepane;
1-{[3-(azepan-1-ylcarbonyl)azetidin-1-yl]carbonyl}-4-cyclobutyl-1,4-diazepane;
1-cyclobutyl-4-({3-[(4-fluoropiperidin-1-yl)carbonyl]azetidin-1-yl}carbonyl)-1,4-diazepane;
1-cyclobutyl-4-({3-[(4,4-difluoropiperidin-1-yl)carbonyl]azetidin-1-yl}carbonyl)-1,4-diazepane;

1-[(4-cyclobutyl-1,4-diazepan-1-yl)carbonyl]-N-cyclohexylazetidine-3-carboxamide;
1-[(4-cyclobutyl-1,4-diazepan-1-yl)carbonyl]-N-(6-methylpyridin-3-yl)azetidine-3-carboxamide;
1-[(4-cyclobutyl-1,4-diazepan-1-yl)carbonyl]-N-methylazetidine-3-carboxamide;
{1-[(4-cyclobutyl-1,4-diazepan-1-yl)carbonyl]azetidin-3-yl}methanol;
1-({3-[(4-chlorophenoxy)methyl]azetidin-1-yl}carbonyl)-4-cyclobutyl-1,4-diazepane;
6-({1-[(4-cyclobutyl-1,4-diazepan-1-yl)carbonyl]azetidin-3-yl}methoxy)-3,4-dihydroisoquinolin-1(2H)-one;
6-({1-[(4-cyclobutyl-1,4-diazepan-1-yl)carbonyl]azetidin-3-yl}methoxy)-2-methyl-3,4-dihydroisoquinolin-1(2H)-one;
5-({1-[(4-cyclobutyl-1,4-diazepan-1-yl)carbonyl]azetidin-3-yl}methoxy)-N-methylpyridine-2-carboxamide;
N-{1-[(4-cyclobutyl-1,4-diazepan-1-yl)carbonyl]azetidin-3-yl}-6-methylpyridine-3-carboxamide;
4-chloro-N-{1-[(4-cyclobutyl-1,4-diazepan-1-yl)carbonyl]azetidin-3-yl}benzamide;
N-{1-[(4-cyclobutyl-1,4-diazepan-1-yl)carbonyl]azetidin-3-yl}cyclohexane carboxamide;
4-chloro-N-{1-[(4-cyclobutyl-1,4-diazepan-1-yl)carbonyl]azetidin-3-yl}-N-methylbenzamide;
N-{1-[(4-cyclobutyl-1,4-diazepan-1-yl)carbonyl]azetidin-3-yl}-N,6-dimethylpyridine-3-carboxamide;
N-{1-[(4-cyclobutyl-1,4-diazepan-1-yl)carbonyl]azetidin-3-yl}-N-methylcyclohexanecarboxamide;
1-[(4-cyclobutyl-1,4-diazepan-1-yl)carbonyl]-N-methyl-N-(6-methylpyridin-3-yl)azetidine-3-carboxamide;
N-(4-chlorophenyl)-1-[(4-cyclobutyl-1,4-diazepan-1-yl)carbonyl]-N-methylazetidine-3-carboxamide;
4-({1-[(4-cyclobutyl-1,4-diazepan-1-yl)carbonyl]azetidin-3-yl}oxy)-N-methylpyridine-2-carboxamide;
1-cyclobutyl-4-{[3-(methoxymethyl)azetidin-1-yl]carbonyl}-1,4-diazepane;
1-cyclobutyl-4-({3-[4-(1-methyl-1H-pyrazol-4-yl)phenoxy]azetidin-1-yl}carbonyl)-1,4-diazepane;
1-cyclobutyl-4-({3-[4-(1,3,5-trimethyl-1H-pyrazol-4-yl)phenoxy]azetidin-1-yl}carbonyl)-1,4-diazepane;
1-cyclobutyl-4-({3-[(3-fluoro-2-methylpyridin-4-yl)oxy]azetidin-1-yl}carbonyl)-1,4-diazepane;
1-cyclobutyl-4-{[3-(naphthalen-2-yloxy)azetidin-1-yl]carbonyl}-1,4-diazepane;
1-cyclobutyl-4-{[3-({[6-(trifluoromethyl)pyridin-3-yl]oxy}methyl)azetidin-1-yl]carbonyl}-1,4-diazepane;
5-({1-[(4-cyclobutyl-1,4-diazepan-1-yl)carbonyl]azetidin-3-yl}oxy)-1H-indole;
5-({1-[(4-cyclobutyl-1,4-diazepan-1-yl)carbonyl]azetidin-3-yl}oxy)-1-methyl-1H-indole;
2-[5-({1-[(4-cyclobutyl-1,4-diazepan-1-yl)carbonyl]azetidin-3-yl}oxy)pyridin-2-yl]-2-methylpropan-1-ol;
2-[5-({1-[(4-ethyl-1,4-diazepan-1-yl)carbonyl]azetidin-3-yl}oxy)pyridin-2-yl]propan-2-ol;
2-{5-[(1-{[4-(1-methylethyl)-1,4-diazepan-1-yl]carbonyl}azetidin-3-yl)oxy]pyridin-2-yl}propan-2-ol;
2-[5-({1-[(4-cyclopentyl-1,4-diazepan-1-yl)carbonyl]azetidin-3-yl}oxy)pyridin-2-yl]propan-2-ol;
1-cyclobutyl-4-({3-[(5-fluoropyrimidin-2-yl)oxy]azetidin-1-yl}carbonyl)-1,4-diazepane;
1-cyclobutyl-4-({3-[(5-methoxypyridin-2-yl)oxy]azetidin-1-yl}carbonyl)-1,4-diazepane;
1-cyclobutyl-4-({3-[(5-ethylpyrimidin-2-yl)oxy]azetidin-1-yl}carbonyl)-1,4-diazepane;
1-cyclobutyl-4-({3-[4-(methylsulfonyl)phenoxy]azetidin-1-yl}carbonyl)-1,4-diazepane;
1-cyclobutyl-4-({3-[(6-methylpyridin-3-yl)methoxy]azetidin-1-yl}carbonyl)-1,4-diazepane;
2-[5-({cis-3-[(4-cyclobutyl-1,4-diazepan-1-yl)carbonyl]cyclobutyl}oxy)pyridin-2-yl]propan-2-ol;
1-cyclobutyl-4-({3-[(6-methylpyridin-3-yl)oxy]azetidin-1-yl}carbonyl)azepane;
1-[(4-ethyl-1,4-diazepan-1-yl)carbonyl]azetidin-3-ol;
1-{[4-(1-methylethyl)-1,4-diazepan-1-yl]carbonyl}azetidin-3-ol;
1-[(4-cyclopentyl-1,4-diazepan-1-yl)carbonyl]azetidin-3-ol;
ethyl 5-({1-[(4-cyclobutyl-1,4-diazepan-1-yl)carbonyl]azetidin-3-yl}oxy)pyridine-2-carboxylate;
1-cyclobutyl-4-{[3-(3-methyl-4-nitrophenoxy)azetidin-1-yl]carbonyl}-1,4-diazepane;
trans-3-[(4-cyclobutyl-1,4-diazepan-1-yl)carbonyl]cyclobutyl acetate; and
methyl 2-[5-({1-[(4-cyclobutyl-1,4-diazepan-1-yl)carbonyl]azetidin-3-yl}oxy)pyridin-2-yl]-2-methylpropanoate.

Prodrugs of the compounds of the invention are also within the scope of the present invention. "Prodrug" means a derivative that is converted into a compound according to the present invention by a reaction with an enzyme, gastric acid or the like under a physiological condition in the living body, e.g. by oxidation, reduction, hydrolysis or the like, each of which is carried out enzymatically. Examples of a prodrug are compounds, wherein the amino group in a compound of the present invention is acylated, alkylated or phosphorylated to form, e.g., eicosanoylamino, alanylamino, pivaloyloxymethylamino or wherein the hydroxyl group is acylated, alkylated, phosphorylated or converted into the borate, e.g. acetyloxy, palmitoyloxy, pivaloyloxy, succinyloxy, fumaryloxy, alanyloxy or wherein the carboxyl group is esterified or amidated. These compounds can be produced from compounds of the present invention according to well-known methods.

Metabolites of compounds of formula (I) are also within the scope of the present invention.

Where tautomerism, like e.g. keto-enol tautomerism, of compounds of formula (I) may occur, the individual forms, like e.g. the keto and enol form, are comprised separately and together as mixtures in any ratio. Same applies for stereoisomers, like e.g. enantiomers, cis/trans isomers, conformers and the like.

Especially, when enantiomeric or diastereomeric forms are given in a compound according to formula (I) each pure form separately and any mixture of at least two of the pure forms in any ratio is comprised by formula (I) and is a subject of the present invention.

Isotopic labeled compounds of formula (I) are also within the scope of the present invention. Methods for isotope labeling are known in the art. Preferred isotopes are those of the elements H, C, N, O and S.

If desired, isomers can be separated by methods well known in the art, e.g. by liquid chromatography. Same applies for enantiomers by using e.g. chiral stationary phases. Additionally, enantiomers may be isolated by converting them into diastereomers, i.e. coupling with an enantiomerically pure auxiliary compound, subsequent separation of the resulting diastereomers and cleavage of the auxiliary residue. Alternatively, any enantiomer of a compound of formula (I) may be obtained from stereoselective synthesis using optically pure starting materials, reagents and/or catalysts.

In case the compounds according to formula (I) contain one or more acidic or basic groups, the invention also comprises their corresponding pharmaceutically or toxicologically acceptable salts, in particular their pharmaceutically utilizable salts. Thus, the compounds of the formula (I) which contain acidic groups can be used according to the invention, for example, as alkali metal salts, alkaline earth metal salts or as ammonium salts. More precise examples of such salts include sodium salts, potassium salts, calcium salts, magnesium salts or salts with ammonia or organic amines such as, for example, ethylamine, ethanolamine, triethanolamine or amino acids. Compounds of the formula (I) which contain one or more basic groups, i.e. groups which can be protonated, can be present and can be used according to the invention in the form of their addition salts with inorganic or organic acids. Examples for suitable acids include hydrogen chloride, hydrogen bromide, phosphoric acid, sulfuric acid, nitric acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, and other acids known to the person skilled in the art. If the compounds of the formula (I) simultaneously contain acidic and basic groups in the molecule, the invention also includes, in addition to the salt forms mentioned, inner salts or betaines (zwitterions). The respective salts according to the formula (I) can be obtained by customary methods which are known to the person skilled in the art like, for example by contacting these with an organic or inorganic acid or base in a solvent or dispersant, or by anion exchange or cation exchange with other salts. The present invention also includes all salts of the compounds of the formula (I) which, owing to low physiological compatibility, are not directly suitable for use in pharmaceuticals but which can be used, for example, as intermediates for chemical reactions or for the preparation of pharmaceutically acceptable salts.

The present invention provides compounds of general formula (I) as Histamine H3 receptor antagonists.

As described before, the histamine H3 receptor is a G protein-coupled receptor (GPCR) and one out of four receptors of the histamine receptor family. Histamine receptors have long been attractive drug targets, mirrored in the development of antihistamines, which were directed at the histamine H1 receptor for the treatment of allergic reactions or at the histamine H2 receptor to ameliorate gastric ulcers by inhibiting gastric acid secretion. The H3 receptor has been identified as a presynaptic autoreceptor, regulating the release of histamine (Arrang et al. (1983) Nature: 302; 832-837), as well as a heteroreceptor that regulates the release of many other important neurotransmitters (acetylcholine, norepinephrine, dopamine, and serotonin). Structurally divergent H3 receptor antagonists/inverse agonists have been developed and shown to comprise activity in a variety of cognition tests in mice and rat (e.g. Esbenshade et al. (2006) Mol Interventions: 6 (2); 77-88) as well as in models for sleeping disorders and energy balance. From these studies it is concluded that such antagonists comprise a potential treatment for a variety of disorders affecting cognition (e.g., Alzheimer's disease, Parkinson's disease, Attention Deficit and Hyperactivity Disorder, Schizophrenia, Foetal Alcohol Syndrome, Mild Cognitive Impairment, Age-related Memory Dysfunction, Down Syndrome and others), as well as sleep (e.g., hypersomnia and narcolepsy), and energy homeostasis (e.g. obesity) (Witkin & Nelson (2004) JPET:103; 1-20; Hancock & Brune (2005) Exp Opin Inves Drugs:14 (3), 223-241).

The pharmacology of the H3 receptor seems not only to be determined by its localization but appears also to be regulated by differential splicing. Today more than 20 splice variants (isoforms) have been described but their functions have yet to be elucidated completely (Bongers et al. (2007) Biochem Pharm: 73; 1195-1204). The H3 receptor is localized primarily to the central nervous system (CNS), with highest expression, in rodents, in the cerebral cortex, hippocampal formations, striatum, and hypothalamus (Drutel et al. (2001) Mol Pharmacol: 59; 1-8). Similarly in human, H3 receptor expression is prominent in the basal ganglia, globus pallidus, hippocampus, and cortex (Martinez-Mir et al. (1990) Brain Res: 526; 322 327). Notably, many of these brain regions are critical for cognition (cortex and hippocampus) and sleep and homeostatic regulation (hypothalamus). The H3 receptor has been shown also to localize to regions which might be involved in pain sensation or transmission and therefore might offer treatment opportunities for different pain states (Cannon et al. (2007) Pain: 129; 76-92).

In addition to agonist-induced signaling, the H3 receptor is constitutively active and capable of signaling independently of agonist both in vitro and in vivo (Morisset et al. (2000) Nature: 408, 860-864).

All these considerations suggest that novel H3 receptor antagonists like the series in this application could be useful in the treatment of cognitive dysfunctions as well as sleeping and energy homeostasis disorders. The term "antagonist" also includes inverse agonists.

Based on the information above and further literature, like WO-A 2007/080140 and WO-A 2006/136924 the following diseases and disorders are preferably affected.
Neurological Disorders:
    Major conditions include
        behavioral/cognitive syndromes (e.g. Alzheimer's disease, Parkinson's disease, Attention Deficit and Hyperactivity Disorder, schizophrenia, Foetal Alcohol Syndrome, Mild Cognitive Impairment, Age-related Memory Dysfunction, Down Syndrome, epilepsy, convulsion, depression, anxiety disorders)
    seizure disorders
    neurodegenerative disorders (e.g. Alzheimer's disease, Parkinson's disease, Multiple
    Sclerosis)
    sleep disorders (e.g. hypersomnia and narcolepsy, excessive daytime sleepiness, diurnal and seasonal variations in sleep patterns)
    Migraine
    Stroke
    tremor.

The term "neurological disorders" also includes psychiatrical disorders within the meaning of the present invention. The term "neurodegenerative disorders" also includes neuroinflammatory disorders within the meaning of the present invention.

Disorders affecting energy homeostasis as well as complications associated therewith, e.g. obesity, eating disorders associated with excessive food intake, bulimia, binge eating, complications associated therewith e.g. diabetes mellitus.

Pain, e.g. neuropathic pain, inflammatory pain, nociception. The term "pain" includes acute and chronic pain within the meaning of the present invention.

Cardiovascular disorders, e.g. acute myocardial infarction, and other disorders, i.e. gastrointestinal disorders, vestibular dysfunction (e.g. Morbus Meniere, motion sickness, drug abuse), nasal congestion, allergic rhinitis (hay fever), asthma.

Preferably, convulsion and epilepsy are excluded.

Preferred disorders are Alzheimer's disease, Parkinson's disease, Attention Deficit and Hyperactivity Disorder, schizophrenia, Foetal Alcohol Syndrome, Mild Cognitive Impairment, Age-related Memory Dysfunction, disease-related cognitive dysfunctions, Lewy body dementia, vascular dementia, Down Syndrome, epilepsy, convulsion, depression, anxiety disorders, idiopathic hypersomnia, narcolepsy, shift-work sleep disorder, disease-related fatigue, chronic fatigue syndrome, Migraine, Stroke, tremor, obesity, eating disorders, diabetes mellitus, neuropathic pain, inflammatory pain, acute myocardial infarction, gastrointestinal disorders, vestibular dysfunction (e.g. Morbus Meniere), motion sickness, drug abuse, nasal congestion, allergic rhinitis (hay fever), asthma.

More preferred disorders are Alzheimer's disease, Parkinson's disease, Attention Deficit and Hyperactivity Disorder, schizophrenia, Mild Cognitive Impairment, disease-related cognitive dysfunctions, Lewy body dementia, vascular dementia, idiopathic hypersomnia, narcolepsy, obesity, diabetes mellitus, neuropathic pain, nasal congestion, allergic rhinitis (hay fever), asthma.

Even more preferred disorders are Alzheimer's disease, Parkinson's disease, Attention Deficit and Hyperactivity Disorder, schizophrenia, idiopathic hypersomnia, narcolepsy, obesity, neuropathic pain.

Accordingly, one aspect of the present invention is a compound or a pharmaceutically acceptable salt thereof of the present invention for use as a medicament.

Yet another aspect of the present invention is a compound or a pharmaceutically acceptable salt thereof of the present invention for use in a method of treating or preventing diseases and disorders associated with the H3 receptor.

Yet another aspect of the present invention is a compound or a pharmaceutically acceptable salt thereof of the present invention for use in a method of treating or preventing neurological disorders, e.g. behavioral/cognitive syndromes (e.g. Alzheimer's disease, Parkinson's disease, Attention Deficit and Hyperactivity Disorder, schizophrenia, Foetal Alcohol Syndrome, Mild Cognitive Impairment, Age-related Memory Dysfunction, Down Syndrome, epilepsy, convulsion, depression, anxiety disorders), seizure disorders, neurodegenerative disorders (e.g. Alzheimer's disease, Parkinson's disease, Multiple Sclerosis), sleep disorders (e.g. hypersomnia and narcolepsy, excessive daytime sleepiness, diurnal and seasonal variations in sleep patterns), Migraine, Stroke, tremor; disorders affecting energy homeostasis as well as complications associated therewith, e.g. obesity, eating disorders associated with excessive food intake, bulimia, binge eating, complications associated therewith e.g. diabetes mellitus; Pain, e.g. neuropathic pain, inflammatory pain, nociception; cardiovascular disorders, e.g. acute myocardial infarction; gastrointestinal disorders; vestibular dysfunction (e.g. Morbus Meniere, motion sickness, drug abuse); nasal congestion; allergic rhinitis (hay fever); or asthma. Preferred disorders are Alzheimer's disease, Parkinson's disease, Attention Deficit and Hyperactivity Disorder, schizophrenia, Foetal Alcohol Syndrome, Mild Cognitive Impairment, Age-related Memory Dysfunction, disease-related cognitive dysfunctions, Lewy body dementia, vascular dementia, Down Syndrome, epilepsy, convulsion, depression, anxiety disorders, idiopathic hypersomnia, narcolepsy, shift-work sleep disorder, disease-related fatigue, chronic fatigue syndrome, Migraine, Stroke, tremor, obesity, eating disorders, diabetes mellitus, neuropathic pain, inflammatory pain, acute myocardial infarction, gastrointestinal disorders, vestibular dysfunction (e.g. Morbus Meniere), motion sickness, drug abuse, nasal congestion, allergic rhinitis (hay fever), asthma. More preferred disorders are Alzheimer's disease, Parkinson's disease, Attention Deficit and Hyperactivity Disorder, schizophrenia, Mild Cognitive Impairment, disease-related cognitive dysfunctions, Lewy body dementia, vascular dementia, idiopathic hypersomnia, narcolepsy, obesity, diabetes mellitus, neuropathic pain, nasal congestion, allergic rhinitis (hay fever), asthma. Even more preferred disorders are Alzheimer's disease, Parkinson's disease, Attention Deficit and Hyperactivity Disorder, schizophrenia, idiopathic hypersomnia, narcolepsy, obesity, neuropathic pain.

Yet another aspect of the present invention is the use of a compound or a pharmaceutically acceptable salt thereof of the present invention for the manufacture of a medicament for the treatment or prophylaxis of diseases and disorders associated with the H3 receptor.

Yet another aspect of the present invention is the use of a compound or a pharmaceutically acceptable salt thereof of the present invention for the manufacture of a medicament for the treatment or prophylaxis of neurological disorders, e.g. behavioral/cognitive syndromes (e.g. Alzheimer's disease, Parkinson's disease, Attention Deficit and Hyperactivity Disorder, schizophrenia, Foetal Alcohol Syndrome, Mild Cognitive Impairment, Age-related Memory Dysfunction, Down Syndrome, epilepsy, convulsion, depression, anxiety disorders), seizure disorders, neurodegenerative disorders (e.g. Alzheimer's disease, Parkinson's disease, Multiple Sclerosis), sleep disorders (e.g. hypersomnia and narcolepsy, excessive daytime sleepiness, diurnal and seasonal variations in sleep patterns), Migraine, Stroke, tremor; disorders affecting energy homeostasis as well as complications associated therewith, e.g. obesity, eating disorders associated with excessive food intake, bulimia, binge eating, complications associated therewith e.g. diabetes mellitus; Pain, e.g. neuropathic pain, inflammatory pain, nociception; cardiovascular disorders, e.g. acute myocardial infarction; gastrointestinal disorders; vestibular dysfunction (e.g. Morbus Meniere, motion sickness, drug abuse); nasal congestion; allergic rhinitis (hay fever); or asthma. Preferred disorders are Alzheimer's disease, Parkinson's disease, Attention Deficit and Hyperactivity Disorder, schizophrenia, Foetal Alcohol Syndrome, Mild Cognitive Impairment, Age-related Memory Dysfunction, disease-related cognitive dysfunctions, Lewy body dementia, vascular dementia, Down Syndrome, epilepsy, convulsion, depression, anxiety disorders, idiopathic hypersomnia, narcolepsy, shift-work sleep disorder, disease-related fatigue, chronic fatigue syndrome, Migraine, Stroke, tremor, obesity, eating disorders, diabetes mellitus, neuropathic pain, inflammatory pain, acute myocardial infarction, gastrointestinal disorders, vestibular dysfunction (e.g. Morbus Meniere), motion sickness, drug abuse, nasal congestion, allergic rhinitis (hay fever), asthma. More preferred disorders are Alzheimer's disease, Parkinson's disease, Attention Deficit and Hyperactivity Disorder, schizophrenia, Mild Cognitive Impairment, disease-related cognitive dysfunctions, Lewy body dementia, vascular dementia, idiopathic hypersomnia, narcolepsy, obesity, diabetes mellitus, neuropathic pain, nasal congestion, allergic rhinitis (hay fever), asthma. Even more preferred disorders are Alzheimer's disease, Parkinson's disease, Attention Deficit and Hyperactivity Disorder, schizophrenia, idiopathic hypersomnia, narcolepsy, obesity, neuropathic pain.

Yet another aspect of the present invention is a method for treating, controlling, delaying or preventing in a mammalian patient in need of the treatment of one or more conditions selected from the group consisting of diseases and disorders associated with the H3 receptor, wherein the method comprises the administration to said patient a therapeutically effective amount of a compound of the present invention or a pharmaceutically acceptable salt thereof.

Yet another aspect of the present invention is a method for treating, controlling, delaying or preventing in a mammalian patient in need of the treatment of one or more conditions selected from the group consisting of neurological disorders, e.g. behavioral/cognitive syndromes (e.g. Alzheimer's disease, Parkinson's disease, Attention Deficit and Hyperactivity Disorder, schizophrenia, Foetal Alcohol Syndrome, Mild Cognitive Impairment, Age-related Memory Dysfunction, Down Syndrome, epilepsy, convulsion, depression, anxiety disorders), seizure disorders, neurodegenerative disorders (e.g. Alzheimer's disease, Parkinson's disease, Multiple Sclerosis), sleep disorders (e.g. hypersomnia and narcolepsy, excessive daytime sleepiness, diurnal and seasonal variations in sleep patterns), Migraine, Stroke, tremor; disorders affecting energy homeostasis as well as complications associated therewith, e.g. obesity, eating disorders associated with excessive food intake, bulimia, binge eating, complications associated therewith e.g. diabetes mellitus; Pain, e.g. neuropathic pain, inflammatory pain, nociception; cardiovascular disorders, e.g. acute myocardial infarction; gastrointestinal disorders; vestibular dysfunction (e.g. Morbus Meniere, motion sickness, drug abuse); nasal congestion; allergic rhinitis (hay fever); and asthma, wherein the method comprises the administration to said patient a therapeutically effective amount of a compound of the present invention or a pharmaceutically acceptable salt thereof. Preferred disorders are Alzheimer's disease, Parkinson's disease, Attention Deficit and Hyperactivity Disorder, schizophrenia, Foetal Alcohol Syndrome, Mild Cognitive Impairment, Age-related Memory Dysfunction, disease-related cognitive dysfunctions, Lewy body dementia, vascular dementia, Down Syndrome, epilepsy, convulsion, depression, anxiety disorders, idiopathic hypersomnia, narcolepsy, shift-work sleep disorder, disease-related fatigue, chronic fatigue syndrome, Migraine, Stroke, tremor, obesity, eating disorders, diabetes mellitus, neuropathic pain, inflammatory pain, acute myocardial infarction, gastrointestinal disorders, vestibular dysfunction (e.g. Morbus Meniere), motion sickness, drug abuse, nasal congestion, allergic rhinitis (hay fever), asthma. More preferred disorders are Alzheimer's disease, Parkinson's disease, Attention Deficit and Hyperactivity Disorder, schizophrenia, Mild Cognitive Impairment, disease-related cognitive dysfunctions, Lewy body dementia, vascular dementia, idiopathic hypersomnia, narcolepsy, obesity, diabetes mellitus, neuropathic pain, nasal congestion, allergic rhinitis (hay fever), asthma. Even more preferred disorders are Alzheimer's disease, Parkinson's disease, Attention Deficit and Hyperactivity Disorder, schizophrenia, idiopathic hypersomnia, narcolepsy, obesity, neuropathic pain.

Preferably, the mammalian patient is a human patient.

Yet another aspect of the present invention is a pharmaceutical composition comprising at least one compound or a pharmaceutically acceptable salt thereof of the present invention together with a pharmaceutically acceptable carrier, optionally in combination with one or more other bioactive compounds or pharmaceutical compositions.

Preferably, the one or more bioactive compounds are lipase inhibitors, anorectic agents, selective serotonin uptake inhibitors, neurotransmitter reuptake blocker, agents that stimulate metabolism of body fat, anti-diabetic agents, lipid lowering agents, or histamine H1 receptor antagonists. A combination of one or more histamine H3 receptor antagonists of the present invention and histamine H1 receptor antagonists is preferred, especially for the treatment of allergic rhinitis, allergic congestion or nasal congestion.

"Pharmaceutical composition" means one or more active ingredients, and one or more inert ingredients that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

A pharmaceutical composition of the present invention may comprise one or more additional compounds as active ingredients like one or more compounds of formula (I) not being the first compound in the composition or other Histamine H3 receptor antagonists.

The active ingredients may be comprised in one or more different pharmaceutical compositions (combination of pharmaceutical compositions).

The term "pharmaceutically acceptable salts" refers to salts prepared from pharmaceutically acceptable non-toxic bases or acids, including inorganic bases or acids and organic bases or acids.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In practical use, the compounds of formula (I) can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or nonaqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally, for example, as liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds of formula (I) may also be administered parenterally. Solutions or suspensions of these active compounds can be prepared in water suitably mixed with a surfactant such as hydroxypropyl-cellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form should be sterile and should be fluid to the extent that easy syringability exists. It should be stable under the conditions of manufacture and storage and should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

Any suitable route of administration may be employed for providing a mammal, especially a human, with an effective dose of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of formula (I) are administered orally.

The effective dosage of active ingredient employed may vary depending on the particular compound employed, the mode of administration, the condition being treated and the severity of the condition being treated. Such dosage may be ascertained readily by a person skilled in the art.

Starting materials for the synthesis of preferred embodiments of the invention may be purchased from commercially available sources such as Array, Sigma Aldrich, Acros, Fisher, Fluka, ABCR or can be synthesized using known methods by one skilled in the art.

In general, several methods are applicable to prepare compounds of the present invention. In some cases various strategies can be combined. Sequential or convergent routes may be used.

One method for the preparation of a compound of the present invention, wherein in formula (I) $X^1$ and $X^3$ are N; $X^2$ is O; n1 and n2 are 0 in the definition of $X^4$ and $R^2$ is an aromatic cycle T, comprises the steps of (a) reacting the amino group of a compound of formula (II) with a suitable chloroformate

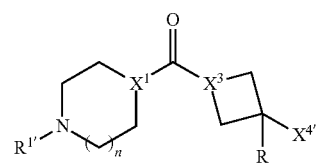

(II)

wherein n and $R^1$ have the meaning as indicated above;

(b) reacting the resulting carbamate compound from step (a) with a compound of formula (III)

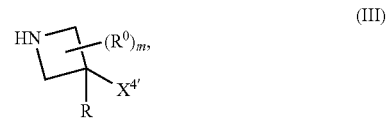

(III)

wherein $X^{4'}$ is OH and R has the meaning as indicated above; and (c) reacting the resulting compound with a compound of formula Cl-T or F-T to yield a compound of formula (I), wherein $X^1$ and $X^3$ are N; $X^2$ is O; n1 and n2 are 0 in the definition of $X^4$ and $R^2$ is an aromatic cycle T.

In general, compounds of formula (I), wherein $X^1$ and $X^3$ are N and $X^2$ is O, can be prepared by a method comprising the steps of (a) reacting the amino group of compound of formula (IIa) with a suitable chloroformate such as 4-nitrophenyl-chloroformate

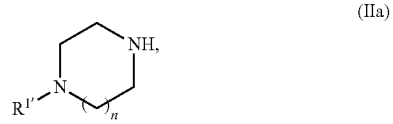

(IIa)

wherein n has the meaning as indicated above and $R^{1'}$ is $R^1$ as indicated above or as suitable N-atom protecting group (b) reacting the resulting carbamate compound from step (a) with a compound of formula (IIIa)

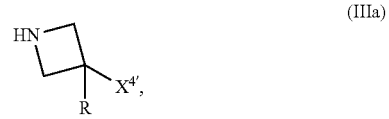

(IIIa)

wherein $X^{4'}$ is H; OH; or $C(O)_2$(alkyl), R has the meaning as indicated above, to yield a compound of formula (I) when $R^{1'}$ is $R^1$ as indicated above and $X^{4'}$ is defined as above.

The method may comprise the further step when $X^{4'}$ is OH
(c1) the alcohol is deprotonated with a strong base (such as NaH or $^tBuOK$) and the resulting alkoxide reacted with a suitable alkyl halide, benzyl halide, activated alcohol (such as OMs or OTs) or (hetero)aromatic halide at room temperature or elevated temperature (up to 200° C.) to yield a compound of formula (I), wherein $X^4$ is $X^5$ $(CH_2)_{n2} R^2$.

In the case when $R^{1'}$ of formula (I) is a suitable N-atom protecting group (such as Boc or cbz), the resulting compound represented by formula (II) requires the following additional steps to synthesise a compound of formula (I);

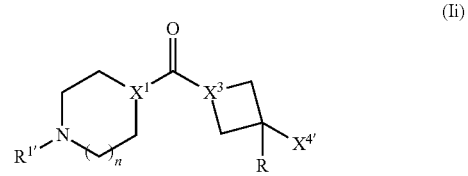

(Ii)

(d1) deprotecting compound of formula (Ii) at the nitrogen atom; and (e1) reacting the resulting compound from step (d1) with $R^1(=O)$ in the presence of a reducing agent such as STAB to yield a compound of formula (I); or alternatively, reacting the resulting compound from step (d1) with a compound of formula $R^1$-halide (optionally in the presence of base) to yield a compound of formula (I).

Alternatively, compounds of formula (I) wherein $X^1$ and $X^3$ are N and $X^2$ is S, may be prepared by a method comprising the steps of (c) reacting the amino group of compound of formula (III) with thio-CDI (usually between 0° C. and room temperature) and reacting the resulting intermediate with a compound of formula (II) at elevated temperature (up to 100° C.), to yield a compound of formula (I) when $X^2=S$ and $X^{4'}$ are defined as above.

Alternatively, compounds of formula (I) wherein $X^1$ and $X^3$ are N and $X^2$ is N—CN, may be prepared by a method comprising the steps of (d) reacting cyanamide with carbon disulfide and then treating the resulting intermediate with dimethyl sulphate to form a compound of formula (IV)

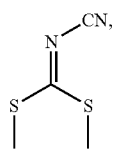

(IV)

(e) reacting the amino group of compound of formula (II) with compound of formula (IV) (usually between room temperature and 80° C.);

(f) reacting the compound from step (e) with a compound of formula (III) at elevated temperature (up to 100° C.), to yield a compound of formula (I) when $X^2=N$—CN and $X^{4'}$ are defined as above.

Alternatively, compounds of general formula (I) wherein $X^2$ is N—OC$_{1-4}$ alkyl and $X^{4'}$ is H or OH, may be prepared from a compound of formula (Ia) by a method comprising the steps of

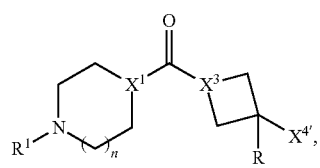

(Ia)

(g) reaction with oxalyl chloride followed by reaction with a compound of formula $NH_2$—OC$_{1-4}$ alkyl, to yield a compound of formula (I), wherein $X^2$ is N—OC$_{1-4}$ alkyl and $X^{4'}$ is H or OH.

Alternatively, compounds of general formula (I) wherein $X^1$ is CH and n is 1, may be prepared from a compound of formula (Ib) by a method comprising the steps of

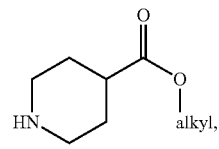

(Ib)

(i) reacting the amino group with a compound of formula $R^1=O$, wherein the oxo group is attached to a carbon atom of $R^1$, followed by reduction of the resulting imine;

(j) saponification of the ester group with base such as LiOH;

(k) activation of the resulting intermediate with amide coupling reagents (such as HOBt and HBTU) and reacting the resulting activated ester with a compound of formula (III), to yield a compound of formula (I) wherein $X^{4'}$ is defined as above.

Alternatively, compounds of general formula (I) wherein $X^1$ is CH and n is 2, may be prepared from a compound of formula (Ic) by a method comprising the steps of

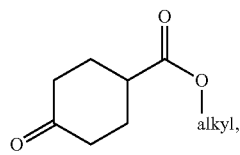

(Ic)

(l) reacting the ketone group with sodium azide and MeSO$_3$H at between RT and 80° C., followed by reduction of the resulting lactam and ester with LAH (usually between RT and 80° C.)

(m) reacting the amino group with a compound of formula $R^1=O$, wherein the oxo group is attached to a carbon atom of $R^1$, followed by reduction of the resulting imine (n) oxidation of the primary alcohol to the carboxylic acid with an oxidising agent (such as chromic acid/Jones oxidation)

(o) activation of the resulting carboxylic acid with amide coupling reagents (such as HOBt and HBTU) and reacting the resulting activated ester with a compound of formula (III), to yield a compound of formula (I) wherein $X^{4'}$ is defined as above.

Alternatively, compounds of general formula (I) wherein $X^1$ is CH and n is 2, may be prepared from a compound of formula (Ih) where PG is a protecting group (usually a carbonate protecting group such as cbz) by a method comprising the steps of

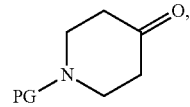

(Ih)

(pp) reacting the ketone group with an alkyl diazoacetate (such as ethyl diazoacetate) in the presence of a Lewis acid (such as boron trifluoride diethyl etherate) usually between −80° C. and RT;

(qq) eliminating the resulting alcohol to give an α,β-unsaturated ester by acid catalysed elimination (Alternatively the alcohol can be converted into a halide (such as bromide using a reagent such as PBr$_3$) or sulfonate (such as a mesylate via reaction with MsCl and TEA) and eliminated in the presence of a base (such as DBU) usually between RT and 100° C.);

(rr) removal of the alkene via hydrogenation (usually using hydrogen gas or ammonium formatate in the presence of a source of palladium such as Pd/C) (ss) hydrolysis of the ester to give the carboxylic acid using aqueous base such as LiOH or acid such as HCl;

(tt) activation of the resulting intermediate with amide coupling reagents (such as HOBt and HBTU) and reacting the resulting activated ester with a compound of formula (III), to yield a compound of formula (I) wherein $X^{4'}$ is defined as above;

(uu) Removal of the protecting group (using H$_2$/Pd/C for a cbz protecting group) and reacting the amino group with a compound of formula $R^1$=O, wherein the oxo group is attached to a carbon atom of $R^1$, followed by reduction of the resulting imine.

In general, compounds of formula (I), wherein $X^1$ is N and $X^3$ is CH can be prepared by a method comprising the following four steps;

(p) reacting a malonate ester (such as diisopropylmalonate) with a strong base (such as NaH) and reacting the resulting di-anion with a 1,3-dihalo-2,2-dialkoxypropane (such as 1,3-dibromo-2,2-dimethoxypropane) to form a compound of formula (Id)

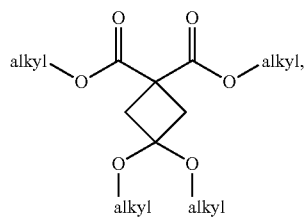
(Id)

(q) treating the compound of formula (Id) with strong acid (such as 5M HCl) at elevated temperature (up to 100° C.) to form a compound represented by formula (Ie)

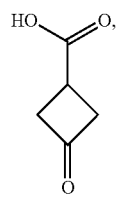
(Ie)

(r) reacting a compound of formula (Ie) with amide coupling reagents (such as CDI) and treating the resulting intermediate with a compound of formula (II);

(s) reducing the ketone group of step (r) product with a reducing agent (such as NaBH$_4$) to give a predominantly (>95:5) cis alcohol of formula (If), wherein $X^5$ is O

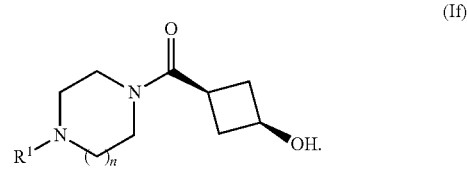
(If)

The method may comprise the further steps where compounds of formula (If), wherein the meanings are as indicated above, are further modified as follows;

(t) converting the alcohol to a suitable leaving group (such as OMs or OTs) by reaction with the appropriate sulfonyl chloride in the presence of base (such as TEA)

(u) reacting the resulting sulfonate ester with an acetate salt (such as potassium acetate) at high temperature (usually up to 120° C.)

(v) hydrolysis of the acetate group with base (such as LiOH) to give a predominantly (>9.5:1) trans alcohol of formula (Ig), wherein $X^5$ is O

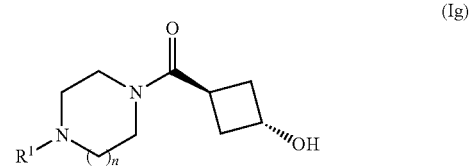
(Ig)

The method may comprise the further step (w) the alcohol is deprotonated with a strong base (such as NaH or $^t$BuOK) and the resulting alkoxide reacted with a suitable alkyl halide, benzyl halide, activated alcohol (such as OMs or OTs) or (hetero)aromatic halide at room temperature or elevated temperature (up to 200° C.) to yield a compound of formula (I), wherein $X^4$ is $X^5$(CH$_2$)$_{n2}$R$^2$.

Similarly, a further method route is given by a method for the preparation of a compound of the present invention, wherein in formula (I) $X^1$ is N and $X^3$ is CH; $X^2$ is O; m is 0; R is H, comprising the steps of (x) reacting a malonate ester with a strong base and reacting the resulting di-anion with a 1,3-dihalo-2,2-dialkoxypropane to form a compound of formula (Id)

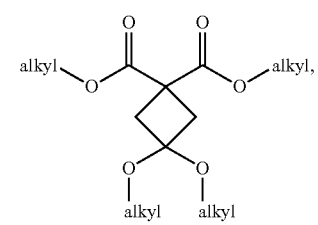
(Id)

(y) treating the compound of formula (Id) with strong acid at elevated temperature to form a compound represented by formula (Ie)

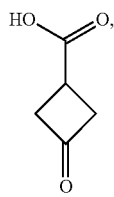
(Ie)

(z) reacting a compound of formula (Ie) with amide coupling reagents and treating the resulting intermediate with a compound of formula (II);

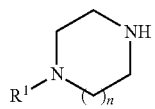
(II)

(aa) reducing the ketone group of step (z) product with a reducing agent to give a predominantly (>95:5) cis alcohol of formula (If), wherein $X^5$ is O and $R^1$ and n have the meaning as indicated above

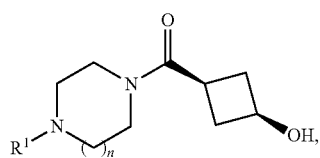
(If)

optionally comprising the further steps (bb) converting the alcohol to a suitable leaving group by reaction with the appropriate sulfonyl chloride in the presence of base or acid;

(cc) reacting the resulting sulfonate ester with an acetate salt such as potassium acetate at high temperature;

(dd) hydrolysis of the acetate group with base to give a predominantly (>9.5:1) trans alcohol of formula (Ig)

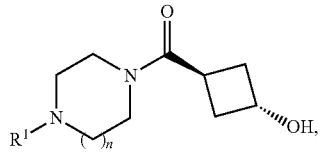
(Ig)

optionally comprising the further step of deprotonating the alcohol with a strong base and reacting the resulting alkoxide with a suitable alkyl halide, benzyl halide, activated alcohol or (hetero)aromatic halide at room temperature or elevated temperature to yield a compound of formula (I), wherein $X^4$ is $O(CH_2)_{n2}R^2$.

The above step may also apply for alcohols of formula (V)

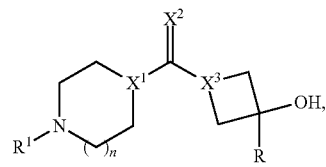
(V)

wherein $R^1$, R, n, $X^1$, $X^2$, $X^3$ have the meaning as indicated above.

The alcohol may be deprotonated with a strong base (such as NaH or 'BuOK, optionally in the presence of CsF) and the resulting alkoxide reacted with a suitable alkyl halide, benzyl halide, activated alcohol (such as OMs or OTs) or (hetero) aromatic halide at room temperature or elevated temperature (up to 200° C.) to yield a compound of formula (I), wherein $X^4$ is $X^5(CH_2)_{n2}R^2$.

Alternatively, compounds of formula (I) wherein $X^5$ is O, can be prepared in a two step process starting from a compound of formula (V), wherein the method comprises the steps of converting the alcohol to a suitable leaving group (such as OMs or OTs) by reaction with the appropriate sulfonyl chloride in the presence of base (such as TEA)

reacting the resulting sulfonate ester with the alkoxide formed by treating a compound of formula HO $(CH_2)_{n2}R^2$ with a suitable base such as NaH or $K_2CO_3$, to yield a compound of formula (I) wherein $X^5$ is O.

Alternatively, compounds of formula (I) wherein $X^5$ is O, can be prepared in a one step Ullmann reaction starting from a compound of formula (V) above, wherein the method comprises the steps of;

reacting the alcohol with a (hetero)aryl halide in the presence of a phenanthroline derivative, copper salt (usually CuI or $Cu_2O$) and base (such as $Cs_2CO_3$) at elevated temperature (usually circa 100° C.), to yield a compound of formula (I) wherein $X^5$ is O.

Alternatively, compounds of formula (I) wherein $X^5$ is O, can be prepared in a one step process starting from a compound of formula (V) above, wherein the method comprises the steps of;

the alcohol is deprotonated with a strong base (such as NaH or 'BuOK) and the resulting alkoxide reacted (usually between room temperature and 180° C.) with a suitable (hetero)aryl fluoride preformed in situ by the reaction of a (hetero)aryl chloride or bromide with KF and a suitable fluorinating agent (such as Kryptofix-222) usually between room temperature and 180° C., to yield a compound of formula (I) wherein $X^5$ is O.

In the case when $X^5$ of formula (I) is C(O), the compounds can be prepared in a two step process starting from a compound of formula (VI) by;

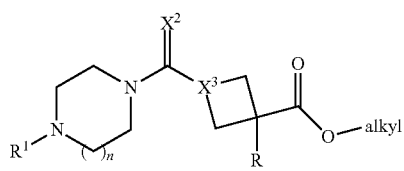
(VI)

saponification of the ester group of formula (VI) with base (such as aqueous LiOH) or acid followed by activation of the resulting intermediate with amide coupling reagents (such as HOBt and HBTU) and reacting the resulting activated ester with either a primary or secondary amine compound, as defined for $R^2$, to yield a compound of formula (I), wherein $X^4$ is $X^5(CH_2)_{n2}R^2$.

In the case when n1 of formula (I) is 1, the compounds can be prepared in a two step process starting from a compound of formula (VI) above by;
  reduction of the ester group of formula (VI) with sodium borohydride
  followed by deprotonation at the resulting alcohol with strong base (such as NaH or $^t$BuOK) and reacting the resulting alkoxide with a suitable alkyl halide, benzyl halide, activated alcohol (such as OMs or OTs) or (hetero)aromatic halide at room temperature or elevated temperature (up to 200° C.) to yield a compound of formula (I), wherein $X^4$ is $(CH_2)_{n1}X^5(CH_2)_{n2}R^2$.

In the case when $X^5$ of formula (I) is $N(R^{1a})$, the compounds represented by formula (VII) can be prepared starting from compound of formula (V) above, in the following three step process;

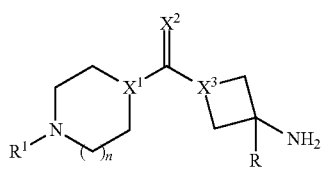

(VII)

deprotonation at the alcohol with strong base (such as NaH or $^t$BuOK) and reacting the resulting alkoxide with MsCl
  displacement of the mesylate by an azide (such as sodium azide) with heating at elevated temperatures (usually up to 100° C.)
  reduction of the azide with $PPh_3$ in the presence of water at room temperature, to yield a compound of formula (I), wherein $X^5$ is NH.

The method may comprise further steps where compounds of formula (VII), wherein the meanings are as indicated above, are further modified as follows;
  (ee) reacting primary amine with a suitable alkyl halide, benzyl halide, activated alcohol (such as OMs or OTs) or (hetero)aromatic halide in the presence of an organic base (such as TEA) at room temperature or elevated temperature (up to 200° C.) to yield a compound of formula (I), wherein $X^4$ is $NH(CH_2)_{n2}R^2$
  (ff) reacting the resulting secondary amine from step (ee) with a suitable alkyl halide or activated alcohol (such as OMs or OTs) in the presence of an organic base (such as TEA) at room temperature or elevated temperature (up to 200° C.) to yield a compound of formula (I), wherein $X^4$ is $N(R^{1a})(CH_2)_{n2}R^2$,
  Alternatively, compounds of formula (I), wherein $X^4$ is $N(R^{1a})(CH_2)_{n2}R^2$, can be prepared in a one step process as follows;
    by reacting the secondary amine from step (ee) with a suitable alkyl aldehyde in the presence of an organic acid (such as AcOH) and reducing agent (such as $NaBH_3CN$) at room temperature or elevated temperature (up to 100° C.), to yield a compound of formula (I), wherein $X^4$ is $N(R^{1a})(CH_2)_{n2}R^2$.

Alternatively step (ee) above may be replaced with step (gg) below, to yield compounds of formula (I), wherein $X^4$ is $NHR^2$;
  (gg) reacting the primary amine of a compound of formula (VII) with a (hetero)aromatic halide at elevated temperature (up to 120° C.) in the presence of palladium catalysed coupling reagents (such as $Pd_2(dba)_3$, BINAP and $^t$BuOK) to yield compounds of formula (I), wherein $X^4$ is $NHR^2$.

In the case when $X^5$ of formula (I) is NHC(O), the compounds represented by formula (VIII) can be prepared by a method comprising of;

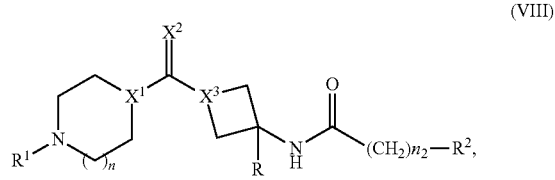

(VIII)

(hh) reacting the amine group of a compound of formula (VII) either with a compound of formula $R^2(CH_2)_{n2}COCl$ in the presence of an organic base (such as TEA), or, with a compound of formula $R^2(CH_2)_{n2}C(O)OH$ in the presence of amide coupling reagents (such as DCC/DMAP) to yield compounds of formula (I), wherein $X^4$ is $NHC(O)(CH_2)_{n2}R^2$ The method may comprise the further step where compounds of formula (VIII), wherein the meanings are as indicated above, are further modified as follows;
  (ii) reacting the primary amide group of a compound of formula (VIII) with a strong base (such as NaH) followed by addition of a compound of formula $R^{1a}$-halide or activated alcohol (such as $R^{1a}$-OMs or $R^{1a}$-OTs) at room temperature or elevated temperature (up to 200° C.) to yield a compound of formula (I), wherein $X^4$ is $N(R^{1a})C(O)(CH_2)_{n2}R^2$.

The same reaction types may apply for compounds of the present invention, where in formula (I) m is other than 0.

In the case when $X^5$ of formula (I) is $NHS(O)_2$, the compounds represented by formula (IX) can be prepared by a method comprising of;

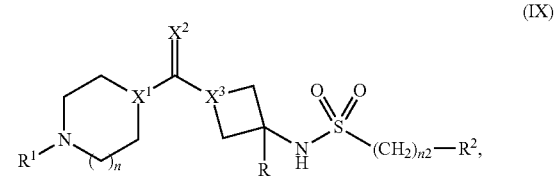

(IX)

(jj) reacting the amine group of a compound of formula (VII) with a compound of formula $R^2(CH_2)_{n2}S(O)_2Cl$ in the presence of an organic base (such as TEA or pyridine) to yield compounds of formula (I), wherein $X^4$ is $NHS(O)_2(CH_2)_{n2}R^2$ The method may comprise the further steps where compounds of formula (I), wherein the meanings are as indicated above and $R^2$ has a potentially chemically reactive group, are further modified as follows:
  (kk) reacting a suitable alcohol or (hetero)aryl alcohol with a strong base (such as NaH or $^t$BuOK) and the resulting alkoxide or (hetero)aryloxide reacted (usually between room temperature and 180° C.) with the halide or activated alcohol (sulfonate ester) substituent of $R^2$, to yield a compound of formula (I); or (ll) reacting a halide or activated alcohol (sulfonate ester) substituent of $R^2$ in a Suzuki reaction using a palladium phosphine catalyst (such as that formed from $Pd_2(dba)_3$ and tricyclohexylphosphine) and suitable boronate ester or boronic acid (usually at room temperature to 150° C.) in the presence of a base (such as $K_3PO_4$ or $K_2CO_3$), to yield a compound of formula (I).

The method may comprise the further steps where compounds of formula (I) represented by formula (X), wherein the meanings are as indicated above, are further modified as follows;

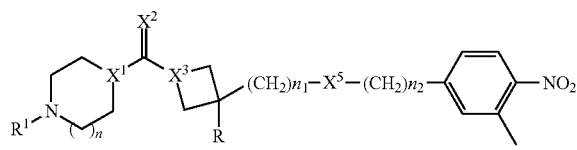

(mm) reacting the nitro group with DMF.DMA and pyrrolidine at elevated temperature (usually >50° C.) and reacting the resulting intermediate with Raney Nickel and hydrazine (usually at room temperature), to yield a compound of formula (I).

The method may comprise the further step where compounds of formula (I) represented by formula ($X^1$), wherein the meanings are as indicated above, are further modified as follows;

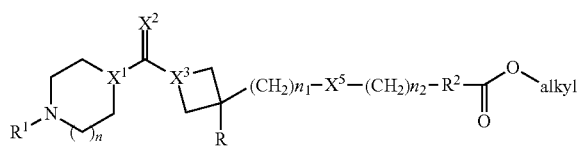

(nn) reacting the ester group with a Grignard reagent (such as MeMgBr), optionally in the presence of lithium chloride, at a temperature usually between −78° C. and 150° C., to yield a compound of formula (I).

The method may comprise the further step where compounds of formula (I) represented by formula (XII), wherein the meanings are as indicated above, are further modified as follows;

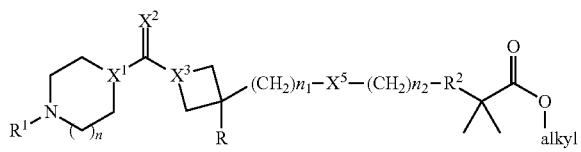

(oo) reducing the ester group (usually with $LiAlH_4$) at temperatures ranging from −50 to 100° C., to yield a compound of formula (I).

The same reaction types may apply for compounds of the present invention, where in formula (I) m is other than 0.

It is clear for a practitioner in the art that the preparation routes mentioned herein can be combined and varied optionally by using activation and protection/deprotection techniques.

EXAMPLES

Biological Evaluation:
Cell-Lines Used to Characterize Invented Compounds In Vitro CHO—K1 cell line expressing human H3 receptors were purchased from Euroscreen (Gosselies, Belgium, Cat. no.: ES-392-C)

Human H3 receptor-expressing cell-lines were grown in Ham's F12 [Sigma, Cat. no. N6658], supplemented with 10% FBS [Sigma, Cat. no. F9665], 400 µg/ml G418 [Sigma, Cat. no. N1876] and 250 µg/ml Zeocin [Invitrogen, Cat. no. 46-0509]) according to the protocol provided by Euroscreen.
cAMP Quantification Protocol for Human H3 Receptor Testing The assay measures the ability of test compounds to inhibit Histamine receptor agonist-induced decrease of intracellular free cAMP (receptor is $G_i$ coupled).

Specifically, a cAMP quantification assay system from DiscoveRx (cAMP XS+; Cat. no. 90-0075) was used.

For the cAMP assay, confluent cells were detached from the culture vessels with 1× trypsin-EDTA solution (Sigma), and seeded into 384-well Costar plates (white, clear bottom, Cat. no. 3707) at a density of 10,000 cells per well. Cells were seeded in a volume of 50 µl in medium without antibiotics and incubated overnight in a humidified atmosphere with 5% $CO_2$ at 37° C. The cAMP assay was performed according to the protocol provided by DiscoveRx.

The cell culture medium was removed and the cells washed once with PBS (50 µl per well). The plates were emptied by inversion and 7.5 µl/well of compound in PBS (containing 1 mM IBMX and 0.03% BSA) were added and incubated for 30 min at 37° C.

Subsequent 7.5 µl/well specific agonist solution was added and the plates for another 30 min incubated at 37° C.

The following agonist solution is used for the individual cell-lines:

hH3:100 nM histamine, 10 µM forskolin in PBS (containing 1 mM IBMX and 0.03% BSA)

After the incubation with the agonist, 5 µl/well cAMP XS antibody solution was added followed by 20 µl/well GaI/EII/Lysis (1:5:19)+ED (1:1). The plates were incubated for one hour at room temperature and afterwards 20 µl/well EA reagent was added. The luminescence was developed for approximately three hours at room temperature and the plates were read out using a 'BMG Novostar' plate reader.
Assaying of Compounds Test compounds were assayed at 8 concentrations in triplicate. Serial 10-fold dilutions in 100% DMSO were made at a 100-times higher concentration than the final concentration and then diluted with a 2 step protocol in assay buffer to reach the required assay concentrations and 1% DMSO.

The specific compounds exemplified below were categorized by the following potency ranges ($IC_{50}$ values):

A: <100 nM; B: >100 nM to 500 nM; C: >500 nM to 5000 nM.

Caco-2 Permeability Assay

The Caco-2 Permeability assay uses an established method for predicting the in vivo absorption of drugs across the gut wall by measuring the rate of transport of a compound across the Caco-2 cell line.

The Caco-2 cell line is derived from a human colon carcinoma. These cells have characteristics that resemble intestinal epithelial cells such as the formation of a polarised monolayer, well-defined brush border on the apical surface and intercellular junctions. Assessing transport in both directions (apical to basolateral (A-B) and basolateral to apical (B-A)) across the cell monolayer enables an efflux ratio to be determined which provides an indicator as to whether a compound undergoes active efflux.

Studying the permeability of compounds across a Caco-2 cell monolayer is widely accepted as an established in vitro model to screen for oral absorption and to evaluate the mechanism of transport. Using LC-MS/MS for the analysis of samples derived from Caco-2 cell studies allows the rapid and accurate determination of drug transport across the Caco-2 cell monolayer. (Wang Z, Hop C. E., Leung K. H. and Pang J. (2000) J Mass Spectrom 35 (1); 71-6).

Preferred compounds of Formula (I) have Caco-2 efflux ratios of <3.0.

Synthesis of Compounds:
Analytical Methods
NMR Spectrometers Used:
Bruker DRX 500 MHz NMR
Bruker AVANCE 400 MHz NMR
Bruker DPX 250 MHz NMR
Bruker DPX 360 MHz NMR
Configuration of the Bruker DRX 500 MHz NMR
High performance digital NMR spectrometer, 2-channel microbay console and Windows XP host workstation running Topspin version 1.3.
  Equipped with:
  Oxford instruments magnet 11.74 Tesla (500 MHz proton resonance frequency)
  B-VT 3000 temperature controller
  GRASP II gradient spectroscopy accessory for fast acquisition of 2D pulse sequences
  Deuterium lock switch for gradient shimming
  5 mm Broad Band Inverse geometry double resonance probe with automated tuning and matching (BBI ATMA). Allows $^1$H observation with pulsing/decoupling of nuclei in the frequency range $^{15}$N and $^{31}$P with $^2$H lock and shielded z-gradient coils.
Configuration of the Bruker DPX 250 MHz NMR
High performance one bay Bruker 250 MHz digital two channel NMR spectrometer console and Windows XP host workstation running XwinNMR version 3.5.
  Equipped with:
  Oxford instruments magnet 5.87 Tesla (250 MHz proton resonance frequency)
  B-VT 3300 variable temperature controller unit
  Four nucleus (QNP) switchable probe for observation of $^1$H, $^{13}$C, $^{19}$F and $^{31}$P with $^2$H lock
Configuration of the Bruker AVANCE 400 MHz NMR
High performance one bay Bruker AVANCE 400 MHz digital two channel NMR spectrometer console
  Equipped with:
  Bruker magnet 9.40 Tesla (400 MHz proton resonance frequency)
  B-VT 3200 variable temperature controller unit
  GRASP II gradient spectroscopy accessory for the generation of one field gradient of up to 50 Gauss cm$^{-1}$
  Four nucleus (QNP) switchable probe for observation of $^1$H, $^{13}$C, $^{19}$F and $^{31}$P with $^2$H lock with z-gradient coils for gradient spectroscopy.
LCMs Methods Used
Example compounds and their intermediates were analysed by HPLC-MS using a combination of the following instrumentation: Shimadzu, Waters or Micromass ZMD, ZQ or LCT mass spectrometers with an Agilent, Waters or Polymer Labs UV and ELS detector. The HPLC conditions are tabulated below. Micromass MassLynx™ Operating Software with OpenLynx™ Browser were used for data acquisition, processing and reporting.

| LCMS Method A (2 min method) | | |
|---|---|---|
| Generic 2 minute method | | |
| Column | Atlantis dC18 2.1 × 30 mm, 3 um | |
| Mobile phase | A = Formic acid (aq) 0.1% B = Formic acid (acetonitrile) 0.1% | |
| Flow rate | 1 mL/min | |
| Injection volume | 3 ul | |
| Detector | 215 nm (nominal) | |
| Gradient | Time (min) | % Organic |
| | 0 | 5 |
| | 1.50 | 100 |
| | 1.60 | 100 |
| | 1.61 | 5 |

| LCMS Method B (3.5 min method) | | |
|---|---|---|
| Standard 3.5 minute method | | |
| Column | Atlantis dC18 2.1 × 50 mm, 5 um | |
| Mobile phase | A = Formic acid (aq) 0.1% B = Formic acid (acetonitrile) 0.1% | |
| Flow rate | 1 mL/min | |
| Injection volume | 3 ul | |
| Detector | 215 nm (nominal) | |
| Gradient | Time (min) | % Organic |
| | 0 | 5 |
| | 2.5 | 100 |
| | 2.7 | 100 |
| | 2.71 | 5 |
| | 3.0 | 5 |

| LCMS Method C (7 min method) | | |
|---|---|---|
| High resolution method' | | |
| Column | Waters Atlantis dC18 100 × 2.1 mm, 3 μm column 40° C. | |
| Mobile phase | A-0.1% Formic acid (water) B-0.1% Formic acid (acetonitrile) | |
| Flow rate | 0.6 mL/min | |
| Injection volume | 3 ul | |
| Detector | 215 nm (nominal) | |
| Gradient | Time (min) | % Organic |
| | 0.00 | 5 |

| LCMS Method C (7 min method) | |
|---|---|
| 5.00 | 100 |
| 5.40 | 100 |
| 5.42 | 5 |
| 7.00 | 5 |

| LCMS Method D (10 min method) | |
|---|---|
| Column | Chromolith Speed Rod RP -18c 4.6 × 50 mm |
| Mobile phase | A – Buffer + Acetonitrile (95:5) Buffer: 0.01% ammonium acetate pH 5.00 (water) B-acetonitrile |
| Flow rate | 1.5 mL/min |
| Injection volume | 10 ul |
| Detector | PDA detector Detection: Spectrum Max |

| Gradient | Time (min) | % Organic |
|---|---|---|
| | 0.00 | 5 |
| | 0.60 | 5 |
| | 5.00 | 95 |
| | 8.00 | 95 |
| | 8.50 | 5 |
| | 10.0 | 5 |

| LCMS Method E (15 min method) | |
|---|---|
| Column | Waters X-terra MS C-18 4.6 × 50 mm, 5 micron |
| Mobile phase | A – Buffer + Acetonitrile (95:5) Buffer: 0.01% ammonium acetate pH 5.00 (water) B-acetonitrile |
| Flow rate | 1.0 mL/min |
| Injection volume | 10 ul |
| Detector | PDA detector Detection: Spectrum Max |

| Gradient | Time (min) | % Organic |
|---|---|---|
| | 0.00 | 5 |
| | 1.00 | 5 |
| | 7.00 | 95 |
| | 12.0 | 95 |
| | 13.0 | 5 |
| | 15.0 | 5 |

Preparative HPLC Methods Used:

Where indicated, Example compounds and their intermediates were purified by one of or any combination of the following methods.

| Prep Method 1 (Low pH) | |
|---|---|
| Column | Waters SunFire Prep C18 OBD 5 um 19 × 100 mm |
| Mobile Phase | A, TFA (aq) 0.1% B, TFA (CH$_3$CN) 0.1% |

| Prep Method 2 | |
|---|---|
| Column | Phenomenex Gemini C18 NX 5 u 100 × 21.2 mm |
| Mobile Phase | A, 2 mM ammonium bicarbonate, buffered to pH10 B, Acetonitrile: 2 mM ammonium bicarbonate 95:5 |

| Prep Method 3 (Low pH) | |
|---|---|
| Column | Waters SunFire Prep C18 OBD 5 um 19 × 100 mm |
| Mobile Phase | A, HCO$_2$H (aq) 0.1% B, HCO$_2$H (MeOH) 0.1% |

| Prep method 4 | |
|---|---|
| Column | Waters SunFire Prep C18 OBD 5 um 19 × 100 mm |
| Mobile Phase | A, H$_2$O B, CH$_3$CN |

| Prep method 5 (Neutral) | |
|---|---|
| Column | Waters SunFire Prep C18 OBD 5 um 19 × 100 mm |
| Mobile Phase | A, H$_2$O B, MeOH |

Compound Naming

All compounds are named using ACD Labs 10.0 naming software which conforms to IUPAC naming protocols. Some compounds are isolated as TFA salts, which is not reflected by the chemical name. Within the meaning of the present invention the chemical name represents the compound in neutral form as well as its TFA salt or any other salt, especially pharmaceutically acceptable salt, if applicable.

| List of Abbreviations | |
|---|---|
| AcOH | acetic acid |
| Ag$_2$CO$_3$ | silver carbonate |
| br s | broad singlet |
| Boc | tert-butoxycarbonyl |
| BINAP | 2,2'-bis(diphenylphosphino)-1,1'binaphthyl |
| $^t$BuOK | potassium tert-butoxide |
| $^n$BuLi | n-butyl lithium |
| $^{sec}$BuLi | secondary-butyl lithium |
| cat | catalytic |
| cbz | benzyloxycarbonyl |
| CDI | 1,1'-carbonyldiimidazole |
| Chloroform-d | deuterated chloroform |
| DCC | dicyclohexylcarbodiimide |
| DCE | 1,2-dichloroethane |
| DCM | dichloromethane |
| DIPEA | N,N-diisopropylethylamine |
| DMAP | N,N-4-dimethylaminopyridine |
| EDCI | 1-ethyl-3-(3-dimethylaminopropyl)carbodiimide hydrochloride |
| eq | equivalent |

List of Abbreviations

| | |
|---|---|
| Ether | diethyl ether |
| Et₂O | diethyl ether |
| EtOAc | ethyl acetate |
| EtOH | ethanol |
| FCC | flash column chromatography |
| h | hours |
| hrs | hours |
| HCl | hydrochloric acid |
| H$_2$SO$_4$ | sulfuric acid |
| HDA | diisopropylamine |
| HOBt | 1-hydroxybenzotriazole |
| HBTU | o-benzotriazol-1-yl-N,N,N',N'-tetramethyluronium tetrafluoroborate |
| IBX | 1-hydroxy-1,2-benziodoxol-3(1h)-one 1-oxide |
| IPA | isopropyl alcohol |
| Kryptofix-222 | 4,7,13,16,21,24-hexaoxa-1,10-diazabicyclo [8.8.8]-hexacosane |
| LAH | lithium aluminium hydride |
| LiAlH$_4$ | lithium aluminium hydride |
| LiTMP | 2,2,6,6-tetramethylpiperidine |
| LCMS | liquid chromatography and mass spectrometry |
| MeCN | acetonitrile |
| MeOH | methanol |
| MeOD | dueterated methanol |
| MsCl | methanesulfonyl chloride |
| MeI | methyl iodide |
| m | multiplet |
| min(s) | minute(s) |
| mL | milliliter |
| ml | milliliter |
| mol/M | mole/molar |
| MW | molecular weight |
| NMR | nuclear magnetic resonance |
| NaBH$_3$CN | sodium cyanoborohydride |
| NaBH$_4$ | sodium borohydride |
| NEt$_3$ | triethylamine |
| OMs | methanesulfonate |
| OTs | para-toluenesulfonate |
| Pd$_2$(dba)$_3$ | bis(dibenzylideneacetone)palladium(0) |
| PBr$_3$ | tribromophospine |
| PMA | phosphomolibdic acid |
| PPh$_3$ | triphenylphosphine |
| PS-DIPEA | polymer-supported N,N-diisopropylethylamine |
| Rt | retention time |
| RT | room temperature |
| SOCl$_2$ | thionyl chloride |
| STAB | sodium triacetoxyborohydride |
| pTSA | para-toluene sulfonic acid |
| thio-CDI | thio-carbonyl diimidazole |
| TBAF | tetra-n-butylammonium fluoride |
| TBAI | tetra-n-butylammonium iodide |
| TBDMSCl | tert-butyldimethylsilyl chloride |
| TEA | triethylamine |
| TFA | 2,2,2-trifluoroacetic acid |
| TFAA | 2,2,2-trifluoroacetic acid anhydride |
| TFE | 2,2,2-trifluoroethanol |
| THF | tetrahydrofuran |
| TLC | thin layer chromatography |
| TMS | trimethylsilyl |
| W | watt(s) |

Route 1

General Procedure A

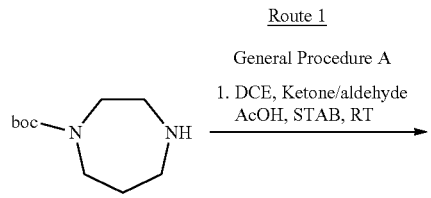

1. DCE, Ketone/aldehyde AcOH, STAB, RT

General Procedure B

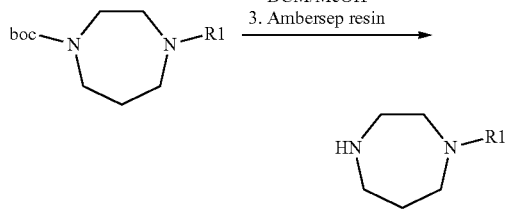

2. 4M HCl in dioxane DCM/MeOH
3. Ambersep resin

General Procedure A

Preparation of tert-butyl 4-cyclobutyl-1,4-diazepane-1-carboxylate

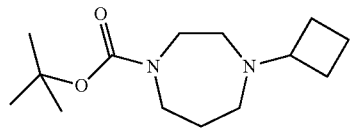 [SMILES: CC(C)(C)OC(=O)N1CCCN(C2CCC2)CC1]

To a stirred solution of [1,4]diazepane-1-carboxylic acid tert-butyl ester (5 g, 24.97 mmol) in DCE (70 ml) at 20 to 25° C. was added cyclobutanone (1.75 g, 24.97 mmol) followed by acetic acid (1.5 g, 24.97 mmol) dropwise. The resulting mixture was stirred at 20 to 25° C. for ca. 2 h. Sodium triacetoxyborohydride (7.94 g, 37.46 mmol) was added in 9 portions, keeping the temperature in the range of 20 to 25° C. The resulting suspension was stirred at 20 to 25° C. overnight. Saturated NaHCO$_3$ (80 ml) was added in four portions and the biphasic mixture stirred at 20 to 25° C. for ca. ½ h. The organic layer was separated, washed with water (20 ml) and the aqueous phase back extracted at pH 9 with DCM (20 ml). The combined organic phases were dried (Na$_2$SO$_4$), filtered and concentrated in vacuo to provide the title compound as yellow oil (6.1 g, 96%).

LCMS data: Calculated MH$^{30}$ (255); Found 100% [2(M-Boc)]H$^1$ m/z (307), Rt=1.4 mins.

NMR data: $^1$H NMR (400 MHz, MeOD) δ ppm 3.38-3.52 (4 H, m), 2.86-2.98 (1 H, m), 2.40-2.54 (4 H, m), 2.02-2.12 (2 H, m), 1.77-1.92 (4 H, m), 1.61-1.75 (2 H, m), 1.46 (9 H, s).

The following intermediates were prepared as described in Route 1, General Procedure A above.

Preparation of tert-butyl 4-(1-methylethyl)-1,4-diazepane-1-carboxylate

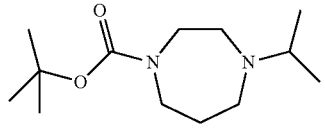 [SMILES: CC(C)N1CCCN(C(=O)OC(C)(C)C)CC1]

In a similar fashion (R1, GP A), tert-butyl 1,4-diazepane-1-carboxylate (500 mg, 2.45 mmol) and acetone (198 μL, 2.69 mmol), gave the title compound (560 mg, 93% yield) as colourless oil. The product was taken through to the next step without further purification.

Preparation of tert-butyl 4-cyclopentyl-1,4-diazepane-1-carboxylate

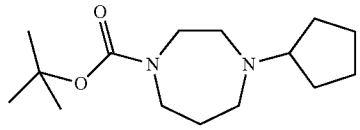 [SMILES: CC(C)(C)OC(=O)N1CCCN(C2CCCC2)CC1]

In a similar fashion (R1, GP A), cyclopentanone (1.36 mL, 15 mmol), gave the title compound (3.68 g, 91% yield) as clear pale yellow oil.

LCMS data: Calculated MH$^+$(269); Found 98% [(M-Boc)] H$^+$ m/z (213), Rt=1.4 mins.

NMR data: $^1$H NMR (400 MHz, Chloroform-d) δ ppm 1.24-1.35 (2 H, m), 1.37 (9 H, s), 1.42-1.49 (2 H, m), 1.53-1.66 (4 H, m), 1.97-2.08 (2 H, m), 1.69-1.84 (4 H, m), 2.55-2.67 (4 H, m), 2.73-2.85 (1 H, m), 3.33-3.47 (4 H, m).

Preparation of tert-butyl 4-cyclobutylpiperazine-1-carboxylate

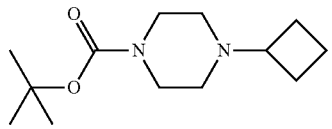 [SMILES: CC(C)(C)OC(=O)N1CCN(C2CCC2)CC1]

In a similar fashion (R1, GP A), tert-butyl piperazine-1-carboxylate (13.0 g, 69.8 mmol) and cyclobutanone (1.36 mL, 15 mmol), gave the title compound (12 g, 71.5% yield) as clear pale yellow oil. This compound showed a single spot by TLC (uv 215 nm) and was taken through to the next step without further purification.

General Procedure B

Preparation of 1-cyclobutyl-1,4-diazepane

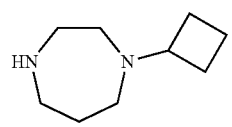

To a stirred solution of tert-butyl 4-cyclobutyl-1,4-diazepane-1-carboxylate (6.1 g, 23.98 mmol) in DCM (70 ml) at 20 to 25° C. was added a solution of 4M HCl in dioxane (30 ml, 120 mmol) dropwise. The resulting mixture was stirred at 20 to 25° C. for ca. 2 h. MeOH (6 ml) was added and the resulting mixture stirred at 20 to 25° C. for 1 to 2 days. The solvent was removed in vacuo and the resulting gummy residue slurried in ether (100 ml) for 0.5 h. The solvent was evaporated and the residue slurried in ether/MeOH (10:1, 66 ml). The resulting white solid was collected by filtration, suspended in DCM (150 ml) and treated with 2M NaOH. The aqueous phase was extracted with DCM until complete transfer of product in the organic layer, as monitored by TLC analysis (eluent, DCM/MeOH/conc.NH$_3$ (90:10:1); stain, PMA) was achieved. The combined organic phases were dried (Na$_2$SO$_4$), filtered and concentrated in vacuo to provide the title compound as orange oil (2.67 g, 73%).

LCMS data: Calculated MH$^+$(155); Found 100% (MH$^+$) m/z 155, Rt=0.44 min.

NMR data: $^1$H NMR (400 MHz, Chloroform-d) δ ppm 2.85-2.97 (5 H, m), 2.43-2.53 (4 H, m), 1.97-2.08 (2 H, m), 1.52-1.91 (7 H, m).

The following intermediate was prepared as described in Route 1, General Procedure B above.

Preparation of 1-(1-methylethyl)-1,4-diazepane

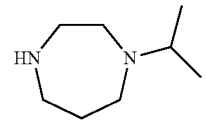

In a similar fashion (R1, GP B), tert-butyl 4-(1-methylethyl)-1,4-diazepane-1-carboxylate (560 mg, 2.31 mmol) gave the title compound (633 mg, 133% yield—$^1$H NMR analysis shows a significant amount of entrained dioxane) as brown oil. $^1$H NMR (500 MHz, CDCl$_3$) δ 3.41-3.85 (9 H, m), 2.27-2.46 (2 H, m), 1.42 (6 H, d).

Preparation of 1-cyclopentyl-1,4-diazepane

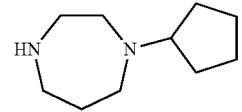

In a similar fashion (R1, GP B), tert-butyl 4-cyclopentyl-1,4-diazepane-1-carboxylate (3.68 g, 13.7 mmol), gave the title compound (1.96 g, 85% yield) as pale yellow semi-solid.

LCMS data: Calculated MH$^+$(169); Found 100% (MH$^+$) m/z 169, Rt=0.25 min.

NMR data: $^1$H NMR (400 MHz, Chloroform-d) δ ppm 2.73-2.84 (5 H, m), 2.53-2.62 (4 H, m), 1.56-1.76 (4 H, m), 1.16-1.56 (6 H, m).

Preparation of 1-cyclobutylpiperazine

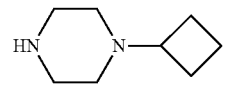

In a similar fashion (R1, GP B), tert-butyl 4-cyclobutylpiperazine-1-carboxylate (12 g, 49.9 mmol), gave the title compound (5.23 g, 74.7% yield) as white semi-crystalline solid.

LC data: Rt=2.74 mins (High pH).

$^1$H NMR (500 MHz, CHLOROFORM-d) δ ppm 5.39 (2 H, br. s.), 3.03 (2 H, t, J=4.8 Hz), 2.63-2.82 (1 H, m), 2.10-2.62 (6 H, m), 1.96 (2 H, q, J=7.7 Hz), 1.73-1.92 (2 H, m), 1.53-1.72 (2 H, m).

Route 2

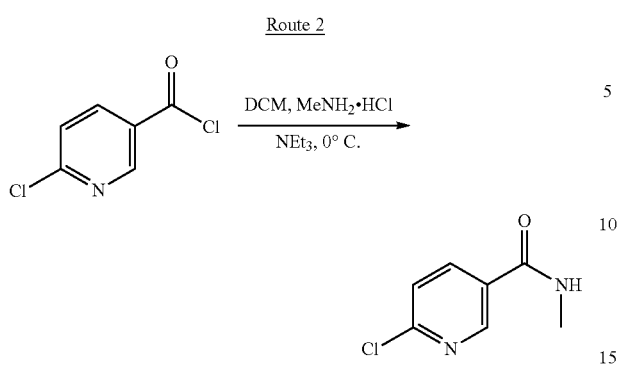

Preparation of
6-chloro-N-methylpyridine-3-carboxamide

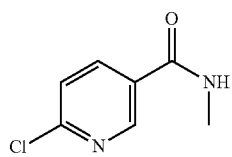

To a stirred solution of 6-chloropyridine-3-carbonyl chloride (1.5 g, 8.52 mmol) in DCM (10 ml) at 0° C. was added methylamine hydrochloride (1.73 g, 25.5 mmol) followed by drop wise additional of triethylamine (3.55 ml, 25.5 mmol) over 10 mins. The reaction mixture was stirred at RT for 2 h then quenched by addition of brine (15 ml) and saturated Na$_2$CO$_3$ (5 ml). The organic layer was collected and the aqueous layer extracted with DCM (2×20 ml). The combined organic phase was washed with brine (10 ml), dried (Na$_2$SO$_4$), filtered and evaporated to dryness. Recrystallisation from hot DCM (~10 ml) provided the title compound (0.995 g, 5.8 mmol, 68%) as white crystals.

LCMS data: Calculated MH$^+$(171); Found 100% (MH$^+$) m/z 171, Rt=2.30 min.

1H NMR (400 MHz, CHLOROFORM-d) δ ppm 8.74 (1 H, d, J=2.4 Hz), 8.09 (1 H, dd, J=8.3, 2.4 Hz), 7.42 (1 H, d, J=8.1 Hz), 6.41 (1 H, br. s.), 3.03 (3H, d, J=4.9 Hz).

Route 3
General Procedure C

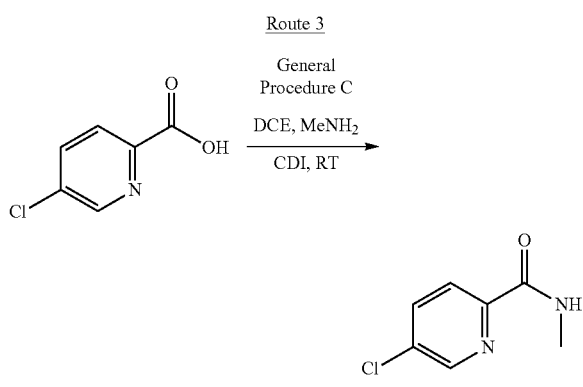

General Procedure C

Preparation of
5-chloro-N-methylpyridine-2-carboxamide

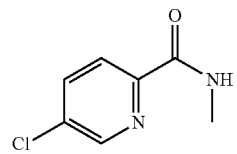

To a stirred solution of 5-chloropyridine-2-carboxylic acid (315 mg, 2.0 mmol) in DCE (2.5 ml) at 20 to 25° C. was added CDI (324 mg, 2.0 mmol) and the mixture was stirred at RT overnight. The reaction mixture was heated to ca. 50° C. and a solution of methylamine in THF (2 M, 5.0 mmol) was added. The resulting mixture was stirred at 50° C. overnight and then cooled to RT and diluted with DCM (20 mL). the reaction mixture was washed with sat. NaHCO$_3$ (10 ml) and the organic layer dried (Na$_2$SO$_4$), filtered and concentrated in vacuo. Purification by silica flash column chromatography (eluting with DCM/MeOH 95:5) provided the title compound as off-white solid (140 mg, 41%).

LCMS data: Calculated MH$^+$ (171); Found 100% (MH$^+$) m/z 171, Rt=1.32 min.

NMR data: $^1$H NMR (400 MHz, MeOD) δ ppm 8.58 (1 H, d, J=2.4 Hz), 8.02-8.08 (1 H, m), 7.94-8.00 (1 H, m), 2.95 (3 H, s).

The following compounds were made as described in Route 3, General Procedure C above.

Preparation of
5-chloro-N,N-dimethylpyridine-2-carboxamide

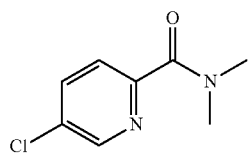

In a similar fashion (Route 3, GP C), 5-chloropyridine-2-carboxylic acid (315 mg, 2.0 mmol) and a solution of dimethyl amine in EtOH (5.6 M, 5.0 mmol) gave the title compound as off white solid (190 mg, 51%).

LCMS data: Calculated MH$^+$(185); Found 100% (MH$^+$) m/z 185, Rt=1.16 min.

NMR data: (400 MHz, MeOD) δ ppm 8.60 (1 H, d, J=2.2 Hz), 7.99 (1 H, dd, J=8.3, 2.4 Hz), 7.62 (1 H, d, J=8.3 Hz), 3.13 (3 H, s), 3.04 (3 H, s).

Preparation of 5-chloro-pyridine-2-carboxamide

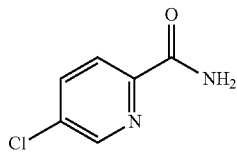

In a similar fashion (Route 3, GP C), 5-chloropyridine-2-carboxylic acid (126 mg, 0.80 mmol) and a solution of ammonia in methanol (7 M, 2.38 mmol) gave the title compound as pale pink solid (40 mg, 32%).

LCMS data: Calculated MH$^+$ (157); Found 99% (MH$^+$) m/z 157, Rt=1.17 min

NMR data: (500 MHz, DMSO) δ ppm 8.68 (1 H, d), 8.09-8.17 (2 H, m), 8.04 (1 H, d), 7.73 (1 H, br. s.).

Preparation of 5-chloro-N,N-dimethylpyridine-2-carboxamide

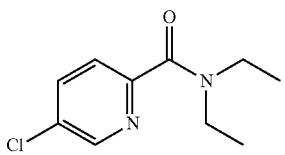

In a similar fashion (Route 3, GP C), 5-chloropyridine-2-carboxylic acid (126 mg, 0.80 mmol) and diethylammonium chloride (259 mg, 2.38 mmol) and DIPEA (0.55 ml, 3.18 mmol) gave the title compound as pink oil (105 mg, 62%).

LCMS data: Calculated MH$^+$ (213); Found 100% (MH$^+$) m/z 213, Rt=1.53 min.

NMR data: (500 MHz, CDCl$_3$) δ ppm 8.48 (1 H, d, J=2.4 Hz), 7.71 (1 H, dd, J=8.3, 2.5 Hz), 7.54 (1 H, d, J=8.4 Hz), 3.50 (2 H, q, J=7.2 Hz), 3.34 (2 H, q, J=7.0 Hz), 1.21 (3 H, t, J=7.2 Hz), 1.12 (3 H, t, J=7.1 Hz).

Preparation of 4-fluoro-N,3-dimethylbenzamide

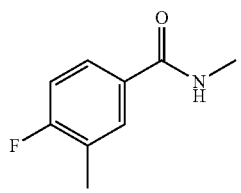

In a similar fashion (Route 3, GP C), 4-fluoro-3-methyl-benzoic acid (97 mg, 0.63 mmol) and a solution of methylamine in MeOH (2 M, 0.89 mmol) gave the title compound as an off white solid (73 mg, 69%).

LCMS data: Calculated MH$^+$ (168); Found 100% (MH$^+$) m/z 168, Rt=1.03 min.

NMR data: (250 MHz, CDCl$_3$) δ ppm 7.64 (1 H, dd, J=7.1, 1.9 Hz), 7.50-7.59 (1 H, m), 7.03 (1 H, 7, J=8.8 Hz), 6.07 (1 H, br s), 3.0 (3 H, d, J=4.9 Hz), 2.30 (3 H, d, J=2.0 Hz).

Route 4

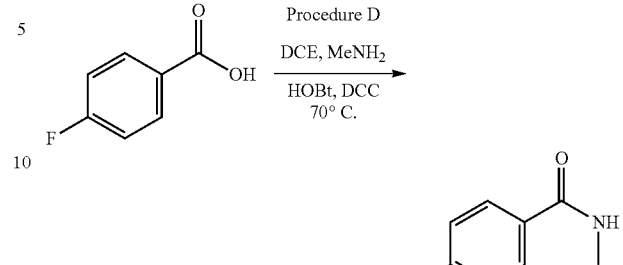

General Procedure D

Preparation of 4-fluoro-N-methylbenzamide

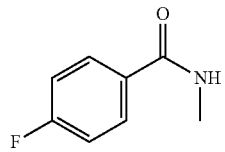

To a stirred solution of 4-fluorobenzoic acid (200 mg, 1.43 mmol) in DCE (3 ml) at RT, was added a solution of methyl amine in THF (2 M, 1.43 mmol) and NEt$_3$ (198 μl, 1.43 mmol) and allowed to stir for ca. 10 mins. HOBt (221 mg, 1.43 mmol) and DCC (295 mg, 1.43 mmol) were added and the reaction mixture heated at 70° C. for 3 h. After cooling to RT, the reaction mixture was washed with sat. NaHCO$_3$ (5 ml) and the aqueous back extracted with DCM. The organics were combined, dried (MgSO$_4$), filtered and concentrated under reduced pressure. Purification by silica flash column chromatography (eluting with DCM/MeOH gradient 100:0 to 80:20) provided the title compound as off-white solid (137 mg, 63%).

LCMS data: Calculated MH$^+$(154); Found 100% (MH$^+$) m/z 154.2, Rt=1.11 min.

The following compound was made as described in Route 4, General Procedure D above.

Preparation of 4-fluoro-N,N-dimethylbenzamide

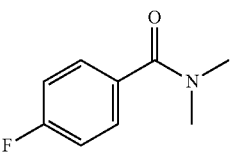

In a similar fashion (Route 4, GP D), 4-fluorobenzoic acid (200 mg, 1.43 mmol) and a solution of dimethyl amine in EtOH (5.6 M, 1.43 mmol) gave the title compound as off white solid (172 mg, 72%).

LCMS data: Calculated MH$^+$ (168); Found 89% (MH$^+$) m/z 168, Rt=1.03 mins.

Route 5

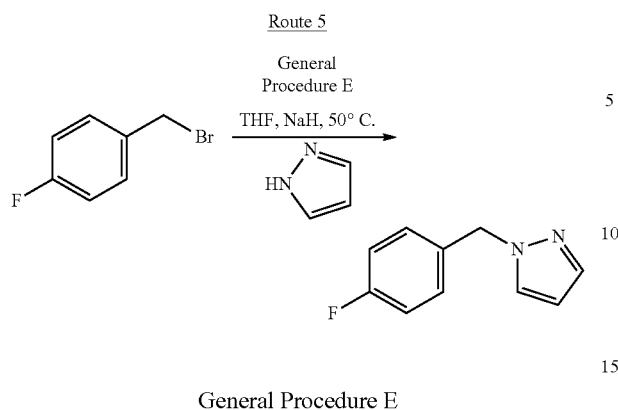

General Procedure E

Preparation of 1-(4-fluorobenzyl)-1H-pyrazole

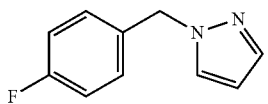 [SMILES: Fc1ccc(Cn2cccn2)cc1]

To a stirred solution of pyrazole (300 mg, 4.4 mmol) in DMSO (2 ml) at RT was added NaH (176 mg, 4.4 mmol, 60% in mineral oil) portionwise. The mixture was stirred at RT for 1 h and 4-fluorobenzylbromide (1.0 g, 5.3 mmol) added dropwise. The mixture was stirred at 50° C. for 0.5 h, cooled to RT and diluted with DCM (20 ml). The resulting mixture was filtered and the filtrate washed with brine (10 ml). The organic layer was then dried (NaSO), filtered and concentrated at reduced pressure. Purification by silica flash column chromatography (eluting with DCM/MeOH 95:5) provided the title compound as colourless oil (650 mg, 84%).

LCMS data: Calculated MH$^+$ (177); Found 100% (MH$^+$) m/z 177, Rt=1.66 min.

NMR data: $^1$H NMR (400 MHz, MeOD) δ ppm 7.68 (1 H, d, J=2.2 Hz), 7.51 (1 H, d, J=1.7 Hz), 7.19-7.27 (2 H, m), 7.01-7.09 (2 H, m), 6.32 (1 H, t, J=2.2 Hz), 5.32 (2 H, s).

The following compounds were made as described in Route 5, General Procedure E above.

Preparation of
2-chloro-5-(1H-pyrazol-1-ylmethyl)pyridine

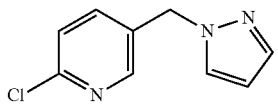

In a similar fashion (Route 5, GP E),2-chloro-5-(chloromethyl)pyridine (450 mg, 2.5 mmol, 90% purity) and pyrazole (170 mg, 2.5 mmol) gave the title compound as colourless oil (372 mg, 77%).

LCMS data: Calculated MH$^+$(194); Found 89% (MH$^+$) m/z 194, Rt=1.39 min.

NMR data: $^1$H NMR (400 MHz, MeOD) δ ppm 8.25 (1 H, d, J=2.2 Hz), 7.77 (1 H, d, J=2.2 Hz), 7.64 (1 H, dd, J=8.2, 2.3 Hz), 7.55 (1 H, d, J=1.5 Hz), 7.42 (1 H, d, J=8.3 Hz), 6.35 (1 H, t, J=2.1 Hz), 5.40 (2 H, s).

Route 6

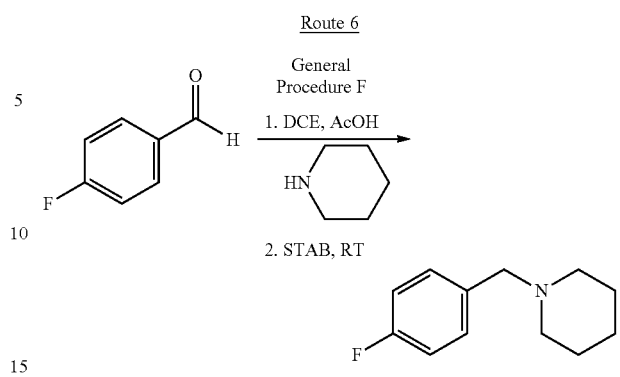

General Procedure F

Preparation of 1-(4-fluorobenzyl)piperidine

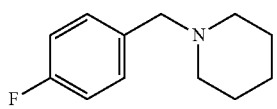 [SMILES: Fc1ccc(CN2CCCCC2)cc1]

To a stirred solution of 4-fluorobenzaldehyde (500 mg, 4.0 mmol) in DCE (3 ml) at RT was added piperidine (309 mg, 3.6 mmol) followed by AcOH (242 mg, 4.0 mmol). The solution was stirred at RT for 2 h, and then STAB (1.3 g, 6.05 mmol) was added in one portion. The resulting mixture was stirred at RT overnight and then quenched with saturated NaHCO$_3$ (10 ml). The organic layer was separated, dried (Na$_2$SO$_4$), filtered and concentrated at reduced pressure. Purification by silica flash column chromatography (eluting with DCM/MeOH/NH$_3$ 90:10:1) provided the title compound as colourless oil (650 mg, 95%).

LCMS data: Calculated MH$^+$(194); Found 100% (MH$^+$) m/z 194, Rt=0.62 min.

NMR data: $^1$H NMR (360 MHz, CHLOROFORM-d) δ ppm 7.23-7.32 (2 H, m), 6.99 (2 H, t, J=8.6 Hz), 3.43 (2 H, s), 2.36 (4 H, br. s.), 1.57 (4 H, quin, J=5.6 Hz), 1.44 (2 H, d, J=5.4 Hz).

The following compounds were made as described in Route 6, General Procedure F above.

Preparation of
1-(4-fluorobenzyl)-4-methylpiperazine

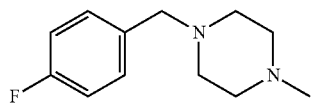

In a similar fashion (Route 6, GP F), 4-fluorobenzaldehyde (500 mg, 4.0 mmol) and N-methylpiperazine (363. mg, 3.63 mmol) gave the title compound as colourless oil (657 mg, 88%).

LCMS data: Calculated MH$^+$ (209); Found 100% (MH$^+$) m/z 209, Rt=0.48 min.

NMR data: ¹H NMR (360 MHz, CHLOROFORM-d) δ ppm 7.28 (2 H, dd, J=8.6, 5.4 Hz), 6.94-7.03 (2 H, m), 3.47 (2 H, s), 2.46 (8 H, d, J=5.9 Hz), 2.29 (3 H, s).

Preparation of 4,4-difluoro-1-(4-fluorobenzyl)piperidine

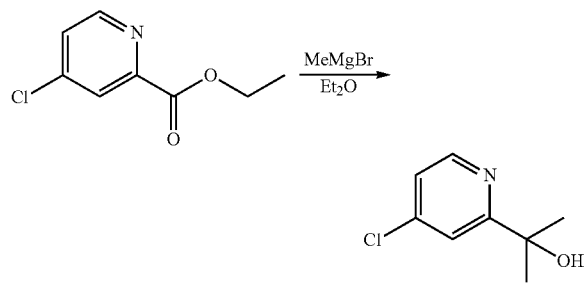

In a similar fashion (Route 6, GP F), 4-fluorobenzaldehyde (250 mg, 2.0 mmol) and 4,4-difluoropiperidine (285. mg, 1.8 mmol) gave the title compound as colourless oil (370 mg, 90%).

LCMS data: Calculated MH⁺(230); Found 100% (MH⁺) m/z 230, Rt=0.66 min.

NMR data: ¹H NMR (250 MHz, CHLOROFORM-d) δ ppm 7.22-7.35 (2 H, m), 6.94-7.08 (2 H, m), 3.51 (2 H, s), 2.53 (4 H, t, J=5.6 Hz), 1.89-2.09 (4 H, m).

Route 7

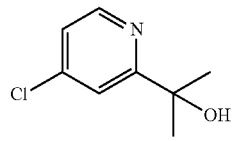

Preparation of 2-(4-chloropyridin-2-yl)propan-2-ol

Ethyl 4-chloropyridine-2-carboxylate (200 mg, 1.08 mmol) was dissolved in diethyl ether (10 ml) and cooled to 0° C. MeMgBr (1.08 ml of a 3M solution in diethyl ether, 3.24 mmol) was added dropwise and the reaction was warmed to room temperature and stirred for 30 minutes. After quenching with saturated NaHCO₃ (2 ml) and diluting with diethyl ether (40 ml), the resulting mixture stirred vigorously for 30 minutes to break up the resulting solid. The mixture was washed twice with saturated NaHCO₃ (20 ml), dried (MgSO₄) and concentrated at reduced pressure. The resulting residue was dissolved in diethyl ether (10 ml) and the Grignard reaction repeated giving the title compound as colourless oil (157 mg, 85%).

LCMS data: Calculated MH⁺(186); Found 92% (MH⁺) m/z 186, Rt=1.57 min.

NMR data: ¹H NMR (500 MHz, CDCl₃) δ ppm 8.43 (1 H, d, J=5.3 Hz), 7.42 (1 H, d, J=1.2 Hz), 7.22 (1 H, dd, J=5.3, 1.8 Hz), 4.56 (1 H, s), 1.55 (6 H, s).

Route 8

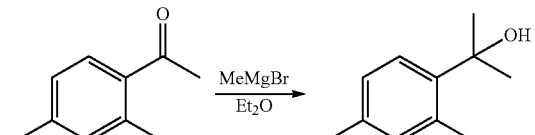

Preparation of 2-(2,4-Difluoro-phenyl)-propan-2-ol

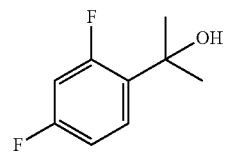

MeMgBr (1.83 ml of a 3M solution in diethyl ether, 5.5 mmol) was added dropwise to a solution of 2,4-difluoroacetophenone (782 mg, 5.0 mmol) in diethyl ether (20 ml) at 0° C. The reaction was warmed to room temperature and after 1 hour was quenched and washed with water (2×20 ml), dried (MgSO₄) and concentrated under reduced pressure to give the title product as colourless oil (800 mg, 93%).

LCMS data: MH⁺(173); Found 75% (M-OH)⁺ m/z 155, Rt=1.75 min.

NMR data: ¹H NMR (500 MHz, CDCl₃) δ ppm 7.49-7.61 (1 H, m), 6.83-6.89 (1 H, m), 6.75-6.83 (1 H, m), 2.02 (1 H, s), 1.63 (6 H, s).

Route 9

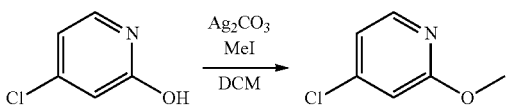

Preparation of 4-chloro-2-methoxy-pyridine

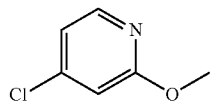

4-Chloro-2-hydroxy-pyridine (247 mg, 1.91 mmol), Ag₂CO₃ (1.58 g, 5.74 mmol) and MeI (0.13 ml, 2.11 mmol) were heated in a sealed tube at 50° C. for 16 hours and then filtered through celite and concentrated at reduced pressure. The residue was purified by FCC (Pentane/Diethyl ether with gradient, 99:1 to 95:5) to provide the title compound as colourless oil (160 mg, 58%).

LCMS data: Calculated MH⁺(144); Found 100% (MH⁺) m/z 144, Rt=1.71 min.

NMR data: ¹H NMR (500 MHz, CDCl₃) δ ppm 8.07 (1 H, d, J=5.5 Hz), 6.89 (1 H, dd, J=5.5, 1.5 Hz), 6.77 (1 H, d, J=1.7 Hz), 3.94 (3 H, s).

Route 10

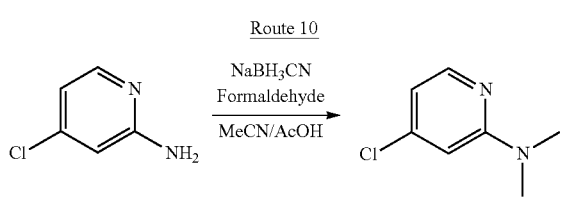

Preparation of
4-chloro-N,N-dimethylpyridin-2-amine

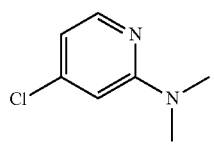

Acetic acid (0.6 ml, 10.5 mmol) was added dropwise to a solution of 2-amino-4-chloropyridine (384 mg, 3.0 mmol), formaldehyde (2.4 ml of a 37% aqueous solution, 29.6 mmol) and NaBH$_3$CN (581 mg, 9.0 mmol) in MeCN (10 ml) and water (2 ml) at 0° C. After 10 minutes the reaction was warmed to room temperature and stirred for 3 days. The reaction was basified to pH4 with 1M aq. NaOH and then extracted with diethyl ether (3×30 ml), dried (MgSO$_4$), filtered and concentrated at reduced pressure. The residue was purified by FCC (Hexane/Diethyl ether with gradient, 98:2 to 8:2) to provide the title compound as colourless oil (260 mg, 56%).

LCMS data: Calculated MH$^+$(157); Found 100% (MH$^+$) m/z 157, Rt=0.63 mins.

NMR data: $^1$H NMR (500 MHz, CDCl$_3$) δ ppm 8.05 (1 H, d, J=5.3 Hz), 6.54 (1 H, d, J=5.5 Hz), 6.49 (1 H, d, J=1.5 Hz), 3.08 (6 H, s).

Route 11

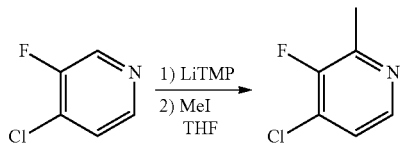

Preparation of 4-chloro-3-fluoro-2-methylpyridine

n-BuLi (8.5 ml of a 1.2 M soln in hexanes, 10.2 mmol) was added dropwise to a solution of 2,2,6,6-tetramethylpiperidine (1.73 ml, 10.2 mmol) in THF (30 ml) at 0° C. The mixture was then cooled to −78° C. and 4-chloro-3-fluoropyridine (1.0 ml, 10.2 mmol) was added dropwise over 15 minutes and then stirred for 25 minutes. MeI (0.64 ml, 10.2 mmol) was added dropwise at −78° C. and the resulting solution was left to warm to room temperature over several hours and quenched with saturated NaHCO$_3$ (5 ml). The reaction was concentrated at reduced pressure, diluted with dichloromethane (50 ml), washed twice with saturated NaHCO$_3$ (25 ml), dried (MgSO$_4$), filtered and concentrated at reduced pressure. The residue was purified by FCC (pentane/diethyl ether with gradient, 9:1 to 8:2) to provide the title compound as colourless oil (833 mg, 56%).

LCMS data: The product did not ionise, 96% UV at Rt=3.59 mins observed (High pH method).

NMR data: $^1$H NMR (500 MHz, CDCl$_3$) δ ppm 8.20 (1 H, d, J=5.2 Hz), 7.17-7.25 (1 H, m), 2.56 (3 H, d, J=3.2 Hz).

Route 12

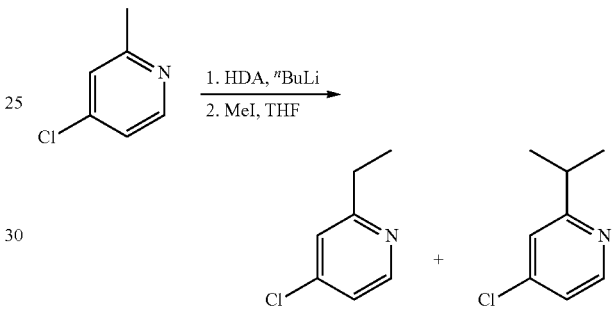

Preparation of 2-ethyl-4-chloropyridine

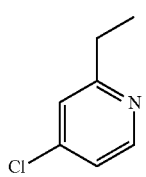

To a stirred solution of diisopropylamine (0.86 ml, 6.1 mmol) in THF (15 ml) at −20° C. was added dropwise a solution of n-butyllithium in hexanes (1.2M, 5.07 ml, 6.1 mmol). The reaction mixture was stirred at −20° C. for 20 minutes and was then cooled to −70° C. A solution of 2-methyl-4-chloropyridine (0.74 g, 5.8 mmol) in THF (10 ml) was added dropwise over 20 minutes and the reaction mixture was stirred for 1 hour at −70° C. Methyl iodide (0.38 ml, 6.1 mmol) was then added dropwise and the reaction was allowed to warm to room temperature with stirring. The solvent was evaporated at reduced pressure and the resulting residue purified by FCC. $^1$H NMR indicated a ~2.2:1 mixture of 2-ethyl and 2-(1-methylethyl) compounds. Re-purification by silica FCC [pentane/ether eluting with gradient 9:1 to 1:1] gave the title compound (209 mg, 24%) as colourless oil.

LCMS data: The product did not ionise, 99% UV at Rt=4.34 mins observed (High pH method).

NMR data: ¹H NMR (250 MHz, CDCl₃) δ ppm 8.43 (1 H, d, J=5.3 Hz), 7.19 (1 H, d, J=2.0 Hz), 7.13 (1 H, dd, J=5.3, 2.0 Hz), 2.82 (2 H, q, J=7.6 Hz), 1.31 (3 H, t, J=7.6 Hz).

Preparation of 4-chloro-2-(1-methylethyl)pyridine

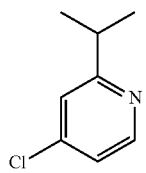

The title compound (97 mg, 10%) was recovered from Route 12 as colourless oil.

LCMS data: The product did not ionise, 91% UV at Rt=3.93 min observed (High pH method).

NMR data: ¹H NMR (250 MHz, CDCl₃) δ ppm 8.44 (1 H, d, J=5.3 Hz), 7.19 (1 H, d, J=1.8 Hz), 7.13 (1 H, dd, J=5.3, 2.0 Hz), 2.97-3.12 (1 H, sept, J=6.8 Hz), 1.30 (6 H, d, J=6.8 Hz).

Route 13

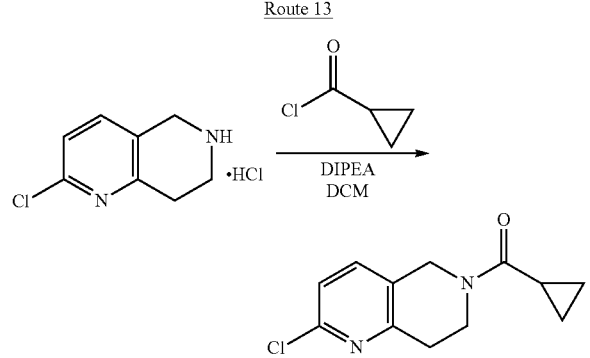

Preparation of 2-chloro-6-(cyclopropylcarbonyl)-5,6,7,8-tetrahydro-1,6-naphthyridine To a room temperature stirred suspension of 2-chloro-5,6,7,8-tetrahydro-1,6-naphthyridine hydrochloride (50 mg, 0.24 mmol) in dichloromethane (2 ml) under a nitrogen atmosphere was added DIPEA (0.12 ml, 0.73 mmol) followed by cyclopropyl carbonyl chloride (24 µl, 0.27 mmol). The resulting mixture was stirred for 16 hours, diluted with dichloromethane (30 ml) and 1M aq. HCl (2 ml). The organic layer was separated and washed with saturated aqueous NaHCO₃ (15 ml) and brine (15 ml), dried (MgSO₄), filtered and concentrated at reduced pressure to provide the title compound (60 mg, 95%) which was used without further purification.

LCMS data: Calculated MH⁺(237); Found 100% (MH⁺) m/z 237, Rt=1.08 mins.

NMR data: ¹H NMR (250 MHz, CDCl₃) δ ppm 7.41 (1 H, d, J=7.5 Hz), 7.18 (1 H, d, J=7.5 Hz), 4.68-4.92 (2 H, m), 3.83-4.10 (2 H, m), 2.90-3.19 (2 H, m), 1.86-1.92 (1 H, m), 0.97-1.08 (2 H, m), 0.77-0.88 (2 H, m).

Route 14

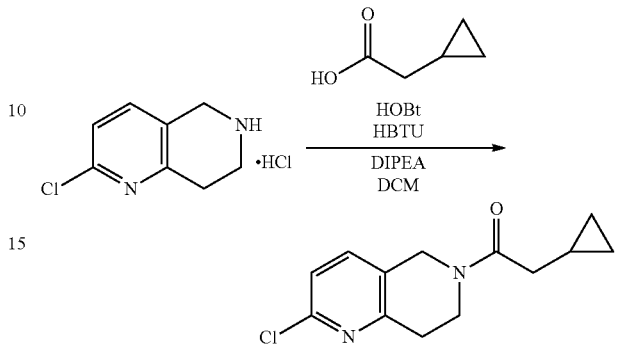

Preparation of 2-chloro-6-(cyclopropylacetyl)-5,6,7,8-tetrahydro-1,6-naphthyridine To a stirred solution of cyclopropylacetic acid (24 mg, 0.24 mmol) in DMF (1 ml) at room temperature was added HBTU (185 mg, 0.49 mmol) and HOBt (72 mg, 0.53 mmol) sequentially and the resulting solution stirred for 15 mins. 2-Chloro-5,6,7,8-tetrahydro-1,6-naphthyridine hydrochloride (50 mg, 0.24 mmol) and DIPEA (89 µl, 0.53 mmol) in DMF (1 ml) were then added and the resulting mixture stirred at room temperature for 16 hours. The reaction mixture was evaporated to dryness and the residue was purified by FCC on silica gel (99:1:1 DCM/MeOH/NH₃) to provide the title compound (56 mg, 95%).

LCMS data: Calculated MH⁺(251); Found 89% (MH⁺) m/z 251, Rt=1.14 mins.

NMR data: ¹H NMR (250 MHz, CDCl₃) δ ppm 7.44 (1 H, d, J=7.5 Hz), , 7.20 (1 H, d, J=7.5 Hz), , 4.76 (2 H, s), 3.78 (2 H, t, J=7.5 Hz), , 3.00-3.06 (2 H, m), 2.40 (2 H, d, J=7.5 Hz), , 1.03-1.16 (1 H, m), 0.56-0.64 (2 H, m), 0.16-0.25 (2 H, m).

Route 15

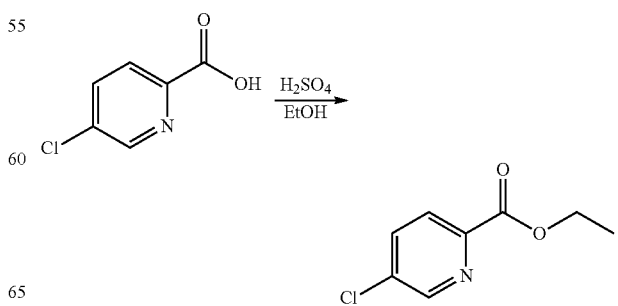

Preparation of ethyl 3-chloropyridine-2-carboxylate

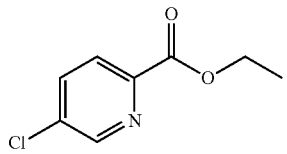

A mixture of 5-chloro-2-pyridinecarboxylic acid (1.0 g, 6.35 mmol) and conc. $H_2SO_4$ (0.1 ml) was heated in EtOH (10 ml) at 80° C. for 16 hours. After cooling and concentrating at reduced pressure, the residue was dissolved in EtOAc (50 ml), washed with saturated $NaHCO_3$ (25 ml) and brine (25 ml), dried ($MgSO_4$), filtered and re-concentrated at reduced pressure giving the title compound (990 mg, 84%).

LCMS data: Calculated MH$^+$(186); Found 98% (MH$^+$) m/z 186, Rt=1.13 min.

NMR data: $^1$H NMR (250 MHz, CDCl$_3$) δ ppm 8.63-8.76 (1 H, m), 8.10 (1 H, d, J=8.4 Hz), 7.82 (1 H, dd, J=8.5, 2.4 Hz), 4.49 (2 H, q, J=7.2 Hz), 1.45 (3 H, t, J=7.2 Hz).

Route 16

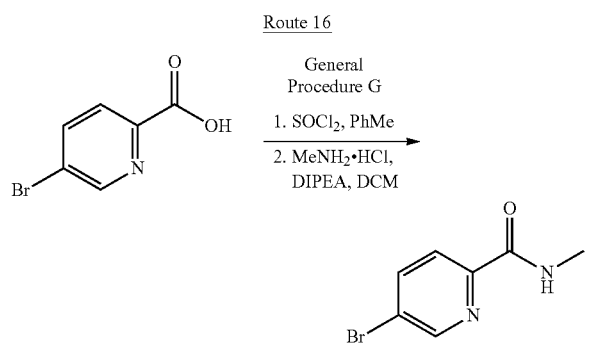

General Procedure G

Preparation of 5-bromo-N-methylpyridine-2-carboxamide

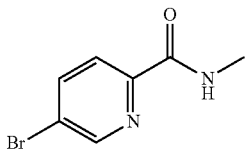

5-Bromo-pyridine-2-carboxylic acid (2.59 g, 12.8 mmol) and thionylchloride (2.79 ml) were heated at reflux in toluene (25 ml) for 16 hours. Excess reagents were removed in vacuo and the residue was diluted in dichloromethane (50 ml). A mixture of methyl amine hydrochloride (2.60 g, 38.5 mmol) and DIPEA (6.7 ml, 38.5 mmol) in dichloromethane (10 ml) was added dropwise to the stirred solution and the resulting mixture was maintained at room temperature for 5 hours. The solution was washed with saturated aqueous $NaHCO_3$ (25 ml), dried ($MgSO_4$), filtered and concentrated in vacuo. The resulting brown solid was recrystallised (Heptane/EtOAc) to provide the title compound as off-white needles (1.74 g, 63%).

LCMS data: Calculated MH$^+$(215/217); Found 100% (MH$^+$) m/z 215/217, Rt=1.36 min.

$^1$H NMR data: (250 MHz, MeOD) δ ppm 8.70 (1 H, d, J=2.3 Hz), 8.06-8.19 (1 H, m), 7.99 (1 H, d, J=8.4 Hz), 2.95 (3 H, s).

The following compounds were made as described in Route 16, General Procedure G above.

Preparation of 5-chloro-2-(piperidin-1-ylcarbonyl)pyridine

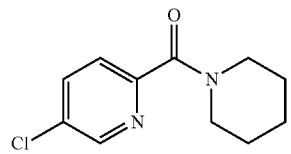 [SMILES: O=C(c1ccc(Cl)cn1)N1CCCCC1]

In a similar fashion (Route 16, GP G), 5-Chloropyridine-2-carboxylic acid (100 mg, 0.64 mmol) and piperidine (189 μl, 1.91 mmol) gave the title compound as light brown oil (122 mg, 86%) after purification by SiO$_2$ plug (Heptane/EtOAc).

LCMS data: Calculated MH$^+$(225); Found 92% (MH$^+$) m/z 225, Rt=1.17 min.

$^1$H NMR data: (250 MHz, Chloroform-d) δ ppm 8.54 (1 H, dd, J=2.4, 0.6 Hz), 7.77 (1 H, dd, J=8.4, 2.4 Hz), 7.58 (1 H, dd, J=8.3, 0.7 Hz), 3.73 (2 H, br.s.), 3.37-3.53 (2 H, m), 1.48-1.77 (7 H, m).

Preparation of 5-chloro-N-(cyclopropylmethyl)pyridine-2-carboxamide

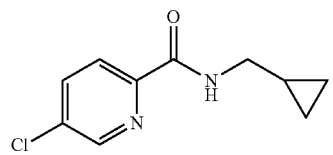 [SMILES: O=C(NCC1CC1)c1ccc(Cl)cn1]

In a similar fashion (Route 16, GP G), 5-Chloropyridine-2-carboxylic acid (100 mg, 0.64 mmol) and cyclopropyl methylamine (166 μl, 1.91 mmol) gave the title compound as light brown oil (86 mg, 64%) after purification by SiO$_2$ plug (Heptane/EtOAc).

LCMS data: Calculated MH$^+$(211); Found 94% (MH$^+$) m/z 211, Rt=1.28 min.

$^1$H NMR data: (250 MHz, Chloroform-d) δ ppm 8.47-8.57 (1 H, m), 8.17 (1 H, d, J=8.4 Hz), 7.90-8.09 (1 H, m), 7.83 (1

H, dd, J=8.4, 2.4 Hz), 3.34 (2 H, dd, J=7.0, 5.8 Hz), 1.08 (1 H, s), 0.52-0.66 (2 H, m), 0.21-0.35 (2 H, m).

Preparation of 2,4-difluoro-N-methylbenzamide

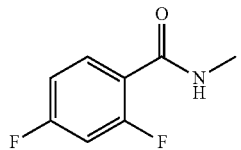

In a similar fashion (Route 16, GP G), 2,4-difluorobenzoic acid (874 mg, 5.5 mmol) and methylamine hydrochloride (1.87 g, 27.6 mmol) gave the title compound as off white solid (393 mg, 42%) after purification by re-crystallising from heptane/EtOAc.
LCMS data: Calculated MH⁺(172); Found 100% (MH⁺) m/z 172, Rt=1.19 min.
NMR data: ¹H NMR (500 MHz, CDCl₃) δ ppm 8.09-8.21 (1 H, m), 6.95-7.06 (1 H, m), 6.81-6.91 (1 H, m), 6.52-6.77 (1 H, s (broad)), 3.03 (3 H, d, J=4.9 Hz).

Preparation of ethyl 4-chloropyridine-2-carboxylate

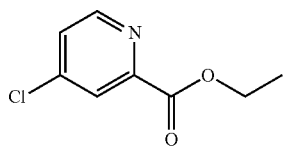

In a similar fashion (Route 16, GP G), 4-chloropyridine-2-carboxylic acid (463 mg, 2.94 mmol) and ethanol (2 ml) gave the title product as colourless oil after purification by silica FCC (310 mg, 79%)
LCMS data: Calculated MH⁺(186); Found 92% (MH⁺) m/z 186, Rt=1.57 min.
NMR data: ¹H NMR (500 MHz, CDCl₃) δ ppm 8.59 (1 H, d, J=5.2 Hz), 8.07 (1 H, d, J=2.1 Hz), 7.42 (1 H, dd, J=5.2, 2.0 Hz), 4.42 (2 H, q, J=7.2 Hz), 1.38 (3 H, t, J=7.2 Hz).

Preparation of 4-chloro-N-(cyclopropylmethyl)pyridine-2-carboxamide

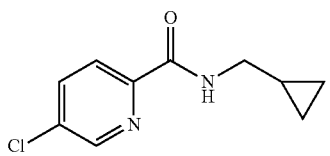 [SMILES: O=C(NCC1CC1)c1ccc(Cl)cn1]

In a similar fashion (Route 16, GP G), 5-chloro-2-pyridinecarboxylic acid (100 mg, 0.63 mmol) and 1-cyclopropylmethanamine (166 μl, 1.91 mmol) gave the title product after purification by recrystallisation (Heptane/EtOAc) as a white solid (86 mg, 65%).

LCMS data: Calculated MH⁺(211); Found 100% (MH⁺) m/z 211, Rt=1.25 min.
NMR data: ¹H NMR (250 MHz, CDCl₃) δ ppm 8.52 (1 H, d, J=2.3 Hz), 8.17 (1 H, d, J=8.4 Hz), 8.00 (1 H, br. s.), 7.83 (1 H, dd, J=8.4, 2.4 Hz), 3.34 (2 H, dd, J=7.0, 5.8 Hz), 1.00-1.16 (1 H, m), 0.52-0.63 (2 H, m), 0.24-0.35 (2 H, m).

Preparation of 4-chloro-2-(piperidin-1-ylcarbonyl)pyridine

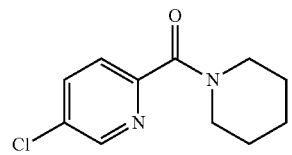 [SMILES: O=C(c1ccc(Cl)cn1)N1CCCCC1]

In a similar fashion (Route 16, GP G), 5-chloro-2-pyridinecarboxylic acid (100 mg, 0.63 mmol) and piperidine (189 μl, 1.91 mmol) gave the title product after purification by recrystallisation (Heptane/EtOAc) as white solid (122 mg, 84%).
LCMS data: Calculated MH⁺(225); Found 100% (MH⁺) m/z 225, Rt=1.55 min.
NMR data: ¹H NMR (250 MHz, CDCl₃) δ ppm 8.54 (1 H, dd, J=2.4, 0.6 Hz), 7.77 (1 H, dd, J=8.4, 2.4 Hz), 7.58 (1 H, dd, J=8.3, 0.7 Hz), 3.65-3.81 (2 H, m), 3.37-3.53 (2 H, m), 1.48-1.77 (6 H, m).

Preparation of 3-fluoro-N-methyl-benzamide

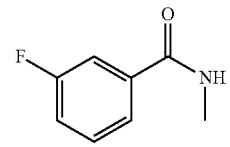

In a similar fashion (Route 16, GP G), 3-fluorobenzoic acid (300 mg, 2.1 mmol) and methylamine hydrochloride (430 mg, 6.4 mmol) gave the title product after workup as a white solid (235 mg, 72%).
LCMS data: Calculated MH⁺(154); Found 90% (MH⁺) m/z 154, Rt=1.15 min.
NMR data: ¹H NMR (250 MHz, MeOD) δ ppm 7.41-7.70 (3 H, m), 7.16-7.36 (1 H, m), 2.91 (3 H, s).

Route 17

General Procedure X

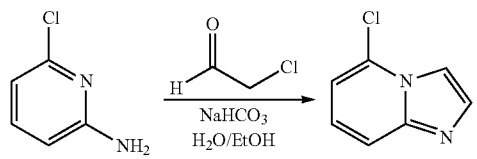

General Procedure X

Preparation of 5-chloroimidazo[1,2-a]pyridine

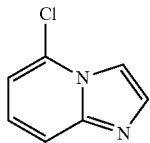

To a solution of pTSA (103 mg, 0.65 mmol) in water (5 ml) and ethanol (20 ml) was added chloroacetaldehyde dimethyl acetal (2.0 g, 16.0 mmol) at room temperature. The reaction was stirred at 65° C. for 30 minutes and then cooled to room temperature and a saturated solution of $NaHCO_3$ was added dropwise until pH 7 was reached. 2-Amino-6-chloropyridine (2.1 g, 16 mmol) in 4:1 ethanol:water (20 ml) was then added and the reaction was heated at reflux for 3 hours. After cooling and concentrating at reduced pressure, the residue was purified by FCC (98:2 DCM/MeOH) to give the title compound (850 mg, 36%) as brown oil.

LCMS data: Calculated $MH^+$ (153/155); Found 97% ($MH^+$) m/z 153/155, Rt=3.35 min (High pH method).

NMR data: $^1H$ NMR (500 MHz, $CDCl_3$) δ ppm 7.79 (1 H, s), 7.73 (1 H, s), 7.64 (1 H, d, J=9.2 Hz), 7.19 (1 H, dd, J=8.9, 7.3 Hz), 6.92 (1 H, d, J=7.3 Hz).

The following compounds were made as described in Route 17, General Procedure X above.

Preparation of 8-Chloroimidazo[1,2-a]pyridine

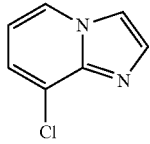

In a similar fashion (Route 17, GP X), 2-amino-3-chloropyridine (2.05 g, 16.0 mmol) gave the title compound (500 mg, 20%) as white solid after purification by recrystallisation from petroleum ether.

LCMS data: Calculated $MH^+$ (153/155); Found 100% ($MH^+$) m/z 153/155, Rt=2.90 min. (High pH method).

NMR data: $^1H$ NMR (250 MHz, $CDCl_3$) δ ppm 8.08 (1 H, dd, J=6.7, 0.9 Hz), 7.66 (2 H, dd, J=8.5, 1.1 Hz), 7.18-7.31 (1 H, m), 6.73 (1 H, t, J=7.1 Hz).

Preparation of 7-Chloroimidazo[1,2-a]pyridine

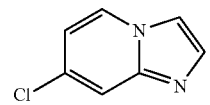

In a similar fashion (Route 17, GP X), 2-amino-4-chloropyridine (2.0 g, 15.5 mmol) gave the title compound (1.0 g, 42%) as orange oil after purification by FCC.

LCMS data: Calculated $MH^+$ (153/155); Found 100% ($MH^+$) m/z 153/155, Rt=3.19 min (High pH method).

NMR data: $^1H$ NMR (250 MHz, $CDCl_3$) δ ppm 8.05 (1 H, dd, J=7.2, 0.7 Hz), 7.62 (2 H, s), 7.56 (1 H, s), 6.78 (1 H, dd, J=7.2, 2.0 Hz).

Route 18

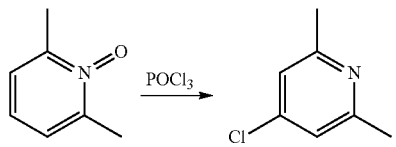

Preparation of 4-Chloro-2,6-dimethylpyridine

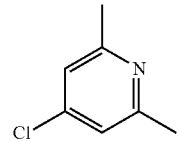

To a solution of concentrated HCl (10 ml) at 10° C. was added 2,6-dimethylpyridine N-oxide (3.0 g, 24.3 mmol) and the resulting white slurry was stirred at room temperature for 3 hours. The product was filtered and washed with $^iPrOH$ (2×10 ml) and dried at reduced pressure. The resulting solid was dissolved in $POCl_3$ (10 ml) and heated at reflux for 8 hours then cooled to 0° C. The reaction was quenched carefully with saturated $K_2CO_3$ (40 ml) and extracted with dichloromethane (2×50 ml), dried ($Na_2SO_4$), filtered and concentrated at reduced pressure. The residue was dissolved in ethanol (20 ml) and $NEt_3$ (5 ml) and heated at reflux for 24 hours then cooled to room temperature and concentrated at reduced pressure. Water (5 ml) was added to the residue the aqueous mixture was extracted with chloroform (2×10 ml). The organics were combined and washed with brine (10 ml), dried ($Na_2SO_4$), filtered and concentrated at reduced pressure to give the title compound as brown solid (1.0 g, 33%).

LCMS data: The product did not ionise, 100% UV at Rt=3.99 mins observed (High pH method).

NMR data: $^1H$ NMR (250 MHz, MeOD) δ ppm 7.88 (2 H, s), 2.76 (6 H, s).

Route 19a

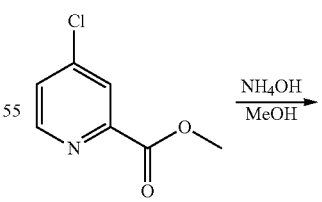

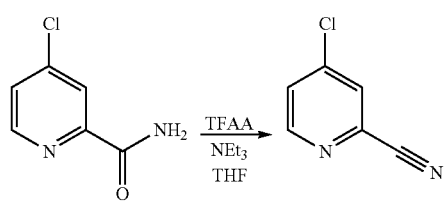

Preparation of 4-chloropyridine-2-carboxamide

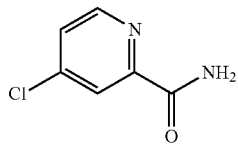

Ammonium hydroxide (2 ml) was added to methyl 4-chloropyridine-2-carboxylate (100 mg, 0.58 mmol) in MeOH (4 ml) in a sealed tube and heated at 50° C. for 4 hours. The reaction was cooled to room temperature and concentrated at reduced pressure. The residue was dissolved in dichloromethane (20 ml), washed with water (2×10 ml), dried ($Na_2SO_4$), filtered and concentrated at reduced pressure to give the title compound (66 mg, 72%).

LCMS data: Calculated $MH^+$(157/159); Found 100% ($MH^+$) m/z 157/159, Rt=3.68 min.

NMR data: $^1$H NMR (250 MHz, $CDCl_3$) δ ppm 8.5 (1 H, dd, J=5, 0.6 Hz), 8.22 (1 H, d, J=1.5 Hz), 7.48 (1 H, dd, J=5, 1.5 Hz).

Preparation of 4-chloropyridine-2-carbonitrile

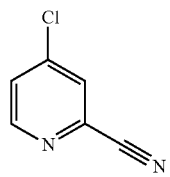

To a stirred solution of 4-chloropyridine-2-carboxamide (150 mg, 0.96 mmol) in THF (5 ml) at −15° C. was added $NEt_3$ (331 μl, 2.40 mmol) followed by TFAA (150 μl, 1.08 mmol). After stirring for 2 hours at 0° C. the reaction was concentrated then diluted with EtOAc (30 ml) and washed with water (2×15 ml), dried ($Na_2SO_4$), filtered and concentrated at reduced pressure. The title compound was obtained as white solid (105 mg, 79%) after purification by FCC.

LCMS data: The product did not ionise, 100% UV at Rt=3.47 min observed (High pH method).

NMR data: $^1$H NMR (250 MHz, $CDCl_3$) δ ppm 8.64 (1 H, d, J=4.9 Hz), 7.72 (1 H, dd, J=2.0, 0.6 Hz), 7.56 (1 H, dd, J=5.3, 2.0 Hz).

Route 19b

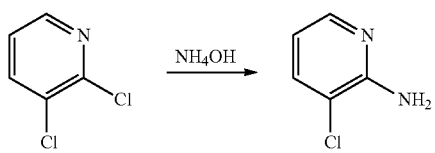

Preparation of 2-amino-3-chloropyridine

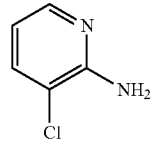

2,3-Dichloropyridine (5.0 g, 34 mmol) and ammonium hydroxide (125 ml) were placed in a steel bomb and heated at 190° C. for 48 hours. After cooling to room temperature the reaction was diluted with EtOAc (150 ml), washed with water (3×50 ml), dried ($MgSO_4$), filtered and concentrated at a reduced pressure. Recrystallisation (EtOAc) gave the title compound (2.0 g, 45%) as pale yellow solid.

LCMS data: Calculated $MH^+$(129/131); Found 100% ($MH^+$) m/z 129/131, Rt=solvent front.

NMR data: $^1$H NMR (250 MHz, $CDCl_3$) δ ppm 8.0 (1 H, dd, J=2, 0.6 Hz), 7.49 (1 H, d, J=4.9, 0.6 Hz), 6.6 (1 H, dd, J=4.9, 2 Hz).

Route 20

General Procedure H

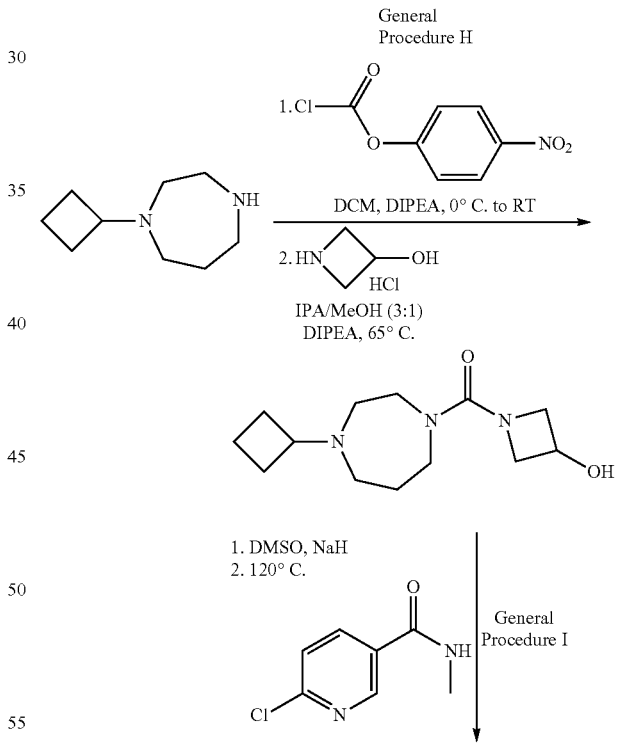

General Procedure I

General Procedure H

Example 1

Preparation of 1-[(4-cyclobutyl-1,4-diazepan-1-yl)carbonyl]azetidin-3-ol. Potency range A

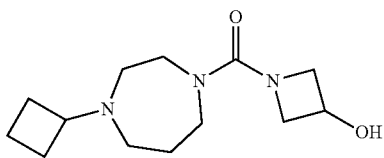 [SMILES: O=C(N1CCCN(C2CCC2)CC1)N1CC(O)C1]

To a stirred RT solution of 4-nitrophenylchloroformate (2.63 g, 13.05 mmol) in DCM (10 ml) was added drop wise a solution of 1-cyclobutyl-1,4-diazepane (1.83 g, 11.86 mmol) and pyridine (1.03 g, 13.05 mmol) in DCM (2 ml). The resulting mixture was stirred at RT for approximately 3 days. The solvent was evaporated in vacuo and the residue dissolved in MeOH/IPA (1:3, 40 ml). Azetidin-3-ol hydrochloride (1.3 g, 11.86 mmol) and DIPEA (3.37 g, 26.1 mmol) were added and the resulting mixture was heated to reflux (~90° C.) overnight. After cooling to RT, the solvent was evaporated and the residue partitioned between DCM (40 ml) and 2M $K_2CO_3$ aq (20 ml). The organic layer was separated and the aq. phase re-extracted with DCM (20 ml). The combined organic phases were dried ($Na_2SO_4$), filtered and concentrated under reduced pressure. Purification by silica flash column chromatography (eluting with DCM/MeOH/$NH_3$ 90:10:1) provided the title compound as yellow solid (1.16 g, 39%).

LCMS data: Calculated $MH^+$(254); Found 100% ($MH^+$) m/z 254, Rt=3.00 min.

NMR data: $^1H$ NMR (360 MHz, chloroform-d) δ ppm 4.47-4.60 (1 H, m), 4.16 (2 H, dd, J=9.5, 6.8 Hz), 3.84 (2 H, dd, J=9.5, 4.5 Hz), 3.33-3.46 (4 H, m), 2.76-2.89 (1 H, m), 2.36-2.55 (4 H, m), 1.95-2.09 (2 H, m), 1.74-1.91 (4 H, m), 1.52-1.73 (2 H, m).

The following compounds were made as described in Route 20, General Procedure H above.

Example 2

Preparation of 1-[(4-cyclobutylpiperazin-1-yl)carbonyl]azetidin-3-ol. Potency range C

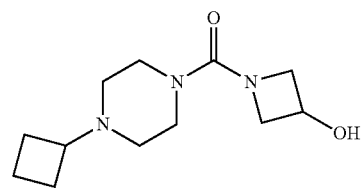 [SMILES: O=C(N1CCN(C2CCC2)CC1)N1CC(O)C1]

In a similar fashion (Route 20, GP H), 1-cyclobutylpiperazine (200 mg, 1.42 mmol) gave the title compound as yellow oil (198 mg, 59%).

LCMS data: Calculated $MH^+$(240); Runs in solvent front.

NMR data: $^1H$ NMR (360 MHz, MeOH) δ ppm 4.38-4.57 (1 H, m), 4.15-4.24 (2 H, m), 3.69-3.84 (2 H, m), 3.34-3.38 (3 H, m), 2.71-2.83 (2 H, m), 2.27-2.37 (4 H, m), 1.99-2.11 (2 H, m), 1.85-1.93 (2 H, m), 1.70-1.78 (2 H, m).

Example 2a

Preparation of 1-[(4-ethyl-1,4-diazepan-1-yl)carbonyl]azetidin-3-ol

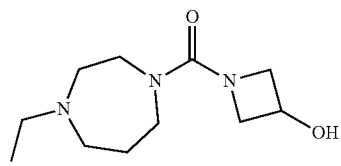 [SMILES: CCN1CCCN(C(=O)N2CC(O)C2)CC1]

In a similar fashion (Route 20, GP H), 1-ethyl-1,4-diazepane (292 mg, 2.23 mmol) gave the title compound as yellow oil (90 mg, 16%).

LCMS data: Calculated $MH^+$(228); Found ($MH^+$) m/z 228. The product eluted in the solvent front.

NMR data: $^1H$ NMR (500 MHz, $CDCl_3$) δ ppm 4.52-4.61 (1 H, m), 4.14-4.21 (2 H, m), 3.80-3.87 (2 H, m), 3.43-3.49 (2 H, m), 3.36-3.43 (2 H, m), 2.64-2.72 (2 H, m), 2.57-2.64 (2 H, m), 2.53 (2 H, q, J=7.1 Hz), 1.83-1.92 (2 H, m), 1.06 (3 H, t, J=7.2 Hz).

Example 2b

Preparation of 1-{[4-(1-methylethyl)-1,4-diazepan-1-yl]carbonyl}azetidin-3-01

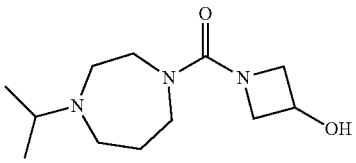 [SMILES: CC(C)N1CCCN(C(=O)N2CC(O)C2)CC1]

In a similar fashion (Route 20, GP H), 1-(1-methylethyl)-1,4-diazepane (662 mg, 3.07 mmol) gave the title compound as yellow oil (335 mg, 45%).

LCMS data: Calculated $MH^+$(242); Found 100% ($MH^+$) m/z 242, Rt=1.25 min.

NMR data: $^1H$ NMR (500 MHz, $CDCl_3$) δ ppm 4.50-4.61 (1 H, m), 4.11-4.22 (2 H, m), 3.79-3.90 (2 H, m), 3.32-3.45 (4

H, m), 2.82-2.95 (1 H, m), 2.62-2.71 (2 H, m), 2.53-2.62 (2 H, m), 1.73-1.87 (2 H, m), 0.99 (6 H, d, J=6.6 Hz).

Example 2c

Preparation of 1-[(4-cyclopentyl-1,4-diazepan-1-yl) carbonyl]azetidin-3-ol

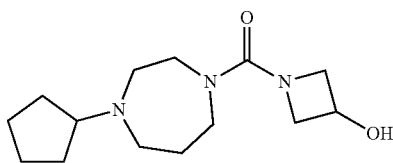 [SMILES: O=C(N1CCCN(C2CCCC2)CC1)N1CC(O)C1]

In a similar fashion (Route 20, GP H), 1-cyclopentyl-1,4-diazepane (387 mg, 2.23 mmol) gave the title compound as yellow oil (350 mg, 59%).

LCMS data: Calculated MH$^+$(268); Found 100% (MH$^+$) m/z 286, Rt=1.36 min.

NMR data: $^1$H NMR (500 MHz, CDCl$_3$) δ 4.47-4.61 (1 H, m), 4.08-4.21 (2 H, m), 3.76-3.90 (2 H, m), 3.32-3.52 (4 H, m), 2.76-2.87 (1 H, m), 2.69-2.76 (2 H, m), 2.59-2.68 (2 H, m), 1.74-1.92 (4 H, m), 1.59-1.73 (2 H, m), 1.45-1.59 (2 H, m), 1.30-1.43 (2 H, m).

General Procedure I

Example 3

Preparation of 6-({1-[(4-cyclobutyl-1,4-diazepan-1-yl)carbonyl]azetidin-3-yl}oxy)-N-methylpyridine-3-carboxamide. Potency range A

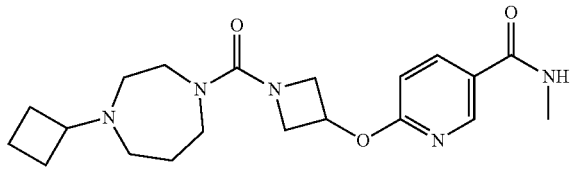 [SMILES: CNC(=O)c1ccc(OC2CN(C(=O)N3CCCN(C4CCC4)CC3)C2)nc1]

To a stirred solution of 1-[(4-cyclobutyl-1,4-diazepan-1-yl)carbonyl]azetidin-3-ol (40 mg, 0.158 mmol) in DMSO (2 ml) was added NaH (14 mg, 0.316 mmol, 60 in mineral oil) at RT in one portion. The suspension was stirred for 2 h at RT then 6-chloro-N-methylpyridine-3-carboxamide (54 mg, 0.316 mmol) was added in one portion. The mixture was heated at 80-100° C. in a sealed tube over night. After cooling to RT, the solution was partitioned between brine/water (1:1 mixture, 15 ml) and DCM (20 ml). The organic layer was separated, washed with brine (2×20 ml), dried (Na$_2$SO$_4$), filtered and concentrated at reduced pressure. The residue was purified by preparative HPLC to provide the title compound as white solid (83 mg, 56% yield).

LCMS data: Calculated MH$^+$(388); Found 100% (MH$^+$) m/z 388, Rt=2.31 min.

$^1$H NMR (250 MHz, MeOD) δ ppm 8.58 (1 H, s), 8.09 (1 H, d), 6.91 (1 H, d), 5.33-5.45 (1 H, m), 4.34-4.48 (2 H, m), 3.95-4.06 (2 H, m), 3.41-3.54 (4 H, m), 2.85-3.06 (4 H, m), 2.44-2.65 (4 H, m), 2.03-2.18 (2 H, m), 1.87-1.94 (4 H, m), 1.65-1.78 (2 H, m).

The following compounds were made as described in Route 20, General Procedure I above.

Example 4

Preparation of 5-({1-[(4-cyclobutyl-1,4-diazepan-1-yl)carbonyl]azetidin-3-yl}oxy)pyridine-2-carboxamide. Potency range A

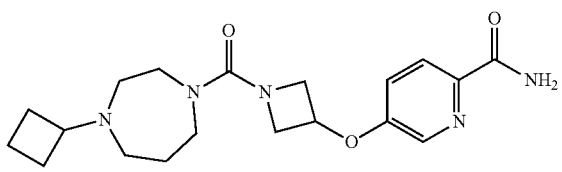 [SMILES: NC(=O)c1ccc(OC2CN(C(=O)N3CCCN(C4CCC4)CC3)C2)cn1]

In a similar fashion (Route 20, GP I), 1-[(4-cyclobutyl-1,4-diazepan-1-yl)carbonyl]azetidin-3-ol (54 mg, 0.21 mmol) and 5-chloropyridine-2-carboxamide (40 mg, 0.26 mmol) gave the title compound as white solid after purification by FCC (20 mg, 26%).

LCMS data: Calculated MH$^+$(374); Found 100% (MH$^+$) m/z 374, Rt=2.24 min.

NMR data: $^1$H NMR (500 MHz, MeOD) δ ppm 8.25 (1 H, d, J=2.8 Hz), 8.07 (1 H, d, J=8.8 Hz), 7.35 (1 H, dd, J=8.7, 2.8 Hz), 5.08-5.19 (1 H, m), 4.46 (2 H, dd, J=9.4, 6.5 Hz), 4.05 (2 H, dd, J=9.7, 3.7 Hz), 3.39-3.52 (4 H, m), 2.85-2.98 (1 H, m), 2.52-2.61 (2 H, m), 2.42-2.52 (2 H, m), 2.01-2.13 (2 H, m), 1.79-1.95 (4 H, m), 1.57-1.76 (2 H, m).

Example 5

Preparation of 5-({1-[(4-cyclobutyl-1,4-diazepan-1-yl)carbonyl]azetidin-3-yl}oxy)-N-methylpyridine-2-carboxamide. Potency range A

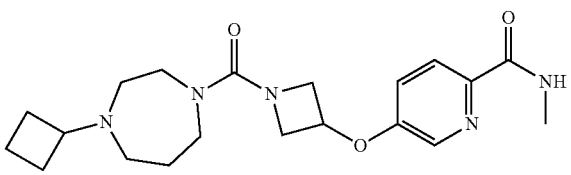 [SMILES: CNC(=O)c1ccc(OC2CN(C(=O)N3CCCN(C4CCC4)CC3)C2)cn1]

In a similar fashion (Route 20, GP I), 1-[(4-cyclobutyl-1,4-diazepan-1-yl)carbonyl]azetidin-3-ol (50 mg, 0.19 mmol) and 5-chloro-N-methylpyridine-2-carboxamide (44 mg, 0.26 mmol) gave the title compound as colourless oil after purification by preparative HPLC (54 mg, 54%).

LCMS data: Calculated MH$^+$(388); Found 100% (MH$^+$) m/z 388, Rt=2.34 min.

NMR data: $^1$H NMR (400 MHz, MeOD) δ ppm 8.22 (1 H, d, J=2.7 Hz), 8.03 (1 H, d, J=8.6 Hz), 7.33 (1 H, dd, J=8.8, 2.7 Hz), 5.09-5.17 (1 H, m), 4.34-4.65 (2 H, m), 3.82-4.19 (3 H, m), 3.72 (1 H, quin, J=8.4 Hz), 3.38-3.61 (5 H, m), 2.87-3.08 (5 H, m), 2.07-2.39 (6 H, m), 1.69-1.91 (2 H, m).

Example 6

Preparation of 5-({1-[(4-cyclobutyl-1,4-diazepan-1-yl)carbonyl]azetidin-3-yl}oxy)-N,N-dimethylpyridine-2-carboxamide. Potency range A

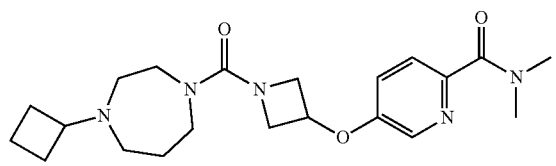 [SMILES: CN(C)C(=O)c1ccc(OC2CN(C(=O)N3CCCN(C4CCC4)CC3)C2)cn1]

In a similar fashion (Route 20, GP I), 1-[(4-cyclobutyl-1,4-diazepan-1-yl)carbonyl]azetidin-3-ol (50 mg, 0.19 mmol) and 5-chloro-N,N-dimethylpyridine-2-carboxamide (47 mg, 0.26 mmol) gave the title compound as colourless oil after purification by preparative HPLC (49 mg, 48%).

LCMS data: Calculated MH$^+$(402); Found 100% (MH$^+$) m/z 402, Rt=2.27 min.

NMR data: $^1$H NMR (400 MHz, MeOD) δ ppm 8.21 (1 H, br. s.), 7.61 (1 H, d, J=8.6 Hz), 7.38 (1 H, dd, J=8.7, 2.8 Hz), 5.10-5.19 (1 H, m), 4.34-4.64 (2 H, m), 3.83-4.21 (3 H, m), 3.72 (1 H, quin, J=8.4 Hz), 3.38-3.62 (5 H, m), 2.89-3.16 (8 H, m), 2.05-2.40 (6 H, m), 1.71-1.91 (2 H, m).

Example 7

Preparation of 5-({1-[(4-cyclobutyl-1,4-diazepan-1-yl)carbonyl]azetidin-3-yl}oxy)-N,N-diethylpyridine-2-carboxamide. Potency range A

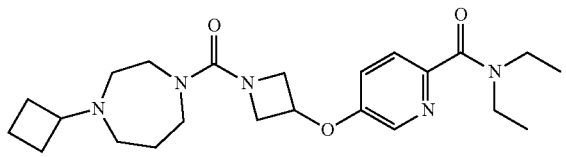 [SMILES: CCN(CC)C(=O)c1ccc(OC2CN(C(=O)N3CCCN(C4CCC4)CC3)C2)cn1]

In a similar fashion (Route 20, GP I), 1-[(4-cyclobutyl-1,4-diazepan-1-yl)carbonyl]azetidin-3-ol (104 mg, 0.41 mmol) and 5-chloro-N,N-diethylpyridine-2-carboxamide (105 mg, 0.49 mmol) gave the title compound as colourless oil after purification by FCC (56 mg, 32%).

LCMS data: Calculated MH$^+$(430); Found 97% (MH$^+$) m/z 430, Rt=2.63 min.

NMR data: $^1$H NMR (400 MHz, MeOD) δ ppm 8.20 (1 H, d, J=2.7 Hz), 7.56 (1 H, d, J=8.7 Hz), 7.36 (1 H, dd, J=8.7, 2.9 Hz), 5.04-5.19 (1 H, m), 4.45 (2 H, dd, J=9.4, 6.5 Hz), 4.04 (2 H, dd, J=9.5, 4.0 Hz), 3.33-3.63 (8 H, m), 2.80-3.00 (1 H, m), 2.40-2.62 (4 H, m), 1.98-2.16 (2 H, m), 1.77-1.98 (4 H, m), 1.56-1.77 (2 H, m), 1.21 (6 H, dt, J=19.9, 7.0 Hz).

Example 8

Preparation of 4-({1-[(4-cyclobutyl-1,4-diazepan-1-yl)carbonyl]azetidin-3-yl}oxy)-N-methylbenzamide. Potency range A

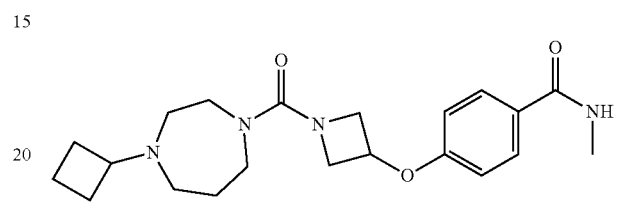

In a similar fashion (Route 20, GP I), 1-[(4-cyclobutyl-1,4-diazepan-1-yl)carbonyl]azetidin-3-ol (40 mg, 0.158 mmol) and 4-fluoro-N-methylbenzamide (48 mg 0.316 mmol) gave the tittle compound as colourless oil after purification by preparative HPLC (11 mg, 18%).

LCMS data: Calculated MH$^+$(388); Found 100% (MH$^+$) m/z 388, Rt=2.32 min.

$^1$H NMR (250 MHz, MeOD) δ ppm 8.55 (1 H, s), 8.08 (1 H, d), 6.91 (1 H, d), 5.31-5.47 (1 H, m), 4.35-4.49 (2 H, m), 3.94-4.09 (2 H, m), 3.37-3.54 (4 H, m), 2.94-3.08 (4 H, m), 2.49-2.67 (4 H, m), 2.03-2.18 (2 H, m), 1.85-1.96 (4 H, m), 1.65-1.77 (2 H, m).

Example 9

Preparation of 4-({1-[(4-cyclobutyl-1,4-diazepan-1-yl)carbonyl]azetidin-3-yl}oxy)-N,N-dimethylbenzamide. Potency range A

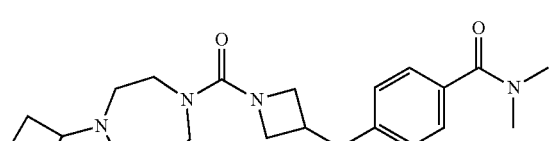

In a similar fashion (Route 20, GP I), 1-[(4-cyclobutyl-1,4-diazepan-1-yl)carbonyl]azetidin-3-ol (40 mg, 0.158 mmol) and 4-fluoro-N,N-dimethylbenzamide (52 mg 0.316 mmol) gave the title compound as colourless oil after purification by preparative HPLC (7 mg, 11%).

LCMS data: Calculated MH$^+$ (401); Found 100% (MH$^+$) m/z 401, Rt=2.51 min.

$^1$H NMR (360 MHz, MeOH) δ ppm 7.41 (2 H, d, J=9.1 Hz), 6.89 (2 H, d, J=8.6 Hz), 5.01-5.09 (1 H, m), 4.54 (1 H, t, J=7.5 Hz), 4.30-4.46 (1 H, m), 4.04-4.18 (1 H, m), 3.82-4.04 (2 H, m), 3.62-3.79 (1 H, m), 3.36-3.61 (5 H, m), 3.05 (8 H, d, J=17.7 Hz), 2.04-2.41 (6 H, m), 1.69-1.93 (2 H, m).

Example 10

Preparation of 1-cyclobutyl-4-({3-[4-(trifluoromethyl)phenoxy]azetidin-1-yl}carbonyl)-1,4-diazepane. Potency range A

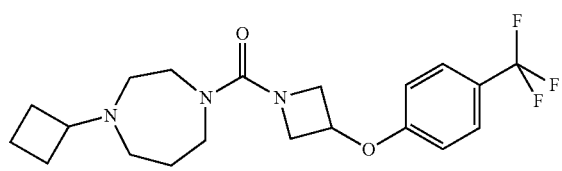 [SMILES: O=C(N1CCCN(C2CCC2)CC1)N1CC(Oc2ccc(C(F)(F)F)cc2)C1]

In a similar fashion (Route 20, GP I), 1-[(4-cyclobutyl-1,4-diazepan-1-yl)carbonyl]azetidin-3-ol (50 mg, 0.19 mmol) and 1-fluoro-4-(trifluoromethyl)benzene (26 mg, 0.24 mmol) gave the title compound as colourless oil after purification by preparative HPLC (35 mg, 34%).

LCMS data: Calculated MH$^+$(398); Found 100% (MH$^+$) m/z 398, Rt=3.17 min.

NMR data: $^1$H NMR (400 MHz, MeOD) δ ppm 7.60 (2 H, d, J=8.6 Hz), 6.97 (2 H, d, J=8.6 Hz), 5.04-5.12 (1 H, m), 4.32-4.63 (2 H, m), 3.85-4.18 (3 H, m), 3.72, (1 H, quin, J=8.4 Hz), 3.38-3.61 (5 H, m), 2.88-3.08 (2 H, m), 2.03-2.40 (6 H, m), 1.71-1.92 (2 H, m).

Example 11

Preparation of 1-cyclobutyl-4-[(3-{[5-(trifluoromethyl)pyridin-2-yl]oxy}azetidin-1-yl)carbonyl]-1,4-diazepane. Potency range A

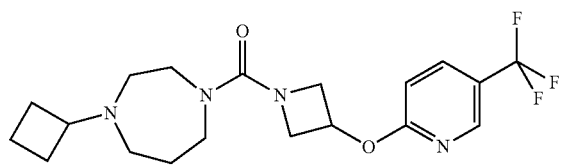 [SMILES: O=C(N1CCCN(C2CCC2)CC1)N1CC(Oc2ccc(C(F)(F)F)cn2)C1]

In a similar fashion (Route 20, GP I), 1-[(4-cyclobutyl-1,4-diazepan-1-yl)carbonyl]azetidin-3-ol (40 mg, 0.158 mmol) and 2-chloro-5-(trifluoromethyl)pyridine (57 mg, 0.316 mmol) gave the title compound as colourless oil after purification by preparative HPLC (15 mg, 24%).

LCMS data: Calculated MH$^+$(399); Found 98% (MH$^+$) m/z 399, Rt=2.95 min.

$^1$H NMR (400 MHz, MeOD) δ ppm 8.45 (1 H, s), 7.99 (1 H, d, J=8.8 Hz), 7.02 (1 H, d, J=8.8 Hz), 5.36-5.48 (1 H, m), 4.43 (2 H, dd), 4.03 (2 H, dd, J=9.5, 4.2 Hz), 3.38-3.52 (4 H, m), 2.94 (1 H, qt), 2.55-2.65 (2 H, m), 2.47-2.54 (2 H, m), 2.04-2.13 (2 H, m), 1.84-1.95 (4 H, m), 1.62-1.75 (2 H, m).

Example 12

Preparation of 4-({1-[(4-cyclobutyl-1,4-diazepan-1-yl)carbonyl]azetidin-3-yl}oxy)benzonitrile. Potency range A

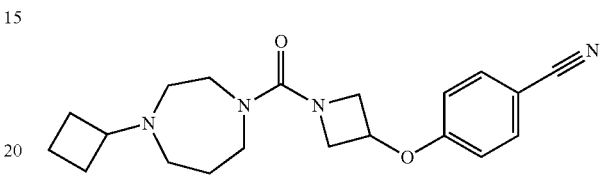

In a similar fashion (Route 20, GP I), 1-[(4-cyclobutyl-1,4-diazepan-1-yl)carbonyl]azetidin-3-ol (50 mg, 0.19 mmol) and 4-fluorobenzonitrile (48 mg, 0.4 mmol) gave the title compound as colourless oil after purification by preparative HPLC (36 mg, 39%).

LCMS data: Calculated MH$^+$(355); Found 100% (MH$^+$) m/z 355, Rt=2.69 min.

NMR data: $^1$H NMR (400 MHz, MeOD) δ ppm 7.65-7.71 (2 H, m), 6.94-7.01 (2 H, m), 5.05-5.13 (1 H, m), 4.32-4.62 (2 H, m), 3.83-4.17 (3 H, m), 3.72 (1 H, quin, J=8.4 Hz), 3.37-3.61 (5 H, m), 2.89-3.10 (2 H, m), 2.04-2.40 (6 H, m), 1.70-1.91 (2 H, m).

Example 13

Preparation of 1-cyclobutyl-4-{[3-(4-fluorophenoxy)azetidin-1-yl]carbonyl}-1,4-diazepane. Potency range A

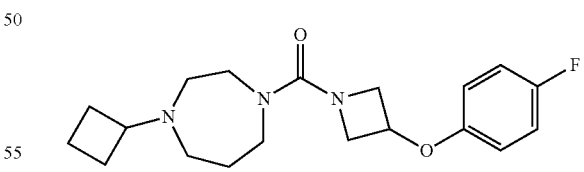

In a similar fashion (Route 20, GP I), 1-[(4-cyclobutyl-1,4-diazepan-1-yl)carbonyl]azetidin-3-ol (50 mg, 0.19 mmol) and 1,4-difluorobenzene (56 mg, 0.49 mmol) gave the title compound as colourless oil after purification by preparative HPLC (19 mg, 21%).

LCMS data: Calculated MH$^+$(348); Found 100% (MH$^+$) m/z 348, Rt=2.86 min.

NMR data: $^1$H NMR (400 MHz, MeOD) δ ppm 6.98-7.07 (2 H, m), 6.76-6.85 (2 H, m), 4.92-4.99 (1 H, m), 4.28-4.57 (2

H, m), 3.84-4.15 (3 H, m), 3.72 (1 H, quin, J=8.4 Hz), 3.37-3.61 (5 H, m), 2.89-3.08 (2 H, m), 2.03-2.40 (6 H, m), 1.71-1.93 (2 H, m).

Example 14

Preparation of 1-{[3-(4-chlorophenoxy)azetidin-1-yl]carbonyl}-4-cyclobutyl-1,4-diazepane. Potency range A

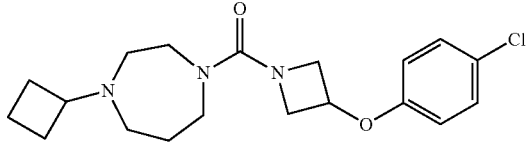 [SMILES: O=C(N1CCCN(C2CCC2)CC1)N1CC(Oc2ccc(Cl)cc2)C1]

In a similar fashion (Route 20, GP I), 1-[(4-cyclobutyl-1,4-diazepan-1-yl)carbonyl]azetidin-3-ol (40 mg, 0.158 mmol) and 1-chloro-4-fluorobenzene (33.7 μl, 41 mg, 0.316 mmol) gave the title compound as colourless oil after purification by FCC (silica, eluting with Heptane/EtOAc 20:80) (47 mg, 84%).

LCMS data: Calculated MH$^+$(364); Found 94% (MH$^+$) m/z 364, Rt=2.98 min.

$^1$H NMR (400 MHz, MeOD) δ ppm 7.21-7.34 (2 H, m), 6.77-6.87 (2 H, m), 4.92-5.01 (1 H, m), 4.40 (2 H, dd, J=9.3, 6.4 Hz), 3.98 (2 H, dd), 3.37-3.53 (4 H, m), 2.80-2.96 (1 H, m), 2.52-2.62 (2 H, m), 2.42-2.50 (2 H, m), 2.01-2.13 (2 H, m), 1.79-1.93 (4 H, m), 1.61-1.74 (2 H, m).

Example 15

Preparation of 1-cyclobutyl-4-[(3-phenoxyazetidin-1-yl)carbonyl]-1,4-diazepane. Potency range A

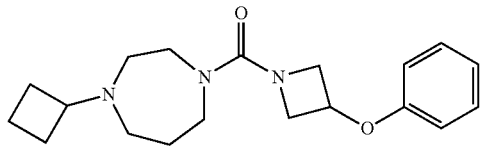 [SMILES: O=C(N1CCCN(C2CCC2)CC1)N1CC(Oc2ccccc2)C1]

In a similar fashion (Route 20, GP I), 1-[(4-cyclobutyl-1,4-diazepan-1-yl)carbonyl]azetidin-3-ol (40 mg, 0.158 mmol) and fluorobenzene (20 μl, 30 mg, 0.316 mmol) gave the title compound as colourless oil after purification by preparative HPLC (13 mg, 25%).

LCMS data: Calculated MH$^+$ (330); Found 100% (MH$^+$) m/z 330, Rt=2.83 min.

$^1$H NMR (360 MHz, MeOH) δ ppm 7.20-7.36 (2 H, m), 6.92-7.03 (1 H, m), 6.74-6.87 (2 H, m), 4.97-5.07 (1 H, m), 4.31-4.57 (2 H, m), 3.86-4.17 (3 H, m), 3.68-3.78 (1 H, m), 3.42-3.58 (5 H, m), 2.93-3.09 (2 H, m), 2.11-2.39 (6 H, m), 1.77-1.93 (2 H, m).

Example 16

Preparation of 1-cyclobutyl-4-({3-[4-(1H-pyrazol-1-ylmethyl)phenoxy]azetidin-1-yl}carbonyl)-1,4-diazepane. Potency range A

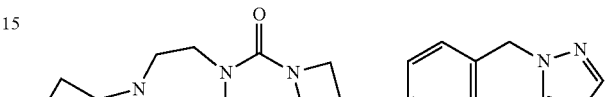

In a similar fashion (Route 20, GP I), 1-[(4-cyclobutyl-1,4-diazepan-1-yl)carbonyl]azetidin-3-ol (50 mg, 0.19 mmol) and 1-(4-fluorobenzyl)-1H-pyrazole (35 mg, 0.19 mmol) gave the title compound as colourless oil after purification by preparative HPLC (42 mg, 40%).

LCMS data: Calculated MH$^+$(410); Found 100% (MH$^+$) m/z 410, Rt=2.76 min.

NMR data: $^1$H NMR (400 MHz, MeOD) δ ppm 7.66 (1 H, d, J=2.2 Hz), 7.51 (1 H, d, J=1.7 Hz), 7.19 (2 H, d, J=8.6 Hz), 6.78 (2 H, d, J=8.6 Hz), 6.31 (1 H, t, J=2.0 Hz), 5.27 (2 H, s), 4.98 (1 H, tt, J=6.4, 3.9 Hz), 4.26-4.56 (2 H, m), 3.82-4.15 (3 H, m), 3.71 (1 H, quin, J=8.4 Hz), 3.49 (5 H, d, J=11.0 Hz), 2.97 (2 H, d, J=9.8 Hz), 2.04-2.39 (6 H, m), 1.71-1.91 (2 H, m).

Example 17

Preparation of 1-cyclobutyl-4-[(3-{[5-(1H-pyrazol-1-ylmethyl)pyridin-2-yl]oxy}azetidin-1-yl)carbonyl]-1,4-diazepane. Potency range A

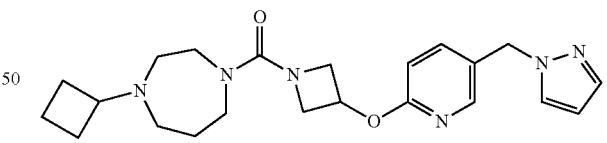

In a similar fashion (Route 20, GP I), 1-[(4-cyclobutyl-1,4-diazepan-1-yl)carbonyl]azetidin-3-ol (50 mg, 0.19 mmol) and 2-chloro-5-(1H-pyrazol-1-ylmethyl)pyridine (35 mg, 0.19 mmol) gave the title compound as colourless oil after purification on silica gel (50 mg, 62%).

LCMS data: Calculated MH$^+$(411); Found 100% (MH$^+$) m/z 411, Rt=2.57 min.

NMR data: $^1$H NMR (360 MHz, MeOH) δ ppm 8.04 (1 H, d, J=1.8 Hz), 7.71 (1 H, d, J=1.8 Hz), 7.60 (1 H, dd, J=8.6, 2.7 Hz), 7.51 (1 H, s), 6.81 (1 H, d, J=8.6 Hz), 6.32 (1 H, t, J=2.0 Hz), 5.24-5.35 (3 H, m), 4.38 (2 H, dd, J=10.0, 6.8 Hz), 3.97 (2 H, dd, J=10.0, 4.5 Hz), 3.36-3.47 (4 H, m), 2.82-2.95 (1 H, m), 2.50-2.57 (2 H, m), 2.41-2.48 (2 H, m), 1.99-2.11 (2 H, m), 1.77-1.93 (4 H, m), 1.57-1.75 (2 H, m).

Hz), 4.98-5.10 (1 H, m), 4.31-4.62 (2 H, m), 4.22 (2 H, s), 3.32-4.16 (11 H, m), 2.80-3.13 (4 H, m), 2.08-2.44 (6 H, m), 1.36-2.01 (8 H, m).

Example 18

Preparation of 1-[4-({1-[(4-cyclobutyl-1,4-diazepan-1-yl)carbonyl]azetidin-3-yl}oxy)phenyl]pyrrolidin-2-one. Potency range A

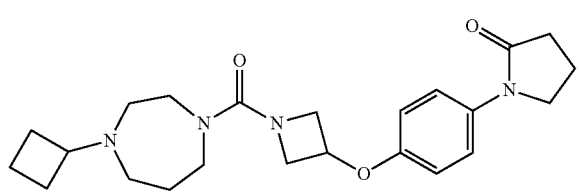 [SMILES: O=C(N1CCCN(C2CCC2)CC1)N1CC(Oc2ccc(N3CCCC3=O)cc2)C1]

In a similar fashion (Route 20, GP I), 1-[(4-cyclobutyl-1,4-diazepan-1-yl)carbonyl]azetidin-3-ol (50 mg, 0.19 mmol) and 1-(4-fluorophenyl)pyrrolidin-2-one (35 mg, 0.19 mmol) gave the title compound as colourless oil after purification on silica gel (50 mg, 62%).

LCMS data: Calculated MH$^+$(413); Found 100% (MH$^+$) m/z 413, Rt=2.65 min.

NMR data: $^1$H NMR (360 MHz, MeOH) δ ppm 8.04 (1 H, d, J=1.8 Hz), 7.71 (1 H, d, J=1.8 Hz), 7.60 (1 H, dd, J=8.6, 2.7 Hz), 7.51 (1 H, s), 6.81 (1 H, d, J=8.6 Hz), 6.32 (1 H, t, J=2.0 Hz), 5.24-5.35 (3 H, m), 4.38 (2 H, dd, J=10.0, 6.8 Hz), 3.97 (2 H, dd, J=10.0, 4.5 Hz), 3.36-3.47 (4 H, m), 2.82-2.95 (1 H, m), 2.50-2.57 (2 H, m), 2.41-2.48 (2 H, m), 1.99-2.11 (2 H, m), 1.77-1.93 (4 H, m), 1.57-1.75 (2 H, m).

Example 19

Preparation of 1-cyclobutyl-4-({3-[4-(piperidin-1-ylmethyl)phenoxy]azetidin-1-yl}carbonyl)-1,4-diazepane. Potency range A

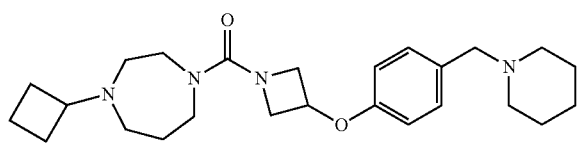 [SMILES: O=C(N1CCCN(C2CCC2)CC1)N1CC(Oc2ccc(CN3CCCCC3)cc2)C1]

In a similar fashion (Route 20, GP I), 1-[(4-cyclobutyl-1,4-diazepan-1-yl)carbonyl]azetidin-3-ol (60 mg, 0.24 mmol) and 1-(4-fluorobenzyl)piperidine (55 mg, 0.28 mmol) gave the title compound as colourless oil after purification by preparative HPLC (22 mg, 17%).

LCMS data: Calculated MH$^+$(427); Found 100% (MH$^+$) m/z 427, Rt=2.17 min.

NMR data: $^1$H NMR (250 MHz, MeOD) δ ppm 7.44 (2 H, d, J=8.7 Hz), 6.92 (2 H, d, J=8.8

Example 20

Preparation of 1-cyclobutyl-4-[(3-{4-[(4-methylpiperazin-1-yl)methyl]phenoxy}azetidin-1-yl)carbonyl]-1,4-diazepane. Potency range A

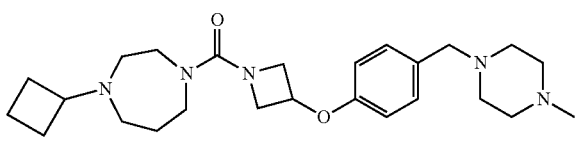 [SMILES: CN1CCN(Cc2ccc(OC3CN(C(=O)N4CCCN(C5CCC5)CC4)C3)cc2)CC1]

In a similar fashion (Route 20, GP I), 1-[(4-cyclobutyl-1,4-diazepan-1-yl)carbonyl]azetidin-3-ol (60 mg, 0.24 mmol) and 1-(4-fluorobenzyl)-4-methylpiperazine (59 mg, 0.28 mmol) gave the title compound as colourless oil after purification by preparative HPLC (33 mg, 25%).

LCMS data: Calculated MH$^+$(442); Found 100% (MH$^+$) m/z 442, Rt=1.91 min.

NMR data: $^1$H NMR (250 MHz, MeOD) δ ppm 7.29-7.38 (2 H, m), 6.78-6.88 (2 H, m), 4.94-5.05 (1 H, m), 4.28-4.61 (2 H, m), 3.36-4.17 (12 H, m), 2.67-3.23 (10 H, m), 2.04-2.42 (6 H, m), 1.67-1.96 (2 H, m).

Example 21

Preparation of 1-cyclobutyl-4-[(3-{4-[(4,4-difluoropiperidin-1-yl)methyl]phenoxy}azetidin-1-yl)carbonyl]-1,4-diazepane. Potency range A

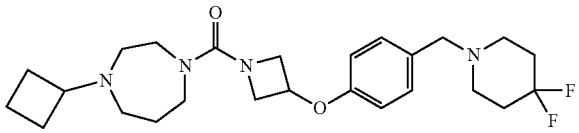 [SMILES: O=C(N1CCCN(C2CCC2)CC1)N1CC(Oc2ccc(CN3CCC(F)(F)CC3)cc2)C1]

In a similar fashion (Route 20, GP I), 1-[(4-cyclobutyl-1,4-diazepan-1-yl)carbonyl]azetidin-3-ol (60 mg, 0.24 mmol) and 4,4-difluoro-1-(4-fluorobenzyl)piperidine (65 mg, 0.28 mmol) gave the title compound as colourless oil after purification by preparative HPLC (25 mg, 18%).

LCMS data: Calculated MH$^+$(463); Found 100% (MH$^+$) m/z 463, Rt=2.17 min.

NMR data: ¹H NMR (250 MHz, MeOD) δ ppm 7.41-7.50 (2 H, m), 6.88-6.98 (2 H, m), 4.98-5.10 (1 H, m), 4.26-4.63 (4 H, m), 3.33-4.18 (12 H, m), 2.77-3.27 (3 H, m), 2.02-2.50 (10 H, m), 1.65-1.96 (2 H, m).

Example 22

Preparation of 1-({3-[(5-bromopyridin-2-yl)oxy]azetidin-1-yl}carbonyl)-4-cyclobutyl-1,4-diazepane.
Potency range A

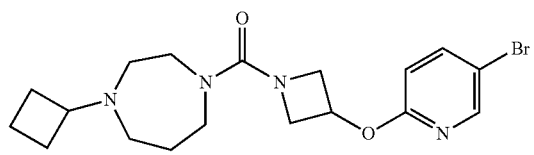 [SMILES: O=C(N1CCCN(C2CCC2)CC1)N1CC(Oc2ccc(Br)cn2)C1]

In a similar fashion (Route 20, GP I), 1-[(4-cyclobutyl-1,4-diazepan-1-yl)carbonyl]azetidin-3-ol (100 mg, 0.395 mmol) and 5-bromo-2-fluoropyridine (81 μl, 139 mg, 0.79 mmol) gave the title compound (89 mg, 54%) as off white solid after purification by FCC (silica, using a gradient of eluents; EtOAc/MeOH/NH₃ 100:0:0 to 80:20:1).

LCMS data: Calculated MH⁺(410); Found 100% (MH⁺) m/z 410, Rt=2.83 min.

¹H NMR (250 MHz, CHLOROFORM-d) δ ppm 8.14 (1 H, d, J=2.6 Hz), 7.68 (1 H, dd, J=8.7, 2.6 Hz), 6.70 (1 H, d, J=8.7 Hz), 5.22-5.33 (1 H, m), 4.34 (2 H, dd, J=9.5, 6.6 Hz), 3.99 (2 H, dd, J=9.9, 4.7 Hz), 2.85 (1 H, t, J=7.6 Hz), 2.34-2.60 (4 H, m), 1.51-2.11 (12 H, m).

Example 23

Preparation of 1-cyclobutyl-4-{[3-(3,4-dichlorophenoxy)azetidin-1-yl]carbonyl}-1,4-diazepane.
Potency range A

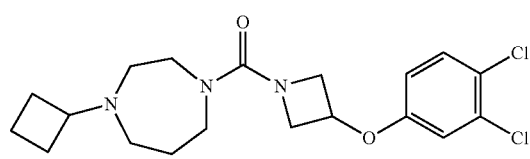 [SMILES: O=C(N1CCCN(C2CCC2)CC1)N1CC(Oc2ccc(Cl)c(Cl)c2)C1]

In a similar fashion (Route 20, GP I), 1-[(4-cyclobutyl-1,4-diazepan-1-yl)carbonyl]azetidin-3-ol (40 mg, 0.158 mmol) and 1,2-dichloro-4-fluorobenzene (37 μl, 52 mg, 0.316 mmol) gave the title compound as colourless oil after purification by preparative HPLC (14 mg, 23%).

LCMS data: Calculated MH⁺(398); Found 100% (MH⁺) m/z 398, Rt=3.06 min.

¹H NMR (250 MHz, MeOD) δ ppm 7.43 (1 H, d, J=8.8 Hz), 7.01 (1 H, d, J=2.9 Hz), 6.79 (1 H, dd, J=8.8, 2.9 Hz), 4.95-5.06 (1 H, m), 4.24-4.60 (2 H, m), 3.81-4.17 (3 H, m), 3.71 (1 H, t, J=8.3 Hz), 3.37-3.62 (5 H, m), 2.81-3.20 (2 H, m), 2.00-2.46 (6 H, m), 1.65-1.97 (2 H, m).

Example 24

Preparation of 1-({3-[(6-bromopyridin-3-yl)oxy]azetidin-1-yl}carbonyl)-4-cyclobutyl-1,4-diazepane.
Potency range A

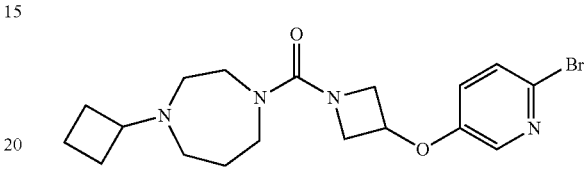

In a similar fashion (Route 20, GP I), 1-[(4-cyclobutyl-1,4-diazepan-1-yl)carbonyl]azetidin-3-ol (100 mg, 0.398 mmol) and 2-bromo-5-fluoropyridine (139 mg, 0.79 mmol) gave the title compound as off white solid after purification by FCC (silica, using a gradient of eluents; EtOAc/MeOH/NH₃ 100:0:0 to 80:20:1), followed by trituration with diethyl ether (106 mg, 65%).

LCMS data: Calculated MH⁺ (410); Found 100% (MH⁺) m/z 410, Rt=2.67 min.

¹H NMR (250 MHz, CHLOROFORM-d) δ ppm 7.91 (1 H, d, J=3.2 Hz), 7.40 (1 H, d, J=8.7 Hz), 6.99 (1 H, dd, J=8.7, 3.2 Hz), 4.84-4.99 (1 H, m), 4.28-4.41 (2 H, m), 4.04 (2 H, dd, J=9.7, 4.1 Hz), 3.33-3.52 (4 H, m), 2.77-2.90 (1 H, m), 2.37-2.58 (4 H, m), 1.95-2.12 (2 H, m), 1.75-1.94 (4 H, m), 1.65-1.72 (2 H, m).

Example 25

Preparation of 1-{[3-(4-chloro-2-methylphenoxy)azetidin-1-yl]carbonyl}-4-cyclobutyl-1,4-diazepane.
Potency range A

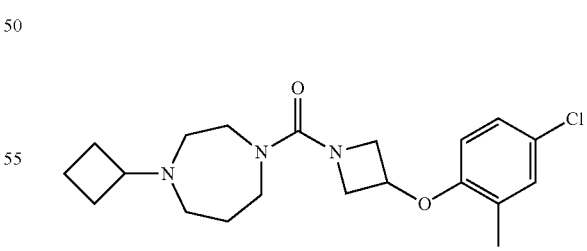

In a similar fashion (Route 20, GP I), 1-[(4-cyclobutyl-1,4-diazepan-1-yl)carbonyl]azetidin-3-ol (50 mg, 0.19 mmol) and 4-chloro-1-fluoro-2-methylbenzene (43 mg, 0.29 mmol) gave the title compound as colourless oil after purification by preparative HPLC (59 mg, 60%).

LCMS data: Calculated MH⁺(378); Found 100% (MH⁺) m/z 378, Rt=3.12 min.

NMR data: ¹H NMR (250 MHz, MeOD) δ ppm 7.00-7.21 (2 H, m), 6.48-6.66 (1 H, m), 5.00-5.05 (1 H, m), 4.26-4.60 (2 H, m), 3.35-4.18 (9 H, m), 3.00 (2 H, br. s.), 2.03-2.42 (9 H, m), 1.82 (2 H, m).

Example 26

Preparation of 1-cyclobutyl-4-({3-[4-(1H-imidazol-1-yl)phenoxy]azetidin-1-yl}carbonyl)-1,4-diazepane. Potency range A

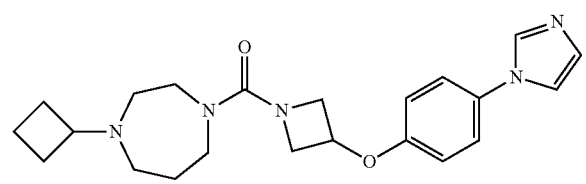 [SMILES: O=C(N1CCCN(C2CCC2)CC1)N1CC(Oc2ccc(-n3ccnc3)cc2)C1]

In a similar fashion (Route 20, GP I), 1-[(4-cyclobutyl-1,4-diazepan-1-yl)carbonyl]azetidin-3-ol (50 mg, 0.19 mmol) and 1-(4-fluorophenyl)-1H-imidazole (48 mg, 0.29 mmol) gave the title compound as colourless oil after purification by preparative HPLC (49 mg, 49%).

LCMS data: Calculated MH⁺(396); Found 100% (MH⁺) m/z 396, Rt=1.92 min.

NMR data: ¹H NMR (250 MHz, MeOD) δ ppm 9.35 (1 H, t, J=1.4 Hz), 7.98 (1 H, t, J=1.8 Hz), 7.71-7.79 (1 H, m), 7.61-7.71 (2 H, m), 7.02-7.12 (2 H, m), 5.11 (1 H, tt, J=6.4, 4.0 Hz), 4.49 (2 H, br. s.), 3.33-4.33 (9 H, m), 2.80-3.28 (2 H, m), 2.09-2.42 (6 H, m), 1.70-1.95 (2 H, m).

Example 27

Preparation of 1-cyclobutyl-4-({3-[(2-methylpyridin-4-yl)oxy]azetidin-1-yl}carbonyl)-1,4-diazepane. Potency range A

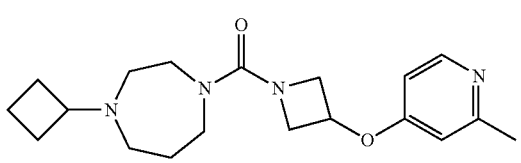 [SMILES: Cc1cc(OC2CN(C(=O)N3CCCN(C4CCC4)CC3)C2)ccn1]

In a similar fashion (Route 20, GP I), 1-[(4-cyclobutyl-1,4-diazepan-1-yl)carbonyl]azetidin-3-ol (50 mg, 0.19 mmol) and 4-chloro-2-methylpyridine (33 mg, 0.26 mmol) gave the title compound as colourless oil after purification on silica gel (27 mg, 40%).

LCMS data: Calculated MH⁺ (345); Found 100% (MH⁺) m/z 345, Rt=0.65 min.

NMR data: ¹H NMR (250 MHz, MeOD) δ ppm 8.23 (1 H, d, J=5.9 Hz), 6.77 (1 H, d, J=2.4 Hz), 6.72 (1 H, dd, J=5.8, 2.4 Hz), 5.08 (1 H, tt, J=6.5, 4.0 Hz), 4.37-4.50 (2 H, m), 3.95-4.06 (2 H, m), 3.37-3.51 (4 H, m), 2.82-2.97 (1 H, m), 2.51-2.60 (2 H, m), 2.41-2.51 (5 H, m), 1.98-2.15 (2 H, m), 1.77-1.96 (4 H, m), 1.57-1.76 (2 H, m).

Example 28

Preparation of 1-cyclobutyl-4-({3-[3-(trifluoromethyl)phenoxy]azetidin-1-yl}carbonyl)-1,4-diazepane. Potency range A

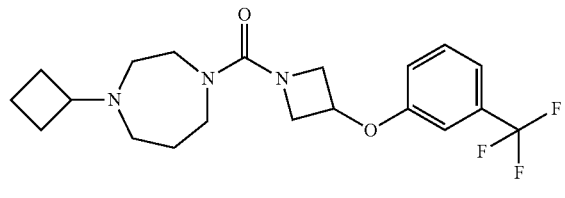 [SMILES: O=C(N1CCCN(C2CCC2)CC1)N1CC(Oc2cccc(C(F)(F)F)c2)C1]

In a similar fashion (Route 20, GP I), 1-[(4-cyclobutyl-1,4-diazepan-1-yl)carbonyl]azetidin-3-ol (40 mg, 0.158 mmol) and 1-fluoro-3-(trifluoromethyl)benzene (52 mg, 0.316 mmol) gave the title compound as colourless oil after purification by preparative HPLC (25 mg, 31%).

LCMS data: Calculated MH⁺(398); Found 100% (MH⁺) m/z 398, Rt=3.02 min.

¹H NMR (360 MHz, MeOH) δ ppm 7.45-7.55 (1 H, m), 7.29 (1 H, d, J=7.7 Hz), 7.09 (2 H, br. s.), 5.06-5.12 (1 H, m), 4.51-4.59 (1 H, m), 4.36-4.43 (1 H, m), 4.09-4.16 (1 H, m), 3.88-4.02 (2 H, m), 3.68-3.76 (1 H, m), 3.40-3.57 (5 H, m), 2.93-3.07 (2 H, m), 2.06-2.36 (6 H, m), 1.75-1.92 (2 H, m).

Example 29

Preparation of 1-cyclobutyl-4-({3-[2-(trifluoromethyl)phenoxy]azetidin-1-yl}carbonyl)-1,4-diazepane. Potency range A

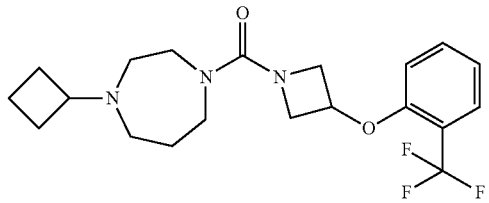 [SMILES: O=C(N1CCCN(C2CCC2)CC1)N1CC(Oc2ccccc2C(F)(F)F)C1]

In a similar fashion (Route 20, GP I), 1-[(4-cyclobutyl-1,4-diazepan-1-yl)carbonyl]azetidin-3-ol (40 mg, 0.158 mmol) and 1-fluoro-2-(trifluoromethyl)benzene (52 mg, 0.316 mmol) gave the title compound as colourless oil after purification by preparative HPLC (27 mg, 33%).

LCMS data: Calculated MH⁺ (398); Found 100% (MH⁺) m/z 398, Rt=2.99 mins.

¹H NMR (360 MHz, MeOH) δ ppm 7.50-7.65 (2 H, m), 7.12 (1 H, t, J=7.5 Hz), 6.90 (1 H, d, J=8.6 Hz), 5.08-5.17 (1 H, m), 4.53-4.61 (1 H, m), 4.36-4.46 (1 H, m), 4.09-4.18 (1 H, m), 3.87-4.04 (2 H, m), 3.64-3.77 (1 H, m), 3.40-3.60 (5 H, m), 2.88-3.09 (2 H, m), 2.08-2.37 (6 H, m), 1.73-1.91 (2 H, m).

Example 30

Preparation of 3-({1-[(4-cyclobutyl-1,4-diazepan-1-yl)carbonyl]azetidin-3-yl}oxy)benzonitrile. Potency range A

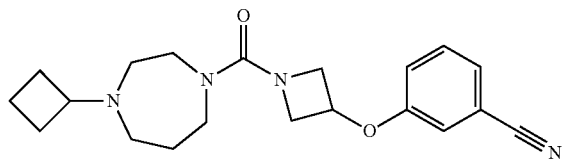 [SMILES: N#Cc1cccc(OC2CN(C(=O)N3CCCN(C4CCC4)CC3)C2)c1]

In a similar fashion (Route 20, GP I), 1-[(4-cyclobutyl-1,4-diazepan-1-yl)carbonyl]azetidin-3-ol (40 mg, 0.158 mmol) and 3-fluorobenzonitrile (38 mg, 0.316 mmol) gave the title compound as colourless oil after purification by preparative HPLC (19 mg, 26%).

LCMS data: Calculated MH$^+$(355); Found 100% (MH$^+$) m/z 355, Rt=2.66 min.

$^1$H NMR (360 MHz, MeOH) δ ppm 7.42-7.54 (1 H, m), 7.36 (1 H, d, J=7.3 Hz), 7.13-7.20 (2 H, m), 5.02-5.11 (1 H, m), 4.32-4.61 (2 H, m), 3.86-4.18 (3 H, m), 3.72 (1 H, q), 3.40-3.60 (5 H, m), 2.87-3.10 (2 H, m), 2.07-2.39 (6 H, m), 1.70-1.92 (2 H, m).

Example 31

Preparation of 2-({1-[(4-cyclobutyl-1,4-diazepan-1-yl)carbonyl]azetidin-3-yl}oxy)benzonitrile. Potency range A

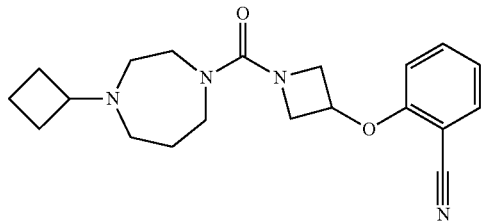 [SMILES: N#Cc1ccccc1OC1CN(C(=O)N2CCCN(C3CCC3)CC2)C1]

In a similar fashion (Route 20, GP I), 1-[(4-cyclobutyl-1,4-diazepan-1-yl)carbonyl]azetidin-3-ol (40 mg, 0.158 mmol) and 2-fluorobenzonitrile (38 mg, 0.316 mmol) gave the title compound as colourless oil after purification by preparative HPLC (21 mg, 26%).

LCMS data: Calculated MH$^+$ (355); Found 100% (MH$^+$) m/z 355, Rt=2.65 min.

$^1$H NMR (360 MHz, MeOH) δ ppm 7.56-7.72 (1 H, m), 7.06-7.18 (1 H, m), 6.92 (1 H, d, J=8.2 Hz), 5.10-5.19 (1 H, m), 4.51-4.62 (1 H, m), 4.38-4.47 (1 H, m), 4.11-4.24 (1 H, m), 4.01-4.08 (1 H, m), 3.90-3.97 (1 H, m), 3.68-3.75 (1 H, m), 3.40-3.58 (5 H, m), 2.91-3.10 (2 H, m), 2.04-2.40 (6 H, m), 1.77-1.90 (2 H, m).

Example 32

Preparation of 1-{[3-(3-chlorophenoxy)azetidin-1-yl]carbonyl}-4-cyclobutyl-1,4-diazepane. Potency range A

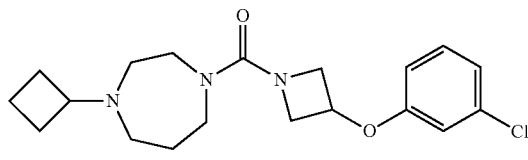 [SMILES: O=C(N1CCCN(C2CCC2)CC1)N1CC(Oc2cccc(Cl)c2)C1]

In a similar fashion (Route 20, GP I), 1-[(4-cyclobutyl-1,4-diazepan-1-yl)carbonyl]azetidin-3-ol (40 mg, 0.158 mmol) and 1-chloro-3-fluorobenzene (48 mg, 0.316 mmol) gave the title compound as colourless oil after purification by preparative HPLC (33 mg, 44%).

LCMS data: Calculated MH$^+$ (364); Found 100% (MH$^+$) m/z 364, Rt=2.95 min.

$^1$H NMR (360 MHz, MeOH) δ ppm 7.22-7.33 (1 H, m), 6.96-7.05 (1 H, m), 6.86 (1 H, s), 6.71-6.81 (1 H, m), 4.97-5.07 (1 H, m), 4.45-4.60 (1 H, m), 4.28-4.44 (1 H, m), 4.04-4.16 (1 H, m), 3.86-4.01 (2 H, m), 3.68-3.78 (1 H, m), 3.43-3.61 (5 H, m), 2.95-3.06 (2 H, m), 2.10-2.39 (6 H, m), 1.72-1.91 (2 H, m).

Example 33

Preparation of 1-{[3-(2-chlorophenoxy)azetidin-1-yl]carbonyl}-4-cyclobutyl-1,4-diazepane. Potency range A

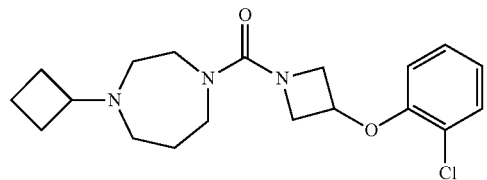 [SMILES: O=C(N1CCCN(C2CCC2)CC1)N1CC(Oc2ccccc2Cl)C1]

In a similar fashion (Route 20, GP I), 1-[(4-cyclobutyl-1,4-diazepan-1-yl)carbonyl]azetidin-3-ol (40 mg, 0.158 mmol) and 1-chloro-2-fluorobenzene (48 mg, 0.316 mmol) gave the title compound as colourless oil after purification by preparative HPLC (5 mg, 7%).

LCMS data: Calculated MH$^+$(364); Found 100% (MH$^+$) m/z 364, Rt=2.92 min.

$^1$H NMR (360 MHz, MeOH) δ ppm 7.40 (1 H, d, J=7.7 Hz), 7.25 (1 H, t, J=7.9 Hz), 6.97 (1 H, t, J=7.7 Hz), 6.80 (1 H, d, J=8.6 Hz), 5.02-5.11 (1 H, m), 4.50-4.59 (1 H, m), 4.35-4.44 (1 H, m), 4.11-4.19 (1 H, m), 3.98-4.06 (1 H, m), 3.88-3.96 (1

H, m), 3.73 (1 H, q), 3.40-3.58 (5 H, m), 2.93-3.07 (2 H, m), 2.16-2.40 (6 H, m), 1.74-1.92 (2 H, m).

Example 34

Preparation of 4-({1-[(4-cyclobutyl-1,4-diazepan-1-yl)carbonyl]azetidin-3-yl}oxy)-N,3-dimethylbenzamide. Potency range A

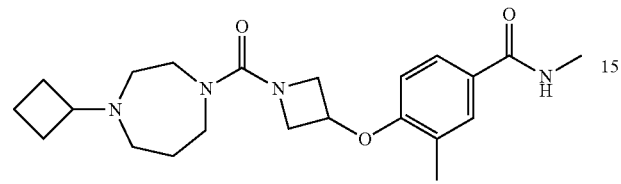

In a similar fashion (Route 20, GP I), 1-[(4-cyclobutyl-1,4-diazepan-1-yl)carbonyl]azetidin-3-ol (40 mg, 0.16 mmol) and 4-fluoro-N,3-dimethylbenzamide (54 mg, 0.32 mmol) gave the title compound as colourless oil after purification on silica gel (24 mg, 38%).

LCMS data: Calculated MH$^+$(401); Found 100% (MH$^+$) m/z 401, Rt=2.35 min.

NMR data: $^1$H NMR (250 MHz, CDCl$_3$) δ ppm 7.52-7.60 (2 H, m), 6.43-6.49 (1 H, d, J=10.8 Hz), 5.99-6.06 (1 H, m), 4.88-4.98 (1 H, m), 4.35 (2 H, dd, J=9.4, 6.6 Hz), 4.05 (2 H, dd, J=9.5, 4.3 Hz), 3.37-3.51 (5 H, m), 3.00 (3 H, d, NCH3), 2.76-2.92 (1 H, m), 2.48-2.57 (2 H, m), 2.39-2.47 (2 H, m), 2.63 (3 H, s), 1.96-2.10 (2 H, m), 1.55-1.94 (8 H, m).

Example 35

Preparation of 5-({1-[(4-cyclobutyl-1,4-diazepan-1-yl)carbonyl]azetidin-3-yl}oxy)-N-(cyclopropylmethyl)pyridine-2-carboxamide. Potency range A

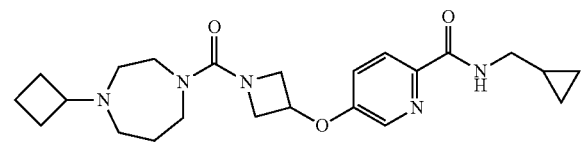 [SMILES: O=C(NCC1CC1)c1ccc(OC2CN(C(=O)N3CCCN(C4CCC4)CC3)C2)cn1]

In a similar fashion (Route 20, GP I; except using DMF instead of DMSO as solvent), 1-[(4-cyclobutyl-1,4-diazepan-1-yl)carbonyl]azetidin-3-ol (50 mg, 0.20 mmol) and 5-chloro-N-(cyclopropylmethyl)pyridine-2-carboxamide (84 mg, 0.40 mmol) gave the title compound as colourless oil (25 mg, 0.48 mmol, 0.047 mmol, 23%) after purification by preparative HPLC.

LCMS data: Calculated MH$^+$ (428); Found 100% (MH$^+$) m/z 428, Rt=2.81 min.

NMR data: $^1$H NMR (500 MHz, Chloroform-d) δ ppm 11.42-11.61 (1 H, m), 7.99 (1 H, d, J=2.7 Hz), 7.87 (1 H, t, J=5.3 Hz), 6.98 (1 H, dd, J=8.7, 2.7 Hz), 5.06 (3 H, br. s.), 4.86-4.92 (1 H, m), 4.37-4.47 (2 H, m), 4.13-4.22 (1 H, m), 4.04-4.12 (1 H, m), 3.84 (2 H, br. s.), 3.36-3.51 (3 H, m), 3.27-3.35 (2 H, m), 3.19 (3 H, t, J=6.4 Hz), 2.74 (1 H, br. s.), 2.28-2.55 (4 H, m), 2.11 (3 H, d, J=6.5 Hz), 1.77 (1 H, q, J=10.2 Hz), 1.52-1.66 (1 H, m), 0.86-1.00 (1 H, m), 0.38-0.49 (2 H, m), 0.11-0.21 (2 H, m).

Example 36

Preparation of 1-cyclobutyl-4-[(3-{[5-(trifluoromethyl)pyridin-3-yl]oxy}azetidin-1-yl)carbonyl]-1,4-diazepane. Potency range A

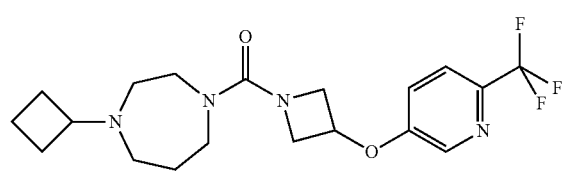 [SMILES: O=C(N1CCCN(C2CCC2)CC1)N1CC(Oc2ccc(C(F)(F)F)nc2)C1]

In similar fashion (Route 7 GP H), 1-[(4-cyclobutyl-1,4-diazepan-1-yl)carbonyl]azetidin-3-ol (50 mg, 0.20 mmol) and 5-Bromo-2-trifluoromethylpyridine (59 mg, 0.26 mmol) gave the title compound (16 mg, 0.031 mmol, 16%) as colourless oil after purification by preparative HPLC.

LCMS data: Calculated MH$^+$(399); Found 100% (MH$^+$) m/z 399, Rt=2.81 min.

NMR data: $^1$H NMR (500 MHz, MeOD-d) δ ppm 8.32 (1 H, d, J=2.7 Hz), 7.77 (1 H, d, J=8.7 Hz), 7.42 (1 H, dd, J=8.6, 2.6 Hz), 5.14-5.21 (1 H, m), 4.54-4.61 (1 H, m), 4.38-4.47 (1 H, m), 4.11-4.20 (1 H, m), 4.00-4.08 (1 H, m), 3.88-3.97 (1 H, m), 3.72 (1 H, quin, J=8.4 Hz), 3.39-3.61 (5 H, m), 3.00 (2 H, m, J=10.9 Hz), 2.30-2.40 (2 H, m), 2.18-2.30 (3 H, m), 2.05-2.18 (1 H, m), 1.73-1.93 (2 H, m).

Example 37

Preparation of 5-({1-[(4-cyclobutylpiperazin-1-yl)carbonyl]azetidin-3-yl}oxy)-N-methylpyridine-2-carboxamide. Potency range A

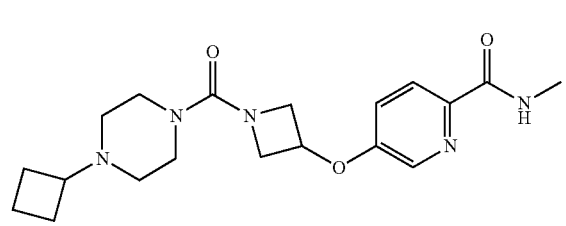 [SMILES: CNC(=O)c1ccc(OC2CN(C(=O)N3CCN(C4CCC4)CC3)C2)cn1]

In a similar fashion (Route 20, GP I; except using DMF instead of DMSO as solvent), 1-[(4-cyclobutylpiperazin-1-yl)carbonyl]azetidin-3-ol (150 mg, 0.63 mmol) and 5-chloro-N-methylpyridine-2-carboxamide (214 mg, 1.26 mmol) gave the title compound (156 mg, 0.42 mmol, 66%) as white solid after purification by FCC [SiO$_2$ eluting with DCM/MeOH/NH$_3$ 98:2:0.5].

LCMS data: Calculated MH$^+$(374); Found 100% (MH$^+$) m/z 374, Rt=2.35 min.

NMR data: $^1$H NMR (500 MHz, MeOD) δ ppm 8.24 (1 H, d, J=2.7 Hz), 8.04 (1 H, d, J=8.7 Hz), 7.34 (1 H, dd, J=8.7, 2.8 Hz), 5.12-5.18 (1 H, m), 4.53-4.60 (1 H, m), 4.39-4.46 (1 H, m), 4.11-4.18 (1 H, m), 3.97-4.06 (1 H, m), 3.84-3.94 (1 H, m), 3.41-3.63 (5 H, m), 3.17-3.29 (2 H, m), 2.94 (6 H, d, J=5.2 Hz), 1.98-2.30 (2 H, m).

3.49 (2 H, m), 3.11-3.22 (2 H, m), 2.81-2.92 (2 H, m), 2.32-2.38 (2 H, m), 2.23-2.26 (2 H, m), 1.79-1.97 (2 H, m).

Example 38

Preparation of 1-cyclobutyl-4-[(3-phenoxyazetidin-1-yl)carbonyl]piperazine. Potency range A

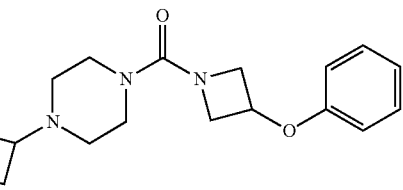

In a similar fashion (Route 20, GP I), 1-[(4-cyclobutylpiperazin-1-yl)carbonyl]azetidin-3-ol (40 mg, 0.167 mmol) and 4-fluorobenzene (32 mg, 0.334 mmol) gave the title compound (11.1 mg, 15%) as colourless oil after purification by preparative HPLC.

LCMS data: Calculated MH$^+$(316); Found 100% (MH$^+$) m/z 316, Rt=2.66 min.

$^1$H NMR (360 MHz, MeOD) δ ppm 7.29 (2 H, t, J=7.9 Hz), 6.97 (1 H, t, J=7.3 Hz), 6.80 (2 H, d, J=8.2 Hz), 4.98-5.05 (1 H, m), 4.47 (2 H, dd, J=9.5, 6.4 Hz), 4.06 (4 H, dd, J=9.3, 3.9 Hz), 3.64-3.76 (1 H, m), 3.43-3.53 (2 H, m), 3.13-3.22 (2 H, m), 2.81-2.93 (2 H, m), 2.30-2.39 (2 H, m), 2.19-2.28 (2 H, m), 1.84-1.95 (2 H, m).

Example 39

Preparation of 1-cyclobutyl-4-({3-[4-(trifluoromethyl)phenoxy]azetidin-1-yl}carbonyl)piperazine. Potency range A

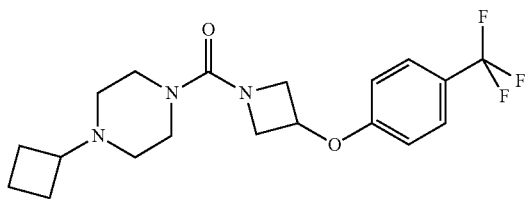 [SMILES: O=C(N1CCN(C2CCC2)CC1)N1CC(Oc2ccc(C(F)(F)F)cc2)C1]

In a similar fashion (Route 20, GP I), 1-[(4-cyclobutylpiperazin-1-yl)carbonyl]azetidin-3-ol (40 mg, 0.167 mmol) and 1-fluoro-4-(trifluoromethyl)benzene (55 mg, 0.334 mmol) gave the title compound (14.5 mg, 18%) as colourless oil after purification by preparative HPLC.

LCMS data: Calculated MH$^+$(384); Found 100% (MH$^+$) m/z 384, Rt=3.12 min.

$^1$H NMR (360 MHz, MeOD) δ ppm 7.61 (2 H, d, J=8.2 Hz), 6.97 (2 H, d, J=8.6 Hz), 5.06-5.14 (1 H, m), 4.50 (2 H, dd, J=9.5, 6.4 Hz), 3.93-4.16 (4 H, m), 3.63-3.76 (1 H, m), 3.36-

Example 40

Preparation of 4-({1-[(4-cyclobutylpiperazin-1-yl)carbonyl]azetidin-3-yl}oxy)benzonitrile. Potency range A

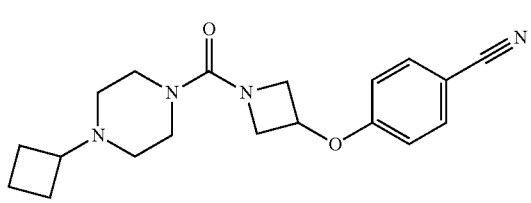 [SMILES: N#Cc1ccc(OC2CN(C(=O)N3CCN(C4CCC4)CC3)C2)cc1]

In a similar fashion (Route 20, GP I), 1-[(4-cyclobutylpiperazin-1-yl)carbonyl]azetidin-3-ol (40 mg, 0.167 mmol) and 4-fluorobenzonitrile (40 mg, 0.334 mmol) gave the title compound (14.8 mg, 19%) as colourless oil after purification by preparative HPLC.

LCMS data: Calculated MH$^+$(341); Found 100% (MH$^+$) m/z 341, Rt=2.56 min.

$^1$H NMR (360 MHz, MeOD) δ ppm 7.69 (2 H, d, J=8.2 Hz), 6.98 (2 H, d, J=8.6 Hz), 5.08-5.15 (1 H, m), 4.45-4.53 (2 H, m), 3.99-4.12 (4 H, m), 3.64-3.73 (1 H, m), 3.39-3.55 (2 H, m), 3.09-3.24 (2 H, m), 2.82-2.94 (2 H, m), 2.28-2.41 (2 H, m), 2.20-2.27 (2 H, m), 1.81-1.95 (2 H, m).

Example 41

Preparation of 1-cyclobutyl-4-{[3-(4-fluorophenoxy)azetidin-1-yl]carbonyl}piperazine. Potency range A

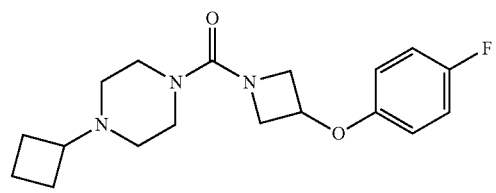 [SMILES: O=C(N1CCN(C2CCC2)CC1)N1CC(Oc2ccc(F)cc2)C1]

In a similar fashion (Route 20, GP I), 1-[(4-cyclobutylpiperazin-1-yl)carbonyl]azetidin-3-ol (40 mg, 0.167 mmol) and 1,4-difluorobenzene (38 mg, 0.334 mmol) gave the title compound (12.9 mg, 18%) as colourless oil after purification by preparative HPLC.

LCMS data: Calculated MH$^+$(334); Found 100% (MH$^+$) m/z 334, Rt=2.70 min.

$^1$H NMR (360 MHz, MeOD) δ ppm 7.03 (2 H, t, J=8.9 Hz), 6.80 (2 H, dd, J=9.1, 4.5 Hz), 4.95-5.01 (1 H, m), 4.46 (2 H, dd, J=9.3, 6.6 Hz), 4.04 (4 H, dd, J=9.3, 3.9 Hz), 3.64-3.75 (1

H, m), 3.37-3.54 (2 H, m), 3.10-3.25 (2 H, m), 2.80-2.98 (2 H, m), 2.18-2.38 (4 H, m), 1.80-1.96 (2 H, m).

Example 42

Preparation of 6-cyclobutyl-2-({1-[(4-cyclobutyl-1,4-diazepan-1-yl)carbonyl]azetidin-3-yl}oxy)-5,6,7,8-tetrahydro-1,6-naphthyridine. Potency range A

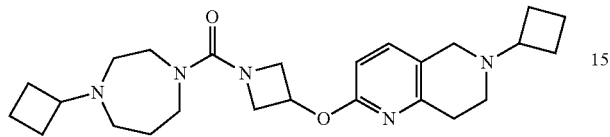

In a similar fashion (Route 20, GP I), (4-cyclobutyl-1,4-diazepan-1-yl)(3-hydroxyazetidin-1-yl)methanone (40 mg, 0.16 mmol) and 2-chloro-6-cyclobutyl-5,6,7,8-tetrahydro-1,6-naphthyridine (39 mg, 0.17 mmol) gave the title compound as colourless oil after purification by FCC on silica (5.6 mg, 8%).

LCMS data: Calculated MH$^+$(440); Found 100% (MH$^+$) m/z 440, Rt=4.87 min.

NMR data: $^1$H NMR (500 MHz, CDCl$_3$) δ ppm 7.25 (1H, d, J=8.3), 6.54 (1H, d, J=8.3), 5.34-5.28 (1H, m), 4.34 (2H, dd, J=9.5 and 6.9 Hz), 3.98 (2H, dd, J=9.7 and 4.5 Hz), 3.51-3.38 (5H, m), 2.65 (2H, t, J=6.1 Hz), 2.57-2.41 (4H, m), 2.19-1.58 (13H, m).

Example 43

Preparation of 4-({1-[(4-cyclobutyl-1,4-diazepan-1-yl)carbonyl]azetidin-3-yl}oxy)-3-fluoro-N-methyl-benzamide. Potency range A

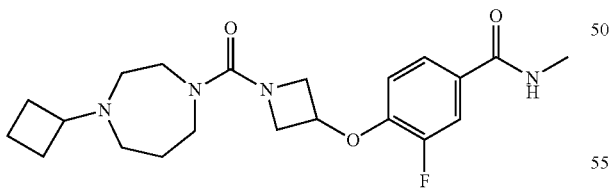

In a similar fashion (Route 20, GP I), 1-[(4-cyclobutyl-1,4-diazepan-1-yl)carbonyl]azetidin-3-ol (40 mg, 0.16 mmol) and 3,4-difluoro-N-methylbenzamide (54 mg, 0.32 mmol) gave the title compound as colourless oil after purification by preparative HPLC (2.2 mg, 3%).

LCMS data: Calculated MH$^+$(405); Found 100% (MH$^+$) m/z 405, Rt=2.27 min.

NMR data: $^1$H NMR (250 MHz, CDCl$_3$) δ ppm 7.37-7.53 (2 H, m), 6.58-6.67 (1 H, m), 6.01-6.12 (1 H, m), 4.88-5.00 (1 H, m), 4.08-4.52 (9 H, m), 3.81-3.99 (2 H, m), 3.18-3.58 (7H, m), 2.92 (3H, d), 2.28-2.61 (2H, m), 1.78-2.26 (1H, m).

Example 44

Preparation of 1-cyclobutyl-4-{[3-(4-iodophenoxy)azetidin-1-yl]carbonyl}-1,4-diazepane. Potency range A

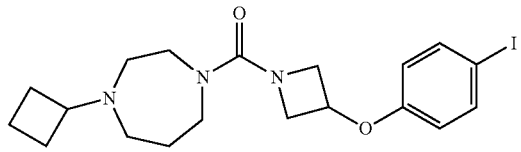 [SMILES: O=C(N1CCCN(C2CCC2)CC1)N1CC(Oc2ccc(I)cc2)C1]

In a similar fashion (Route 20, GP I), 1-[(4-cyclobutyl-1,4-diazepan-1-yl)carbonyl]azetidin-3-ol (300 mg, 1.19 mmol) and 1-fluoro-4-iodobenzene (184 μl, 1.78 mmol) gave the title compound as an off-white solid after purification by silica FCC (200 mg, 37%).

LCMS data: Calculated MH$^+$(456); Found 94% (MH$^+$) m/z 456, Rt=3.13 min.

NMR data: $^1$H NMR (500 MHz, CDCl$_3$) δ ppm 7.56 (2 H, d, J=8.8 Hz), 6.53 (2 H, d, J=8.8 Hz), 4.81-4.88 (1 H, m), 4.32 (2 H, m), 4.01 (2 H, m), 3.37-3.48 (4 H, m), 2.84 (1 H, m), 2.46-2.55 (2 H, m), 2.37-2.46 (2 H, m), 1.97-2.09 (2 H, m), 1.56-1.91 (6 H, m).

Example 45

Preparation of 1-cyclobutyl-4-({3-[(5-fluoropyridin-3-yl)oxy]azetidin-1-yl}carbonyl)-1,4-diazepane. Potency range A

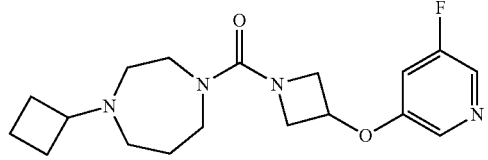 [SMILES: O=C(N1CCCN(C2CCC2)CC1)N1CC(Oc2cncc(F)c2)C1]

In a similar fashion (Route 20, GP I), 1-[(4-cyclobutyl-1,4-diazepan-1-yl)carbonyl]azetidin-3-ol (35 mg, 0.14 mmol) and 3,5-difluoropyridine (38 μl, 0.42 mmol) gave the title compound as colourless oil after purification by preparative HPLC as the TFA salt (29 mg, 44%).

LCMS data: Calculated MH$^+$ (349); Found 100% (MH$^+$) m/z 349, Rt=2.33 min.

NMR data: $^1$H NMR (500 MHz, MeOD) δ ppm 8.19 (1 H, m), 8.12 (1 H, m), 7.29 (1 H, dt, J=10.3, 2.3 Hz), 5.08-5.18 (1 H, m), 4.48-4.63 (1 H, m), 4.34-4.47 (1 H, m), 4.07-4.20 (1 H, m), 3.83-4.07 (2 H, m), 3.66-3.77 (1 H, m), 3.37-3.62 (5 H, m), 2.88-3.08 (2 H, m), 2.07-2.40 (6 H, m), 1.70-1.92 (2 H, m).

Example 46

1-({3-[(6-chloropyridin-3-yl)oxy]azetidin-1-yl}carbonyl)-4-cyclobutyl-1,4-diazepane. Potency range A

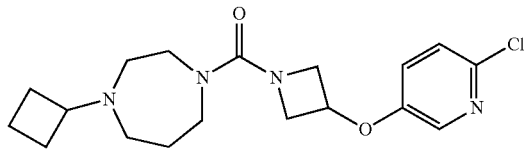 [SMILES: O=C(N1CCCN(C2CCC2)CC1)N1CC(Oc2ccc(Cl)nc2)C1]

In a similar fashion (Route 20, GP I), 1-[(4-cyclobutyl-1,4-diazepan-1-yl)carbonyl]azetidin-3-ol and 2-chloro-5-fluoropyridine gave the title compound as the TFA salt (31 mg, 48%).

LCMS data: Calculated MH$^+$ (365); Found 100% (MH$^+$) m/z 365, Rt=2.45 min.

NMR data: $^1$H NMR (500 MHz, MeOD) δ ppm 7.97 (1 H, d, J=2.9 Hz), 7.36-7.41 (1 H, m), 7.30-7.36 (1 H, m), 5.04-5.11 (1 H, m), 4.46-4.59 (1 H, m), 4.32-4.46 (1 H, m), 4.06-4.17 (1 H, m), 3.84-4.05 (2 H, m), 3.67-3.77 (1 H, m), 3.37-3.61 (5 H, m), 2.98 (2 H, d, J=12.5 Hz), 2.05-2.39 (6 H, m), 1.72-1.91 (2 H, m).

Example 47

Preparation of 4-({1-[(4-cyclobutyl-1,4-diazepan-1-yl)carbonyl]azetidin-3-yl}oxy)-2-fluoro-N-methylbenzamide. Potency range A

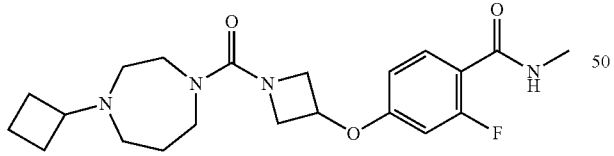

In a similar fashion (Route 20, GP I), 1-[(4-cyclobutyl-1,4-diazepan-1-yl)carbonyl]azetidin-3-ol (125 mg, 0.20 mmol) and 2,4-difluoro-N-methylbenzamide (171 mg, 0.22 mmol) gave the title compound as colourless oil after purification by preparative HPLC as the TFA salt (46 mg, 44%).

LCMS data: Calculated MH$^+$(405); Found 95% (MH$^+$) m/z 405, Rt=2.33 min.

NMR data: $^1$H NMR (500 MHz, MeOD) δ ppm 7.84 (1 H, dd, J=8.5, 6.9 Hz), 6.76-6.87 (1 H, m), 6.61 (1 H, dd, J=10.5, 2.0 Hz), 5.08-5.15 (1 H, m), 4.48-4.62 (1 H, m), 4.34-4.47 (1 H, m), 4.13-4.25 (1 H, m), 4.01-4.12 (1 H, m), 3.86-4.00 (1 H, m), 3.65-3.77 (1 H, m), 3.38-3.61 (5 H, m), 2.86-3.07 (5 H, m), 2.08-2.39 (6 H, m), 1.70-1.90 (2 H, m).

Example 48

Preparation of 1-({3-[(4-chloropyridin-3-yl)oxy]azetidin-1-yl}carbonyl)-4-cyclobutyl-1,4-diazepane. Potency range A

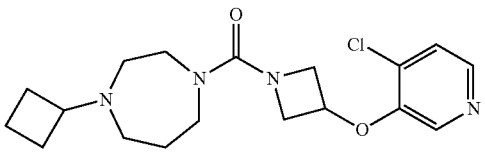 [SMILES: O=C(N1CCCN(C2CCC2)CC1)N1CC(Oc2cnccc2Cl)C1]

In a similar fashion (Route 20, GP I), 1-[(4-cyclobutyl-1,4-diazepan-1-yl)carbonyl]azetidin-3-ol (44 mg, 0.17 mmol) and 4-chloro-3-fluoropyridine (21 μl, 0.20 mmol) gave the title compound as colourless oil after purification by preparative HPLC and SCX (22 mg, 37%).

LCMS data: Calculated MH$^+$ (365); Found 95% (MH$^+$) m/z 365, Rt=3.98 mins (High pH method).

NMR data: $^1$H NMR (500 MHz, MeOD) δ ppm 8.13-8.21 (1 H, m), 8.05-8.13 (1 H, m), 7.54 (1 H, d, J=5.0 Hz), 5.16-5.25 (1 H, m), 4.49 (2 H, dd, J=9.5, 6.6 Hz), 4.11 (2 H, dd, J=9.6, 3.8 Hz), 3.42-3.65 (4 H, m), 3.30 (1 H, m), 2.70-3.02 (4 H, m), 2.13-2.27 (2 H, m), 1.94-2.12 (4 H, m), 1.67-1.85 (2 H, m).

Example 49

Preparation of 1-cyclobutyl-4-({3-[(3-fluoropyridin-4-yl)oxy]azetidin-1-yl}carbonyl)-1,4-diazepane. Potency range A

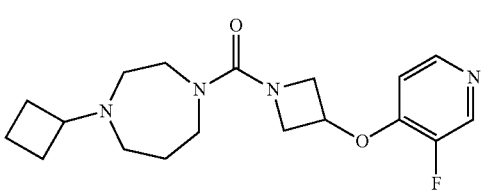 [SMILES: O=C(N1CCCN(C2CCC2)CC1)N1CC(Oc2ccncc2F)C1]

In a similar fashion (Route 20, GP I), 1-[(4-cyclobutyl-1,4-diazepan-1-yl)carbonyl]azetidin-3-ol (44 mg, 0.17 mmol) and 4-chloro-3-fluoropyridine (21 μl, 0.20 mmol) gave the title compound as colourless oil after purification by preparative HPLC as the free base (4 mg, 7%).

LCMS data: Calculated MH$^+$ (349); Found 99% (MH$^+$) m/z 349, Rt=3.59 mins (High pH method).

NMR data: $^1$H NMR (500 MHz, MeOD) δ ppm 8.32-8.41 (1 H, m), 8.19-8.29 (1 H, m), 6.93-7.03 (1 H, m), 5.14-5.25 (1

H, m), 4.43-4.54 (2 H, m), 4.04-4.15 (2 H, m), 3.42-3.68 (5 H, m), 2.65-3.07 (4 H, m), 2.15-2.29 (2 H, m), 1.93-2.14 (4 H, m), 1.66-1.87 (2 H, m).

Example 50

Preparation of 1-({3-[(4-chloro-2-methylpyridin-3-yl)oxy]azetidin-1-yl}carbonyl)-4-cyclobutyl-1,4-diazepane. Potency range A

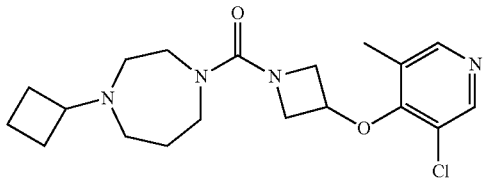 [SMILES: Cc1cncc(Cl)c1OC1CN(C(=O)N2CCCN(C3CCC3)CC2)C1]

In a similar fashion (Route 20, GP I), 1-[(4-cyclobutyl-1,4-diazepan-1-yl)carbonyl]azetidin-3-ol (45 mg, 0.17 mmol) and 4-chloro-3-fluoro-2-methylpyridine (31 mg, 0.21 mmol) gave the title compound as colourless oil after purification by preparative HPLC (8 mg, 13%).

LCMS data: Calculated MH$^+$ (378); Found 100% (MH$^+$) m/z 378, Rt=2.25 mins (High pH method).

NMR data: $^1$H NMR (500 MHz, MeOD) δ ppm 8.24-8.33 (1 H, m), 7.64-7.74 (1 H, m), 4.93-5.02 (1 H, m), 4.43-4.56 (1 H, m), 4.28-4.42 (2 H, m), 4.15-4.29 (1 H, m), 3.87-4.00 (1 H, m), 3.66-3.79 (1 H, m), 3.38-3.61 (5 H, m), 2.98 (2 H, m), 2.62 (3 H, s), 2.04-2.41 (6 H, m), 1.74-1.92 (2 H, m).

Example 51

Preparation of 5-({1-[(4-cyclobutyl-1,4-diazepan-1-yl)carbonyl]azetidin-3-yl}oxy)imidazo[1,5-a]pyridine. Potency range A

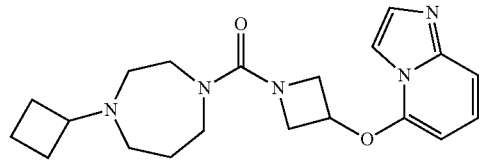 [SMILES: O=C(N1CCCN(C2CCC2)CC1)N1CC(Oc2cccc3nccn23)C1]

In a similar fashion (Route 20, GP I), 1-[(4-cyclobutyl-1,4-diazepan-1-yl)carbonyl]azetidin-3-ol (60 mg, 0.24 mmol) and 5-chloroimidazo[1,2-a]pyridine (43 mg, 0.28 mmol) gave the title compound as a colourless oil after purification by silica FCC (45 mg, 50%).

LCMS data: Calculated MH$^+$ (370); Found 100% (MH$^+$) m/z 370, Rt=3.53 min (High pH method).

NMR data: $^1$H NMR (500 MHz, MeOD) δ ppm 7.68 (1 H, s), 7.61 (1 H, s), 7.26-7.35 (1 H, m), 7.14 (1 H, dd, J=8.9, 7.4 Hz), 5.76 (1 H, d, J=7.5 Hz), 5.07-5.19 (1 H, m), 4.44 (2 H, dd, J=9.8, 6.6 Hz), 4.18 (2 H, dd, J=9.8, 4.1 Hz), 3.34-3.54 (4 H, m), 2.84 (1 H, quin, J=7.9 Hz), 2.48-2.58 (2 H, m), 2.23-2.39 (2 H, m), 1.97-2.11 (2 H, m), 1.75-1.94 (4 H, m), 1.54-1.74 (2 H, m).

Example 52

Preparation of 1-cyclobutyl-4-({3-[(2-methoxypyrimidin-4-yl)oxy]azetidin-1-yl}carbonyl)-1,4-diazepane. Potency range A

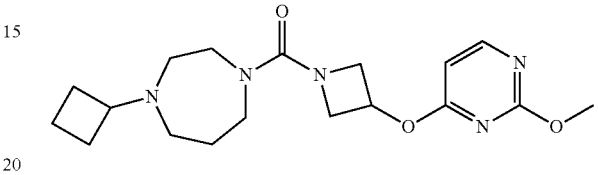

In a similar fashion (Route 20, GP I), 1-[(4-cyclobutyl-1,4-diazepan-1-yl)carbonyl]azetidin-3-ol (333 mg, 1.31 mmol) and 4-chloro-2-methoxypyrimidine (377 mg, 2.63 mmol) in THF (10 ml) gave the title compound as an orange oil after purification by silica FCC (309 mg, 65%).

LCMS data: Calculated MH$^+$ (362); Found 100% (MH$^+$) m/z 362, Rt=3.69 min (High pH method).

NMR data: $^1$H NMR (500 MHz, MeOD) δ ppm 8.23 (1 H, d, J=5.6 Hz), 6.41 (1 H, d, J=5.6 Hz), 5.34-5.43 (1 H, m), 4.36 (2 H, dd, J=9.6, 6.7 Hz), 4.02 (2 H, dd, J=9.8, 4.4 Hz), 3.96 (3 H, s), 3.35-3.50 (4 H, m), 2.77-2.89 (1 H, m), 2.46-2.58 (2 H, m), 2.34-2.46 (2 H, m), 1.92-2.00 (2 H, m), 167-1.83 (4 H, m), 1.54-1.71 (2 H, m).

Example 53

Preparation of 2-[4-({1-[(4-cyclobutyl-1,4-diazepan-1-yl)carbonyl]azetidin-3-yl}oxy)pyridin-2-yl]propan-2-ol. Potency range A

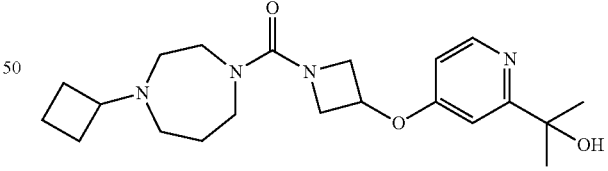

In a similar fashion (Route 20, GP I), 1-[(4-cyclobutyl-1,4-diazepan-1-yl)carbonyl]azetidin-3-ol (64 mg, 0.25 mmol) and 2-(4-chloropyridin-2-yl)propan-2-ol (52 mg, 0.30 mmol) gave the title compound as an orange oil after purification by silica FCC (35 mg, 36%).

LCMS data: Calculated MH$^+$ (389); Found 100% (MH$^+$) m/z 389, Rt=3.57 min (High pH method).

NMR data: $^1$H NMR (500 MHz, MeOD) δ ppm 8.34 (1 H, d, J=5.8 Hz), 6.76 (1 H, d, J=2.3 Hz), 6.53 (1 H, dd, J=5.8, 2.3 Hz), 4.95 (1 H, m), 4.82 (1 H, br. s.), 4.35 (2 H, dd, J=9.4, 6.6 Hz), 4.03 (2 H, dd, J=9.6, 4.1 Hz), 3.35-3.48 (4 H, m), 2.76-

2.88 (1 H, m), 2.45-2.54 (2 H, m), 2.37-2.45 (2 H, m), 1.97-2.07 (2 H, m), 1.74-1.91 (4 H, m), 1.54-1.71 (2 H, m), 1.46-1.53 (6 H, s).

Example 54

Preparation of 1-cyclobutyl-4-({3-[(2-ethylpyridin-4-yl)oxy]azetidin-1-yl}carbonyl)-1,4-diazepane. Potency range A

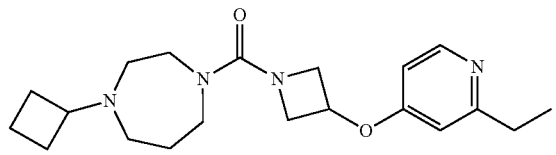 [SMILES: CCc1cc(OC2CN(C(=O)N3CCCN(C4CCC4)CC3)C2)ccn1]

In a similar fashion (Route 20, GP I), 1-[(4-cyclobutyl-1,4-diazepan-1-yl)carbonyl]azetidin-3-ol (60 mg, 0.24 mmol) and 4-chloro-2-ethylpyridine (40 mg, 0.28 mmol) gave the title compound as orange oil after purification by preparative HPLC as the free base (21 mg, 24%).

LCMS data: Calculated MH$^+$ (359); Found 100% (MH$^+$) m/z 359, Rt=3.84 min (High pH method).

NMR data: $^1$H NMR (500 MHz, MeOD) δ ppm 8.26 (1 H, d, J=5.8 Hz), 6.77 (1 H, d, J=2.1 Hz), 6.72 (1 H, dd, J=5.8, 2.3 Hz), 5.05-5.14 (1 H, m), 4.44 (2 H, dd, J=9.3, 6.6 Hz), 4.01 (2 H, dd, J=9.5, 3.9 Hz), 3.38-3.50 (4 H, m), 2.90 (1 H, m), 2.75 (2 H, q, J=7.5 Hz), 2.51-2.62 (2 H, m), 2.40-2.51 (2 H, m), 1.99-2.12 (2 H, m), 1.78-1.93 (4 H, m), 1.59-1.74 (2 H, m), 1.27 (3 H, t, J=7.6 Hz).

Example 55

Preparation of 1-cyclobutyl-4-[(3-{[2-(1-methylethyl)pyridin-4-yl]oxy}azetidin-1-yl)carbonyl]-1,4-diazepane. Potency range A

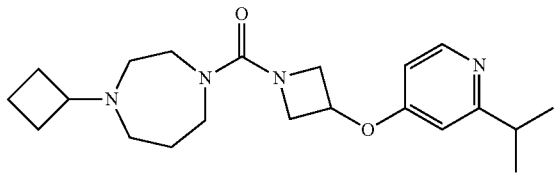 [SMILES: CC(C)c1cc(OC2CN(C(=O)N3CCCN(C4CCC4)CC3)C2)ccn1]

In a similar fashion (Route 20, GP I), 1-[(4-cyclobutyl-1,4-diazepan-1-yl)carbonyl]azetidin-3-ol (60 mg, 0.24 mmol) and 4-chloro-2-(1-methylethyl)pyridine (44 mg, 0.28 mmol) gave the title compound as an colourless oil after purification by silica FCC (70 mg, 78%).

LCMS data: Calculated MH$^+$ (373); Found 95% (MH$^+$) m/z 373, Rt=4.06 min (High pH method).

NMR data: $^1$H NMR (500 MHz, MeOD) δ ppm 8.35 (1 H, d, J=5.6 Hz), 6.54 (1 H, d, J=2.4 Hz), 6.44 (1 H, dd, J=5.8, 2.4 Hz), 4.86-4.97 (1 H, m), 4.33 (2 H, dd, J=9.7, 6.6 Hz), 4.01 (2 H, dd, J=9.9, 4.1 Hz), 3.33-3.49 (4 H, m), 2.89-3.04 (1 H, m), 2.75-2.88 (1 H, m), 2.30-2.54 (4 H, m), 1.94-2.08 (2 H, m), 1.72-1.91 (4 H, m), 1.53-1.72 (2 H, m), 1.26 (6 H, d, J=6.9 Hz).

Example 56

Preparation of 1-cyclobutyl-4-({3-[(2-methoxypyridin-4-yl)oxy]azetidin-1-yl}carbonyl)-1,4-diazepane. Potency range A

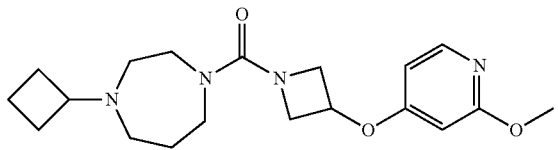 [SMILES: COc1cc(OC2CN(C(=O)N3CCCN(C4CCC4)CC3)C2)ccn1]

In a similar fashion (Route 20, GP I), 1-[(4-cyclobutyl-1,4-diazepan-1-yl)carbonyl]azetidin-3-ol (94 mg, 0.37 mmol) and 4-chloro-2-methoxy-pyridine (160 mg, 1.11 mmol) gave the title compound as an colourless oil after purification by silica FCC (50 mg, 36%).

LCMS data: Calculated MH$^+$ (361); Found 100% (MH$^+$) m/z 361, Rt=3.87 mins (High pH method).

NMR data: $^1$H NMR (500 MHz, CDCl$_3$) δ ppm 7.97 (1 H, d, J=6.0 Hz), 6.38 (1 H, dd, J=5.9, 2.2 Hz), 5.95 (1 H, d, J=2.1 Hz), 4.82-4.91 (1 H, m), 4.32 (2 H, dd, J=9.5, 6.5 Hz), 4.01 (2 H, dd, J=9.5, 4.2 Hz), 3.90 (3 H, s), 3.35-3.47 (4 H, m), 2.82 (1 H, quin, J=7.9 Hz), 2.45-2.52 (2 H, m), 2.37-2.44 (2 H, m), 1.97-2.05 (2 H, m), 1.73-1.89 (4 H, m), 1.53-1.70 (2 H, m).

Example 57

Preparation of 4-({1-[(4-cyclobutyl-1,4-diazepan-1-yl)carbonyl]azetidin-3-yl}oxy)pyridin-2-amine. Potency range A

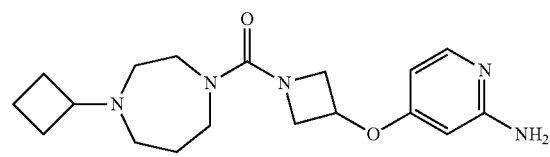 [SMILES: Nc1cc(OC2CN(C(=O)N3CCCN(C4CCC4)CC3)C2)ccn1]

In a similar fashion (Route 20, GP I), 1-[(4-cyclobutyl-1,4-diazepan-1-yl)carbonyl]azetidin-3-ol (91 mg, 0.36 mmol) and 2-amino-4-chloropyridine (55 mg, 0.43 mmol) gave the title compound as an white solid (4 mg, 3%) after purification by silica FCC and recrystallisation (Heptane/EtOAc).

LCMS data: Calculated MH$^+$ (346); Found 99% (MH$^+$) m/z 346, Rt=3.37 min (High pH method).

NMR data: $^1$H NMR (500 MHz, MeOD) δ ppm 7.73 (1 H, d, J=6.0 Hz), 6.17 (1 H, dd, J=6.1, 2.3 Hz), 5.93 (1 H, d, J=2.1 Hz), 4.93-5.02 (1 H, m), 4.40 (2 H, dd, J=9.4, 6.6 Hz), 3.99 (2 H, dd, J=9.6, 4.0 Hz), 3.38-3.52 (4 H, m), 2.91 (1 H, m), 2.51-2.61 (2 H, m), 2.40-2.49 (2 H, m), 2.03-2.12 (2 H, m), 1.78-1.93 (4 H, m), 1.60-1.76 (2 H, m).

Example 58

Preparation of 4-({1-[(4-cyclobutyl-1,4-diazepan-1-yl)carbonyl]azetidin-3-yl}oxy)-N,N-dimethylpyridin-2-amine. Potency range A

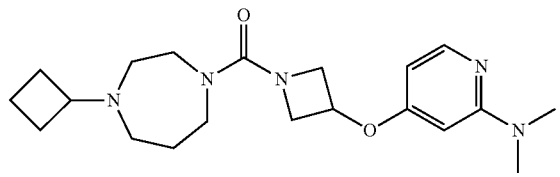 [SMILES: CN(C)c1cc(OC2CN(C(=O)N3CCCN(C4CCC4)CC3)C2)ccn1]

In a similar fashion (Route 20, GP I), 1-[(4-cyclobutyl-1,4-diazepan-1-yl)carbonyl]azetidin-3-ol (118 mg, 0.47 mmol) and 4-chloro-N,N-dimethylpyridin-2-amine (87 mg, 0.56 mmol) gave the title compound as a colourless oil (70 mg, 39%).

LCMS data: Calculated MH$^+$ (374); Found 100% (MH$^+$) m/z 374, Rt=3.94 min (High pH method).

NMR data: $^1$H NMR (500 MHz, CDCl$_3$) δ ppm 7.99 (1 H, d, J=5.6 Hz), 5.98 (1 H, dd, J=5.7, 1.9 Hz), 5.79 (1 H, d, J=1.8 Hz), 4.85-4.97 (1 H, m), 4.31 (2 H, dd, J=9.2, 6.8 Hz), 4.01 (2 H, dd, J=9.5, 4.0 Hz), 3.34-3.51 (4 H, m), 2.99-3.11 (6 H, s), 2.76-2.89 (1 H, m), 2.36-2.55 (4 H, m), 1.96-2.06 (2 H, m), 1.75-1.92 (4 H, m), 1.52-1.73 (2 H, m).

Example 59

Preparation of 1-cyclobutyl-4-({3-[(6-methylpyridazin-3-yl)oxy]azetidin-1-yl}carbonyl)-1,4-diazepane. Potency range A

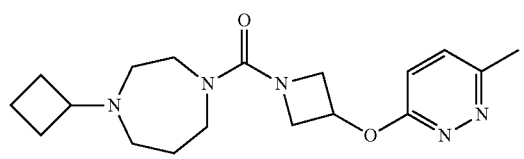 [SMILES: Cc1ccc(OC2CN(C(=O)N3CCCN(C4CCC4)CC3)C2)nn1]

In a similar fashion (Route 20, GP I), 1-[(4-cyclobutyl-1,4-diazepan-1-yl)carbonyl]azetidin-3-ol (1.09 g, 4.3 mmol) and 3-chloro-6-methylpyridazine (611 mg, 4.7 mmol) in THF at 50° C. gave the title compound as a pale pink oil after purification by silica FCC (975 mg, 66%).

LCMS data: Calculated MH$^+$ (345); Found 100% (MH$^+$) m/z 345, Rt=3.51 min (High pH method).

NMR data: $^1$H NMR (500 MHz, CDCl$_3$) δ ppm 7.23-7.30 (1 H, d, J=9.0 Hz), 6.94 (1 H, d, J=9.0 Hz), 5.42-5.55 (1 H, m), 4.42 (2 H, dd, J=9.6, 6.7 Hz), 4.05 (2 H, dd, J=9.7, 4.3 Hz), 3.35-3.51 (4 H, m), 2.77-2.89 (1 H, m), 2.61 (3 H, s), 2.35-2.54 (4 H, m), 1.96-2.08 (2 H, m), 1.72-1.92 (4 H, m), 1.52-1.72 (2 H, m).

Example 60

Preparation of 2-[4-({1-[(4-cyclobutyl-1,4-diazepan-1-yl)carbonyl]azetidin-3-yl}oxy)-2-fluorophenyl]propan-2-ol. Potency range A

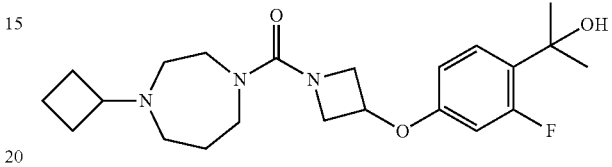

In a similar fashion (Route 20, GP I), 1-[(4-cyclobutyl-1,4-diazepan-1-yl)carbonyl]azetidin-3-ol (88 mg, 0.35 mmol) and 2-(2,4-difluoro-phenyl)-propan-2-ol (66 mg, 0.38 mmol) gave the title compound as a colourless oil after purification by preparative HPLC as the TFA salt (24 mg, 13%).

LCMS data: Calculated MH$^+$ (406); Found 99% (MH$^+$) m/z 406, Rt=4.17 min (High pH method).

NMR data: $^1$H NMR (500 MHz, CDCl$_3$) δ ppm 7.60 (1 H, dd, J=8.5, 7.0 Hz), 6.63-6.75 (1 H, m), 6.47 (1 H, dd, J=10.7, 2.3 Hz), 4.95-5.09 (1 H, m), 4.46 (2 H, dd, J=9.0, 6.7 Hz), 4.04 (2 H, dd, J=9.4, 3.7 Hz), 3.47 (5 H, t, J=6.0 Hz), 3.08-3.27 (1 H, m), 2.54-2.99 (4 H, m), 2.11-2.26 (2 H, m), 1.85-2.07 (4 H, m), 1.66-1.82 (2 H, m), 1.60 (6 H, s).

Example 61

Preparation of 1-cyclobutyl-4-({3-[(3,5-dimethylpyrazin-2-yl)oxy]azetidin-1-yl}carbonyl)-1,4-diazepane. Potency range A

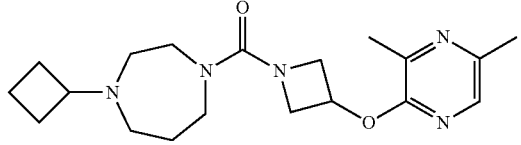 [SMILES: Cc1cnc(OC2CN(C(=O)N3CCCN(C4CCC4)CC3)C2)c(C)n1]

In a similar fashion (Route 20, GP I), 1-[(4-cyclobutyl-1,4-diazepan-1-yl)carbonyl]azetidin-3-ol (333 mg, 1.31 mmol) and 2-chloro-3,5-dimethylpyrazine (207 mg, 1.44 mmol) gave the title compound as a brown oil after purification by FCC (297 mg, 63%).

LCMS data: Calculated MH$^+$ (360); Found 99% (MH$^+$) m/z 360, Rt=3.92 min (High pH method).

NMR data: $^1$H NMR (500 MHz, CDCl$_3$) δ ppm 7.71 (1 H, s), 5.25-5.35 (1 H, m), 4.36 (2 H, dd, J=9.6, 6.9 Hz), 4.02 (2 H, dd, J=9.7, 4.5 Hz), 3.36-3.52 (4 H, m), 2.84 (1 H, m), 2.49-2.54 (2 H, m), 2.47 (3 H, s), 2.40-2.45 (5 H, m), 1.99-2.07 (2 H, m), 1.72-1.91 (4 H, m), 1.57-1.71 (2 H, m).

Example 62

Preparation of 1-cyclobutyl-4-({3-[(2-methoxypyrimidin-4-yl)oxy]azetidin-1-yl}carbonyl)-1,4-diazepane. Potency range A

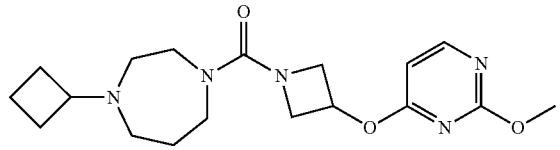 [SMILES: COc1nccc(OC2CN(C(=O)N3CCCN(C4CCC4)CC3)C2)n1]

In a similar fashion (Route 20, GP I), 1-[(4-cyclobutyl-1,4-diazepan-1-yl)carbonyl]azetidin-3-ol (333 mg, 1.31 mmol) and 4-chloro-2-methoxypyrimidine (377 mg, 2.63 mmol) at 50° C. in THF gave the title compound as light orange oil (309 mg, 65%).

LCMS data: Calculated MH$^+$ (362); Found 97% (MH$^+$) m/z 362, Rt=3.71 min (High pH method).

NMR data: $^1$H NMR (500 MHz, CDCl$_3$) δ ppm 8.24 (1 H, d, J=5.6 Hz), 6.42 (1 H, d, J=5.6 Hz), 5.34-5.44 (1 H, m), 4.36 (2 H, dd, J=9.6, 6.9 Hz), 4.03 (2 H, dd, J=9.6, 4.4 Hz), 3.96 (3 H, s), 3.35-3.51 (4 H, m), 2.83 (1 H, m), 2.46-2.56 (2 H, m), 2.35-2.46 (2 H, m), 1.97-2.08 (2 H, m), 1.74-1.93 (4 H, m), 1.50-1.72 (2 H, m).

Example 63

Preparation of 1-cyclobutyl-4-({3-[(6-methylpyrazin-2-yl)oxy]azetidin-1-yl}carbonyl)-1,4-diazepane. Potency range A

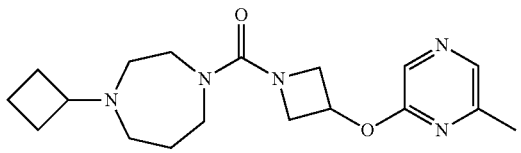 [SMILES: Cc1cncc(OC2CN(C(=O)N3CCCN(C4CCC4)CC3)C2)n1]

In a similar fashion (Route 20, GP I), 1-[(4-cyclobutyl-1,4-diazepan-1-yl)carbonyl]azetidin-3-ol (120 mg, 0.47 mmol) and 2-chloro-6-methylpyrazine (61 μl, 0.52 mmol) gave the title compound as a yellow oil after purification by FCC (114 mg, 70%).

LCMS data: Calculated MH$^+$ (346); Found 99% (MH$^+$) m/z 346, Rt=3.81 min (High pH method).

NMR data: $^1$H NMR (500 MHz, CDCl$_3$) δ ppm 8.01 (1 H, s), 7.99 (1 H, s), 5.27-5.34 (1 H, m), 4.32 (2 H, dd, J=9.7, 6.8 Hz), 3.98 (2 H, dd, J=9.8, 4.4 Hz), 3.35-3.47 (4 H, m), 2.74-2.85 (1 H, m), 2.43-2.52 (2 H, m), 2.32-2.42 (5 H, m), 1.93-2.03 (2 H, m), 1.71-1.87 (4 H, m), 1.50-1.68 (2 H, m).

Example 64

Preparation of 1-cyclobutyl-4-({3-[(3,6-dimethylpyrazin-2-yl)oxy]azetidin-1-yl}carbonyl)-1,4-diazepane. Potency range A

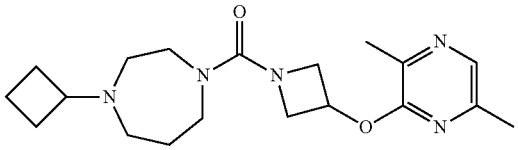 [SMILES: Cc1cnc(C)c(OC2CN(C(=O)N3CCCN(C4CCC4)CC3)C2)n1]

In a similar fashion (Route 20, GP I), 1-[(4-cyclobutyl-1,4-diazepan-1-yl)carbonyl]azetidin-3-ol (120 mg, 0.47 mmol) and 3-chloro-2,5-dimethylpyrazine (62 μl, 0.52 mmol) gave the title compound as a colourless oil after purification by FCC (131 mg, 77%).

LCMS data: Calculated MH$^+$ (360); Found 99% (MH$^+$) m/z 360, Rt=4.01 min (High pH method).

NMR data: $^1$H NMR (500 MHz, CDCl$_3$) δ ppm 7.87 (1 H, s), 5.25-5.37 (1 H, m), 4.34 (2 H, dd, J=9.5, 6.7 Hz), 4.01 (2 H, dd, J=9.5, 4.7 Hz), 3.35-3.51 (4 H, m), 2.77-2.90 (1 H, m), 2.47-2.55 (2 H, m), 2.38-2.46 (5 H, m), 2.34 (3 H, s), 1.97-2.08 (2 H, m), 1.74-1.92 (4 H, m), 1.50-1.71 (2 H, m).

Example 65

Preparation of 1-cyclobutyl-4-({3-[(2-methylpyrimidin-4-yl)oxy]azetidin-1-yl}carbonyl)-1,4-diazepane. Potency range A

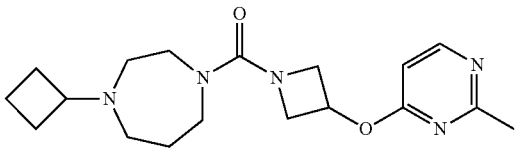

In a similar fashion (Route 20, GP I), 1-[(4-cyclobutyl-1,4-diazepan-1-yl)carbonyl]azetidin-3-ol (354 mg, 1.40 mmol) and 4-chloro-2-methylpyrimidine (197 mg, 1.53 mmol) gave the title compound as a yellow oil after purification by FCC (270, 56%).

LCMS data: Calculated MH$^+$ (346); Found 100% (MH$^+$) m/z 346, Rt=3.59 min (High pH method).

NMR data: $^1$H NMR (500 MHz, CDCl$_3$) δ ppm 8.35 (1 H, d, J=5.8 Hz), 6.57 (1 H, d, J=5.8 Hz), 5.34-5.48 (1 H, m), 4.35 (2 H, dd, J=9.9, 6.9 Hz), 4.01 (2 H, dd, J=9.9, 4.4 Hz), 3.38-3.52 (4 H, m), 2.79-2.89 (1 H, m), 2.57 (3 H, s), 2.47-2.55 (2 H, m), 2.39-2.47 (2 H, m), 1.99-2.08 (2 H, m), 1.55-1.92 (6 H, m).

Example 66

Preparation of 1-cyclobutyl-4-({3-[(6-methoxypyrazin-2-yl)oxy]azetidin-1-yl}carbonyl)-1,4-diazepane. Potency range A

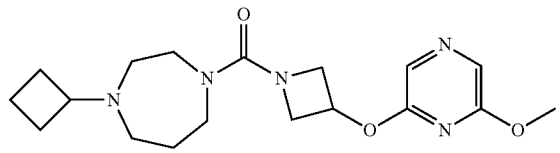 [SMILES: COc1cncc(OC2CN(C(=O)N3CCCN(C4CCC4)CC3)C2)n1]

In a similar fashion (Route 20, GP I), 1-[(4-cyclobutyl-1,4-diazepan-1-yl)carbonyl]azetidin-3-ol (110 mg, 0.43 mmol) and 2-chloro-6-methoxypyrazine (70 mg, 0.47 mmol) gave the title compound as a colourless oil after purification by FCC (114 mg, 73%).

LCMS data: Calculated MH$^+$ (362); Found 99% (MH$^+$) m/z 362, Rt=3.92 min (High pH method).

NMR data: $^1$H NMR (500 MHz, CDCl$_3$) δ ppm 7.81 (1 H, s), 7.79 (1 H, s), 5.25-5.33 (1 H, m), 4.34 (2 H, dd, J=9.5, 6.8 Hz), 4.04 (2 H, dd, J=9.7, 4.5 Hz), 3.88 (3 H, s), 3.34-3.50 (4 H, m), 2.82 (1 H, m), 2.45-2.53 (2 H, m), 2.37-2.44 (2 H, m), 1.97-2.06 (2 H, m), 1.73-1.90 (4 H, m), 1.51-1.70 (2 H, m).

Example 67

Preparation of 1-({3-[(3-chloropyridin-2-yl)oxy]azetidin-1-yl}carbonyl)-4-cyclobutyl-1,4-diazepane. Potency range A

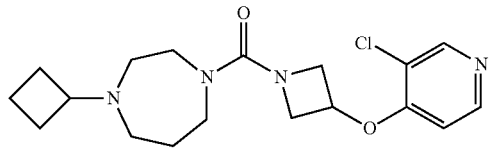 [SMILES: O=C(N1CCCN(C2CCC2)CC1)N1CC(Oc2ccncc2Cl)C1]

In a similar fashion (Route 20, GP I) 1-[(4-cyclobutyl-1,4-diazepan-1-yl)carbonyl]azetidin-3-ol (50 mg, 0.20 mmol) and 3,4-dichloropyridine (35 mg, 0.24 mmol) gave the title compound as colourless oil after purification by FCC (32 mg, 45%).

LCMS data: Calculated MH$^+$(365); Found 100% (MH$^+$) m/z 365, Rt=2.11 min.

NMR data: $^1$H NMR (500 MHz, CDCl$_3$) δ ppm 8.43 (1 H, s), 8.28 (1 H, d, J=5.5 Hz), 6.44 (1 H, d, J=5.5 Hz), 4.88-4.97 (1 H, m), 4.32 (2 H, dd, J=9.6, 6.6 Hz), 4.05 (2 H, dd, J=9.7, 4.2 Hz), 3.38-3.44 (2 H, m), 3.35 (2 H, m), 2.77 (1 H, m), 2.41-2.49 (2 H, m), 2.31-2.39 (2 H, m), 1.91-2.06 (2 H, m), 1.68-1.85 (4 H, m), 1.47-1.65 (2 H, m).

Example 68

Preparation of 4-({1-[(4-cyclobutyl-1,4-diazepan-1-yl)carbonyl]azetidin-3-yl}oxy)quinoline. Potency range A

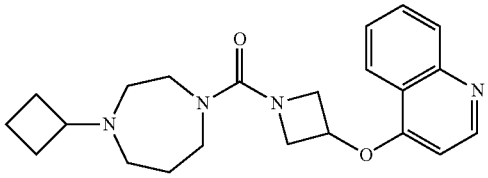 [SMILES: O=C(N1CCCN(C2CCC2)CC1)N1CC(Oc2ccnc3ccccc23)C1]

In a similar fashion (Route 20, GP I) 1-[(4-cyclobutyl-1,4-diazepan-1-yl)carbonyl]azetidin-3-ol (50 mg, 0.20 mmol) and 4-chloroquinoline (42 mg, 0.26 mmol) gave the title compound as colourless oil after purification by FCC (35 mg, 47%).

LCMS data: Calculated MH$^+$(381); Found 93% (MH$^+$) m/z 381, Rt=1.96 min.

NMR data: $^1$H NMR (500 MHz, CDCl$_3$) δ ppm 8.73 (1 H, d, J=5.0 Hz), 8.24 (1 H, d, J=8.2 Hz), 8.06 (1 H, d, J=8.4 Hz), 7.69-7.78 (1 H, m), 7.55 (1 H, m), 6.42 (1 H, d, J=5.2 Hz), 5.09-5.19 (1 H, m), 4.48 (2 H, dd, J=9.5, 6.6 Hz), 4.20 (2 H, dd, J=9.5, 4.2 Hz), 3.39-3.55 (4 H, m), 2.85 (1 H, m), 2.49-2.59 (2 H, m), 2.39-2.48 (2 H, m), 1.99-2.11 (2 H, m), 1.76-1.94 (4 H, m), 1.55-1.73 (2 H, m).

Example 69

Preparation of 1-cyclobutyl-4-({3-[(2,6-dimethylpyridin-4-yl)oxy]azetidin-1-yl}carbonyl)-1,4-diazepane. Potency range A

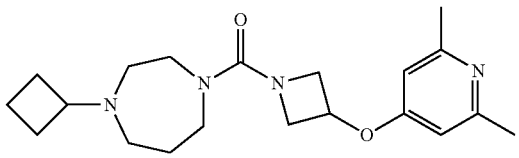 [SMILES: Cc1cc(OC2CN(C(=O)N3CCCN(C4CCC4)CC3)C2)cc(C)n1]

In a similar fashion (Route 20, GP I) 1-[(4-cyclobutyl-1,4-diazepan-1-yl)carbonyl]azetidin-3-ol (50 mg, 0.20 mmol) and 4-chloro-2,6-dimethylpyridine hydrochloride (42 mg, 0.24 mmol) gave the title compound as colourless oil after purification by FCC (30 mg, 42%).

LCMS data: Calculated MH$^+$ (359); Found 99% (MH$^+$) m/z 359, Rt=3.71 min (High pH method).

NMR data: $^1$H NMR (500 MHz, CDCl$_3$) δ ppm 6.27 (2 H, s), 4.83 (1 H, m), 4.27 (2 H, dd, J=9.3, 6.6 Hz), 3.94 (2 H, dd, J=9.5, 4.1 Hz), 3.37-3.43 (2 H, m), 3.35 (2 H, m), 2.72-2.82 (1

H, m), 2.42-2.47 (2 H, m), 2.39 (6 H, s), 2.32-2.37 (2 H, m), 1.96 (2 H, m), 1.69-1.83 (4 H, m), 1.48-1.64 (2 H, m).

Example 70

Preparation of 8-({1-[(4-cyclobutyl-1,4-diazepan-1-yl)carbonyl]azetidin-3-yl}oxy)imidazo[1,2-a]pyridine. Potency range A

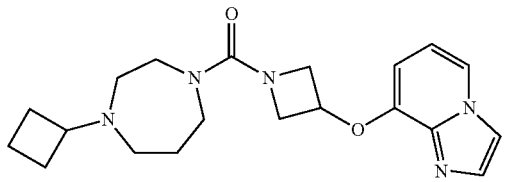 [SMILES: O=C(N1CCCN(C2CCC2)CC1)N1CC(Oc2cccn3ccnc23)C1]

In a similar fashion (Route 20, GP I) 1-[(4-cyclobutyl-1,4-diazepan-1-yl)carbonyl]azetidin-3-ol (50 mg, 0.20 mmol) and 8-chloroimidazo[1,2-a]pyridine (36 mg, 0.24 mmol) gave the title compound as white solid after purification by preparative HPLC (16.7 mg, 23%).

LCMS data: Calculated MH$^+$ (370); Found 100% (MH$^+$) m/z 370, Rt=3.49 min (High pH method).

NMR data: $^1$H NMR (500 MHz, MeOD) δ ppm 8.10 (1 H, d, J=6.9 Hz), 7.85 (1 H, d, J=1.1 Hz), 7.54 (1 H, d, J=1.1 Hz), 6.81 (1 H, t, J=7.2 Hz), 6.47 (1 H, d, J=7.6 Hz), 5.19 (1 H, m), 4.50 (2 H, dd, J=9.5, 6.6 Hz), 4.18 (2 H, dd, J=9.5, 4.0 Hz), 3.44-3.52 (4 H, m), 2.92 (1 H, m), 2.56-2.61 (2 H, m), 2.46-2.51 (2 H, m), 2.08 (2 H, m), 1.83-1.94 (4 H, m), 1.69 (2 H, m).

Example 71

Preparation of 7-({1-[(4-cyclobutyl-1,4-diazepan-1-yl)carbonyl]azetidin-3-yl}oxy)imidazo[1,2-a]pyridine. Potency range A

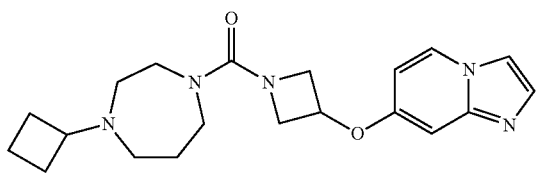 [SMILES: O=C(N1CCCN(C2CCC2)CC1)N1CC(Oc2ccn3ccnc3c2)C1]

In a similar fashion (Route 20, GP I) 1-[(4-cyclobutyl-1,4-diazepan-1-yl)carbonyl]azetidin-3-ol (50 mg, 0.20 mmol) and 7-chloroimidazo[1,2-a]pyridine (36 mg, 0.24 mmol) gave the title compound as colourless oil after purification by preparative HPLC (15 mg, 21%).

LCMS data: Calculated MH$^+$ (370); Found 100% (MH$^+$) m/z 370, Rt=3.54 min (High pH method).

NMR data: $^1$H NMR (500 MHz, MeOD) δ ppm 8.31 (1 H, d, J=7.5 Hz), 7.66 (1 H, d, J=1.2 Hz), 7.41 (1 H, d, J=1.2 Hz), 6.61-6.67 (2 H, m), 5.07 (1 H, m), 4.47 (2 H, dd, J=9.5, 6.5 Hz), 4.05 (2 H, dd, J=9.5, 4.0 Hz), 3.41-3.49 (4 H, m), 2.80 (1 H, m), 2.54-2.58 (2 H, m), 2.44-2.48 (2 H, m), 2.02-2.10 (2 H, m), 1.81-1.91 (4 H, m), 1.67 (2 H, m).

Example 72

Preparation of 4-({1-[(4-cyclobutyl-1,4-diazepan-1-yl)carbonyl]azetidin-3-yl}oxy)pyridine-2-carboxamide. Potency range A

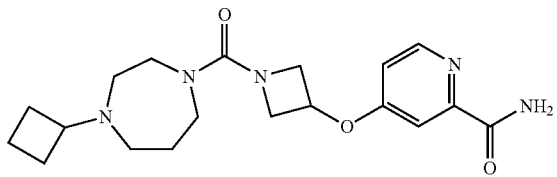 [SMILES: NC(=O)c1cc(OC2CN(C(=O)N3CCCN(C4CCC4)CC3)C2)ccn1]

In a similar fashion (Route 20, GP I) 1-[(4-cyclobutyl-1,4-diazepan-1-yl)carbonyl]azetidin-3-ol (50 mg, 0.20 mmol) was reacted with and 4-chloro-pyridine-2-carbonitrile (32 mg, 0.24 mmol). The hydrolysed product was recovered as colourless oil after purification by preparative HPLC as the TFA salt (40 mg, 54%).

LCMS data: Calculated MH$^+$(374); Found 97% (MH$^+$) m/z 374, Rt=2.04 min.

NMR data: $^1$H NMR (500 MHz, MeOD) δ ppm 8.51 (1 H, d, J=5.8 Hz), 7.59-7.65 (1 H, m), 7.10-7.15 (1 H, m), 5.20-5.26 (1 H, m), 4.55-4.64 (1 H, m), 4.42-4.49 (1 H, m), 4.13-4.20 (1 H, m), 4.01-4.07 (1 H, m), 3.88-3.97 (1 H, m), 3.68-3.77 (1 H, m), 3.39-3.60 (5 H, m), 2.92-3.07 (2 H, m), 2.30-2.39 (2 H, m), 2.17-2.28 (3 H, m), 2.05-2.17 (1 H, m), 1.74-1.92 (2 H, m).

Example 73

Preparation of 5-({1-[(4-cyclobutyl-1,4-diazepan-1-yl)carbonyl]azetidin-3-yl}oxy)-N-(cyclopropylmethyl)pyridine-2-carboxamide. Potency range A

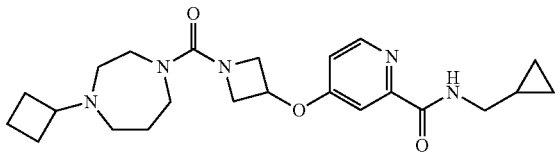 [SMILES: O=C(NCC1CC1)c1cc(OC2CN(C(=O)N3CCCN(C4CCC4)CC3)C2)ccn1]

In a similar fashion (Route 20, GP I) 1-[(4-cyclobutyl-1,4-diazepan-1-yl)carbonyl]azetidin-3-ol (50 mg, 0.20 mmol) and 4-chloro-N-(cyclopropylmethyl)pyridine-2-carboxamide (84 mg, 0.40 mmol) gave the title compound as brown oil after purification by preparative HPLC as the TFA salt (25 mg, 23%).

LCMS data: Calculated MH$^+$(428); Found 100% (MH$^+$) m/z 428, Rt=2.81 min.

NMR data: $^1$H NMR (500 MHz, CDCl$_3$) δ ppm 8.08-8.22 (2 H, m), 7.94-8.07 (1 H, m), 7.12 (1 H, dd, J=8.7, 2.7 Hz), 4.97-5.07 (1 H, m), 4.48-4.62 (1 H, m), 4.15-4.38 (2 H, m), 3.91-4.05 (2 H, m), 3.50-3.65 (3 H, m), 3.25-3.49 (5 H, m), 2.79-2.98 (1 H, m), 2.37-2.72 (4 H, m), 2.10-2.33 (3 H, m), 1.82-2.01 (1 H, m), 1.62-1.80 (1 H, m), 0.97-1.15 (1 H, m), 0.47-0.61 (2 H, m), 0.22-0.37 (2 H, m).

Example 74

Preparation of 1-cyclobutyl-4-[(3-{[6-(piperidin-1-ylcarbonyl)pyridin-3-yl]oxy}azetidin-1-yl)carbonyl]-1,4-diazepane. Potency range A

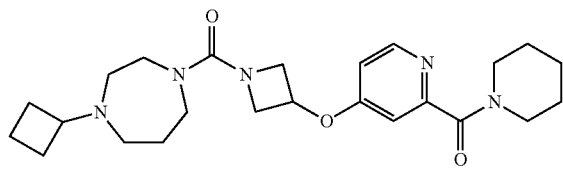 [SMILES: O=C(c1cc(OC2CN(C(=O)N3CCCN(C4CCC4)CC3)C2)ccn1)N1CCCCC1]

In a similar fashion (Route 20, GP I) 1-[(4-cyclobutyl-1,4-diazepan-1-yl)carbonyl]azetidin-3-ol (50 mg, 0.20 mmol) and 4-chloro-2-(piperidin-1-ylcarbonyl)pyridine (90 mg, 0.40 mmol) gave the title compound as colourless oil after purification by preparative HPLC (16 mg, 18%).

LCMS data: Calculated MH$^+$(442); Found 100% (MH$^+$) m/z 442, Rt=2.56 min.

NMR data: $^1$H NMR (500 MHz, MeOD) δ ppm 8.20 (1 H, d, J=2.7 Hz), 7.55 (1 H, d, J=8.5 Hz), 7.37 (1 H, dd, J=8.7, 2.8 Hz), 5.08-5.16 (1 H, m), 4.46 (2 H, dd, J=9.3, 6.5 Hz), 4.05 (2 H, dd, J=9.5, 3.8 Hz), 3.66-3.75 (2 H, m), 3.38-3.53 (6 H, m), 2.95-3.07 (1 H, m), 2.50-2.70 (4 H, m), 2.06-2.15 (2 H, m), 1.84-1.96 (4 H, m), 1.62-1.77 (6 H, m), 1.57 (2 H, m).

Example 75

Preparation of 3-({1-[(4-cyclobutyl-1,4-diazepan-1-yl)carbonyl]azetidin-3-yl}oxy)-N-methylbenzamide. Potency range A

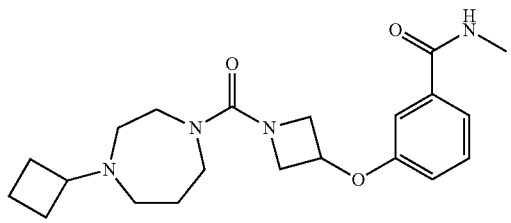 [SMILES: CNC(=O)c1cccc(OC2CN(C(=O)N3CCCN(C4CCC4)CC3)C2)c1]

In a similar fashion (Route 20, GP I) 1-[(4-cyclobutyl-1,4-diazepan-1-yl)carbonyl]azetidin-3-ol (50 mg, 0.20 mmol) and 3-fluoro-N-methyl-benzamide (46 mmol, 0.30 mmol) gave the title compound as colourless oil after purification by preparative HPLC as the TFA salt (4 mg, 3%).

LCMS data: Calculated MH$^+$(387); Found 100% (MH$^+$) m/z 387, Rt=2.37 min.

NMR data: $^1$H NMR (500 MHz, MeOD) δ ppm 7.35-7.44 (2 H, m), 7.21-7.27 (1 H, m), 7.00 (1 H, m), 5.02-5.09 (1 H, m), 4.55 (1 H, m), 4.40 (1 H, m), 4.12 (1 H, m), 3.87-4.04 (2 H, m), 3.73 (1 H, quin, J=8.4 Hz), 3.38-3.62 (5 H, m), 3.00 (2 H, m), 2.91 (3 H, s), 2.35 (2 H, m), 2.23 (3 H, m), 2.05-2.15 (1 H, m), 1.74-1.95 (2 H, m).

Example 76

Preparation of 1-({3-[(5-chloropyridin-2-yl)oxy]azetidin-1-yl}carbonyl)-4-cyclobutyl-1,4-diazepane. Potency range A

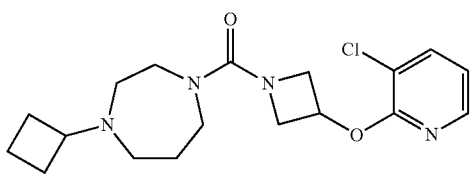 [SMILES: O=C(N1CCCN(C2CCC2)CC1)N1CC(Oc2ncccc2Cl)C1]

In a similar fashion (Route 20, GP I) 1-[(4-cyclobutyl-1,4-diazepan-1-yl)carbonyl]azetidin-3-ol (50 mg, 0.20 mmol) and 2,3-dichloropyridine (38 mg, 0.26 mmol) gave the title compound as yellow oil after purification by FCC (28 mg, 39%).

LCMS data: Calculated MH$^+$(367); Found 97% (MH$^+$) m/z 367, Rt=2.78 min (High pH method).

NMR data: $^1$H NMR (500 MHz, CDCl$_3$) δ ppm 8.00 (1 H, dd, J=4.9, 1.6 Hz), 7.66 (1 H, dd, J=7.7, 1.7 Hz), 6.88 (1 H, dd, J=7.7, 5.0 Hz), 5.37 (1 H, m), 4.38 (2 H, dd, J=9.7, 6.8 Hz), 4.09 (2 H, dd, J=9.9, 4.6 Hz), 3.40-3.51 (4 H, m), 2.85 (1 H, quin, J=7.8 Hz), 2.49-2.56 (2 H, m), 2.40-2.47 (2 H, m), 2.00-2.08 (2 H, m), 1.77-1.91 (4 H, m), 1.63-1.72 (2 H, m).

Example 77

Preparation of 1-({3-[(5-chloropyridin-2-yl)oxy]azetidin-1-yl}carbonyl)-4-cyclobutyl-1,4-diazepane. Potency range A

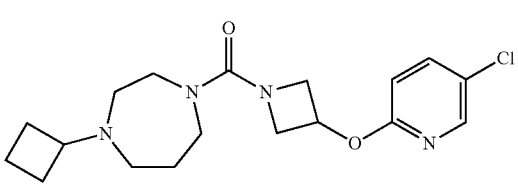 [SMILES: O=C(N1CCCN(C2CCC2)CC1)N1CC(Oc2ccc(Cl)cn2)C1]

In a similar fashion (Route 20, GP I) 1-[(4-cyclobutyl-1,4-diazepan-1-yl)carbonyl]azetidin-3-ol (50 mg, 0.20 mmol) and 2,5-dichloropyridine (38 mg, 0.26 mmol) gave the title compound as orange oil after purification by FCC (38 mg, 53%).

LCMS data: Calculated MH$^+$(367); Found 100% (MH$^+$) m/z 367, Rt=2.79 min (High pH method).

NMR data: $^1$H NMR (500 MHz, CDCl$_3$) δ ppm 8.05 (1 H, d, J=2.4 Hz), 7.56 (1 H, dd, J=8.8, 2.8 Hz), 6.74 (1 H, d, J=8.8 Hz), 5.25-5.32 (1 H, m), 4.34 (2 H, dd, J=9.4, 6.7 Hz), 4.00 (2 H, dd, J=9.6, 4.5 Hz), 3.44-3.49 (2 H, m), 3.42 (2 H, m), 2.84

(1 H, quin, J=7.8 Hz), 2.49-2.55 (2 H, m), 2.40-2.45 (2 H, m), 1.99-2.08 (2 H, m), 1.77-1.90 (4 H, m), 1.62-1.72 (2 H, m).

Example 78

Preparation of 1-cyclobutyl-4-({3-[(3,5-dimethylpyrazin-2-yl)oxy]azetidin-1-yl}carbonyl)-1,4-diazepane. Potency range A

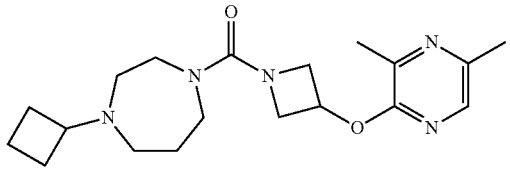 [SMILES: Cc1cnc(OC2CN(C(=O)N3CCCN(C4CCC4)CC3)C2)c(C)n1]

In a similar fashion (Route 20, GP I) 1-[(4-cyclobutyl-1,4-diazepan-1-yl)carbonyl]azetidin-3-ol (333 mg, 1.31 mmol) and 2-chloro-3,5-dimethylpyrazine (207 mg, 1.44 mmol) gave the title compound as brown oil after purification by FCC (297 mg, 63%).

LCMS data: Calculated MH+ (360); Found 97% (MH+) m/z 360, Rt=3.93 min (High pH method).

NMR data: $^1$H NMR (500 MHz, CDCl$_3$) δ ppm 7.71 (1 H, s), 5.25-5.32 (1 H, m), 4.36 (2 H, dd, J=9.8, 6.8 Hz), 4.02 (2 H, dd, J=9.8, 4.5 Hz), 3.45-3.50 (2 H, m), 3.43 (2 H, m), 2.84 (1 H, quin, J=7.9 Hz), 2.49-2.56 (2 H, m), 2.46-2.48 (3 H, s), 2.38-2.45 (5 H, m), 1.99-2.08 (2 H, m), 1.77-1.91 (4 H, m), 1.57-1.72 (2 H, m).

Example 79

Preparation of 1-({3-[(3-chloropyridin-4-yl)oxy]azetidin-1-yl}carbonyl)-4-cyclobutyl-1,4-diazepane. Potency range A

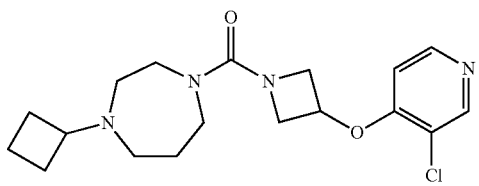 [SMILES: O=C(N1CCCN(C2CCC2)CC1)N1CC(Oc2ccncc2Cl)C1]

In a similar fashion (Route 20, GP I) 1-[(4-cyclobutyl-1,4-diazepan-1-yl)carbonyl]azetidin-3-ol (50 mg, 0.20 mmol) and 3,4-dichloropyridine (35 mg, 0.24) gave the title compound as colourless oil after purification by FCC (32 mg, 45%).

LCMS data: Calculated MH+ (365); Found 100% (MH+) m/z 365, Rt=2.11 min (High pH method).

NMR data: $^1$H NMR (500 MHz, CDCl$_3$) δ ppm 8.43 (1 H, s), 8.28 (1 H, d, J=5.5 Hz), 6.44 (1 H, d, J=5.5 Hz), 4.88-4.97 (1 H, m), 4.32 (2 H, dd, J=9.6, 6.6 Hz), 4.05 (2 H, dd, J=9.7, 4.2 Hz), 3.38-3.44 (2 H, m), 3.35 (2 H, m), 2.77 (1 H, m), 2.41-2.49 (2 H, m), 2.31-2.39 (2 H, m), 1.91-2.06 (2 H, m), 1.68-1.85 (4 H, m), 1.47-1.65 (2 H, m).

Example 80

Preparation of 1-({3-[(5-chloropyridin-3-yl)oxy]azetidin-1-yl}carbonyl)-4-cyclobutyl-1,4-diazepane. Potency range A

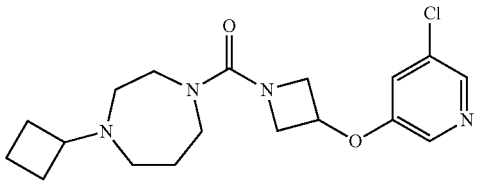 [SMILES: O=C(N1CCCN(C2CCC2)CC1)N1CC(Oc2cncc(Cl)c2)C1]

In a similar fashion (Route 20, GP I) 1-[(4-cyclobutyl-1,4-diazepan-1-yl)carbonyl]azetidin-3-ol (50 mg, 0.20 mmol) and 3,5-dichloropyridine (37 mg, 0.26 mmol) gave the title compound as brown oil after purification by FCC (36 mg, 52% yield).

LCMS data: Calculated MH+ (365); Found 100% (MH+) m/z 365, Rt=2.55 min.

NMR data: $^1$H NMR (500 MHz, CDCl$_3$) δ ppm 8.25 (1 H, d, J=2.0 Hz), 8.08 (1 H, d, J=2.4 Hz), 7.08 (1 H, t, J=2.2 Hz), 4.94 (1 H, m), 4.37 (2 H, dd, J=9.4, 6.5 Hz), 4.06 (2 H, dd J=9.7, 3.9 Hz), 3.35-3.56 (4 H, m), 2.89 (1 H, m), 2.39-2.58 (4 H, m), 2.01-2.11 (2 H, m), 1.82-1.92 (4 H, m), 1.69 (2 H, m).

Example 81

Preparation of 1-cyclobutyl-4-{[3-(pyridin-4-yloxy)azetidin-1-yl]carbonyl}-1,4-diazepane. Potency range A

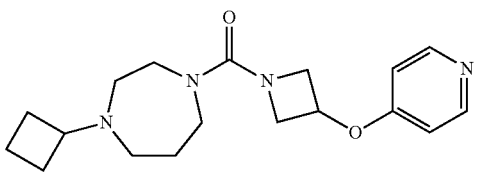 [SMILES: O=C(N1CCCN(C2CCC2)CC1)N1CC(Oc2ccncc2)C1]

In a similar fashion (Route 20, GP I) 1-[(4-cyclobutyl-1,4-diazepan-1-yl)carbonyl]azetidin-3-ol (315 mg, 1.24 mmol) and 4-chloropyridine (240 mg, 1.61 mmol) gave the title compound as pale yellow oil after purification by FCC (200 mg, 44% yield).

LCMS data: Calculated MH+ (330); Found 98% (MH+) m/z 330, Rt=3.47 mins (High pH method).

NMR data: $^1$H NMR (500 MHz, MeOD) δ ppm 8.39 (2 H, dd, J=4.9, 1.5 Hz), 6.93 (2 H, dd, J=4.9, 1.5 Hz), 5.09-5.16 (1 H, m), 4.47 (2 H, dd, J=9.6, 6.6 Hz), 4.04 (2 H, dd, J=9.8, 3.9

Hz), 3.42-3.51 (4 H, m), 2.88-2.98 (1 H, m), 2.53-2.61 (2 H, m), 2.45-2.54 (2 H, m), 2.05-2.13 (2 H, m), 1.82-1.94 (4 H, m), 1.62-1.76 (2 H, m).

Example 82

Preparation of 1-cyclobutyl-4-({3-[(5-methoxypyridin-3-yl)oxy]azetidin-1-yl}carbonyl)-1,4-diazepane. Potency range A

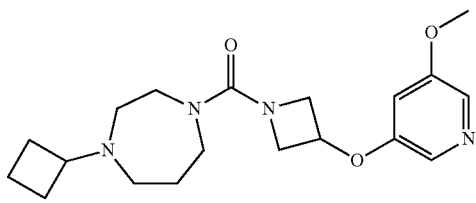 [SMILES: COc1cncc(OC2CN(C(=O)N3CCCN(C4CCC4)CC3)C2)c1]

In a similar fashion (Route 20, GP I) 1-[(4-cyclobutyl-1,4-diazepan-1-yl)carbonyl]azetidin-3-ol (260 mg, 1.03 mmol) and 3-chloro-5-methoxypyridine (191 mg, 1.34 mmol) gave the title compound as dark yellow oil after purification by preparative HPLC (54 mg, 15% yield).

LCMS data: Calculated MH$^+$ (360); Found 96% (MH$^+$) m/z 360, Rt=3.68 min (High pH method).

NMR data: $^1$H NMR (500 MHz, CDCl$_3$) δ ppm 8.00 (1 H, d, J=2.3 Hz), 7.76 (1 H, d, J=2.3 Hz), 6.62 (1 H, t, J=2.4 Hz), 4.94 (1 H, m), 4.29-4.41 (2 H, dd, J=9.5, 6.5 Hz), 4.05 (2 H, dd, J=9.4, 3.9 Hz), 3.85 (3 H, s), 3.56 (2 H, m), 3.42 (2 H, m), 2.93-3.05 (1 H, m), 2.44-2.84 (4 H, m), 1.93-2.15 (5 H, m), 1.54-1.80 (3 H, m).

Example 83

Preparation of 2-({1-[(4-cyclobutyl-1,4-diazepan-1-yl)carbonyl]azetidin-3-yl}oxy)-6-(cyclopropylcarbonyl)-5,6,7,8-tetrahydro-1,6-naphthyridine. Potency range A

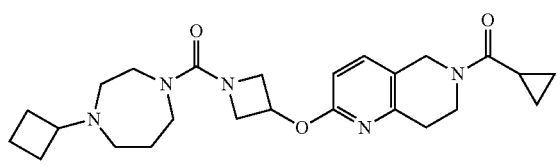 [SMILES: O=C(C1CC1)N1CCc2nc(OC3CN(C(=O)N4CCCN(C5CCC5)CC4)C3)ccc2C1]

In a similar fashion (Route 20, GP I) 1-[(4-cyclobutyl-1,4-diazepan-1-yl)carbonyl]azetidin-3-ol (32 mg, 0.13 mmol) and 2-chloro-6-(cyclopropylcarbonyl)-5,6,7,8-tetrahydro-1,6-naphthyridine (60 mg, 0.25 mmol) gave the title compound as orange oil after FCC (7 mg, 11%).

LCMS data: Calculated MH$^+$(454); Found 95% (MH$^+$) m/z 454, Rt=2.72 mins.

NMR data: $^1$H NMR (250 MHz, MeOD) δ ppm 7.42-7.58 (1 H, m), 6.63-6.75 (1 H, m), 5.23-5.40 (1 H, m), 4.55-4.69 (1 H, m), 4.38 (2 H, dd, J=9.4, 6.5 Hz), 3.92-4.10 (3 H, m), 3.79-3.91 (1 H, m), 3.38-3.51 (4 H, m), 2.72-2.98 (3 H, m), 2.60-2.70 (1 H, m), 2.39-2.61 (4 H, m), 1.97-2.14 (3 H, m), 1.76-1.93 (4 H, m), 1.58-1.74 (2 H, m), 0.76-0.97 (4 H, m).

Example 84

Preparation of 2-({1-[(4-cyclobutyl-1,4-diazepan-1-yl)carbonyl]azetidin-3-yl}oxy)-6-(cyclopropylacetyl)-5,6,7,8-tetrahydro-1,6-naphthyridine. Potency range A

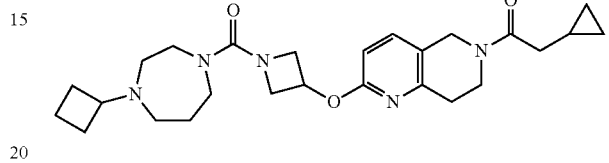

In a similar fashion (Route 20, GP I) 1-[(4-cyclobutyl-1,4-diazepan-1-yl)carbonyl]azetidin-3-ol (28 mg, 0.11 mmol) and 2-chloro-6-(cyclopropylacetyl)-5,6,7,8-tetrahydro-1,6-naphthyridine (56 mg, 0.22 mmol) gave the title compound after preparative HPLC (29 mg, 56%).

LCMS data: Calculated MH$^+$(468); Found (MH$^+$) m/z 468. The product eluted in the solvent front.

NMR data: $^1$H NMR (250 MHz, MeOD) δ ppm 8.17-8.34 (1 H, m), 7.37 (1 H, d, J=8.8 Hz), 5.44-5.62 (1 H, m), 4.60-5.04 (4 H, m), 3.90-4.15 (3 H, m), 3.65-3.84 (3 H, m), 3.41-3.63 (5 H, m), 2.81-3.22 (4 H, m), 2.02-2.51 (8 H, m), 1.71-1.98 (2 H, m), 0.94-1.17 (1 H, m), 0.44-0.68 (2 H, m), 0.10-0.32 (2 H, m).

Example 85

Preparation of 4-({1-[(4-cyclobutyl-1,4-diazepan-1-yl)carbonyl]azetidin-3-yl}oxy)-N-methylpyridine-3-carboxamide. Potency range A

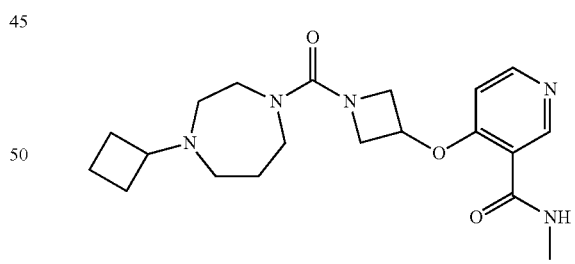

In a similar fashion (Route 20, GP I) 1-[(4-cyclobutyl-1,4-diazepan-1-yl)carbonyl]azetidin-3-ol (25 mg, 0.10 mmol), 4-chloro-N-methylpyridine-3-carboxamide (25 mg, 0.15 mmol) with KO$^t$Bu (13 mg, 0.12 mmol) gave the title compound after purification by FCC (23 mg, 59%).

LCMS data: Calculated MH$^+$ (388); Found 100% (MH$^+$) m/z 388, Rt=3.17 mins (High pH method).

NMR data: $^1$H NMR (500 MHz, MeOD) δ ppm 8.76 (1 H, s), 8.48 (1 H, d, J=6.0 Hz), 6.90 (1 H, d, J=6.0 Hz), 5.16-5.26 (1 H, m), 4.48 (2 H, dd, J=9.7, 6.6 Hz), 4.13 (2 H, dd, J=9.7, 4.0 Hz), 3.40-3.51 (4 H, m), 2.96 (3 H, s), 2.91 (1 H, quin, J=7.9 Hz), 2.52-2.62 (2 H, m), 2.40-2.50 (2 H, m), 1.99-2.12 (2 H, m), 1.78-1.96 (4 H, m), 1.57-1.75 (2 H, m).

Example 85a

Preparation of ethyl 5-({1-[(4-cyclobutyl-1,4-diazepan-1-yl)carbonyl]azetidin-3-yl}oxy)pyridine-2-carboxylate

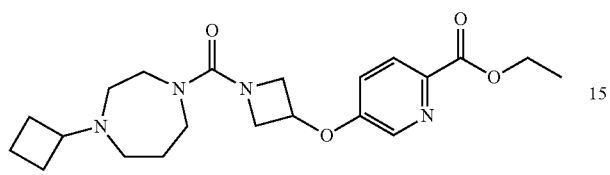

In a similar fashion (Route 20, GP I) 1-[(4-cyclobutyl-1,4-diazepan-1-yl)carbonyl]azetidin-3-ol (415 mg, 1.64 mmol) and ethyl 3-chloropyridine-2-carboxylate (530 mg, 2.87 mmol) gave the title compound after purification by FCC (124 mg, 65%).

LCMS data: Calculated MH$^+$(403); Found 98% (MH$^+$) m/z 403, Rt=0.9 min.

NMR data: $^1$H NMR (500 MHz, CDCl$_3$) δ ppm 8.30 (1 H, d, J=2.7 Hz), 8.12 (1 H, d, J=8.7 Hz), 7.11 (1 H, dd, J=8.7, 2.7 Hz), 4.94-5.06 (1 H, m), 4.41-4.51 (2 H, q, J=7.2 Hz), 4.38 (2 H, dd, J=9.5, 6.4 Hz), 4.07 (2 H, dd, J=9.6, 4.1 Hz), 3.37-3.51 (4 H, m), 2.84 (1 H, s), 2.48-2.58 (2 H, m), 2.38-2.48 (2 H, m), 1.98-2.11 (2 H, m), 1.75-1.92 (4 H, m), 1.59-1.74 (2 H, m), 1.44 (3 H, t, J=7.2 Hz).

Example 85b

Preparation of 1-cyclobutyl-4-{[3-(3-methyl-4-nitrophenoxy)azetidin-1-yl]carbonyl}-1,4-diazepane

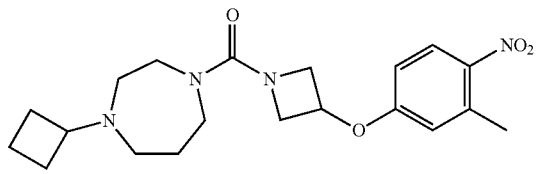 [SMILES: Cc1cc(OC2CN(C(=O)N3CCCN(C4CCC4)CC3)C2)ccc1[N+](=O)[O-]]

In a similar fashion (Route 20, GP I) 1-[(4-cyclobutyl-1,4-diazepan-1-yl)carbonyl]azetidin-3-ol (125 mg, 0.49 mmol) and 4-fluoro-2-methyl-1-nitrobenzene (115 mg, 0.74 mmol) gave the title compound as colourless oil after purification by FCC (124 mg, 65%).

LCMS data: Calculated MH$^+$(389); Found (MH$^+$) m/z 389, Rt=1.39 min.

NMR data: $^1$H NMR (500 MHz, CDCl$_3$) δ ppm 8.04-8.11 (1 H, m), 6.60-6.69 (2 H, m), 4.91-5.01 (1 H, m), 4.37 (2 H, dd, J=9.5, 6.6 Hz), 4.04 (2 H, dd, J=9.5, 4.1 Hz), 3.39-3.50 (4 H, m), 2.79-2.91 (1 H, m), 2.63 (3 H, s), 2.47-2.56 (2 H, m), 2.37-2.47 (2 H, m), 1.98-2.10 (2 H, m), 1.76-1.94 (4 H, m), 1.54-1.74 (2 H, m).

Route 21

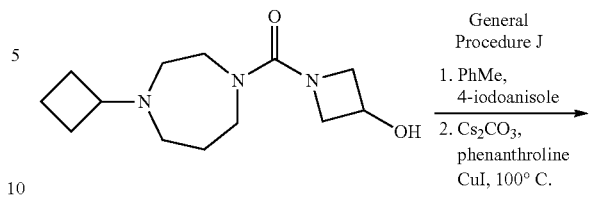

General Procedure J
1. PhMe, 4-iodoanisole
2. Cs$_2$CO$_3$, phenanthroline CuI, 100° C.

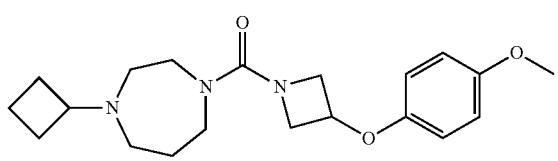

General Procedure J

Example 86

Preparation of 1-cyclobutyl-4-{[3-(4-methoxyphenoxy)azetidin-1-yl]carbonyl}-1,4-diazepane. Potency range A

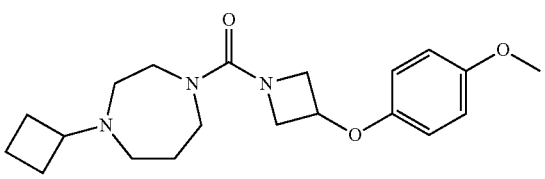 [SMILES: COc1ccc(OC2CN(C(=O)N3CCCN(C4CCC4)CC3)C2)cc1]

To a stirred suspension of 4-cyclobutyl-[1,4]diazepan-1-yl)-(3-hydroxy-azetidin-1-yl)-methanone (50 mg, 0.197 mmol) in toluene (2 ml) was added 4-iodoanisole (69 mg, 0.296 mmol), Cs$_2$CO$_3$ (128 mg, 0.394 mmol), CuI (3.7 mg, 0.0197 mmol) and 1,10-phenanthroline (7.1 mg, 0.04 mmol). The resulting mixture was heated at 100° C. overnight, then cooled to RT and filtered through a plug of silica gel, eluting with EtOAc. The filtrate was concentrated in vacuo and the residue purified by FCC [silica, eluting with DCM/MeOH/NH$_3$; 90:10:1] to provide the title compound as colourless oil (27 mg, 39%).

LCMS data: Calculated MH$^+$(360); Found 98% (MH$^+$) m/z 360, Rt=2.71 min.

NMR data: $^1$H NMR (360 MHz, MeOH) δ ppm 6.81-6.87 (2 H, m), 6.70-6.77 (2 H, m), 4.85-4.92 (1 H, m), 4.36 (2 H, dd, J=9.5, 6.4 Hz), 3.96 (2 H, dd, J=9.5, 4.1 Hz), 3.73 (3 H, s), 3.39-3.50 (4 H, m), 2.90-3.02 (1 H, m), 2.47-2.65 (4 H, m), 2.03-2.14 (2 H, m), 1.82-1.96 (4 H, m), 1.58-1.76 (2 H, m).

The following compounds were made as described in Route 21, General Procedure J above

Example 87

Preparation of 1-cyclobutyl-4-({3-[4-(1H-pyrazol-1-yl)phenoxy]azetidin-1-yl}carbonyl)-1,4-diazepane. Potency range A

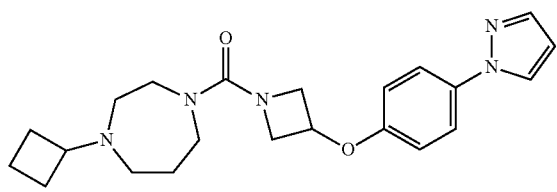 [SMILES: O=C(N1CCCN(C2CCC2)CC1)N1CC(Oc2ccc(-n3cccn3)cc2)C1]

In a similar fashion (Route 21, GP J), 1-[(4-cyclobutyl-1,4-diazepan-1-yl)carbonyl]azetidin-3-ol (50 mg, 0.19 mmol) and 1-(4-iodophenyl)-1H-pyrazole (69 mg, 0.26 mmol) gave the title compound as colourless oil after purification by preparative HPLC (41 mg, 41%).

LCMS data: Calculated MH$^+$(396); Found 100% (MH$^+$) m/z 396, Rt=2.82 min.

NMR data: $^1$H NMR (360 MHz, MeOH) δ ppm 8.10 (1 H, d, J=2.7 Hz), 7.69 (1 H, d, J=1.8 Hz), 7.61-7.67 (2 H, m), 6.90-6.97 (2 H, m), 6.50 (1 H, t, J=2.3 Hz), 5.00-5.08 (1 H, m), 4.46 (2 H, m), 3.85-4.16 (3 H, m), 3.64-3.76 (1 H, m), 3.38-3.61 (5 H, m), 2.88-3.07 (2 H, m), 2.05-2.38 (6 H, m), 1.72-1.92 (2 H, m).

Example 88

Preparation of 1-cyclobutyl-4-({3-[4-(trifluoromethoxy)phenoxy]azetidin-1-yl}carbonyl)-1,4-diazepane. Potency range A

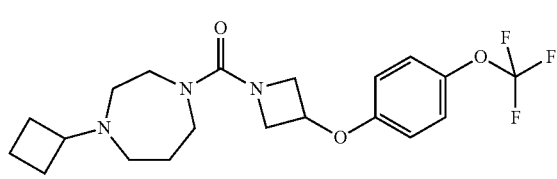 [SMILES: O=C(N1CCCN(C2CCC2)CC1)N1CC(Oc2ccc(OC(F)(F)F)cc2)C1]

In a similar fashion (Route 21, GP J) except for replacing phenanthroline with 3,4,7,8-tetramethylphenanthroline, 1-[(4-cyclobutyl-1,4-diazepan-1-yl)carbonyl]azetidin-3-ol (50 mg, 0.19 mmol) and 1-iodo-4-(trifluoromethoxy)benzene (86 mg, 0.3 mmol) gave the title compound as colourless oil after purification by preparative HPLC (44 mg, 52%).

LCMS data: Calculated MH$^+$(414); Found 100% (MH$^+$) m/z 414, Rt=3.15 min.

NMR data: $^1$H NMR (250 MHz, MeOD) δ ppm 7.14-7.29 (2 H, m), 6.81-6.97 (2 H, m), 4.98-5.09 (1 H, m), 4.28-4.62 (2 H, m), 3.81-4.20 (3 H, m), 3.63-3.82 (1 H, m), 3.34-3.62 (5 H, m), 2.82-3.15 (2 H, m), 1.99-2.45 (6 H, m), 1.65-1.99 (2 H, m).

Example 89

Preparation of 1-cyclobutyl-4-({3-[4-(difluoromethoxy)phenoxy]azetidin-1-yl}carbonyl)-1,4-diazepane. Potency range A

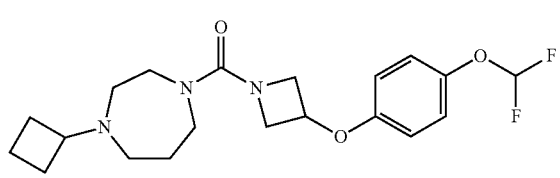 [SMILES: O=C(N1CCCN(C2CCC2)CC1)N1CC(Oc2ccc(OC(F)F)cc2)C1]

In a similar fashion (Route 21, GP J) except for replacing phenanthroline with 3,4,7,8-tetramethylphenanthroline, 1-[(4-cyclobutyl-1,4-diazepan-1-yl)carbonyl]azetidin-3-ol (50 mg, 0.19 mmol) and 1-(difluoromethoxy)-4-iodobenzene (81 mg, 0.3 mmol) gave the title compound as colourless oil after purification by preparative HPLC (47 mg, 57%).

LCMS data: Calculated MH$^+$(396); Found 100% (MH$^+$) m/z 396, Rt=2.92 min.

NMR data: $^1$H NMR (250 MHz, MeOD) δ ppm 7.04-7.14 (2 H, m), 6.78-6.88 (2 H, m), 6.69 (1 H, t), 4.97-5.03 (1 H, m), 4.28-4.60 (2 H, m), 3.82-4.16 (3 H, m), 3.63-3.81 (1 H, m), 3.35-3.62 (5 H, m), 2.83-3.13 (2 H, m), 2.03-2.42 (6 H, m), 1.67-1.95 (2 H, m).

Example 90

Preparation of 1-{[3-(4-chloro-2-fluorophenoxy)azetidin-1-yl]carbonyl}-4-cyclobutyl-1,4-diazepane. Potency range A

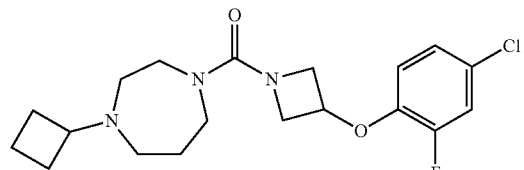

In a similar fashion (Route 21, GP J) except for replacing phenantroline with 3,4,7,8-tetramethylphenanthroline, 1-[(4-cyclobutyl-1,4-diazepan-1-yl)carbonyl]azetidin-3-ol (50 mg, 0.19 mmol) and 4-chloro-2-fluoro-1-iodobenzene (77 mg, 0.3 mmol) gave the title compound as colourless oil after purification by preparative HPLC (60 mg, 61%).

LCMS data: Calculated MH$^+$(382); Found 100% (MH$^+$) m/z 382, Rt=3.06 min.

NMR data: $^1$H NMR (250 MHz, MeOD) δ ppm 7.23 (1 H, dd, J=11.0, 2.4 Hz), 7.11 (1 H, dt, J=8.8, 1.9 Hz), 6.86 (1 H, t, J=8.8 Hz), 4.97-5.14 (1 H, m), 4.26-4.63 (2 H, m), 3.83-4.25

(3 H, m), 3.62-3.82 (1 H, m, J=8.3, 8.3, 8.3, 8.3 Hz), 3.52 (5 H, br. s.), 2.82-3.17 (2 H, m), 2.01-2.43 (6 H, m), 1.67-1.96 (2 H, m).

Example 91

Preparation of 1-cyclobutyl-4-{[3-(3-methoxyphenoxy)azetidin-1-yl]carbonyl}-1,4-diazepane. Potency range A

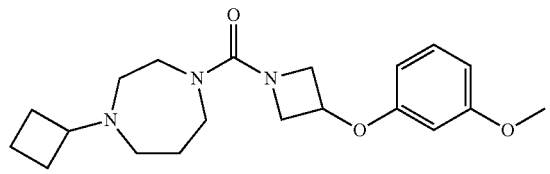 [SMILES: COc1cccc(OC2CN(C(=O)N3CCCN(C4CCC4)CC3)C2)c1]

In a similar fashion (Route 21, GP J), 1-[(4-cyclobutyl-1,4-diazepan-1-yl)carbonyl]azetidin-3-ol (50 mg, 0.19 mmol) and 1-iodo-3-methoxybenzene (69 mg, 0.3 mmol) gave the title compound as colourless oil after purification by preparative HPLC (6 mg, 6%).

LCMS data: Calculated MH$^+$(360); Found 100% (MH$^+$) m/z 360, Rt=2.76 min.

NMR data: $^1$H NMR (360 MHz, MeOH) δ ppm 7.12-7.22 (1 H, m), 6.51-6.58 (1 H, m), 6.32-6.40 (2 H, m), 4.93-5.01 (1 H, m), 4.28-4.57 (2 H, m), 3.84-4.15 (3 H, m), 3.65-3.79 (4 H, m), 3.35-3.59 (5 H, m), 2.87-3.08 (2 H, m), 2.01-2.40 (6 H, m), 1.70-1.92 (2 H, m).

Example 92

Preparation of 1-cyclobutyl-4-{[3-(2-methoxyphenoxy)azetidin-1-yl]carbonyl}-1,4-diazepane. Potency range A

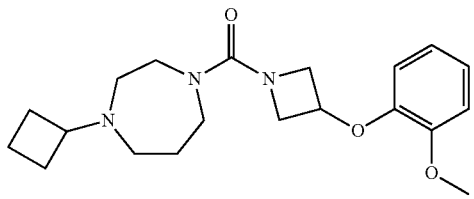 [SMILES: COc1ccccc1OC1CN(C(=O)N2CCCN(C3CCC3)CC2)C1]

In a similar fashion (Route 21, GP J), 1-[(4-cyclobutyl-1,4-diazepan-1-yl)carbonyl]azetidin-3-ol (50 mg, 0.19 mmol) and 1-iodo-2-methoxybenzene (69 mg, 0.3 mmol) gave the title compound as colourless oil after purification by preparative HPLC (24 mg, 26%).

LCMS data: Calculated MH$^+$ (360); Found 100% (MH$^+$) m/z 360, Rt=2.65 min.

NMR data: $^1$H NMR (360 MHz, MeOH) δ ppm 6.93-7.03 (2 H, m), 6.82-6.91 (1 H, m), 6.72 (1 H, d, J=7.7 Hz), 4.93-5.01 (1 H, m), 4.27-4.54 (2 H, m), 4.08-4.20 (1 H, m), 3.79-4.07 (5 H, m), 3.73 (1 H, quin, J=8.3 Hz), 3.37-3.61 (5 H, m), 2.88-3.09 (2 H, m), 2.00-2.41 (6 H, m), 1.73-1.95 (2 H, m).

Example 93

Preparation of 6-({1-[(4-cyclobutyl-1,4-diazepan-1-yl)carbonyl]azetidin-3-yl}oxy)-2-methylquinoline. Potency range A

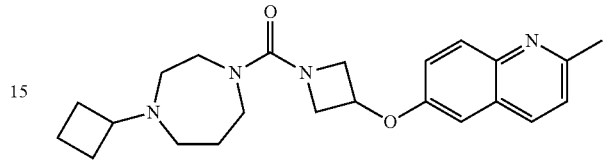

In a similar fashion (Route 21, GP J) except for replacing phenantroline with 3,4,7,8-tetramethylphenantroline, 1-[(4-cyclobutyl-1,4-diazepan-1-yl)carbonyl]azetidin-3-ol (128 mg, 0.51 mmol) and 6-bromo-2-methylquinoline (224 mg, 1.01 mmol) gave the title compound as brown oil after purification by FCC (52 mg, 25%).

LCMS data: Calculated MH$^+$(395); Found 100% (MH$^+$) m/z 395, Rt=4.02 min.

NMR data: $^1$H NMR (500 MHz, CDCl$_3$) δ ppm 7.88-7.98 (2 H, m), 7.28-7.33 (1 H, m), 7.26 (1 H, d, J=8.4 Hz), 6.78 (1 H, d, J=2.8 Hz), 4.98-5.05 (1 H, m), 4.42 (2 H, dd, J=9.3, 6.5 Hz), 4.11 (2 H, dd, J=9.4, 4.1 Hz), 3.37-3.56 (4 H, m), 2.86 (1 H, t, J=7.6 Hz), 2.72 (3 H, s), 2.50-2.60 (2 H, m), 2.32-2.49 (2 H, m), 1.99-2.10 (2 H, m), 1.77-1.93 (4 H, m), 1.55-1.74 (2 H, m).

Example 94

Preparation of 1-cyclobutyl-4-[(3-{[6-(trifluoromethyl)pyridin-3-yl]oxy}azetidin-1-yl)carbonyl]-1,4-diazepane. Potency range A

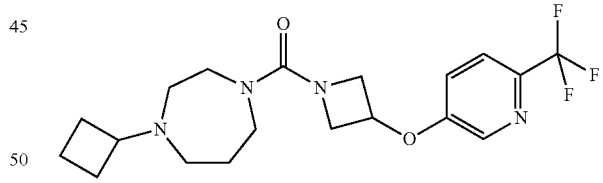

In a similar fashion (Route 21, GP J) except for replacing phenantroline with 3,4,7,8-tetramethylphenantroline, 1-[(4-cyclobutyl-1,4-diazepan-1-yl)carbonyl]azetidin-3-ol (50 mg, 0.20 mmol) and 5-bromo-2-trifluoromethylpyridine (59 mg, 0.26 mmol) gave the title compound as a brown oil after purification by preparative HPLC (15 mg, 14%).

LCMS data: Calculated MH$^+$(399); Found 100% (MH$^+$) m/z 399, Rt=2.81 min.

NMR data: $^1$H NMR (500 MHz, MeOD) δ ppm 8.32 (1 H, d, J=2.7 Hz), 7.77 (1 H, d, J=8.7 Hz), 7.42 (1 H, dd, J=8.6, 2.6 Hz), 5.14-5.21 (1 H, m), 4.54-4.61 (1 H, m), 4.38-4.47 (1 H, m), 4.11-4.20 (1 H, m), 4.00-4.08 (1 H, m), 3.88-3.97 (1 H, m), 3.72 (1 H, quin, J=8.4 Hz), 3.39-3.61 (5 H, m), 3.00 (2 H, m, J=10.9 Hz), 2.30-2.40 (2 H, m), 2.18-2.30 (3 H, m), 2.05-2.18 (1 H, m), 1.73-1.93 (2 H, m).

Route 22

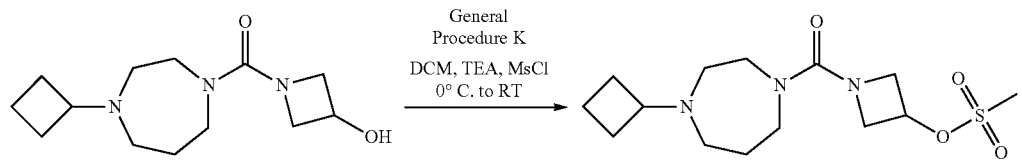

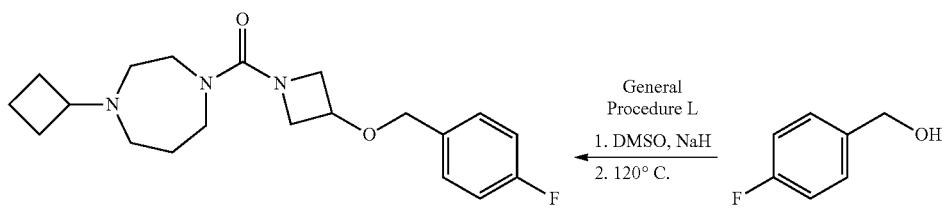

General Procedure K

Preparation of 1-[(4-cyclobutyl-1,4-diazepan-1-yl)carbonyl]azetidin-3-yl methanesulfonate

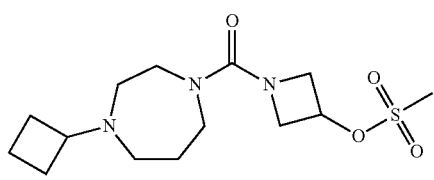 [SMILES: CS(=O)(=O)OC1CN(C(=O)N2CCCN(C3CCC3)CC2)C1]

To a stirred solution of 1-[(4-cyclobutyl-1,4-diazepan-1-yl)carbonyl]azetidin-3-ol (100 mg, 0.395 mmol) in DCM (5 ml) at 0° C. was added TEA (120 mg, 1.2 mmol) and methansulphonyl chloride (110 mg, 0.94 mmol). The mixture was stirred for 2 h at RT, then diluted with DCM (15 ml) and washed with saturated NaHCO$_3$ (10 ml). The organic layer was separated, dried (Na$_2$SO$_4$), filtered and concentrated providing the title compound as pale yellow solid (130 mg, 92%).

LCMS data: Calculated MH$^+$(332); Found 100% (MH$^+$) m/z 332, Rt=0.74 min.

NMR data: $^1$H NMR (360 MHz, chloroform-d) δ ppm 5.18-5.26 (1 H, m), 4.29 (2 H, dd, J=10.9, 6.8 Hz), 4.12 (2 H, dd, J=10.9, 4.5 Hz), 3.35-3.47 (4 H, m), 3.07 (3 H, s), 2.83 (1 H, quin, J=7.8 Hz), 2.47-2.54 (2 H, m), 2.36-2.45 (2 H, m), 1.98-2.09 (2 H, m), 1.74-1.91 (4 H, m), 1.55-1.73 (2 H, m).

General Procedure L

Example 95

Preparation of 1-cyclobutyl-4-({3-[(4-fluorobenzyl)oxy]azetidin-1-yl}carbonyl)-1,4-diazepane. Potency range A

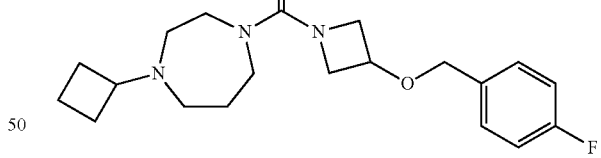

To a stirred solution of (4-fluorophenyl)methanol (27 mg, 0.2 mmol) in DMSO (1.5 mL) was added NaH (8.5 mg, 0.2 mmol, 60% purity) at RT. The mixture was stirred for 1 h and a solution of 1 1-[(4-cyclobutyl-1,4-diazepan-1-yl)carbonyl]azetidin-3-yl methanesulfonate (33 mg, 0.1 mmol) in DMSO (0.5 mL) was added. The resulting mixture was stirred at 100° C. overnight, cooled to RT and diluted with EtOAc. The crude mixture and washed with water/brine; 1/1 solution, dried (Na$_2$SO$_4$), filtered and concentrated at reduced pressure. Purification by preparative HPLC provided the title compound as colourless oil (8 mg, 18%).

LCMS data: Calculated MH$^+$(362); Found 100% (MH$^+$) m/z 362, Rt=2.79 min.

NMR data: $^1$H NMR (250 MHz, MeOD) δ ppm 7.29-7.44 (2 H, m), 7.00-7.15 (2 H, m), 4.47 (2 H, s), 4.32-4.43 (1 H, m), 4.02-4.31 (2 H, m), 3.63-4.01 (4 H, m), 3.34-3.62 (5 H, m), 2.86-3.09 (2 H, m), 1.96-2.43 (6 H, m), 1.68-1.96 (2 H, m).

The following compounds were made as described in Route 22, General Procedure L above

Example 96

Preparation of 1-cyclobutyl-4-[(3-methoxyazetidin-1-yl)carbonyl]-1,4-diazepane. Potency range A

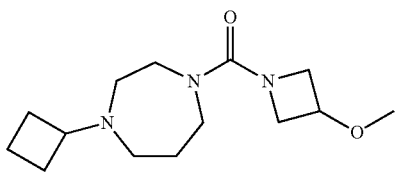 [SMILES: COC1CN(C(=O)N2CCCN(C3CCC3)CC2)C1]

In a similar fashion (Route 22, GP L), 1-[(4-cyclobutyl-1,4-diazepan-1-yl)carbonyl]azetidin-3-yl methanesulfonate (33 mg, 0.1 mmol) and sodium methoxide (11 mg, 0.2 mmol) gave the title compound as colourless oil after purification by preparative HPLC (8 mg, 20%).

LCMS data: Calculated MH$^+$(268); Found 100% (MH$^+$) m/z 268, Rt=3.43 min.

NMR data: $^1$H NMR (250 MHz, MeOD) δ ppm 4.04-4.35 (2 H, m), 3.67-3.99 (4 H, m), 3.34-3.67 (6 H, m), 3.29 (3 H, br. s.), 2.85-3.12 (2 H, m), 2.00-2.44 (6 H, m), 1.70-1.96 (2 H, m).

Route 23

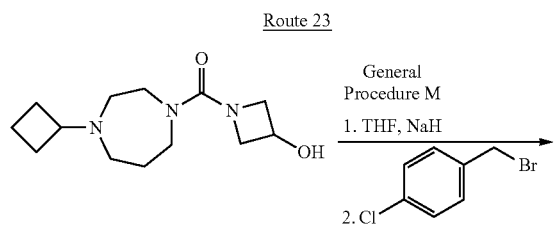

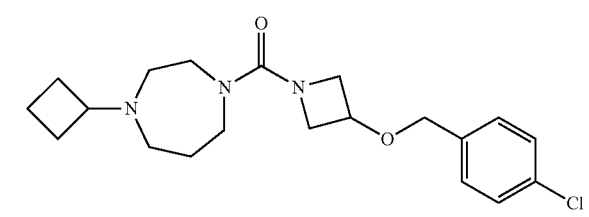

General Procedure M

Example 97

Preparation of 1-({3-[(4-chlorobenzyl)oxy]azetidin-1-yl}carbonyl)-4-cyclobutyl-1,4-diazepane. Potency range A

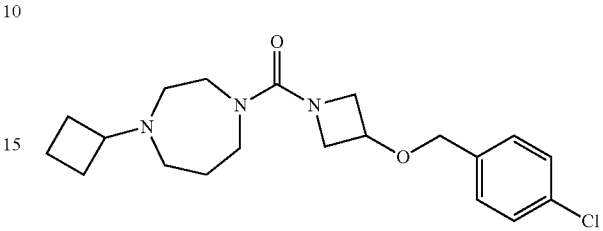

To a stirred solution of 1-[(4-cyclobutyl-1,4-diazepan-1-yl)carbonyl]azetidin-3-ol (40 mg, 0.158 mmol) in THF (3 mL) was added NaH (13 mg, 0.316 mmol, 60% in mineral oil). The suspension was stirred at RT for 1 h before 1-(bromomethyl)-4-chlorobenzene (65 mg, 0.316 mmol) was added in one portion. The resulting mixture was heated at 80° C. for 1 H, cooled to RT and concentrated at reduced pressure. The crude residue was dissolved in MeOH and filtered through a short pad of silica before purification by preparative HPLC to provide the title compound (31 mg, 40%) as colourless oil.

LCMS data: Calculated MH$^+$(378); Found 100% (MH$^+$) m/z 378, Rt=2.66 min.

$^1$H NMR (250 MHz, MeOD) δ ppm 7.35 (4 H, s), 4.47 (2 H, s), 4.33-4.43 (1 H, m), 4.19-4.32 (1 H, m), 4.03-4.18 (1 H, m), 3.77-4.02 (3 H, m), 3.62-3.77 (1 H, m), 3.37-3.60 (5 H, m), 2.81-3.09 (2 H, m), 2.02-2.44 (6 H, m), 1.65-1.96 (2 H, m).

The following compounds were made as described in Route 23, General Procedure M above.

Example 98

Preparation of 4-[({1-[(4-cyclobutyl-1,4-diazepan-1-yl)carbonyl]azetidin-3-yl}oxy)methyl]benzonitrile. Potency range A

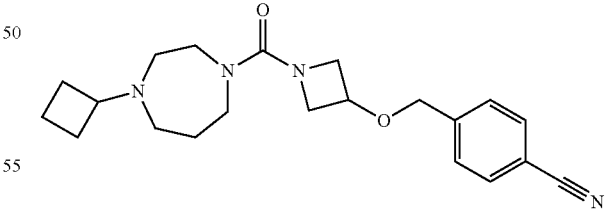

In a similar fashion (Route 23, GP M), 1-[(4-cyclobutyl-1,4-diazepan-1-yl)carbonyl]azetidin-3-ol (40 mg, 0.158 mmol) and 4-(bromomethyl)benzonitrile (62 mg, 0.158 mmol) gave the title compound as colourless oil after purification by preparative HPLC (17 mg, 22%).

LCMS data: Calculated MH$^+$(369); Found 99% (MH$^+$) m/z 369, Rt=2.66 min.

$^1$H NMR (250 MHz, MeOD) δ ppm 7.72 (2 H, d), 7.54 (2 H, d, J=8.5 Hz), 4.58 (2 H, s), 4.36-4.48 (1 H, m), 4.06-4.35

(2 H, m), 3.80-4.06 (3 H, m), 3.62-3.80 (1 H, m), 3.35-3.62 (5 H, m), 2.83-3.12 (2 H, m), 2.03-2.43 (6 H, m), 1.69-1.96 (2 H, m).

Example 99

Preparation of 1-cyclobutyl-4-{[3-(prop-2-yn-1-yloxy)azetidin-1-yl]carbonyl}-1,4-diazepane. Potency range A

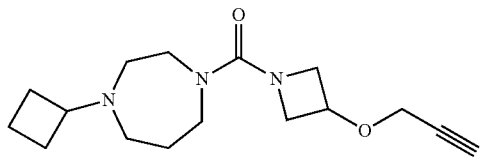 [SMILES: C#CCOC1CN(C(=O)N2CCCN(C3CCC3)CC2)C1]

In a similar fashion (Route 23, GP M), 1-[(4-cyclobutyl-1,4-diazepan-1-yl)carbonyl]azetidin-3-ol (52 mg, 0.20 mmol) and propargyl bromide (60 µl of a 80% wt solution in toluene, 0.23 mmol) gave the title compound as yellow oil after purification by preparative HPLC (10 mg, 17%).

LCMS data: Calculated MH$^+$(292); Found 100% (MH$^+$) m/z 292, Rt=3.67 min.

NMR data: $^1$H NMR (250 MHz, MeOD) δ ppm 4.37-4.52 (1 H, m), 4.11-4.25 (4 H, m), 3.90 (2 H, dd, J=9.3, 4.3 Hz), 3.36-3.50 (4 H, m), 2.81-2.99 (2 H, m), 2.40-2.61 (4 H, m), 1.98-2.15 (2 H, m), 1.76-1.96 (4 H, m), 1.55-1.76 (2 H, m).

Preparation of bis(1-methylethyl) 3,3-dimethoxycyclobutane-1,1-dicarboxylate

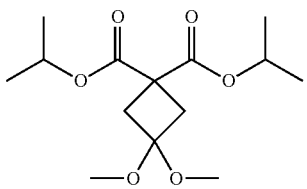 [SMILES: COC1(OC)CC(C(=O)OC(C)C)(C(=O)OC(C)C)C1]

To a stirred suspension of NaH (11.7 g, 293 mmol, 60% purity) in DMF (100 ml) was added diisopropylmalonic ester dropwise, keeping the temperature below 40° C. The resulting mixture was stirred for 1 h at RT and then 1,3-dibromo-2,2-dimethoxypropane (34.8 g, 133 mmol) was added in one portion. The resulting mixture was heated at 140° C. for 24 h and then cooled to RT. Saturated NH$_4$Cl aqueous (400 ml) was added and the mixture extracted with hexane (2×190 ml). The combined organic phases were washed with H$_2$O (2×250 ml) saturated NaHCO$_3$ (2×250 ml), H$_2$O (2×250 ml) and brine (250 ml). The organic phase was dried (Na$_2$SO$_4$), filtered and concentrated at reduced pressure to provide an orange oil. Purification by in vacuo distillation to remove excess of 1,3-dibromo-2,2-dimethoxypropane (b.p. 60-62° C., 0.1 mmHg) and diisopropylmalonic ester (b.p 78-80° C., 0.1 mmHg) provided the title compound (20 g, 52%) as Route 24

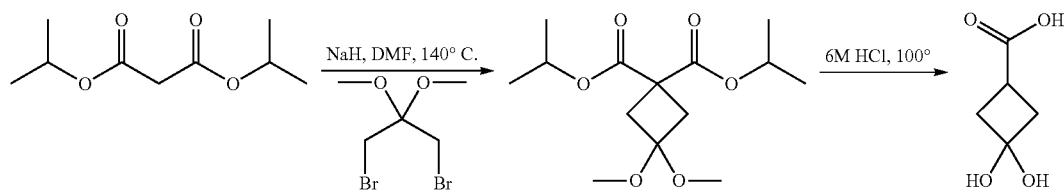

General Procedure N

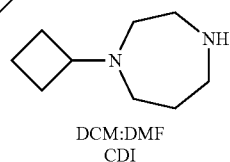

DCM:DMF
CDI

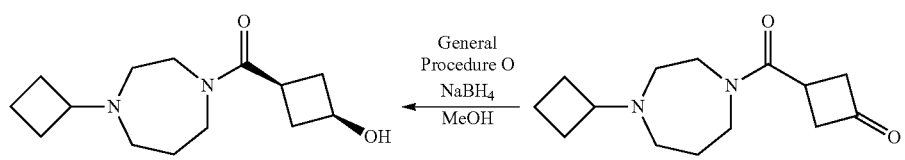

General Procedure O
NaBH$_4$
MeOH

MS data: Calculated MH$^+$(289); Found 100% (MH$^+$) m/z 289.

NMR data: $^1$H NMR (360 MHz, CHLOROFORM-d) δ ppm 5.07 (2 H, spt, J=6.3 Hz), 3.16 (6 H, s), 2.70 (4 H, s), 1.24 (12 H, d, J=6.4 Hz).

Preparation of 3,3-dihydroxycyclobutanecarboxylic acid

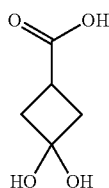

To a stirred solution of 20% HCl (7 ml) was added bis(1-methylethyl) 3,3-dimethoxycyclobutane-1,1-dicarboxylate (2.5 g, 8.7 mmol) at RT. The resulting mixture was heated at 100° C. overnight and then cooled to RT and extracted with diethyl ether (3×20 ml). The organic phases were combined, dried (Na$_2$SO$_4$), filtered and concentrated at reduced pressure. The resulting light brown oil was slurried in DCM (2 ml) and the resulting solid collected by filtration, washed with pentane and dried at reduced pressure to yield a pale brown solid (530 mg, 47%).

LCMS data: Calculated MH$^+$(133); compound below 150 amu detection limit.

NMR data: $^1$H NMR (250 MHz, CHLOROFORM-d) δ ppm 3.07-3.43 (5 H, m).

General Procedure N

Example 100

Preparation of 3-[(4-cyclobutyl-1,4-diazepan-1-yl)carbonyl]cyclobutanone. Potency range A

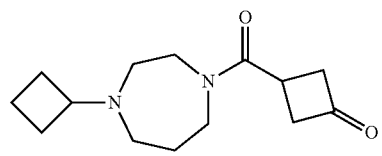 [SMILES: O=C1CC(C(=O)N2CCCN(C3CCC3)CC2)C1]

To a stirred solution of 3,3-dihydroxycyclobutanecarboxylic acid (80 mg, 0.61 mmol) in 4:1 DCM/DMF (2.5 ml) was added CDI (103 mg, 0.64 mmol) at RT. The mixture was stirred for 1.5 h at RT and 1-cyclobutyl-1,4-diazepane (98 mg, 0.64 mmol) was added. The resulting solution was stirred at RT for 3 H, diluted with DCM (20 ml) and washed with 1:1 H$_2$O/brine (20 ml). The organic layer was dried (Na$_2$SO$_4$), filtered and concentrated at reduced pressure. Purification by silica gel FCC (eluting with DCM/MeOH/NH$_3$ 90:10:1) provided the title compound as colourless oil (84 mg, 56%).

LCMS data: Calculated MH$^+$(251); Found 100% (MH$^+$) m/z 251, Rt=1.31 min.

NMR data: $^1$H NMR (250 MHz, CHLOROFORM-d) δ ppm 3.63-3.74 (2 H, m), 3.45-3.62 (4 H, m), 3.27-3.43 (1 H, m), 3.09-3.26 (2 H, m), 2.78-2.95 (1 H, m), 2.37-2.58 (4 H, m), 1.97-2.13 (2 H, m), 1.53-1.97 (6 H, m).

General Procedure O

Example 101

Preparation of cis-3-[(4-cyclobutyl-1,4-diazepan-1-yl)carbonyl]cyclobutanol. Potency range B

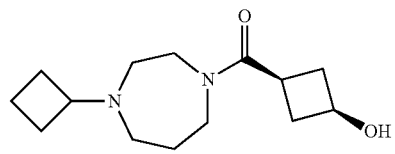 [SMILES: O=C([C@H]1C[C@@H](O)C1)N1CCCN(C2CCC2)CC1]

To a stirred solution of 3-[(4-cyclobutyl-1,4-diazepan-1-yl)carbonyl]cyclobutanone (50 mg, 0.2 mmol) in MeOH (2.5 ml) at 0° C. was added NaBH$_4$ (3.7 mg, 0.1 mmol). After 10 mins the reaction mixture was warmed to RT and stirred for a further 1 h. The solvent was evaporated in vacuuo and the crude solid was partitioned between DCM and 0.5 M NaOH. The organic phase was separated, dried (Na$_2$SO$_4$), filtered and concentrated at reduced pressure. The resulting yellow oil was purified by silica gel FCC (eluant DCM.MeOH/NH$_3$ 90:10:1) to provide the title compound as off white solid (35 mg, 70%).

LCMS data: Calculated MH$^+$(253); Found 100% (MH$^+$) m/z 253, Rt=3.10 min.

NMR data: $^1$H NMR (250 MHz, CHLOROFORM-d) δ ppm 4.06-4.24 (1 H, m), 3.00-3.66 (5 H, m), 2.66-2.91 (2 H, m), 2.34-2.62 (6 H, m), 2.15-2.32 (2 H, m), 1.94-2.10 (2 H, m), 1.50-1.92 (6 H, m).

The following compounds were made as described in Route 20, General Procedure I above.

Example 102

Preparation of 6-({cis-3-[(4-cyclobutyl-1,4-diazepan-1-yl)carbonyl]cyclobutyl}oxy)-N-methylpyridine-3-carboxamide. Potency range A

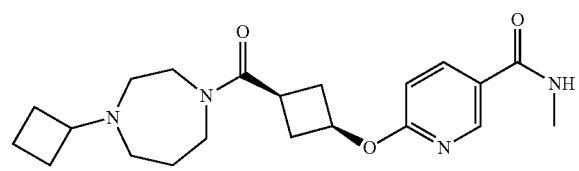 [SMILES: CNC(=O)c1ccc(O[C@H]2C[C@@H](C(=O)N3CCCN(C4CCC4)CC3)C2)nc1]

In a similar fashion (Route 20, GP I), cis-3-[(4-cyclobutyl-1,4-diazepan-1-yl)carbonyl]cyclobutanol (40 mg, 0.16 mmol) and 6-chloro-N-methylpyridine-3-carboxamide (35 mg, 0.21 mmol) gave the title compound as colourless oil after purification by silica FCC (12 mg, 20%).

LCMS data: Calculated MH$^+$(387); Found 100% (MH$^+$) m/z 387, Rt=2.26 min.

NMR data: $^1$H NMR (250 MHz, CHLOROFORM-d) δ ppm 8.54 (1 H, d, J=2.4 Hz), 7.98 (1 H, dd, J=8.7, 2.4 Hz), 6.71 (1 H, d, J=8.7 Hz), 6.29-6.46 (1 H, m), 5.07-5.24 (1 H, m), 3.54-3.68 (2 H, m), 3.39-3.53 (2 H, m), 2.99 (3 H, d, J=4.9 Hz), 2.79-2.95 (2 H, m), 2.61-2.79 (2 H, m), 2.35-2.54 (6 H, m), 1.50-2.10 (9 H, m).

Example 103

Preparation of 4-({cis-3-[(4-cyclobutyl-1,4-diazepan-1-yl)carbonyl]cyclobutyl}oxy)benzonitrile. Potency range A

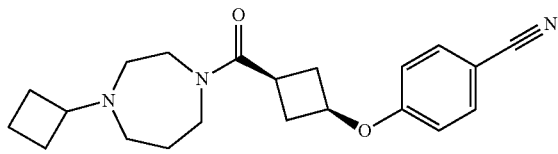 [SMILES: N#Cc1ccc(O[C@H]2C[C@@H](C(=O)N3CCCN(C4CCC4)CC3)C2)cc1]

In a similar fashion (Route 20, GP I), cis-3-[(4-cyclobutyl-1,4-diazepan-1-yl)carbonyl]cyclobutanol (30 mg, 0.12 mmol) and 4-fluorobenzonitrile (17 mg, 0.14 mmol) gave the title compound as white solid after purification by silica FCC (8 mg, 20%).

LCMS data: Calculated MH+(354); Found 94% (MH+) m/z 354, Rt=2.83 min.

NMR data: $^1$H NMR (500 MHz, CDCl$_3$) δ ppm 7.56 (2 H, d, J=8.8 Hz), 6.85 (2 H, d, J=8.8 Hz), 4.65 (1 H, m), 3.57-3.70 (2 H, m), 3.42-3.54 (2 H, m), 2.77-3.00 (2 H, m), 2.64-2.76 (2 H, m), 2.44-2.62 (4 H, m), 2.34-2.44 (2 H, m), 1.99-2.09 (2 H, m), 1.74-1.94 (4 H, m), 1.54-1.74 (2 H, m).

Example 104

Preparation of 1-cyclobutyl-4-[(cis-3-{[5-(trifluoromethyl)pyridin-2-yl]oxy}cyclobutyl)carbonyl]-1,4-diazepane. Potency range A

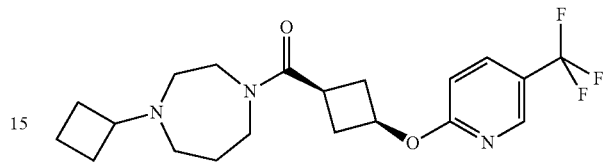

In a similar fashion (Route 20, GP I), cis-3-[(4-cyclobutyl-1,4-diazepan-1-yl)carbonyl]cyclobutanol (30 mg, 0.12 mmol) and 2-chloro-5-(trifluoromethyl)pyridine (26 mg, 0.14 mmol) gave the title compound as colourless oil after purification by silica FCC (15 mg, 31%).

LCMS data: Calculated MH+(398); Found 97% (MH+) m/z 398, Rt=3.04 min.

NMR data: $^1$H NMR (500 MHz, CDCl$_3$) δ ppm 8.39 (1 H, s), 7.75 (1 H, dd, J=8.7, 2.1 Hz), 6.78 (1 H, d, J=8.8 Hz), 5.14-5.24 (1 H, m), 3.58-3.68 (2 H, m), 3.45-3.52 (2 H, m), 2.79-2.98 (2 H, m), 2.67-2.78 (2 H, m), 2.45-2.58 (4 H, m), 2.36-2.44 (2 H, m), 1.99-2.10 (2 H, m), 1.74-1.92 (4 H, m), 1.55-1.73 (2 H, m).

Route 25

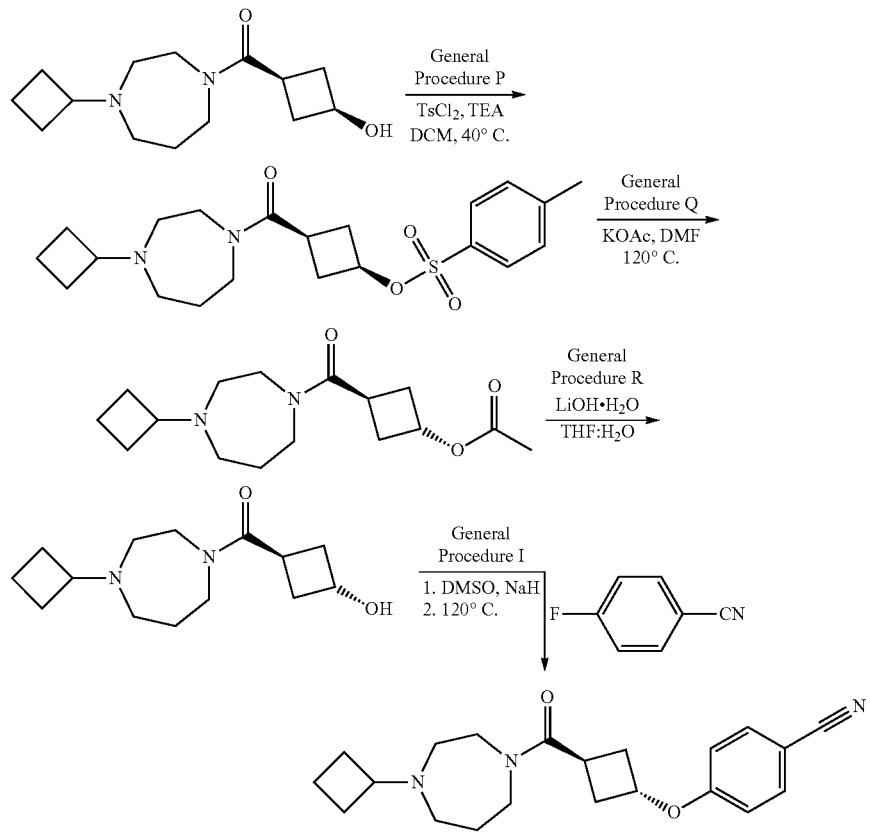

General Procedure P

Preparation of cis-3-[(4-cyclobutyl-1,4-diazepan-1-yl)carbonyl]cyclobutyl 4-methylbenzenesulfonate

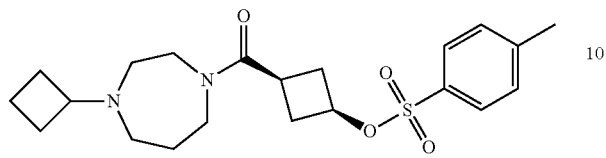

To a stirred solution of cis-3-[(4-cyclobutyl-1,4-diazepan-1-yl)carbonyl]cyclobutanol (50 mg, 0.19 mmol) in DCM (2 ml) at RT was added triethylamine (77 mg, 0.7 mmol) and toluene-4-sulfonyl chloride (108 mg, 0.57 mmol). The mixture was stirred at RT for 1 h and then at 35° C. for 2 h. After cooling to RT and dilution with DCM the mixture was washed with 1:1 $H_2O$/saturated $NaHCO_3$. The organic layer was dried ($Na_2SO_4$), filtered and concentrated at reduced pressure. Purification by silica FCC (eluting with DCM/MeOH/$NH_3$ 90:10:1) provided the title compound as colourless oil (73 mg, 91%).

LCMS data: Calculated $MH^+$(407); Found 100% ($MH^+$) m/z 407, Rt=1.36 min.

NMR data: $^1H$ NMR (250 MHz, CHLOROFORM-d) δ ppm 7.76 (2 H, d, J=8.4 Hz), 7.32 (2 H, d, J=7.9 Hz), 4.77 (1 H, m, J=7.6, 7.6, 7.6, 7.6, 1.6 Hz), 3.50-3.60 (2 H, m), 3.30-3.41 (2 H, m), 2.62-2.88 (2 H, m), 2.29-2.52 (11 H, m), 1.92-2.07 (2 H, m), 1.49-1.87 (6 H, m).

General Procedure Q

Example 104a

Preparation of trans-3-[(4-cyclobutyl-1,4-diazepan-1-yl)carbonyl]cyclobutyl acetate

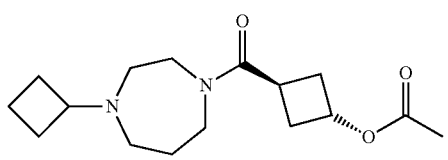

To a stirred solution cis-3-[(4-cyclobutyl-1,4-diazepan-1-yl)carbonyl]cyclobutyl 4-methylbenzenesulfonate (73 mg, 0.18 mmol) in DMF (3 ml) at RT was added potassium acetate (108 mg, 1.1 mmol). The mixture was heated at 110° C. overnight and then cooled to RT and diluted with DCM. The resulting mixture was washed with 1:1 $H_2O$/brine and the organic phase dried ($Na_2SO_4$), filtered and concentrated at reduced pressure to yield the title compound (50 mg, 94%), which was used without further purification.

LCMS data: Calculated $MH^+$(295); Found 100% ($MH^+$) m/z 295, Rt=0.9 min.

NMR data: $^1H$ NMR (250 MHz, CHLOROFORM-d) δ ppm 4.95-5.08 (1 H, m), 3.50-3.61 (2 H, m), 3.18-3.37 (3 H, m), 2.58-2.85 (3 H, m), 2.12-2.46 (6 H, m), 1.89-2.04 (5 H, m), 1.45-1.87 (6 H, m).

General Procedure R

Example 105

Preparation of trans-3-[(4-cyclobutyl-1,4-diazepan-1-yl)carbonyl]cyclobutanol. Potency range A

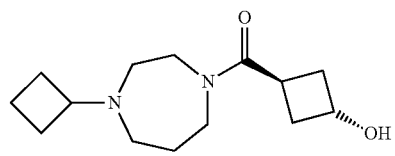

To a stirred solution trans-3-[(4-cyclobutyl-1,4-diazepan-1-yl)carbonyl]cyclobutyl acetate (50 mg, 0.17 mmol) in 5:1 THF/$H_2O$ (93 ml) at RT was added $LiOH.H_2O$ (8.5 mg, 0.2 mmol). The mixture was stirred at RT overnight, diluted with $H_2O$ and extracted with DCM. The organic layer was then dried ($Na_2SO_4$), filtered and concentrated at reduced pressure to yield the title compound as pale yellow oil (40 mg, 93%).

LCMS data: Calculated $MH^+$(253); Found 100% ($MH^+$) m/z 253, Rt=3.07 min.

NMR data: $^1H$ NMR (250 MHz, CHLOROFORM-d) δ ppm 4.45-4.59 (1 H, m), 3.57-3.68 (2 H, m), 3.36-3.45 (2 H, m), 3.18-3.32 (1 H, m), 2.77-2.93 (1 H, m), 2.54-2.69 (2 H, m), 2.34-2.52 (4 H, m), 1.96-2.24 (4 H, m), 1.55-1.93 (7 H, m).

The following compounds were made as described in Route 20, General Procedure I above.

Example 106

Preparation of 4-({trans-3-[(4-cyclobutyl-1,4-diazepan-1-yl)carbonyl]cyclobutyl}oxy)benzonitrile. Potency range A

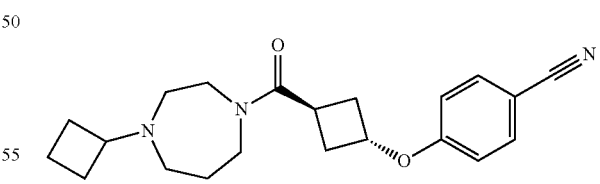

In a similar fashion (Route 20, GP I), trans-3-[(4-cyclobutyl-1,4-diazepan-1-yl)carbonyl]cyclobutanol (33 mg, 0.13 mmol) and 4-fluorobenzonitrile (19 mg, 0.16 mmol) gave the title compound as yellow oil after purification by silica FCC (13 mg, 28%).

LCMS data: Calculated $MH^+$(354); Found 94% ($MH^+$) m/z 354, Rt=2.83 min.

NMR data: $^1H$ NMR (500 MHz, $CDCl_3$) δ ppm 7.56 (2 H, d, J=8.6 Hz), 6.84 (2 H, d, J=8.6 Hz), 4.83-4.93 (1 H, m), 3.59-3.70 (2 H, m), 3.34-3.50 (3 H, m), 2.82 (3 H, m), 2.49 (2 H, m), 2.34-2.45 (4 H, m), 2.03 (2 H, m), 1.74-1.93 (4 H, m), 1.55-1.71 (2 H, m).

Example 107

Preparation of 1-cyclobutyl-4-[(trans-3-{[5-(trifluoromethyl)pyridin-2-yl]oxy}cyclobutyl)carbonyl]-1,4-diazepane. Potency range A

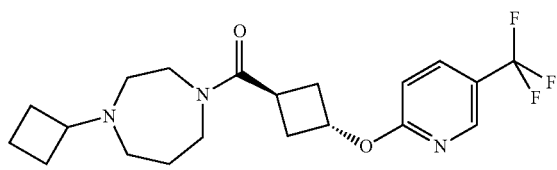 [SMILES: O=C([C@H]1C[C@H](Oc2ccc(C(F)(F)F)cn2)C1)N1CCCN(C2CCC2)CC1]

In a similar fashion (Route 20, GP I), trans-3-[(4-cyclobutyl-1,4-diazepan-1-yl)carbonyl]cyclobutanol (33 mg, 0.13 mmol) and 2-chloro-5-(trifluoromethyl)pyridine (29 mg, 0.16 mmol) gave the title compound as colourless oil after purification by silica FCC (12 mg, 24%).

LCMS data: Calculated MH$^+$ (398); Found 94% (MH$^+$) m/z 398, Rt=3.08 min.

NMR data: $^1$H NMR (500 MHz, CDCl$_3$) δ ppm 8.41 (1 H, s), 7.76 (1 H, dd, J=8.6, 2.0 Hz), 6.79 (1 H, d, J=8.8 Hz), 5.35 (1 H, m), 3.59-3.71 (2 H, m), 3.32-3.46 (3 H, m), 2.79-2.91 (3 H, m), 2.46-2.54 (2 H, m), 2.32-2.46 (4 H, m), 1.98-2.08 (2 H, m), 1.74-1.94 (4 H, m), 1.54-1.72 (2 H, m).

Route 26

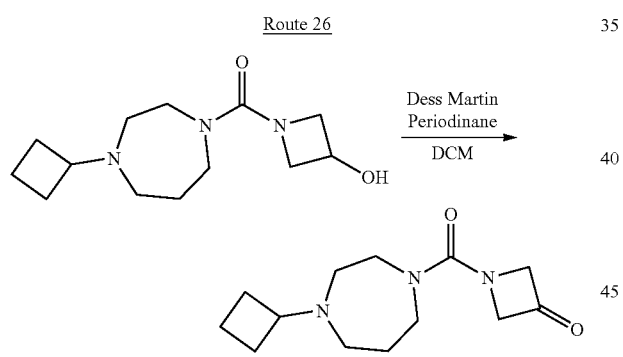

Example 108

Preparation of 1-[(4-cyclobutyl-1,4-diazepan-1-yl)carbonyl]azetidin-3-one. Potency range A

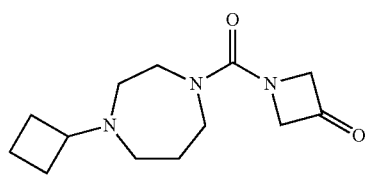 [SMILES: O=C1CN(C(=O)N2CCCN(C3CCC3)CC2)C1]

To a stirred solution of 1-[(4-cyclobutyl-1,4-diazepan-1-yl)carbonyl]azetidin-3-ol (27 mg, 0.11 mmol) in dichloromethane (2 ml) was added Dess Martin periodinane (80 mg, 0.19 mmol) at room temperature. The mixture was stirred for 3 hours and then concentrated and purified by FCC (eluting with DCM/MeOH/NH$_3$ gradient 95:5:1 to 90:10:1) to provide the title compound as colourless oil (17 mg, 63%).

LCMS data: Calculated MH$^+$ (252); Found 86% (MH$^+$) m/z 252, Rt=3.26 min.

NMR data: $^1$H NMR (250 MHz, CDCl$_3$) δ ppm 3.53-3.61 (2 H, m), 3.41-3.52 (2 H, m), 2.83-3.02 (1 H, m), 2.62-2.73 (2 H, m), 2.48-2.60 (2 H, m), 1.86-2.15 (8 H, m), 1.51-1.81 (2 H, m).

Route 27

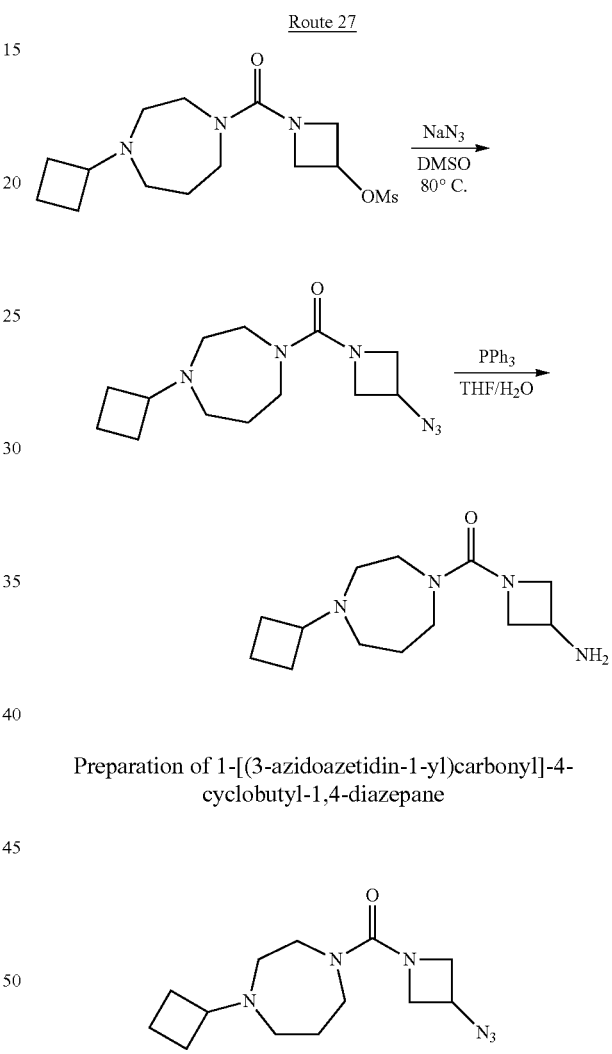

Preparation of 1-[(3-azidoazetidin-1-yl)carbonyl]-4-cyclobutyl-1,4-diazepane

1-[(4-cyclobutyl-1,4-diazepan-1-yl)carbonyl]azetidin-3-yl methanesulfonate (200 mg, 0.61 mmol) was dissolved in DMSO (4 ml) and sodium azide (157 mg, 2.41 mmol) was added. The reaction was heated at 80° C. for 48 hours and then diluted with DCM (30 ml) and washed with water (10 ml), dried (MgSO$_4$), filtered and concentrated at reduced pressure giving a yellow solid (140 mg, 83%), which was used directly in the next step.

LCMS data: Calculated MH$^+$ (279); Found 100% (MH$^+$) m/z 279, Rt=0.65 min.

NMR data: $^1$H NMR (250 MHz, MeOD) δ ppm 4.19-4.40 (3 H, m), 3.88 (2 H, dd, J=8.9, 3.7 Hz), 3.36-3.49 (4 H, m), 2.91 (1 H, m), 2.51-2.60 (2 H, m), 2.41-2.51 (2 H, m), 2.06 (2 H, m), 1.76-2.00 (4 H, m), 1.56-1.76 (2 H, m).

Example 109

Preparation of 1-[(4-cyclobutyl-1,4-diazepan-1-yl) carbonyl]azetidin-3-amine. Potency range A

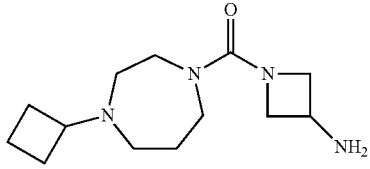 [SMILES: NC1CN(C(=O)N2CCCN(C3CCC3)CC2)C1]

1-[(3-azidoazetidin-1-yl)carbonyl]-4-cyclobutyl-1,4-diazepane (140 mg, 0.50 mmol), was dissolved in THF (5 ml) and water (0.28 ml, 5 mmol) was added. PPh₃ was then added as a solid and the reaction was stirred for 16 hours giving a clear solution. The reaction was concentrated in vacuo and purified by FCC (DCM/MeOH/MH₃ gradient, 95:5:1 to 70:30:1) to provide the title compound as pale yellow solid (51 mg, 40%).

LCMS data: Calculated MH⁺(253); Found 99% (MH⁺) m/z 253, Rt=2.94 min (High pH method).

NMR data: ¹H NMR (500 MHz, MeOD) δ ppm 4.11-4.21 (2 H, m), 3.66-3.75 (3 H, m), 3.38-3.48 (4 H, m), 2.88-2.98 (1 H, m), 2.53-2.60 (2 H, m), 2.42-2.52 (2 H, m), 2.02-2.12 (2 H, m), 1.81-1.93 (4 H, m), 1.61-1.76 (2 H, m).

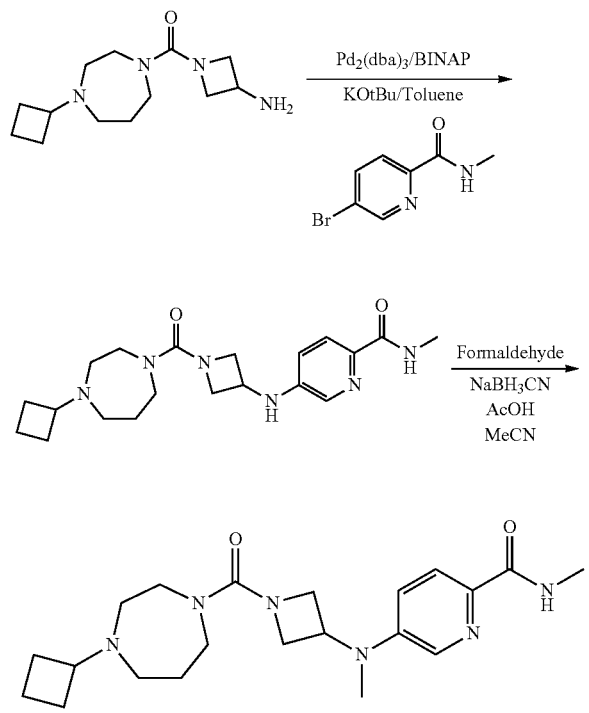

Example 110

Preparation of 5-({1-[(4-cyclobutyl-1,4-diazepan-1-yl)carbonyl]azetidin-3-yl}amino)-N-methylpyridine-2-carboxamide. Potency range A

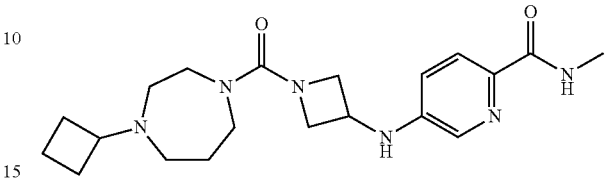

To a solution of 1-[(4-cyclobutyl-1,4-diazepan-1-yl)carbonyl]azetidin-3-amine (22 mg, 87 μmol) in degassed toluene (2 ml) was added 5-bromo-N-methylpyridine-2-carboxamide (19 mg, 87 μmol), racemic BINAP (8 mg, 13 μmol), ᵗBuOK (12 mg, 0.10 mmol), followed by Pd₂(dba)₃ (8 mg, 9 μmol). The reaction was heated at 100° C. for 16 hours, concentrated and purified by FCC (DCM/MeOH/NH₃ gradient, 98:2:1 to 95:5:1) giving the title compound as colourless oil (26 mg, 78%).

LCMS data: Calculated MH⁺ (387); Found 96% (MH⁺) m/z 387, Rt=2.22 min (High pH method).

NMR data: ¹H NMR (500 MHz, MeOD) δ ppm 7.94 (1 H, d, J=2.4 Hz), 7.84 (1 H, d, J=8.6 Hz), 6.92 (1 H, dd, J=8.6, 2.6 Hz), 4.34-4.41 (2 H, m), 4.25-4.33 (1 H, m), 3.84 (2 H, dd, J=8.3, 5.0 Hz), 3.40-3.49 (4 H, m), 2.86-2.97 (4 H, m), 2.52-2.60 (2 H, m), 2.44-2.52 (2 H, m), 2.03-2.11 (2 H, m), 1.79-1.91 (4H, m), 1.59-1.75 (2 H, m).

Example 111

Preparation of 5-[{1-[(4-cyclobutyl-1,4-diazepan-1-yl)carbonyl]azetidin-3-yl}(methyl)amino]-N-methylpyridine-2-carboxamide. Potency range A

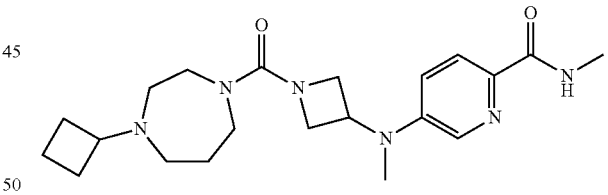

5-({1-[(4-cyclobutyl-1,4-diazepan-1-yl)carbonyl]azetidin-3-yl}amino)-N-methylpyridine-2-carboxamide (34 mg, 92 μmol) was dissolved in 1:1 MeCN/water (3 ml) and formaldehyde (50 μl of a 37% wt. soln, 1.8 mmol) followed by NaBH₃CN (34 mg, 0.56 mmol) were added. After 10 minutes, acetic acid (40 μl, 0.72 mmol) was added and the reaction stirred at room temperature for 16 hours. The reaction mixture was concentrated at reduced pressure and purified by FCC (DCM/MeOH/NH₃ gradient, 98:2:1 to 90:10:1) giving the title compound as colourless oil (7 mg, 19%).

LCMS data: Calculated MH⁺(401); Found 96% (MH⁺) m/z 401, Rt=2.38 min.

NMR data: ¹H NMR (500 MHz, CDCl₃) δ ppm 8.04 (1 H, d, J=8.6 Hz), 7.97 (1 H, d, J=2.9 Hz), 7.74 (1 H, br. s.), 7.02 (1 H, dd, J=8.8, 2.9 Hz), 4.45-4.55 (1 H, m), 4.25 (2 H, t, J=8.2 Hz), 4.03 (2 H, dd, J=8.8, 5.9 Hz), 3.39-3.52 (4 H, m), 3.03-

3.08 (3 H, m), 3.01 (3 H, d, J=5.1 Hz), 2.78-2.92 (1 H, m), 2.49-2.60 (2 H, m), 2.36-2.48 (2 H, m), 2.00-2.09 (2 H, m), 1.54-1.96 (6 H, m).

Route 29

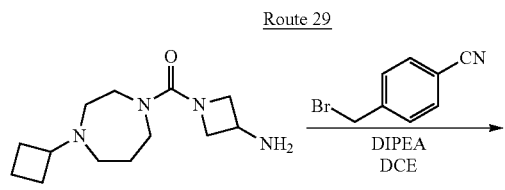

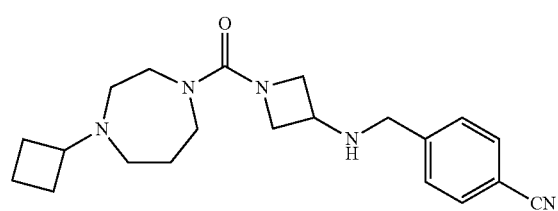

Example 112

Preparation of 4-[({1-[(4-cyclobutyl-1,4-diazepan-1-yl)carbonyl]azetidin-3-yl}amino)methyl]benzonitrile. Potency range A

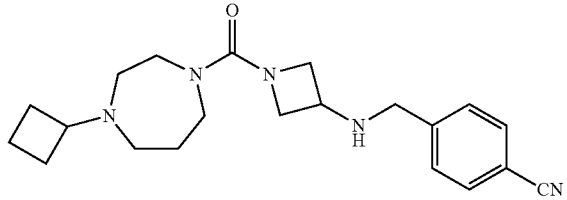 [SMILES: N#Cc1ccc(CNC2CN(C(=O)N3CCCN(C4CCC4)CC3)C2)cc1]

To a solution of 1-[(4-cyclobutyl-1,4-diazepan-1-yl)carbonyl]azetidin-3-amine (20 mg, 80 μmol) in dichloroethane (2 ml) was added 4-(bromomethyl)benzonitrile (17 mg, 87 μmol) and DIPEA (15 μl, 87 μmol). The reaction was heated at 100° C. for 16 hours, concentrated at reduced pressure and purified by FCC (DCM/MeOH/NH$_3$ with gradient, 98:2:1 to 90:10:1) to provide the title compound as colourless oil (10 mg, 33%).

LCMS data: Calculated MH$^+$ (368); Found 96% (MH$^+$) m/z 368, Rt=3.93 min (High pH method).

NMR data: $^1$H NMR (250 MHz, MeOD) δ ppm 7.71 (2 H, d, J=8.4 Hz), 7.55 (2 H, d, J=8.4 Hz), 4.02-4.15 (2 H, m), 3.80 (2 H, s), 3.72 (2 H, dd, J=8.2, 5.5 Hz), 3.53-3.67 (1 H, m), 3.35-3.51 (4 H, m), 2.98 (1 H, s), 2.57 (4 H, dt, J=19.0, 5.1 Hz), 2.01-2.18 (2 H, m), 1.79-2.01 (4 H, m), 1.57-1.79 (2 H, m).

Route 30

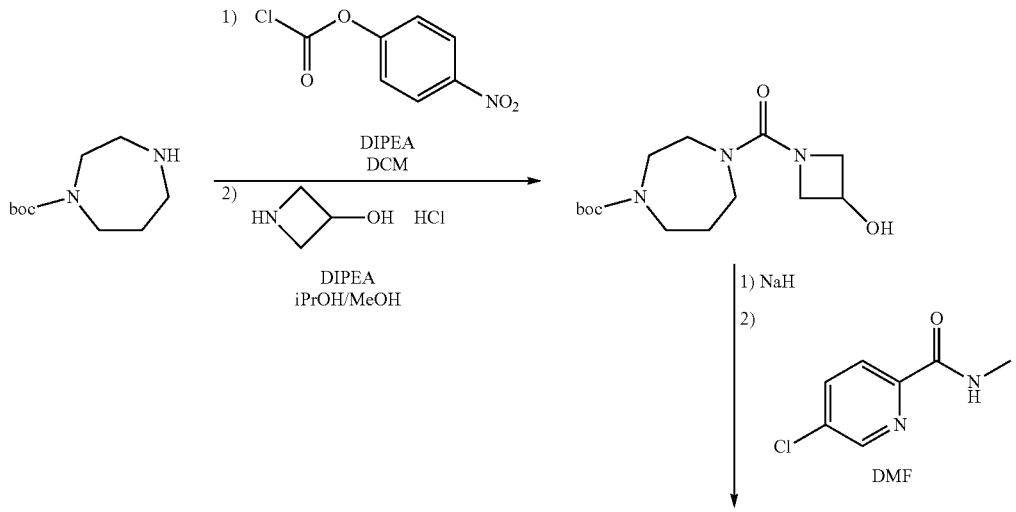

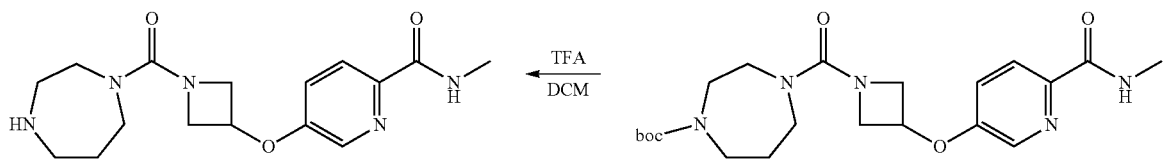

Preparation of tert-butyl 4-[(3-hydroxyazetidin-1-yl)carbonyl]-1,4-diazepane-1-carboxylate

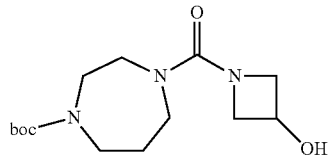

In a similar fashion (Route 20, GP H), [1,4]diazepane-1-carboxylic acid tert-butyl ester (877 mg, 4.4 mmol) gave the title compound as yellow oil (1.10 g, 84%).

LCMS data: Calculated MH$^+$ (300); Found 86% MH$^+$ m/z (300), Rt=0.97 min.

NMR data: $^1$H NMR (250 MHz, MeOD) δ ppm 4.39-4.56 (1 H, m), 4.09-4.26 (2 H, m), 3.80 (2 H, m), 3.31-3.58 (8 H, m), 1.81 (2 H, m), 1.46 (9 H, s).

Preparation of tert-butyl 4-[(3-hydroxyazetidin-1-yl)carbonyl]-1,4-diazepane-1-carboxylate

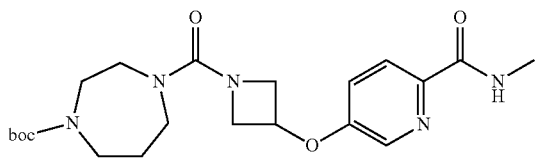

In a similar fashion (Route 20, GP I), tert-butyl 4-[(3-hydroxyazetidin-1-yl)carbonyl]-1,4-diazepane-1-carboxylate (1.22 g, 4.10 mmol) and 5-chloro-N-methylpyridine-2-carboxamide (835 mg, 4.91 mmol) gave the title compound as yellow solid after purification by FCC (1.0 g, 56%).

LCMS data: Calculated MH$^+$(434); Found 100% (MH$^+$) m/z 434, Rt=1.37 min.

NMR data: $^1$H NMR (400 MHz, MeOD) δ ppm 8.23 (1 H, d, J=2.7 Hz), 8.03 (1 H, d, J=8.7 Hz), 7.34 (1 H, d, J=8.5 Hz), 5.13 (1 H, d, J=2.9 Hz), 4.46 (2 H, dd, J=9.2, 6.6 Hz), 4.01-4.08 (2 H, m), 3.35-3.57 (8 H, m), 2.94 (3 H, s), 1.81 (2 H, br. s.), 1.45 (9 H, d, J=7.0 Hz).

Preparation of 5-{[1-(1,4-diazepan-1-ylcarbonyl)azetidin-3-yl]oxy}-N-methylpyridine-2-carboxamide

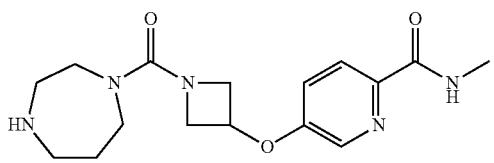 [SMILES: CNC(=O)c1ccc(OC2CN(C(=O)N3CCCNCC3)C2)cn1]

To a stirred solution of tert-butyl 4-[(3-hydroxyazetidin-1-yl)carbonyl]-1,4-diazepane-1-carboxylate (651 mg, 1.5 mmol) in DCM (6 ml) was added TFA (1 ml) at 0° C. The mixture was allowed to warm to RT and was stirred at this temperature over night. The reaction mixture was concentrated in vacuo. The residue was taken up in DCM, AMBERSEP resin (500 mg) was added and the mixture was shaken over night. The mixture was filtered and the filtrate concentrated in vacuo to afford title compound as light brown oil (262 mg, 52%).

$^1$H NMR data: (250 MHz, CDCl$_3$) δ ppm 8.24 (1 H, d, J=2.7 Hz), 8.04 (1 H, d, J=8.7 Hz), 7.28-7.41 (1 H, m), 5.13 (1 H, tt, J=6.4, 4.0 Hz), 4.40-4.55 (2 H, m), 3.99-4.13 (2 H, m), 3.42-3.52 (4 H, m), 2.79-3.03 (7 H, m), 1.79-1.93 (2 H, m).

The following compounds were made as described in Route 1, General Procedure A above.

Example 113

Preparation of 5-({1-[(4-methyl-1,4-diazepan-1-yl)carbonyl]azetidin-3-yl}oxy)-N-methylpyridine-2-carboxamide. Potency range C

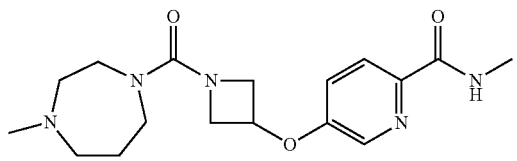

In a similar fashion (Route 1, GP A; except that MeCN was used as solvent), 5-{[1-(1,4-diazepan-1-ylcarbonyl)azetidin-3-yl]oxy}-N-methylpyridine-2-carboxamide (25 mg, 0.075 mmol) and formaldehyde (6.1 μl of a 37% aq solution, 0.075 mmol) gave the title compound as colourless oil (5.3 mg, 20%) after purification by preparative HPLC.

LCMS data: Calculated MH$^+$(348); Found 99% (MH$^+$) m/z 348, Rt=2.19 min.

NMR data: $^1$H NMR (500 MHz, MeOD) δ ppm 8.24 (1 H, d, J=2.7 Hz), 8.04 (1 H, d, J=8.7 Hz), 7.34 (1 H, dd, J=8.7, 2.8 Hz), 5.12-5.18 (1 H, m), 4.53-4.60 (1 H, m), 4.39-4.46 (1 H, m), 4.11-4.18 (1 H, m), 3.97-4.06 (1 H, m), 3.84-3.94 (1 H, m), 3.41-3.63 (6 H, m), 3.17-3.29 (2 H, m), 2.94 (7 H, d, J=5.2 Hz), 1.98-2.30 (1 H, m).

Example 114

Preparation of 5-({1-[(4-(1-methylethyl)-1,4-diazepan-1-yl)carbonyl]azetidin-3-yl}oxy)-N-methylpyridine-2-carboxamide. Potency range A

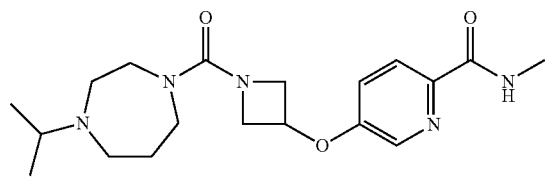 [SMILES: CNC(=O)c1ccc(OC2CN(C(=O)N3CCCN(C(C)C)CC3)C2)cn1]

In a similar fashion (Route 1, GP A; except that MeCN was used as solvent), 5-{[1-(1,4-diazepan-1-ylcarbonyl)azetidin-3-yl]oxy}-N-methylpyridine-2-carboxamide (25 mg, 0.075 mmol) and acetone (5.5 μl, 0.075 mmol) gave the title compound as colourless oil (4 mg, 14%) after purification by preparative HPLC.

LCMS data: Calculated MH$^+$(376); Found 100% (MH$^+$) m/z 376, Rt=2.31 min.

NMR data: $^1$H NMR (500 MHz, MeOD) δ ppm 8.24 (1 H, d, J=2.7 Hz), 8.04 (1 H, d, J=8.7 Hz), 7.34 (1 H, dd, J=8.7, 2.8 Hz), 5.12-5.19 (1 H, m), 4.58 (1 H, dd, J=9.2, 6.5 Hz), 4.43 (1

H, dd, J=9.3, 6.6 Hz), 4.16 (1 H, dd, J=9.5, 3.7 Hz), 4.03 (1 H, dd, J=9.5, 3.7 Hz), 3.88-3.96 (1 H, m), 3.62-3.70 (1 H, m), 3.56-3.62 (1 H, m), 3.38-3.56 (4 H, m), 3.15-3.29 (2 H, m), 2.93-2.96 (3 H, s), 2.19-2.28 (1 H, m), 2.05-2.17 (1 H, m), 1.35 (6 H, s).

Example 115

Preparation of 5-({1-[(4-cyclopentyl-1,4-diazepan-1-yl)carbonyl]azetidin-3-yl}oxy)-N-methylpyridine-2-carboxamide. Potency range A

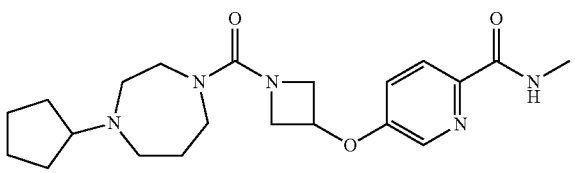 [SMILES: CNC(=O)c1ccc(OC2CN(C(=O)N3CCCN(C4CCCC4)CC3)C2)cn1]

In a similar fashion (Route 1, GP A; except TEA (46 μl, 0.33 mmol) was used as base), 5-{[1-(1,4-diazepan-1-ylcarbonyl)azetidin-3-yl]oxy}-N-methylpyridine-2-carboxamide (50 mg, 0.11 mmol) and cyclopentanone (9.7 μl, 0.11 mmol) gave the title compound (2 mg, 5%) as colourless oil after purification by preparative HPLC.

LCMS data: Calculated MH⁺(402); Found 98% (MH⁺) m/z 402, Rt=2.48 min.

NMR data: $^1$H NMR (500 MHz, MeOD) δ ppm 8.14 (1 H, d, J=2.6 Hz), 7.94 (1 H, d, J=8.8 Hz), 7.24 (1 H, dd, J=8.6, 2.8 Hz), 5.01-5.08 (1 H, m), 4.34-4.44 (2 H, m), 3.98 (2 H, dd, J=9.6, 3.2 Hz), 3.49-3.64 (2 H, m), 3.36-3.45 (4 H, m), 2.82-2.87 (3 H, m), 1.96-2.06 (4 H, m), 1.65-1.77 (2 H, m), 1.52-1.63 (4 H, m), 1.14-1.24 (3 H, m).

Route 31

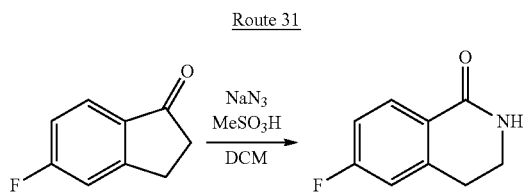 [SMILES: O=C1CCc2cc(F)ccc21 ; O=C1NCCc2cc(F)ccc21]

Preparation of 6-fluoro-3,4-dihydroisoquinolin-1(2H)-one

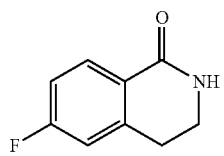

To a stirred solution of 5-fluoro-2,3-dihydro-1H-inden-1-one (433 mg, 2.9 mmol) in dichloromethane (2.5 ml) and methanesulfonic acid (2.5 ml) was added sodium azide (378 mg, 5.8 mmol) portionwise at room temperature. Gas evolution was seen immediately and after 3 hours, complete conversion was observed by TLC. The reaction mixture was added dropwise to a rapidly stirred 5M NaOH solution (8 ml) in ice maintaining the internal temperature below 15° C. On complete addition, the aqueous phase (pH 14) was extracted with dichloromethane (3×25 ml). The organics were combined and washed with water (2×25 ml), dried (MgSO₄), filtered and concentrated in vacuo. NMR showed a 7:3 mixture of regioisomers that were separated by FCC (using a gradient of eluents 1:1 Hexane/EtOAc to EtOAc) providing the title compound as white solid (267 mg, 58%).

LCMS data: Calculated MH⁺(166); Found 100% [MH⁺] m/z (166), Rt=1.27 min.

NMR data: $^1$H NMR (250 MHz, CDCl₃) δ ppm 8.09 (1 H, dd, J=8.6, 5.9 Hz), 7.04 (1 H, ddd, J=8.6, 5.9, 2.6 Hz), 6.92 (1 H, dd, J=8.9, 2.5 Hz), 6.20 (1 H, br. s.), 3.59 (2 H, td, J=6.6, 2.8 Hz), 3.01 (2 H, t, J=6.5 Hz).

Route 32

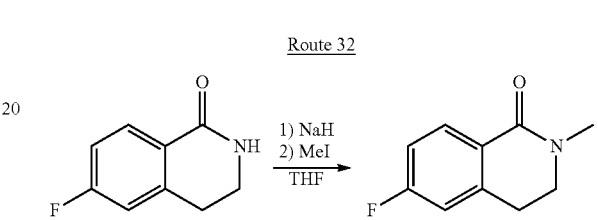

Preparation of 6-fluoro-2-methyl-3,4-dihydroisoquinolin-1(2H)-one

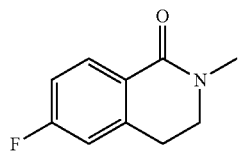

To a stirred solution of 6-fluoro-3,4-dihydroisoquinolin-1(2H)-one (102 mg, 0.62 mmol) in THF (5 ml) was added NaH (49 mg of a 60% dispersion in mineral oil, 1.23 mmol) giving a thick white precipitate. After 30 minutes, methyl iodide (76 μl, 1.23 mmol) was added and the reaction was heated at 50° C. for 1 hour. Complete conversion was observed by TLC and the reaction was concentrated, diluted with dichloromethane (30 ml), washed with saturated NaHCO₃ (15 ml), dried (MgSO₄), filtered and concentrated in vacuo. The residue was purified by FCC (using a gradient of eluents 1:1 Hexane/EtOAc to EtOAc) to provide the title compound as colourless oil (106 mg, 96%).

LCMS data: Calculated MH⁺(180); Found 100% [MH⁺] m/z (180), Rt=1.61 min.

NMR data: $^1$H NMR (250 MHz, CDCl₃) δ ppm 8.09 (1 H, dd, J=8.6, 5.9 Hz), 7.00 (1 H, ddd, J=8.6, 5.9, 2.4 Hz), 6.86 (1 H, dd, J=8.8, 2.4 Hz), 3.57 (2 H, t, J=6.7 Hz), 3.00 (2 H, t, J=6.7 Hz).

The following compounds were made as described in Route 20, General Procedure I above.

Example 116

Preparation of 6-({1-[(4-cyclobutyl-1,4-diazepan-1-yl)carbonyl]azetidin-3-yl}oxy)-3,4-dihydroisoquinolin-1(2H)-one. Potency range A

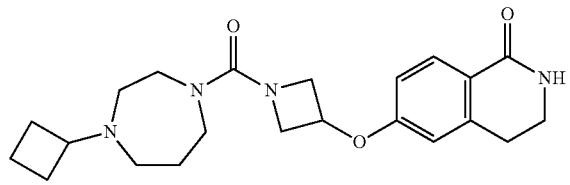 [SMILES: O=C1NCCc2cc(OC3CN(C(=O)N4CCCN(C5CCC5)CC4)C3)ccc21]

In a similar fashion (Route 20, GP I), 1-[(4-cyclobutyl-1,4-diazepan-1-yl)carbonyl]azetidin-3-ol (38 mg, 0.15 mmol) and 6-fluoro-3,4-dihydroisoquinolin-1(2H)-one (30 mg, 0.18 mmol) gave the title compound as white solid after purification by FCC (44 mg, 73%).

LCMS data: Calculated MH$^+$(399); Found 100% (MH$^+$) m/z 399, Rt=2.46 min.

NMR data: $^1$H NMR (500 MHz, MeOD) δ ppm 8.00 (1 H, d, J=8.6 Hz), 6.67 (1 H, dd, J=8.6, 2.0 Hz), 6.56 (1 H, s), 6.38 (1 H, br. s.), 4.88-4.97 (1 H, m), 4.35 (2 H, dd, J=9.0, 7.0 Hz), 4.03 (2 H, dd, J=9.4, 4.1 Hz), 3.50-3.60 (2 H, m), 3.35-3.49 (4 H, m), 2.95 (2 H, t, J=6.5 Hz), 2.83 (1 H, quin), 2.47-2.55 (2 H, m), 2.38-2.45 (2 H, m), 2.03 (2 H, q, J=8.1 Hz), 1.75-1.90 (4 H, m), 1.54-1.72 (2 H, m).

Example 117

Preparation of 6-({1-[(4-cyclobutyl-1,4-diazepan-1-yl)carbonyl]azetidin-3-yl}oxy)-2-methyl-3,4-dihydroisoquinolin-1(2H)-one. Potency range A

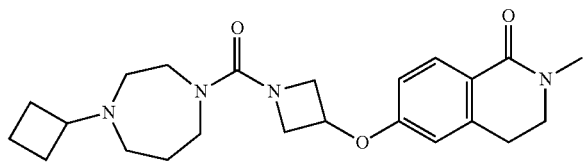 [SMILES: CN1CCc2cc(OC3CN(C(=O)N4CCCN(C5CCC5)CC4)C3)ccc2C1=O]

In a similar fashion (Route 20, GP I), 1-[(4-cyclobutyl-1,4-diazepan-1-yl)carbonyl]azetidin-3-ol (32 mg, 0.13 mmol) and 6-fluoro-2-methyl-3,4-dihydroisoquinolin-1(2H)-one (25 mg, 0.14 mmol) gave the title compound as white solid after purification by FCC (18 mg, 34%).

LCMS data: Calculated MH$^+$(413); Found 100% (MH$^+$) m/z 413, Rt=2.58 min.

NMR data: $^1$H NMR (500 MHz, MeOD) δ ppm 8.01 (1 H, d, J=8.4 Hz), 6.65 (1 H, dd, J=8.5, 2.3 Hz), 6.51 (1 H, d, J=1.8 Hz), 4.88-4.95 (1 H, m), 4.34 (2 H, dd, J=9.3, 6.7 Hz), 4.03 (2 H, dd, J=9.4, 4.1 Hz), 3.54 (2 H, t, J=6.7 Hz), 3.44-3.50 (2 H, m), 3.41 (2 H, t, J=6.1 Hz), 3.13 (3 H, s), 2.96 (2 H, t, J=6.6 Hz), 2.79-2.89 (1 H, m), 2.48-2.56 (2 H, m), 2.38-2.47 (2 H, m), 1.99-2.07 (2 H, m), 1.77-1.92 (4 H, m), 1.55-1.72 (2 H, m).

Route 33

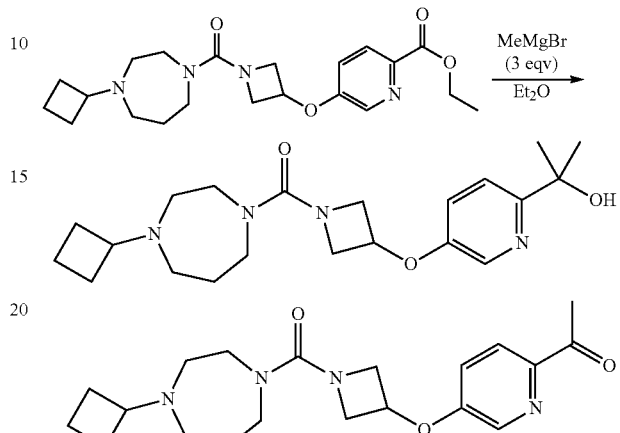

Example 118

Preparation of 2-[5-({1-[(4-cyclobutyl-1,4-diazepan-1-yl)carbonyl]azetidin-3-yl}oxy)pyridin-2-yl]propan-2-ol. Potency range A

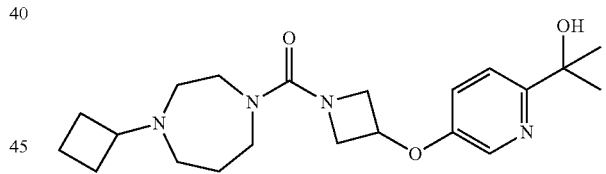

MeMgBr (0.96 ml of a 3M solution in diethyl ether, 2.88 mmol) was added dropwise to a solution of ethyl 5-({1-[(4-cyclobutyl-1,4-diazepan-1-yl)carbonyl]azetidin-3-yl}oxy)pyridine-2-carboxylate (386 mg, 0.96 mmol) in diethyl ether (20 ml) at 0° C. The reaction was warmed to room temperature and after 1 hour was quenched and washed with water (2×20 ml), dried (MgSO$_4$) and concentrated under reduced pressure. The crude material was purified by preparative HPLC to give the title compound (179 mg, 37%) as colourless oil and 1-[5-({1-[(4-cyclobutyl-1,4-diazepan-1-yl)carbonyl]azetidin-3-yl}oxy)pyridin-2-yl]ethanone (2.5 mg, 1%) as colourless oil.

LCMS data: Calculated MH$^+$(389); Found 100% (MH$^+$) m/z 389, Rt=1.73 min.

NMR data: $^1$H NMR (500 MHz, CDCl$_3$) δ ppm 8.03 (1 H, d, J=2.6 Hz), 7.32 (1 H, d, J=8.6 Hz), 7.11 (1 H, dd, J=8.6, 2.8 Hz), 4.86-5.01 (1 H, m), 4.36 (2 H, dd, J=9.3, 6.7 Hz), 4.05 (2 H, dd, J=9.4, 4.1 Hz), 3.35-3.54 (4 H, m), 2.80-2.95 (1 H, m), 2.35-2.62 (4 H, m), 2.00-2.10 (2 H, m), 1.89 (4 H, d, J=15.0 Hz), 1.57-1.75 (2 H, m), 1.53 (6 H, s).

Example 119

Preparation of 1-[5-({1-[(4-cyclobutyl-1,4-diazepan-1-yl)carbonyl]azetidin-3-yl}oxy)pyridin-2-yl]ethanone. Potency range A

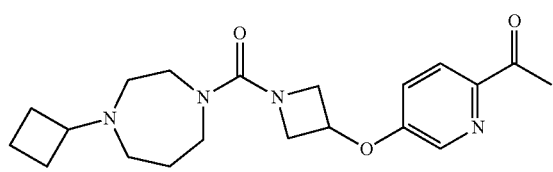 [SMILES: CC(=O)c1ccc(OC2CN(C(=O)N3CCCN(C4CCC4)CC3)C2)cn1]

The title compound (2.5 mg, 1%) was formed in the reaction illustrated in Route 33.

LCMS data: Calculated MH$^+$(373); Found 95% (MH$^+$) m/z 373, Rt=2.36 min.

NMR data: $^1$H NMR (500 MHz, CDCl$_3$) δ ppm 8.21 (1 H, d, J=2.6 Hz), 8.05 (1 H, d, J=8.7 Hz), 7.11 (1 H, dd, J=8.7, 2.9 Hz), 4.97-5.07 (1 H, m), 4.39 (2 H, dd, J=9.4, 6.6 Hz), 4.08 (2H, dd, J=9.5, 4.0 Hz), 3.36-3.52 (4 H, m), 2.79-2.91 (1 H, m), 2.69 (3 H, s), 2.48-2.55 (2 H, m), 2.38-2.47 (2 H, m), 2.04 (2 H, d, J=8.1 Hz), 1.75-1.95 (4 H, m), 1.61-1.73 (2 H, m).

Route 34

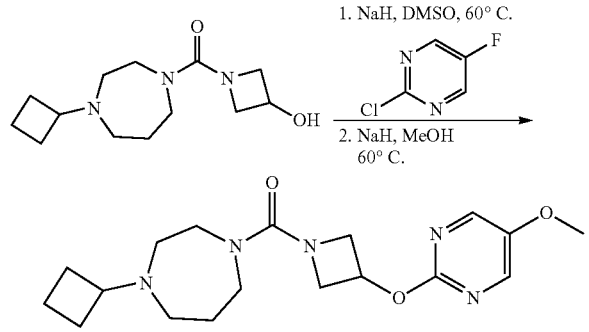

Example 120

Preparation of 1-cyclobutyl-4-({3-[(5-methoxypyrimidin-2-yl)oxy]azetidin-1-yl}carbonyl)-1,4-diazepane. Potency range A

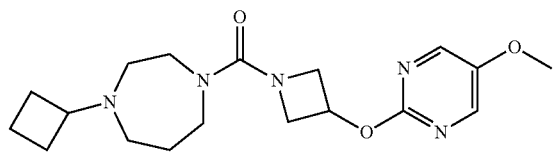 [SMILES: COc1cnc(OC2CN(C(=O)N3CCCN(C4CCC4)CC3)C2)nc1]

To a stirred solution of 1-[(4-cyclobutyl-1,4-diazepan-1-yl)carbonyl]azetidin-3-ol (50 mg, 0.197 mmol) in DMSO (2 ml) was added NaH (16 mg of a 60% dispersion in mineral oil, 0.40 mmol) at room temperature in one portion. The suspension was stirred for 2 hours at room temperature then 2-chloro-5-fluoro-pyrimidine (26 mg, 0.20 mmol) was added in one portion. The mixture was heated at 60° C. in a sealed tube for 16 hours. After cooling to room temperature the solution was treated with MeOH (8 μl, 0.20 mmol) and NaH (16 mg, 0.40 mmol, 60 in mineral oil) and heated at 60° C. in a sealed tube for 16 hours. After cooling to room temperature the reaction was diluted with dichloromethane (30 ml) and washed twice with saturated NaHCO$_3$ (15 ml), dried (Na$_2$SO$_4$), filtered and concentrated at reduced pressure. The residue was purified by FCC (DCM/MeOH/NH$_3$ with gradient, 98:2:1 to 90:10:1) to provide the title compound as colourless oil (20 mg, 28%).

LCMS data: Calculated MH$^+$(362); Found 100% (MH$^+$) m/z 362, Rt=2.17 min.

NMR data: $^1$H NMR (500 MHz, CDCl$_3$) δ ppm 8.09 (2 H, s), 4.85-4.91 (1 H, m), 4.32 (2 H, dd, J=9.5, 6.5 Hz), 4.05 (2 H, dd, J=9.6, 4.1 Hz), 3.97 (3 H, s), 3.44-3.49 (2 H, m), 3.42 (2 H, m), 2.80-2.89 (1 H, m), 2.48-2.55 (2 H, m), 2.40-2.46 (2 H, m), 1.99-2.09 (2 H, m), 1.87 (4 H, m), 1.56-1.73 (2 H, m).

Route 35

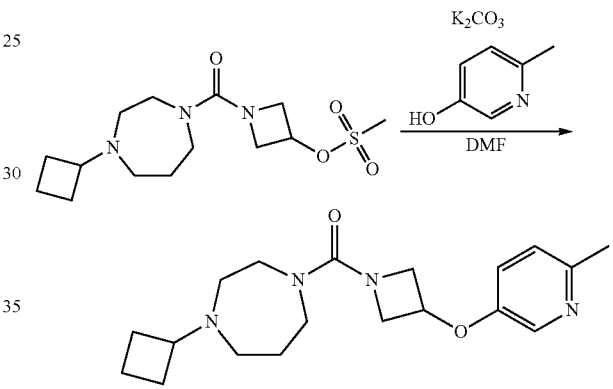

Example 121

Preparation of 1-cyclobutyl-4-({3-[(6-methylpyridin-3-yl)oxy]azetidin-1-yl}carbonyl)-1,4-diazepane. Potency range A

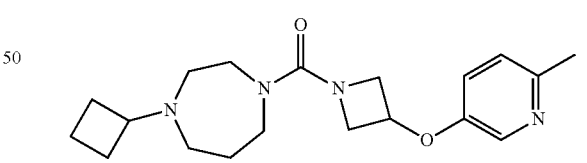

3-Hydroxy-6-methylpyridine (24 mg, 0.22 mmol) and K$_2$CO$_3$ (33 mg, 0.24 mmol) were stirred in DMF (1 ml) for 30 minutes and 1-[(4-cyclobutyl-1,4-diazepan-1-yl)carbonyl]azetidin-3-yl methanesulfonate (66 mg, 0.20) was added. The reaction was stirred at 90° C. for 3 days and then diluted with dichloromethane (30 ml) and washed with saturated NaHCO$_3$ (3×15 ml), dried (MgSO$_4$), filtered and concentrated at reduced pressure. The residue was purified by FCC (DCM/MeOH/NH$_3$ with gradient, 98:2:1 to 90:10:1) to give the title product as off-white solid (24 mg, 35%).

LCMS data: Calculated MH$^+$(345); Found 99% (MH$^+$) m/z 345, Rt=3.68 mins (High pH method).

NMR data: $^1$H NMR (500 MHz, MeOD) δ ppm 8.01 (1 H, s), 7.20-7.26 (2 H, m), 4.99-5.06 (1 H, m), 4.41 (2 H, dd, J=9.2, 6.5 Hz), 4.00 (2 H, dd, J=9.4, 4.0 Hz), 3.40-3.49 (4 H, m), 2.90 (1 H, quin, J=8.0 Hz), 2.53-2.58 (2 H, m), 2.43-2.49 (5 H, m), 2.03-2.11 (2 H, m), 1.80-1.92 (4 H, m), 1.60-1.74 (2 H, m).

ration of the solvent and co-evaporation with MeOH (2×20 ml) at reduced pressure provided the title compound as viscous brown oil that crystallized on standing (3.17 g, 100%). The material was used without purification.

LCMS data: Calculated MH$^+$(116); Found 100% (MH$^+$) m/z 116, Rt=0.18 min.

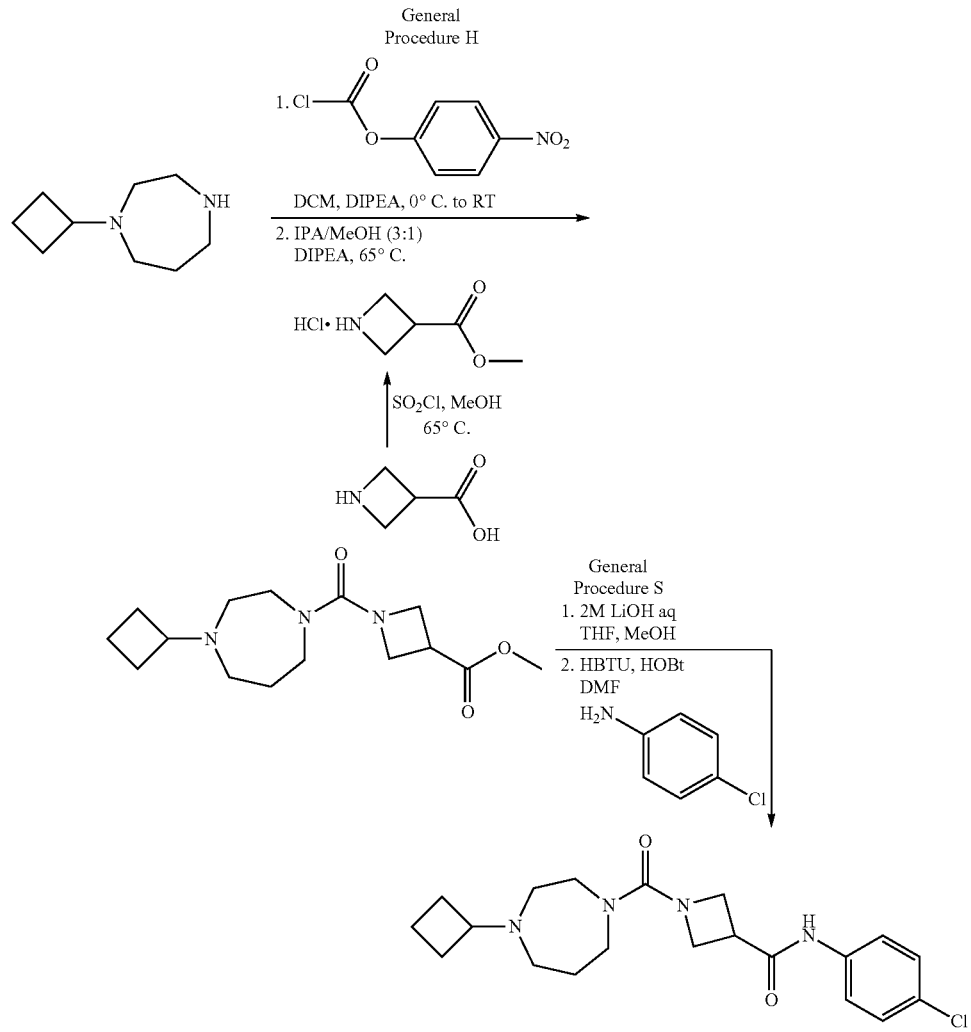

Preparation of methyl azetidine-3-carboxylate hydrochloride

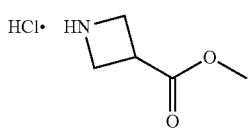

A stirred suspension of azetidine-3-carboxylic acid (2 g, 19.8 mmol) in MeOH (8 ml) was cooled to 5° C. in an ice-water bath. Thionyl chloride (4.3 ml, 59 mmol) was added dropwise at such a rate as to maintain reaction temperature below 30° C. A further portion of MeOH (8 ml) was added carefully and the mixture heated at 65° C. overnight. Evapo- NMR data: $^1$H NMR (250 MHz, DMSO) δ ppm 9.60-8.90 (2H, br m), 4.05 (4H, br s), 3.65 (3H, s)

Preparation of 4-nitrophenyl-4-cyclobutyl-1,4-diazepane-1-carboxylate

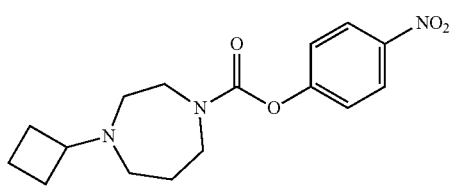 [SMILES: O=C(Oc1ccc([N+](=O)[O-])cc1)N1CCCN(C2CCC2)CC1]

To a stirred solution of 1-cyclobutyl-1,4-diazepane (4.81 g, 31 mmol) and DIPEA (5.4 ml, 34 mmol) in DCM (85 ml) at 5° C. was added dropwise a solution of 4-nitrophenyl chloroformate (6.29 g, 31 mmol) in DCM (40 ml). An ice-water bath was used to maintain the reaction temperature below 10° C. during addition. When addition was complete, the reaction was allowed to warm to RT overnight with stirring. The reaction mixture was quenched by the careful addition of water (20 ml). The organic fraction was washed with water (2×30 ml), dried ($Na_2SO_4$), filtered and evaporated at reduced pressure. Purification by FCC on silica provided the title compound as yellow oil (3.79 g, 39%).

LCMS data: Calculated $MH^+$ (320); Found 100% ($MH^+$) m/z 320, Rt=0.85 min.

NMR data: $^1H$ NMR (500 MHz, $CDCl_3$) δ ppm 8.27 (2H, d, J=9 Hz), 7.32 (2H, d, J=9 Hz), 3.73 (2H, t, J=5.4 Hz), 3.68-3.63 (2 H, m), 2.99-2.89 (1H, m), 2.63-2.56 (2H, m), 2.56-2.49 (2H, m), 2.14-2.04 (2H, m), 2.00-1.60 (6H, m).

Example 122

Preparation of methyl 1-[(4-cyclobutyl-1,4-diazepan-1-yl)carbonyl]azetidine-3-carboxylate. Potency range A

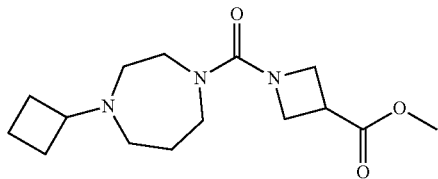 [SMILES: COC(=O)C1CN(C(=O)N2CCCN(C3CCC3)CC2)C1]

To a stirred solution of 4-nitrophenyl 4-cyclobutyl-1,4-diazepane-1-carboxylate (2.4 g, 7.5 mmol) in isopropyl alcohol (6 ml) and methanol (3 ml) was added DIPEA (3.80 ml, 24 mmol) followed by methyl azetidine-3-carboxylate hydrochloride (1.70 g, 11 mmol) portion wise over 2 minutes. The resulting suspension was heated at 85° C. for 72 h. The mixture was allowed to cool and the solvent was removed in vacuo. The residue was dissolved in DCM (100 ml) and washed with 1M sodium carbonate solution (3×30 ml), dried ($Na_2SO_4$), filtered and evaporated at reduced pressure. Purification by FCC on silica provided the title compound as pale yellow oil (0.95 g, 43%).

LCMS data: Calculated $MH^+$(296); Found 100% ($MH^+$) m/z 296, Rt=3.53 min.

NMR data: $^1H$ NMR (500 MHz, $CDCl_3$) δ ppm 4.17-4.10 (5H, m), 3.76 (3H, s), 3.50-3.36 (5H, m), 2.90-2.79 (1H, m), 2.57-2.38 (4H, m), 2.09-2.00 (2H, m), 1.96-1.78 (4H, m), 1.77-1.57 (3H, m), 1.31-1.24 (2H, m).

General Procedure S

Example 123

Preparation of N-(4-chlorophenyl)-1-[(4-cyclobutyl-1,4-diazepan-1-yl)carbonyl]azetidine-3-carboxamide. Potency range A

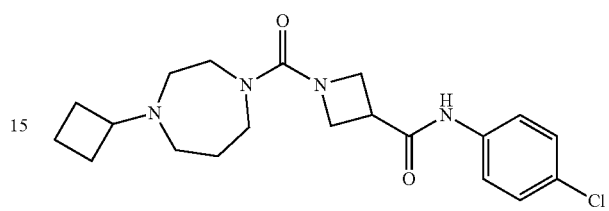

To a solution of methyl methyl 1-[(4-cyclobutyl-1,4-diazepan-1-yl)carbonyl]azetidine-3-carboxylate (40 mg, 0.14 mmol) in THF (0.3 ml) and MeOH (0.3 ml) was added 2M LiOH solution (0.09 ml, 0.18 mmol). The reaction mixture was stirred overnight at room temperature. The solvent was removed in vacuo and the residue co-evaporated with toluene (2×10 ml) to dryness. The residue was suspended in DMF (2 ml) and HBTU (67 mg, 0.18 mmol) and HOBt (26 mg, 0.19 mmol) added. The resulting solution was stirred for 1 hr, 4-chloroaniline (26 mg, 0.20 mmol) was added in one portion and the reaction mixture stirred at RT for 64 h. Solvent was evaporated in vacuo and the residue dissolved in MeOH (1 ml), loaded onto an SCX column and eluted with 2M $NH_3$ in MeOH. The basic fractions were combined and concentrated in vacuo and the residue purified by FCC on silica to afford the title compound as white solid (12 mg, 23%).

LCMS data: Calculated $MH^+$(391); Found 100% ($MH^+$) m/z 391, Rt=2.85 min.

NMR data: $^1H$ NMR (250 MHz, $CDCl_3$) δ ppm 7.79 (1H, br s, NH), 7.44 (2H, d, J=8.8 Hz), 7.24-7.20 (2H, m), 4.17-4.04 (4H, m), 3.41-3.27 (5H, m), 2.81-2.71 (1H, m), 2.49-2.31 (4H, m), 2.01-1.91 (2H, m), 1.85-1.47 (6H, m).

The following compounds were made as described in Route 36, General Procedure S above.

Example 124

Preparation of 1-cyclobutyl-4-{[3-(piperidin-1-ylcarbonyl)azetidin-1-yl]carbonyl}-1,4-diazepane. Potency range A

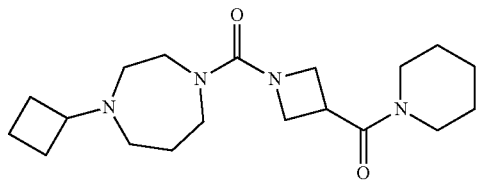 [SMILES: O=C(C1CN(C(=O)N2CCCN(C3CCC3)CC2)C1)N1CCCCC1]

In a similar fashion (Route 21, GP S), methyl 1-[(4-cyclobutyl-1,4-diazepan-1-yl)carbonyl]azetidine-3-carboxylate (20 mg, 0.07 mmol) and piperidine (6.3 mg, 0.07 mmol) gave the title compound (1.8 mg, 8%, free base) as colourless oil after purification by FCC.

LCMS data: Calculated MH⁺ (349); Found 100% (MH⁺) m/z 349, Rt=2.48 min.

NMR data: $^1$H NMR (500 MHz, CDCl$_3$) δ ppm 4.24-4.20 (1H, m), 4.17-4.08 (3H, m), 3.77 (1H, m), 3.60-3.56 (1H, m), 3.49-3.36 (5H, m), 3.24-3.20 (1H, m), 2.90-2.81 (1H, m), 2.56-2.40 (4H, m), 2.09-2.01 (2H, m), 1.93-1.78 (4H, m), 1.75-1.51 (9H, m).

Example 125

Preparation of 1-cyclobutyl-4-{[3-(morpholin-4-ylcarbonyl)azetidin-1-yl]carbonyl}-1,4-diazepane. Potency range A

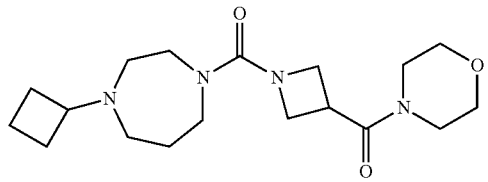 [SMILES: O=C(C1CN(C(=O)N2CCCN(C3CCC3)CC2)C1)N1CCOCC1]

In a similar fashion (Route 36, GP S), methyl 1-[(4-cyclobutyl-1,4-diazepan-1-yl)carbonyl]azetidine-3-carboxylate (50 mg, 0.18 mmol) and morpholine (22.1 mg, 0.25 mmol) gave the title compound as white solid (7.4 mg, 12%) after purification by FCC on silica.

LCMS data: Calculated MH⁺(351); Found 100% (MH⁺) m/z 351, Rt=3.27 min.

NMR data: $^1$H NMR (500 MHz, CDCl$_3$) δ ppm 4.02-4.27 (4 H, m), 3.55-3.79 (8 H, m), 3.36-3.52 (3 H, m), 3.22-3.33 (2 H, m), 2.98-3.14 (1 H, m), 2.00-2.97 (10 H, m), 1.74-1.89 (1 H, m), 1.58-1.72 (1 H, m).

Example 126

Preparation of 1-{[3-(azetidin-1-ylcarbonyl)azetidin-1-yl]carbonyl}-4-cyclobutyl-1,4-diazepane. Potency range A

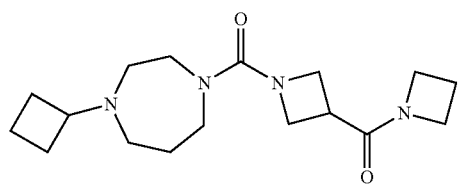 [SMILES: O=C(C1CN(C(=O)N2CCCN(C3CCC3)CC2)C1)N1CCC1]

In a similar fashion (Route 36, GP S), methyl 1-[(4-cyclobutyl-1,4-diazepan-1-yl)carbonyl]azetidine-3-carboxylate (40 mg, 0.14 mmol) and azetidine (35 mg, 0.61 mmol) gave the title compound as colourless oil after purification by FCC (18 mg, 40%).

LCMS data: Calculated MH⁺(321); Found 100% (MH⁺) m/z 321, Rt=3.20 min.

NMR data: $^1$H NMR (500 MHz, CDCl$_3$) δ ppm 4.10-4.27 (2 H, m), 3.91-4.10 (6 H, m), 3.81-3.91 (1 H, m), 3.17-3.54 (7 H, m), 2.73-2.84 (1 H, m), 2.51-2.62 (1 H, m), 2.32-2.50 (3 H, m), 2.27 (2 H, m), 2.02-2.22 (3 H, m), 1.77-1.88 (1 H, m), 1.57-1.71 (1 H, m).

Example 127

Preparation of 1-cyclobutyl-4-{[3-(pyrrolidin-1-ylcarbonyl)azetidin-1-yl]carbonyl}-1,4-diazepane. Potency range A

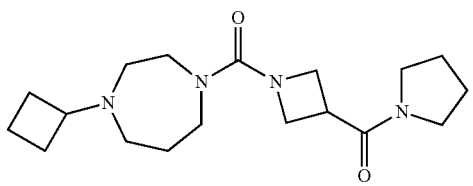 [SMILES: O=C(C1CN(C(=O)N2CCCN(C3CCC3)CC2)C1)N1CCCC1]

In a similar fashion (Route 36, GP S), methyl 1-[(4-cyclobutyl-1,4-diazepan-1-yl)carbonyl]azetidine-3-carboxylate (40 mg, 0.14 mmol) and pyrrolidine (43 mg, 0.61 mmol) gave the title compound as colourless oil after purification by FCC (18.8 mg, 41%).

LCMS data: Calculated MH⁺(335); Found 100% (MH⁺) m/z 335, Rt=3.40 min.

NMR data: $^1$H NMR (500 MHz, CDCl$_3$) δ ppm 4.36 (1 H, m), 4.29 (1 H, m), 4.04-4.16 (2 H, m), 3.89-4.00 (1 H, m), 3.26-3.62 (11 H, m), 2.81-2.94 (1 H, m), 2.60-2.72 (1 H, m), 2.39-2.57 (3 H, m), 2.08-2.30 (3 H, m), 1.83-2.06 (5 H, m), 1.64-1.80 (1 H, m).

Example 128

Preparation of 1-{[3-(azepan-1-ylcarbonyl)azetidin-1-yl]carbonyl}-4-cyclobutyl-1,4-diazepane. Potency range A

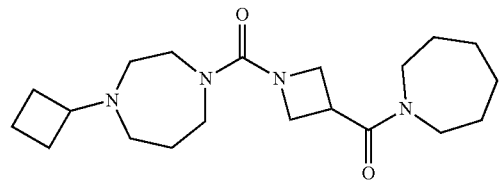 [SMILES: O=C(C1CN(C(=O)N2CCCN(C3CCC3)CC2)C1)N1CCCCCC1]

In a similar fashion (Route 36, GP S), methyl 1-[(4-cyclobutyl-1,4-diazepan-1-yl)carbonyl]azetidine-3-carboxylate (40 mg, 0.14 mmol) and azepane (60 mg, 0.61 mmol) gave the title compound as colourless oil after purification by FCC (16 mg, 31%).

LCMS data: Calculated MH⁺(363); Found 100% (MH⁺) m/z 363, Rt=3.84 min.

NMR data: $^1$H NMR (500 MHz, CDCl$_3$) δ ppm 4.30-4.39 (1 H, m), 4.22-4.30 (1 H, m), 4.08-4.15 (1 H, m), 4.00-4.08 (1 H, m), 3.90-3.99 (1 H,), 3.38-3.61 (8 H, m), 3.24-3.38 (3 H, m), 2.80-2.92 (1 H, m), 2.58-2.67 (1 H, m), 2.41-2.57 (3 H, m), 2.10-2.29 (3 H, m), 1.83-1.96 (1 H, m), 0.64-1.79 (5 H, m), 1.58 (4 H, m).

Example 129

Preparation of 1-cyclobutyl-4-({3-[(4-fluoropiperidin-1-yl)carbonyl]azetidin-1-yl}carbonyl)-1,4-diazepane. Potency range A

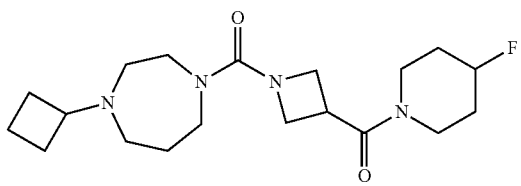 [SMILES: O=C(C1CN(C(=O)N2CCCN(C3CCC3)CC2)C1)N1CCC(F)CC1]

In a similar fashion (Route 36, GP S), methyl 1-[(4-cyclobutyl-1,4-diazepan-1-yl)carbonyl]azetidine-3-carboxylate (40 mg, 0.14 mmol) and 4-fluoropiperidine (85 mg, 0.61 mmol) gave the title compound as colourless oil after purification by FCC (13 mg, 25%).

LCMS data: Calculated MH$^+$(367); Found 100% (MH$^+$) m/z 367, Rt=3.50 min.

NMR data: $^1$H NMR (500 MHz, CDCl$_3$) δ ppm 4.89-4.99 (1 H, m), 4.22-4.39 (2 H, m), 4.01-4.16 (2 H, m), 3.87-4.01 (2 H, m), 3.39-3.63 (8 H, m), 3.29-3.39 (1 H, m), 3.17-3.29 (1 H, m), 2.85 (1 H, m), 2.57-2.69 (1 H, m), 2.38-2.57 (3 H, m), 2.10-2.30 (3 H, m), 1.65-1.97 (6 H, m).

Example 130

Preparation of 1-cyclobutyl-4-({3-[(4,4-difluoropiperidin-1-yl)carbonyl]azetidin-1-yl}carbonyl)-1,4-diazepane. Potency range A

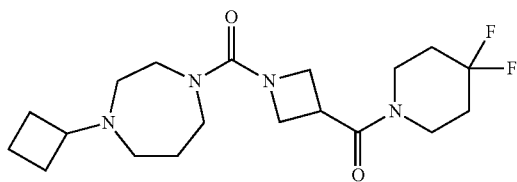 [SMILES: O=C(C1CN(C(=O)N2CCCN(C3CCC3)CC2)C1)N1CCC(F)(F)CC1]

In a similar fashion (Route 36, GP S), methyl 1-[(4-cyclobutyl-1,4-diazepan-1-yl)carbonyl]azetidine-3-carboxylate (40 mg, 0.14 mmol) and 4,4-difluoropiperidine hydrochloride (96 mg, 0.61 mmol) gave the title compound as colourless oil after purification by FCC (10 mg, 19%).

LCMS data: Calculated MH$^+$(385); Found 100% (MH$^+$) m/z 385, Rt=3.72 min.

NMR data: $^1$H NMR (500 MHz, CDCl$_3$) ppm 4.18-4.36 (2 H, m), 3.99-4.13 (2 H, m), 3.85-3.99 (1 H, m), 3.70-3.84 (2 H, m), 3.35-3.63 (8 H, m), 3.24-3.34 (1 H, m), 2.70-2.88 (1 H, m), 2.44-2.66 (4 H, m), 2.07-2.26 (3 H, m), 1.84-2.06 (4 H, m), 1.61-1.84 (2 H, m).

Example 131

Preparation of 1-[(4-cyclobutyl-1,4-diazepan-1-yl)carbonyl]-N-cyclohexylazetidine-3-carboxamide. Potency range A

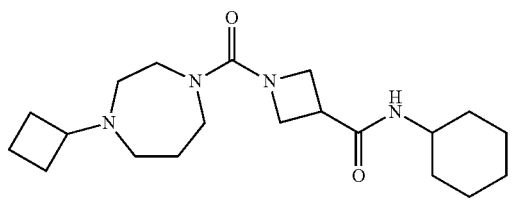 [SMILES: O=C(NC1CCCCC1)C1CN(C(=O)N2CCCN(C3CCC3)CC2)C1]

In a similar fashion (Route 36, GP S), methyl 1-[(4-cyclobutyl-1,4-diazepan-1-yl)carbonyl]azetidine-3-carboxylate (40 mg, 0.14 mmol) and cyclohexylamine (60 mg, 0.61 mmol) gave the title compound as colourless oil after purification by FCC (12 mg, 24%).

LCMS data: Calculated MH$^+$(363); Found 100% (MH$^+$) m/z 363, Rt=3.80 min.

NMR data: $^1$H NMR (500 MHz, CDCl$_3$) δ ppm 5.50 (1 H, d, J=8.1 Hz), 4.21-4.32 (2 H, m), 4.00-4.10 (2 H, m), 3.89-3.99 (1 H, m), 3.74-3.84 (1 H, m), 3.29-3.60 (6 H, m), 3.14-3.24 (1 H, m), 2.82-2.93 (1 H, m), 2.58-2.70 (1 H, m), 2.40-2.57 (3 H, m), 2.09-2.31 (3 H, m), 1.86-1.98 (3 H, m), 1.68-1.79 (3 H, m), 1.61-1.68 (1 H, m), 1.32-1.43 (2 H, m), 1.08-1.24 (3 H, m).

Example 132

Preparation of 1-[(4-cyclobutyl-1,4-diazepan-1-yl)carbonyl]-N-(6-methylpyridin-3-yl)azetidine-3-carboxamide. Potency range A

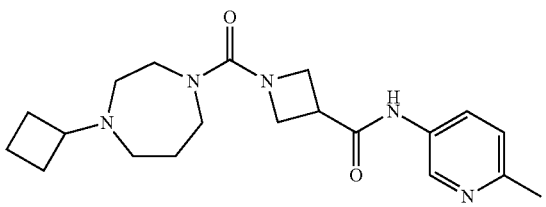 [SMILES: Cc1ccc(NC(=O)C2CN(C(=O)N3CCCN(C4CCC4)CC3)C2)cn1]

In a similar fashion (Route 36, GP S), methyl 1-[(4-cyclobutyl-1,4-diazepan-1-yl)carbonyl]azetidine-3-carboxylate (102 mg, 0.35 mmol) and 3-amino-6-methylpyridine (83 mg, 0.77 mmol) gave the title compound after purification by FCC (51 mg, 39%).

LCMS data: Calculated MH$^+$(371); Found 99% (MH$^+$) m/z 371, Rt=3.37 min.

NMR data: $^1$H NMR (500 MHz, MeOD) δ ppm 8.62 (1 H, d, J=2.1 Hz), 8.02 (1 H, dd, J=8.4, 2.6 Hz), 7.28 (1 H, d, J=8.5 Hz), 4.89-5.00 (1 H, m), 4.14-4.27 (4 H, m), 3.39-3.64 (4 H, m), 2.79-3.02 (1 H, m), 2.40-2.64 (7 H, m), 2.01-2.18 (2 H, m), 1.80-1.98 (4 H, m), 1.58-1.78 (2 H, m).

Route 37

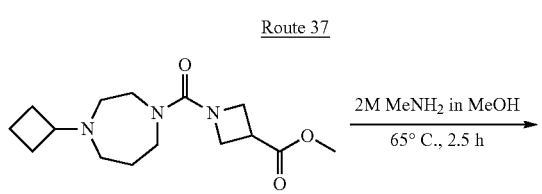

Example 133

Preparation of 1-[(4-cyclobutyl-1,4-diazepan-1-yl)carbonyl]-N-methylazetidine-3-carboxamide. Potency range B

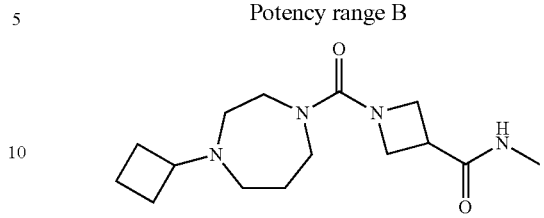

A solution of methyl 1-[(4-cyclobutyl-1,4-diazepan-1-yl)carbonyl]azetidine-3-carboxylate (6.5 mg, 0.02 mmol) in methylamine (2M in MeOH, 1 ml) was heated to 65° C. for 2.5 h. After cooling to room temperature the solvent was removed in vacuo and the residue purified by FCC on silica to afford the title compound as colourless oil (4 mg, 61%).

LCMS data: Calculated $MH^+$(295); Found 100% ($MH^+$) m/z 295, Rt=3.11 min.

NMR data: $^1$H NMR (500 MHz, $CDCl_3$) δ ppm 5.56 (1H, br s), 4.07-4.00 (4H, m), 3.40-3.30 (4H, m), 3.16-3.08 (1H, m), 2.78 (3H, d, J=4.8), 2.77-2.72 (1H, m), 2.46-2.41 (2H, m), 2.37-2.33 (2H, m), 2.00-1.92 (2H, m), 1.82-1.49 (6H, m).

Route 38

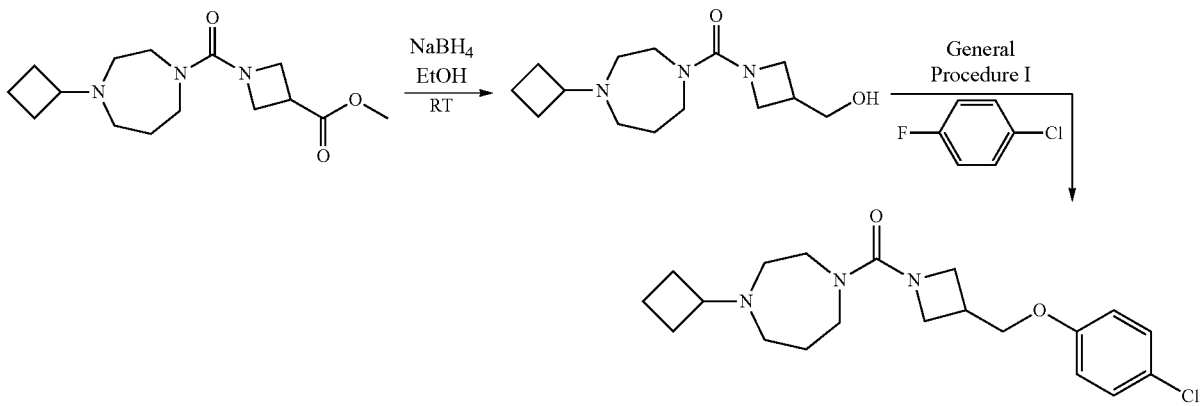

Example 134

Preparation of {1-[(4-cyclobutyl-1,4-diazepan-1-yl)carbonyl]azetidin-3-yl}methanol. Potency range A

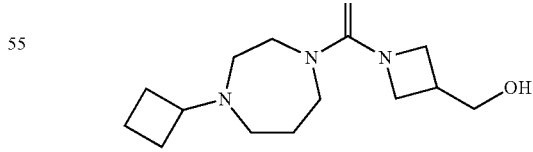

To a stirred solution of {1-[(4-cyclobutyl-1,4-diazepan-1-yl)carbonyl]azetidin-3-yl}methanol (72 mg, 0.02 mmol) in ethanol (1 ml) was added sodium borohydride (18 mg, 0.05 mmol) portion wise over 3 minutes. The mixture was stirred overnight at room temperature. Evaporation at reduced pressure and purification by FCC on silica provided the title compound (18.1 mg, 28%) as colourless oil.

LCMS data: Calculated MH⁺(268); Found 100% (MH⁺) m/z 268, Rt=3.10 min.

NMR data: ¹H NMR (250 MHz, CDCl$_3$) δ ppm 4.08-3.95 (2H, m), 3.82-3.67 (4H, m), 3.50-3.31 (4H, m), 2.91-2.62 (2H, m), 2.55-2.34 (4H, m), 2.32-1.50 (9H, m).

The following compounds were made as described in Route 20, General Procedure I above.

Example 135

Preparation of 1-({3-[(4-chlorophenoxy)methyl] azetidin-1-yl}carbonyl)-4-cyclobutyl-1,4-diazepane. Potency range A

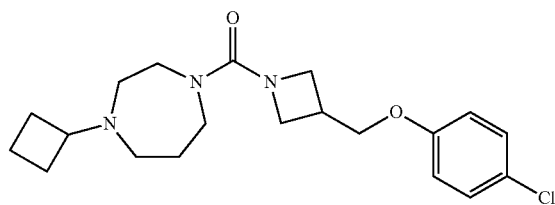 [SMILES: O=C(N1CCCN(C2CCC2)CC1)N1CC(COc2ccc(Cl)cc2)C1]

In a similar fashion (Route 20, GP I), {1-[(4-cyclobutyl-1,4-diazepan-1-yl)carbonyl]azetidin-3-yl}methanol (20 mg, 0.07 mmol) and 4-fluoro-1-chlorobenzene (19 mg, 0.15 mmol) gave the title compound as colourless oil after purification by preparative HPLC (11.6 mg, 32%).

LCMS data: Calculated MH⁺ (378); Found 100% (MH⁺) m/z 378, Rt=3.05 min.

NMR data: ¹H NMR (500 MHz, CDCl$_3$) δ ppm 7.29-7.23 (2 H, m), 6.86-6.79 (2 H, m), 4.30 (1H, t, J=8.5), 4.11-3.93 (5 H, m), 3.80 (1 H, dd, J=8.4, 5.5), 3.63-3.32 (6H, m), 3.11-3.01 (1H, m), 2.97-2.87 (1H, m), 2.72-2.61 (1H, m), 2.57-2.41 (3H, m), 1.91 (1H, q, J=10.2), 1.79-1.67 (1H, m).

Example 136

Preparation of 6-({1-[(4-cyclobutyl-1,4-diazepan-1-yl)carbonyl]azetidin-3-yl}methoxy)-3,4-dihydroisoquinolin-1(2H)-one. Potency range A

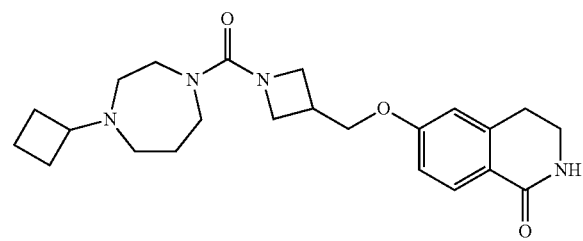 [SMILES: O=C1NCCc2cc(OCC3CN(C(=O)N4CCCN(C5CCC5)CC4)C3)ccc21]

In a similar fashion (Route 20, GP I), {1-[(4-cyclobutyl-1,4-diazepan-1-yl)carbonyl]azetidin-3-yl}methanol (39 mg, 0.15 mmol) and 6-fluoro-3,4-dihydroisoquinolin-1(2H)-one (31 mg, 0.19 mmol) gave the title compound as colourless oil after purification by preparative HPLC (26.2 mg, 34%).

LCMS data: Calculated MH⁺ (413); Found 100% (MH⁺) m/z 413, Rt=3.74 min.

NMR data: ¹H NMR (500 MHz, CDCl$_3$) δ ppm 8.07 (1 H, s), 8.01 (1 H, d, J=8.6 Hz), 6.88 (1H, dd, J=8.7 and 2.5 Hz), 6.76 (1 H, d, J=2.2 Hz), 4.30 (1H, t, J=8.5), 4.18 (2H, d, J=6.4 Hz), 4.12-3.92 (3H, m), 3.77 (1H, dd, J=8.4 and 5.5 Hz), 3.66-3.49 (8H, m), 3.44 (2H, dd, J=7.9 and 5.6 Hz), 3.39-3.29 (1H, m), 3.17-3.04 (1H, m), 3.00 (2H, t, J=6.8), 2.93-2.81 (1H, m), 2.68-2.45 (4H, m), 2.28-2.12 (3H, m), 1.96-1.87 (1H, m), 1.79-1.67 (1H, m).

Example 137

Preparation of 6-({1-[(4-cyclobutyl-1,4-diazepan-1-yl)carbonyl]azetidin-3-yl}methoxy)-2-methyl-3,4-dihydroisoquinolin-1(2H)-one. Potency range A

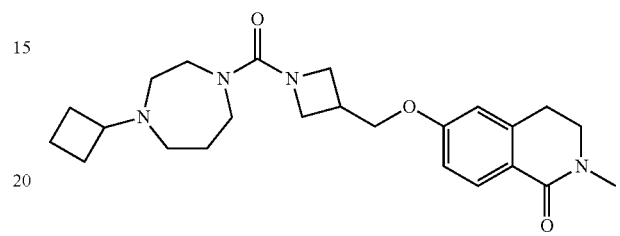

In a similar fashion (Route 20, GP I), {1-[(4-cyclobutyl-1,4-diazepan-1-yl)carbonyl]azetidin-3-yl}methanol (39 mg, 0.15 mmol) and 6-fluoro-2-methyl-3,4-dihydroisoquinolin-1(2H)-one (34 mg, 0.19 mmol) gave the title compound as colourless oil after purification by preparative HPLC (15.3 mg, 19%).

LCMS data: Calculated MH⁺(427); Found 100% (MH⁺) m/z 427, Rt=4.02 min.

NMR data: ¹H NMR (500 MHz, CDCl$_3$) δ ppm 8.03 (1 H, d, J=8.6), 6.85 (1H, dd, J=8.7 and 2.3 Hz), 6.70 (1 H, d, J=2.0 Hz), 4.35-4.26 (1H, m), 4.15 (2H, d, J=6.4 Hz), 4.11-3.94 (3H, m), 3.84-3.73 (1H, m), 3.64-3.48 (5H, m), 3.48-3.41 (2H, m), 3.39-3.29 (1H, m), 3.19 (3H, s), 3.12-3.08 (1H, m), 3.00 (2H, t, J=6.7), 2.96-2.85 (1H, m), 2.73-2.46 (4H, m), 2.30-2.11 (3H, m), 1.96-1.88 (1H, m), 1.79-1.70 (1H, m).

Example 138

Preparation 5-({1-[(4-cyclobutyl-1,4-diazepan-1-yl)carbonyl]azetidin-3-yl}methoxy)-N-methylpyridine-2-carboxamide. Potency range A

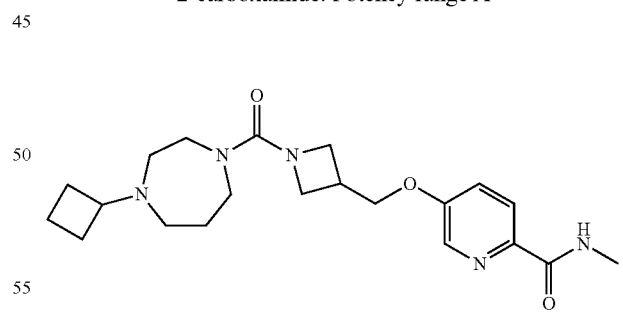

In a similar fashion (Route 20, GP I), {1-[(4-cyclobutyl-1,4-diazepan-1-yl)carbonyl]azetidin-3-yl}methanol (39 mg, 0.15 mmol) and 5-chloro-N-methylpyridine-2-carboxamide (37 mg, 0.22 mmol) gave the title compound as colourless oil after purification by preparative HPLC (11.2 mg, 15%).

LCMS data: Calculated MH⁺(402); Found 100% (MH⁺) m/z 402, Rt=3.75 min.

NMR data: ¹H NMR (500 MHz, CDCl$_3$) δ ppm 8.24 (1H, d, J=2.8 Hz), 8.19 (1 H, d, J=8.6), 8.10-8.05 (1H, br m), 7.36-7.31 (1H, m), 4.39-4.32 (1H, m), 4.23 (2H, d, J=6.4), 4.16-4.05 (3H, m), 4.03-3.95 (1H, m), 3.88-3.80 (1H, m), 3.64-3.34 (6H, m), 3.18-3.10 (1H, m), 3.07 (3H, d, J=5.1), 3.00-2.89 (1H, m), 2.73-2.63 (1H, m), 2.60-2.42 (3H, m), 2.33-2.15 (3H, m), 1.98-1.88 (1H, m), 1.81-1.70 (1H, m).

Route 39

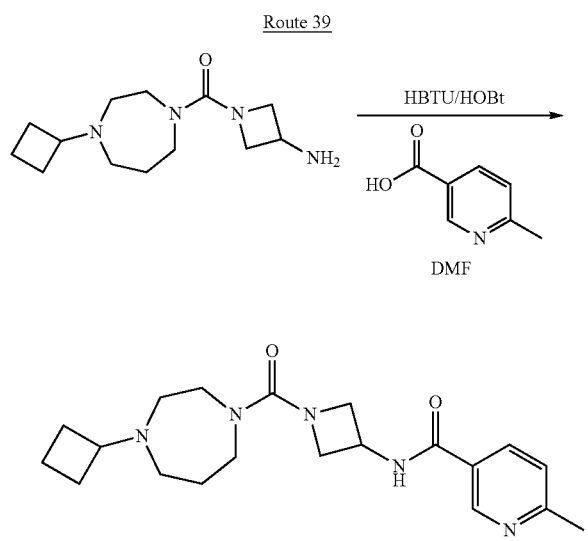

Example 139

Preparation of N-{1-[(4-cyclobutyl-1,4-diazepan-1-yl)carbonyl]azetidin-3-yl}-6-methylpyridine-3-carboxamide. Potency range A

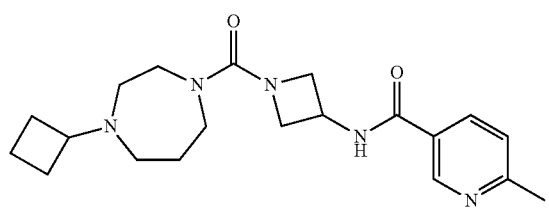

To a stirred solution of 6-methylnicotinic acid (5.5 mg, 40 μmol) in 1:1 DCM:DMF (1 ml) was added HOBt (12 mg, 87 μmol) followed by HBTU (30 mg, 80 μmol) at room temperature. After 15 minutes 1-[(4-cyclobutyl-1,4-diazepan-1-yl)carbonyl]azetidin-3-amine (10 mg, 40 μmol) was added and the reaction was stirred for 16 hours. The reaction was concentrated at reduced pressure and purified directly via preparative HPLC to give the title compound (5 mg, 34%).

LCMS data: Calculated MH$^+$(372); Found 99% (MH$^+$) m/z 372, Rt=1.68 min.

NMR data: $^1$H NMR (500 MHz, MeOD) δ ppm 8.88 (1 H, d, J=2.2 Hz), 8.15 (1 H, dd, J=8.2, 2.2 Hz), 7.41 (1 H, d, J=8.2 Hz), 4.70-4.80 (1 H, m), 4.29-4.38 (2 H, m), 4.00 (2 H, dd, J=8.7, 5.8 Hz), 3.39-3.50 (4 H, m), 2.91 (1 H, quin, J=8.0 Hz), 2.59 (3 H, s), 2.53-2.58 (2 H, m), 2.43-2.50 (2 H, m), 2.01-2.13 (2 H, m), 1.80-1.93 (4 H, m), 1.60-1.75 (2 H, m).

Route 40

General Procedure T

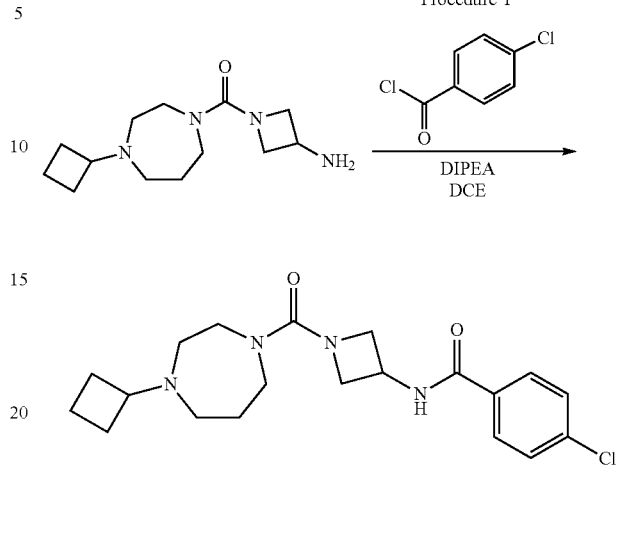

General Procedure T

Example 140

Preparation of 4-chloro-N-{1-[(4-cyclobutyl-1,4-diazepan-1-yl)carbonyl]azetidin-3-yl}benzamide. Potency range A

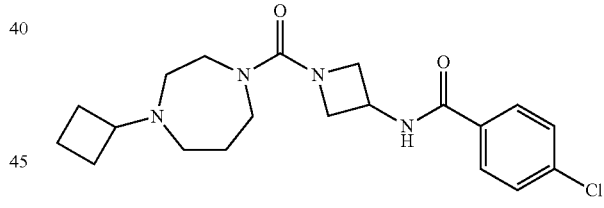

To a solution of 1-[(4-cyclobutyl-1,4-diazepan-1-yl)carbonyl]azetidin-3-amine (46 mg, 0.18 mmol) in dichloroethane (3 ml) was added 4-chlorobenzoyl chloride (20 μl, 0.18 mmol) and DIPEA (38 μl, 0.22 mmol). The reaction was stirred at room temperature for 3 hours and then diluted with dichloromethane (30 ml) and washed twice with saturated NaHCO$_3$ (15 ml), dried (MgSO$_4$), filtered and concentrated at reduced pressure. The residue was purified by FCC (DCM/MeOH/NH$_3$ with gradient, 98:2:1 to 90:10:1) to provide the title compound as white solid (26 mg, 37%).

LCMS data: Calculated MH$^+$(391); Found 100% (MH$^+$) m/z 391, Rt=2.77 min.

NMR data: $^1$H NMR (500 MHz, CDCl$_3$) δ ppm 7.89 (1 H, d, J=6.6 Hz), 7.84 (2 H, d, J=8.6 Hz), 7.38 (2 H, d, J=8.6 Hz), 4.78-4.88 (1 H, m), 4.27 (2H, dd, J=8.4, 6.1 Hz), 3.97 (2 H, dd, J=8.4, 6.1 Hz), 3.30-3.40 (4 H, m), 2.73-2.82 (1 H, m), 2.37 (4 H, m), 1.95-2.05 (2 H, m), 1.71-1.84 (4 H, m), 1.54-1.70 (2 H, m).

The following compounds were made as described in Route 40, General Procedure T above.

Example 141

Preparation of N-{1-[(4-cyclobutyl-1,4-diazepan-1-yl)carbonyl]azetidin-3-yl}cyclohexanecarboxamide. Potency range A

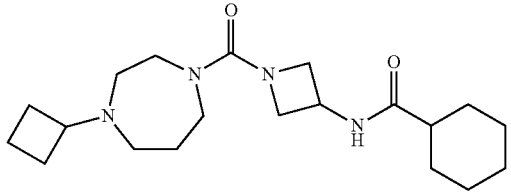 [SMILES: O=C(NC1CN(C(=O)N2CCCN(C3CCC3)CC2)C1)C1CCCCC1]

In a similar fashion (Route 40, GP T), 1-[(4-cyclobutyl-1,4-diazepan-1-yl)carbonyl]azetidin-3-amine (46 mg, 0.18 mmol) and cyclohexanecarbonyl chloride (25 μl, 0.18 mmol) gave the title compound as white solid after purification by silica FCC (40 mg, 62%).

LCMS data: Calculated MH$^+$(363); Found 99% (MH$^+$) m/z 363, Rt=2.59 min.

NMR data: $^1$H NMR (500 MHz, CDCl$_3$) δ ppm 6.61 (1 H, d, J=7.0 Hz), 4.54-4.64 (1 H, m), 4.19 (2 H, dd, J=8.5, 6.0 Hz), 3.75 (2 H, dd, J=8.5, 6.0 Hz), 3.30-3.44 (4 H, m), 2.80 (1 H, quin, J=7.8 Hz), 2.42-2.50 (2 H, m), 2.34-2.42 (2 H, m), 2.09 (1 H, m), 2.00 (2 H, m), 1.69-1.87 (8 H, m), 1.52-1.69 (3 H, m), 1.34-1.47 (2 H, m), 1.12-1.29 (3 H, m).

General Procedure U

Example 142

Preparation of 4-chloro-N-{1-[(4-cyclobutyl-1,4-diazepan-1-yl)carbonyl]azetidin-3-yl}-N-methylbenzamide. Potency range A

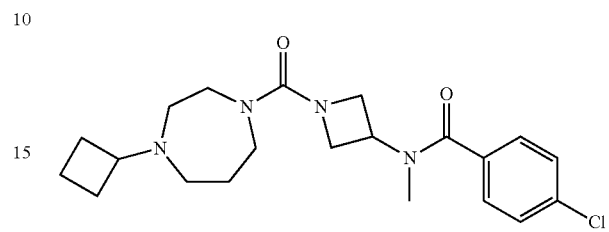

To a solution of 4-chloro-N-{1-[(4-cyclobutyl-1,4-diazepan-1-yl)carbonyl]azetidin-3-yl}benzamide (15 mg, 38 μmol) in THF (2 ml) was added NaH (3 mg of a 60% dispersion in mineral oil, 76 μmol). The reaction was stirred at room temperature for 30 minutes and then MeI (2.6 μmol, 46 μmol) was added. The reaction was heated in a sealed tube at 50° C. for 3 hours and then concentrated at reduced pressure, diluted with dichloromethane (30 ml), washed twice with saturated NaHCO$_3$ (15 ml), dried (MgSO$_4$), filtered and concentrated at reduced pressure. The residue was purified by FCC (DCM/MeOH/NH$_3$ with gradient, 95:5:1 to 90:10:1) to provide the title compound as colourless oil (10 mg, 66%).

LCMS data: Calculated MH$^+$(405); Found 91% (MH$^+$) m/z 405, Rt=2.69 min.

NMR data: $^1$H NMR (500 MHz, CDCl$_3$) δ ppm 7.12-7.47 (4 H, m), 4.44-5.14 (1 H, m), 3.93-4.34 (4 H, m), 3.33-3.53 (4 H, m), 3.09 (3 H, m), 2.83 (1 H, m), 2.47-2.58 (2 H, m), 2.32-2.47 (2 H, m), 1.97-2.09 (2 H, m), 1.73-1.93 (4 H, m), 1.54-1.72 (2 H, m).

The following compounds were made as described in Route 41, General Procedure U above.

Example 143

Preparation of N-{1-[(4-cyclobutyl-1,4-diazepan-1-yl)carbonyl]azetidin-3-yl}-N,6-dimethylpyridine-3-carboxamide. Potency range A

Route 41

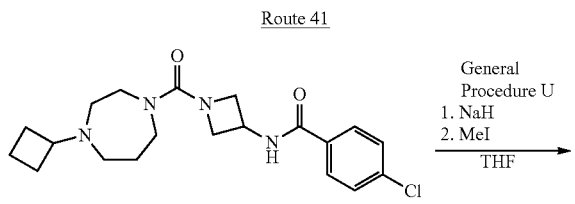

General Procedure U
1. NaH
2. MeI
THF

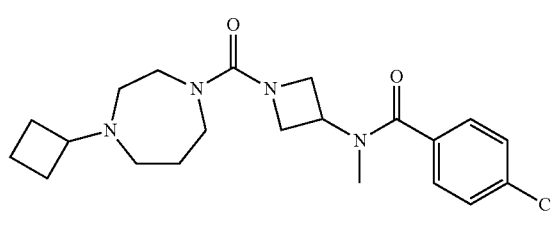

In a similar fashion (Route 41, GP U), N-{1-[(4-cyclobutyl-1,4-diazepan-1-yl)carbonyl]azetidin-3-yl}-6-methylpyridine-3-carboxamide (49 mg, 0.13 mmol) gave the title compound after purification by silica FCC (8 mg, 16%).

LCMS data: Calculated MH$^+$(386); Found 94% (MH$^+$) m/z 386, Rt=3.39 min.

NMR data—a 1:1 mixture of rotamers was observed: $^1$H NMR (500 MHz, MeOD) δ ppm 8.33-8.62 (1 H, m), 7.65-7.91 (1 H, m), 7.40 (1 H, d, J=8.1 Hz), 4.92-5.13 (0.5 H, m), 4.55-4.78 (0.5 H, m), 4.05-4.38 (4 H, m), 3.44 (4 H, m), 2.98-3.28 (3 H, m), 2.90 (1 H, quin, J=8.0 Hz), 2.59 (3 H, s), 2.51-2.58 (2 H, m), 2.39-2.50 (2 H, m), 2.00-2.13 (2 H, m), 1.80-1.97 (4 H, m), 1.54-1.78 (2 H, m).

Example 144

Preparation of N-{1-[(4-cyclobutyl-1,4-diazepan-1-yl)carbonyl]azetidin-3-yl}-N-methylcyclohexanecarboxamide. Potency range A

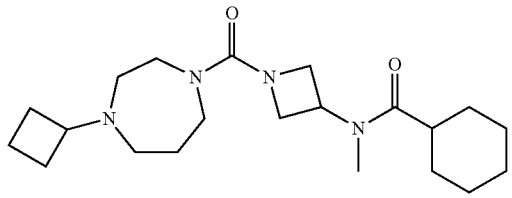 [SMILES: CN(C(=O)C1CCCCC1)C1CN(C(=O)N2CCCN(C3CCC3)CC2)C1]

In a similar fashion (Route 41, GP U), N-{1-[(4-cyclobutyl-1,4-diazepan-1-yl)carbonyl]azetidin-3-yl}cyclohexanecarboxamide (14 mg, 38 μmol) gave the title compound after purification by silica FCC as colourless oil (9 mg, 64%).

LCMS data: Calculated MH$^+$(377); Found 97% (MH$^+$) m/z 377, Rt=2.67 min.

NMR data—a 7:3 mixture of rotamers was observed: $^1$H NMR (500 MHz, CDCl$_3$) δ ppm 5.02-5.16 (0.7 H, m), 4.83 (0.3 H, m), 4.09-4.28 (2 H, m), 3.96-4.09 (0.6 H, m), 3.80-3.96 (1.4 H, m), 3.29-3.57 (4 H, m), 3.08 (2.1 H, s), 3.03 (0.9 H, s), 2.78-2.92 (1 H, m), 2.33-2.59 (5 H, m), 2.04 (2 H, m), 1.56-1.94 (11 H, m), 1.39-1.56 (2 H, m), 1.14-1.38 (3 H, m).

Example 145

Preparation of 1-[(4-cyclobutyl-1,4-diazepan-1-yl)carbonyl]-N-methyl-N-(6-methylpyridin-3-yl)azetidine-3-carboxamide. Potency range A

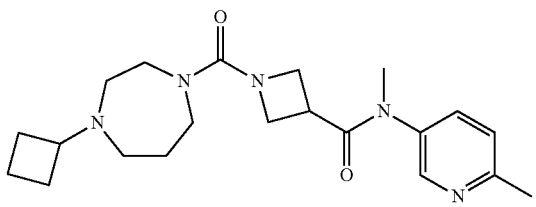 [SMILES: Cc1ccc(N(C)C(=O)C2CN(C(=O)N3CCCN(C4CCC4)CC3)C2)cn1]

In a similar fashion (Route 41, GP U) 1-[(4-cyclobutyl-1,4-diazepan-1-yl)carbonyl]-N-(6-methylpyridin-3-yl)azetidine-3-carboxamide (51 mg, 0.14 mmol) gave the title compound (1.3 mg, 3%) after purification by silica FCC.

LCMS data: Calculated MH$^+$(386); Found 93% (MH$^+$) m/z 386, Rt=3.51 min.

NMR data: $^1$H NMR (500 MHz, MeOD) δ ppm 8.31-8.38 (1 H, m), 7.62-7.71 (1 H, m), 7.38-7.47 (1 H, m), 4.05-4.14 (2 H, m), 3.69-3.80 (2 H, m), 3.25-3.48 (8 H, m), 2.83-2.94 (1 H, m), 2.49-2.62 (5 H, m), 2.40-2.49 (2 H, m), 2.01-2.13 (2 H, m), 1.77-1.92 (4 H, m), 1.56-1.74 (2 H, m).

Example 146

Preparation of N-(4-chlorophenyl)-1-[(4-cyclobutyl-1,4-diazepan-1-yl)carbonyl]-N-methylazetidine-3-carboxamide. Potency range A

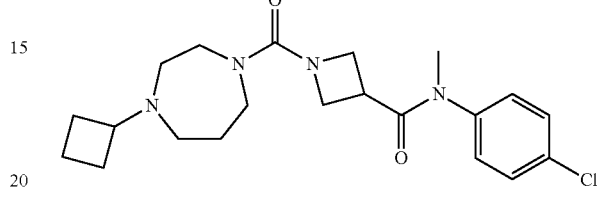

In a similar fashion (Route 41, GP U) 1-[(4-cyclobutyl-1,4-diazepan-1-yl)carbonyl]-N-(6-methylpyridin-3-yl)azetidine-3-carboxamide (51 mg, 0.14 mmol) gave the title compound (2.3 mg, 3%) after purification by silica FCC.

LCMS data: Calculated MH$^+$(405); Found 100% (MH$^+$) m/z 405, Rt=2.96 min.

NMR data:—a 6:4 mixture of rotamers was observed: $^1$H NMR (500 MHz, MeOD) δ ppm 7.54-7.63 (0.6 H, d, J=8.5 Hz), 7.47-7.53 (0.4 H, d, J=8.5 Hz), 7.30-7.37 (0.6 H, d, J=8.5 Hz), 7.22-7.30 (0.4 H, d, J=8.5 Hz), 4.00-4.39 (2 H, m), 3.64-3.98 (2 H, m), 3.21-3.63 (12 H, m), 2.85-3.13 (1 H, m), 2.31-2.41 (2 H, m), 1.99-2.29 (4 H, m), 1.73-1.93 (2 H, m).

Example 147

Preparation of 4-({1-[(4-cyclobutyl-1,4-diazepan-1-yl)carbonyl]azetidin-3-yl}oxy)-N-methylpyridine-2-carboxamide. Potency range A

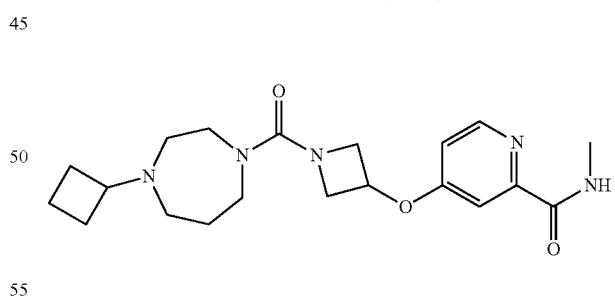

In a similar fashion (Route 41, GP U), 4-({1-[(4-cyclobutyl-1,4-diazepan-1-yl)carbonyl]azetidin-3-yl}oxy)pyridine-2-carboxamide (15 mg, 40 μmol) in DMF (2 ml) gave the title compound (10 mg, 50%) as colourless oil after purification by preparative HPLC (TFA salt).

LCMS data: Calculated MH$^+$ (388); Found 100% (MH$^+$) m/z 388, Rt=2.23 min

NMR data: $^1$H NMR (500 MHz, MeOD) δ ppm 8.49 (1 H, d, J=4.7 Hz), 7.52-7.57 (1 H, m), 7.03-7.08 (1 H, m), 5.18-5.24 (1 H, m), 4.58-4.65 (1 H, m), 4.43-4.49 (1 H, m), 4.14-4.21 (1 H, m), 4.01-4.07 (1 H, m), 3.91-3.98 (1 H, m), 3.70-

3.79 (1 H, m), 3.41-3.61 (5 H, m), 2.98 (5 H, m), 2.33-2.42 (2 H, m), 2.05-2.31 (4 H, m), 1.76-1.94 (2 H, m).

Example 148

Preparation of 1-cyclobutyl-4-{[3-(methoxymethyl)azetidin-1-yl]carbonyl}-1,4-diazepane. Potency range A

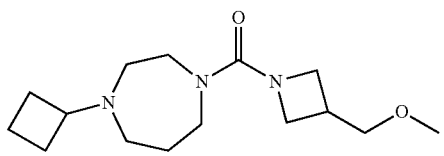 [SMILES: COCC1CN(C(=O)N2CCCN(C3CCC3)CC2)C1]

In a similar fashion (Route 41, GP U), {1-[(4-cyclobutyl-1,4-diazepan-1-yl)carbonyl]azetidin-3-yl}methanol (20 mg, 74 µmol) in DMSO (2 ml) gave the title compound after purification by FCC (6 mg, 30%).

LCMS data: Calculated MH$^+$(282); Found 90% (MH$^+$) m/z 282, Rt=3.60 min

NMR data: $^1$H NMR (500 MHz, CDCl$_3$) δ ppm 4.04 (2 H, t, J=8.3 Hz), 3.70 (2 H, dd, J=8.2, 5.6 Hz), 3.53 (2 H, d, J=7.0 Hz), 3.43-3.47 (2 H, m), 3.35-3.41 (5 H, m), 2.73-2.88 (2 H, m), 2.47-2.55 (2 H, m), 2.38-2.46 (2 H, m), 1.98-2.08 (2 H, m), 1.77-1.93 (4 H, m), 1.56-1.75 (2 H, m).

1-Methyl-4-(4,4,5,5-tetramethyl-1,3,2-dioxaborolan-2-yl)-1H-pyrazole (21 mg, 101 µmol), tricyclohexylphosphine (3.1 mg, 11 µmol) and Pd$_2$(dba)$_3$ (4.2 mg, 5 µmol) were dissolved in dioxane (0.25 ml) under a nitrogen atmosphere. Solid 1-cyclobutyl-4-{[3-(4-iodophenoxy)azetidin-1-yl]carbonyl}-1,4-diazepane (42 mg, 92 µmol) was added followed by K$_3$PO$_4$ (122 µl of a 1.27 M aqueous solution, 156 µmol). The reaction was stirred at room temperature for 30 minutes and then at 110° C. for 16 hours. The reaction was diluted with dichloromethane (30 ml), filtered through celite, washed twice with saturated NaHCO$_3$ (15 ml), dried (MgSO$_4$), filtered and concentrated at reduced pressure. The residue was purified by FCC (DCM/MeOH/NH$_3$ with gradient, 98:2:1 to 90:10:1) and then recrystallised (Heptane/EtOAc) to give the title product as white solid (16 mg, 42%).

LCMS data: Calculated MH$^+$(410); Found 99% (MH$^+$) m/z 410, Rt=2.63 min.

NMR data: $^1$H NMR (250 MHz, CDCl$_3$) δ ppm 7.69 (1 H, s), 7.53 (1 H, s), 7.38 (2 H, d, J=8.7 Hz), 6.75 (2 H, d, J=8.7 Hz), 4.82-4.99 (1 H, m), 4.34 (2 H, dd, J=9.3, 6.5 Hz), 4.05 (2 H, dd, J=9.4, 4.1 Hz), 3.94 (3 H, s), 3.35-3.53 (4 H, m), 2.73-2.93 (1 H, m), 2.34-2.59 (4 H, m), 1.95-2.14 (2 H, m), 1.47-1.95 (6 H, m).

The following compounds were made as described in Route 42, General Procedure V above.

Route 42

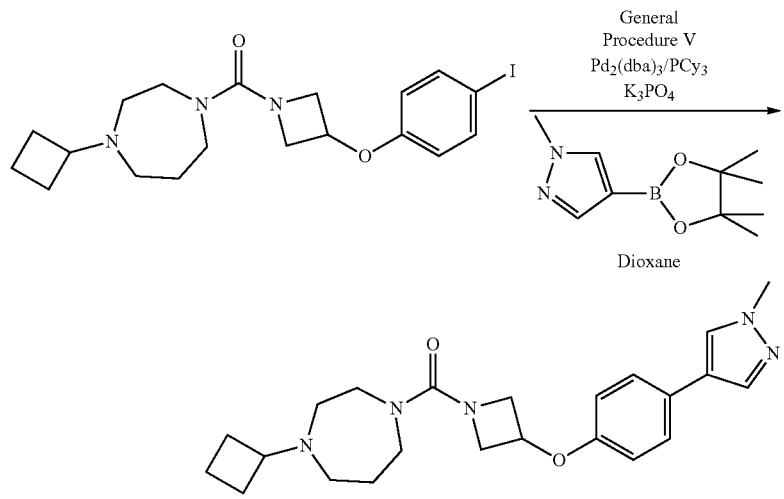

General Procedure V

Example 149

Preparation of 1-cyclobutyl-4-({3-[4-(1-methyl-1H-pyrazol-4-yl)phenoxy]azetidin-1-yl}carbonyl)-1,4-diazepane. Potency range A

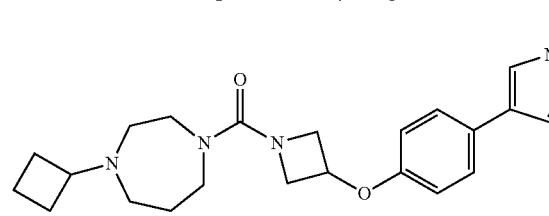

Example 150

Preparation of 1-cyclobutyl-4-({3-[4-(1,3,5-trimethyl-1H-pyrazol-4-yl)phenoxy]azetidin-1-yl}carbonyl)-1,4-diazepane. Potency range A

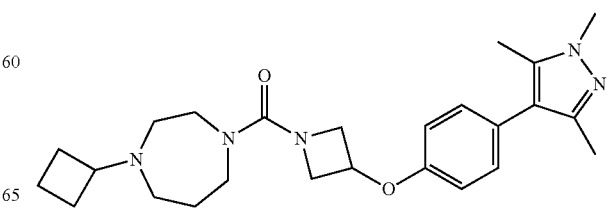

In a similar fashion (Route 42, GP V), 1-cyclobutyl-4-{[3-(4-iodophenoxy)azetidin-1-yl]carbonyl}-1,4-diazepane (42 mg, 92 μmol) and 1-methyl-4-(4,4,5,5-tetramethyl-1,3,2-dioxaborolan-2-yl)-1H-pyrazole (24 mg, 101 μmol) gave the title compound (15 mg, 37%) as yellow oil after purification by silica FCC.

LCMS data: Calculated MH+(438); Found 98% (MH+) m/z 438, Rt=2.70 min.

NMR data: $^1$H NMR (500 MHz, CDCl$_3$) δ ppm 7.15 (2 H, d, J=8.7 Hz), 6.79 (2 H, d, J=8.7 Hz), 4.88-4.95 (1 H, m), 4.35 (2 H, dd, J=9.3, 6.7 Hz), 4.07 (2 H, dd, J=9.5, 4.3 Hz), 3.77 (3 H, s), 3.39-3.52 (4 H, m), 2.78-2.90 (1 H, m), 2.48-2.57 (2 H, m), 2.38-2.47 (2 H, m), 2.22 (6 H, d, J=3.1 Hz), 1.98-2.08 (2 H, m), 1.74-1.92 (4 H, m), 1.54-1.73 (2 H, m).

Route 43

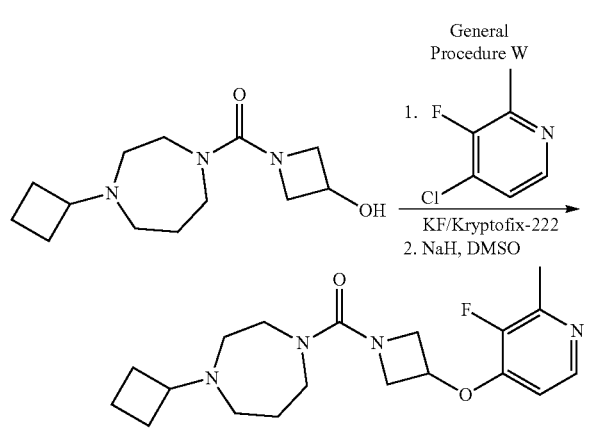

General Procedure W

Example 151

Preparation of 1-cyclobutyl-4-({3-[(3-fluoro-2-methylpyridin-4-yl)oxy]azetidin-1-yl}carbonyl)-1,4-diazepane. Potency range A

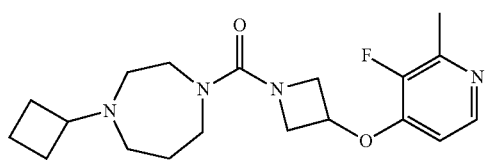 [SMILES: Cc1nccc(OC2CN(C(=O)N3CCCN(C4CCC4)CC3)C2)c1F]

KF (73 mg, 1.25 mmol) was dried under vacuum for 2 hours and then stirred with Kryptofix-222 (282 mg, 0.75 mmol) and 4-chloro-3-fluoro-2-methylpyridine (40 mg, 0.28 mmol) in DMSO (3 ml) at 120° C. for 16 hours in a sealed tube. After cooling to room temperature, NaH (100 mg of a 60% dispersion in mineral oil, 2.5 mmol) and 1-[(4-cyclobutyl-1,4-diazepan-1-yl)carbonyl]azetidin-3-ol (63 mg, 0.25 mmol) were added and stirred for a further 8 hours. The reaction was diluted with EtOAc (30 ml) and washed with saturated NaHCO$_3$ (3×15 ml), dried (MgSO$_4$), filtered and concentrated at reduced pressure. The residue was purified by FCC (DCM/MeOH/NH$_3$ with gradient, 98:2:1 to 90:10:1) to give the title compound (32 mg, 35%) as yellow oil.

LCMS data: Calculated MH+ (363); Found 99% (MH+) m/z 363, Rt=3.76 mins (High pH method).

NMR data: $^1$H NMR (500 MHz, CDCl$_3$) δ ppm 8.07 (1 H, d, J=5.5 Hz), 6.37-6.47 (1 H, m), 4.88-4.98 (1 H, m), 4.32 (2 H, dd, J=9.7, 6.6 Hz), 4.05 (2 H, dd, J=9.7, 4.0 Hz), 3.32-3.46 (4 H, m), 2.75-2.85 (1 H, m), 2.41-2.49 (5 H, m), 2.33-2.41 (2 H, m), 1.92-2.05 (2 H, m), 1.70-1.89 (4 H, m), 1.58 (2 H, m).

The following compounds were made as described in Route 43, General Procedure W above.

Example 152

Preparation of 1-cyclobutyl-4-{[3-(naphthalen-2-yloxy)azetidin-1-yl]carbonyl}-1,4-diazepane. Potency range A

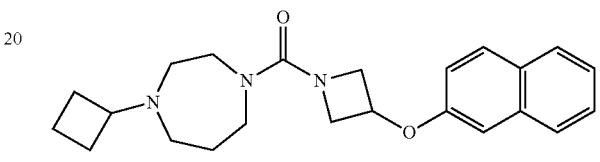

In a similar fashion (Route 43, GP W), 1-[(4-cyclobutyl-1,4-diazepan-1-yl)carbonyl]azetidin-3-ol (30 mg, 0.12 mmol) and 2-chloronapthalene (39 mg, 0.24 μmol) gave the title compound after purification by preparative HPLC (7 mg, 10%).

LCMS data: Calculated MH+ (380); Found 79% (MH+) m/z 380, Rt=3.17 min. Approximately 95% purity by NMR was observed.

NMR data: $^1$H NMR (500 MHz, CDCl$_3$) δ ppm 7.79 (2 H, d, J=8.8 Hz), 7.71 (1 H, d, J=8.3 Hz), 7.44-7.50 (1 H, m), 7.35-7.41 (1 H, m), 7.12 (1 H, dd, J=9.0, 2.6 Hz), 6.83 (1 H, d, J=2.4 Hz), 5.01-5.11 (1 H, m), 4.59 (1 H, dd, J=9.1, 6.9 Hz), 4.29-4.40 (1 H, m), 4.25 (1 H, dd, J=9.4, 3.9 Hz), 3.93-4.06 (2 H, m), 3.40-3.64 (5 H, m), 3.28-3.39 (1 H, m), 2.84-2.95 (1 H, m), 2.41-2.71 (4 H, m), 2.10-2.29 (3 H, m), 1.84-1.96 (1 H, m), 1.64-1.79 (1 H, m).

Route 44

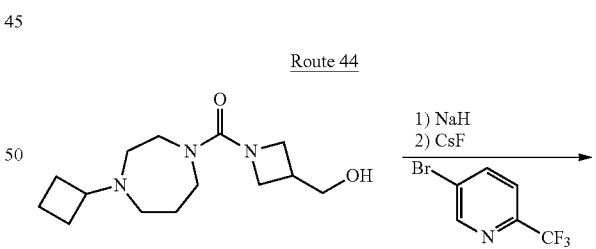

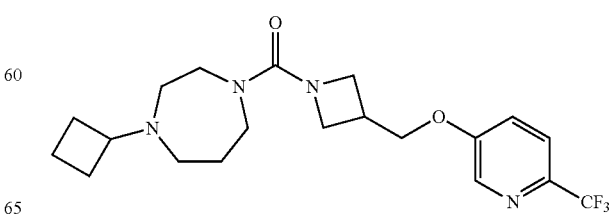

Example 153

Preparation of 1-cyclobutyl-4-{[3-({[6-(trifluoromethyl)pyridin-3-yl]oxy}methyl)azetidin-1-yl]carbonyl}-1,4-diazepane. Potency range A

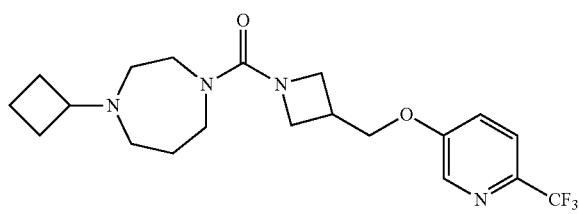 [SMILES: O=C(N1CCCN(C2CCC2)CC1)N1CC(COc2ccc(C(F)(F)F)nc2)C1]

To a solution of {1-[(4-cyclobutyl-1,4-diazepan-1-yl)carbonyl]azetidin-3-yl}methano 1 (20 mg, 74 μmol) in DMSO (1 ml) was added NaH (6 mg of a 60% dispersion in mineral oil, 0.15 mmol). After 30 minutes CsF (12 mg, 74 μmol) and 5-bromo-2-trifluoromethylpyridine (34 mg, 0.15 mmol) were added and the mixture was heated at 85° C. for 2 hours. The reaction was cooled to room temperature, diluted with dichloromethane (20 ml), washed with water (20 ml), dried (MgSO$_4$), filtered and concentrated at reduced pressure. The residue was purified by preparative HPLC to give the title compound (14 mg, 45%).

LCMS data: Calculated MH$^+$(413); Found 86% (MH$^+$) m/z 413, Rt=2.87 mins. 95% purity by NMR was observed.

NMR data: $^1$H NMR (500 MHz, CDCl$_3$) δ ppm 8.42 (1 H, d, J=2.6 Hz), 7.66 (1 H, d, J=8.6 Hz), 7.33 (1 H, dd, J=8.7, 2.5 Hz), 4.32 (1 H, m), 4.23 (2 H, d, J=6.4 Hz), 4.07-4.14 (1 H, m), 4.00-4.06 (1 H, m), 3.91-4.00 (1 H, m), 3.79 (1 H, dd, J=8.4, 5.5 Hz), 3.48-3.63 (3 H, m), 3.30-3.48 (3 H, m), 3.06-3.18 (1 H, m), 2.84-2.96 (1 H, m), 2.59-2.70 (1 H, m), 2.41-2.59 (3 H, m), 2.11-2.31 (3 H, m), 1.85-1.97 (1 H, m), 1.67-1.82 (1 H, m).

Route 45

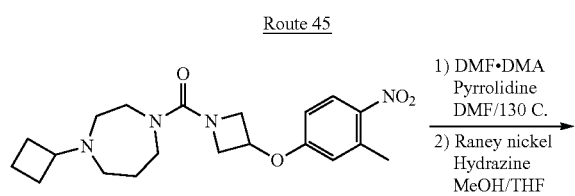

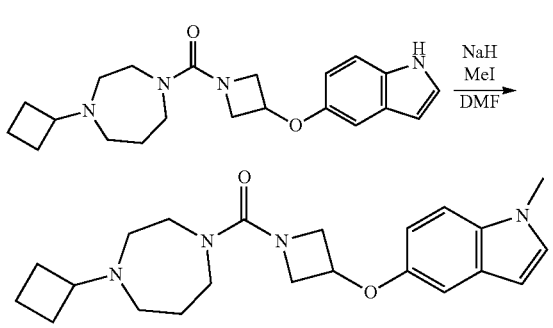

Example 154

Preparation of 5-({1-[(4-cyclobutyl-1,4-diazepan-1-yl)carbonyl]azetidin-3-yl}oxy)-1H-indole. Potency range A

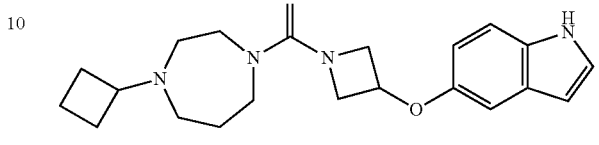

To a stirred solution of 1-cyclobutyl-4-{[3-(3-methyl-4-nitrophenoxy)azetidin-1-yl]carbonyl}-1,4-diazepane (40 mg, 0.16 mmol) in DMF (2 ml) was added DMF.DMA (100 μl, 0.75 mmol) and pyrrolidine (100 μl, 0.75 mmol) at 130° C. in one portion. The suspension was stirred for 2 h at 130° C. then cooled to room temperature and concentrated at reduced pressure. The residue was dissolved in 1:1 THF/MeOH (4 ml) and Raney Nickel (0.7 ml, 50% w/v in H$_2$O) and hydrazine (0.7 ml, 1M solution in THF) were added. The reaction was stirred at room temperature for 3 hours then filtered over celite and concentrated at reduced pressure. The residue was purified by FCC (DCM/MeOH/NH$_3$ with gradient, 98:2:1 to 95:5:1) to give the title compound (43 mg, 37%) as light brown oil.

LCMS data: Calculated MH$^+$(369); Found 98% (MH$^+$) m/z 369, Rt=4.12 min.

NMR data: $^1$H NMR (250 MHz, CDCl$_3$) δ 8.48 (1 H, br. s.), 7.16-7.28 (1 H, m), 7.12 (1 H, m), 6.64-6.83 (2 H, m), 6.38 (1 H, m), 4.84 (1 H, m), 4.27 (2 H, dd, J=9.7, 6.4 Hz), 4.00 (2 H, dd, J=9.8, 4.3 Hz), 3.27-3.47 (4 H, m), 2.66-2.84 (1 H, m), 2.27-2.52 (4 H, m), 1.86-2.07 (2 H, m), 1.44-1.86 (6 H, m).

Example 155

Preparation of 5-({1-[(4-cyclobutyl-1,4-diazepan-1-yl)carbonyl]azetidin-3-yl}oxy)-1-methyl-1H-indole. Potency range A

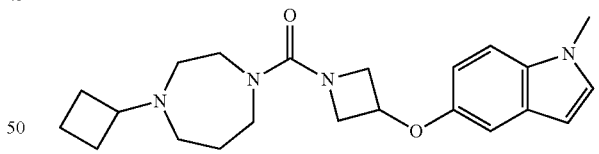

To a stirred solution of 5-({1-[(4-cyclobutyl-1,4-diazepan-1-yl)carbonyl]azetidin-3-yl}oxy)-1H-indole (30 mg, 81 μmol) in DMF (2 ml) was added NaH (4 mg of a 60% dispersion in mineral oil, 97 μmol) at room temperature in one portion. The suspension was stirred for 30 min at room temperature under a nitrogen atmosphere then cooled to 0° C. and MeI (6 μl, 97 μmol) was added. The reaction was allowed to warm to room temperature and stirred for 16 hours then diluted with dichloromethane (30 ml) and washed twice with saturated NaHCO$_3$ (15 ml), dried (MgSO$_4$), filtered and concentrated at reduced pressure. The residue was purified by FCC (DCM/MeOH/NH$_3$ with gradient, 98:2:1 to 90:10:1) to provide the title compound (23 mg, 74%) as light brown oil.

LCMS data: Calculated MH$^+$(383); Found 99% (MH$^+$) m/z 383, Rt=2.89 min.

NMR data: ¹H NMR (500 MHz, CDCl₃) 7.15 (1 H, d, J=8.7 Hz), 6.93-6.98 (1 H, d, J=3.1 Hz m), 6.71-6.79 (2 H, m), 6.31 (1 H, d, J=3.1 Hz), 4.81-4.90 (1 H, m), 4.27 (2 H, dd, J=9.2, 6.6 Hz), 4.00 (2 H, dd, J=9.3, 4.3 Hz), 3.69 (3 H, s), 3.37-3.43 (2 H, m), 3.35 (2 H, m), 2.77 (1 H, m), 2.41-2.49 (2 H, m), 2.32-2.39 (2 H, m), 1.96 (2 H, m), 1.70-1.83 (4 H, m), 1.48-1.64 (2 H, m).

Route 46

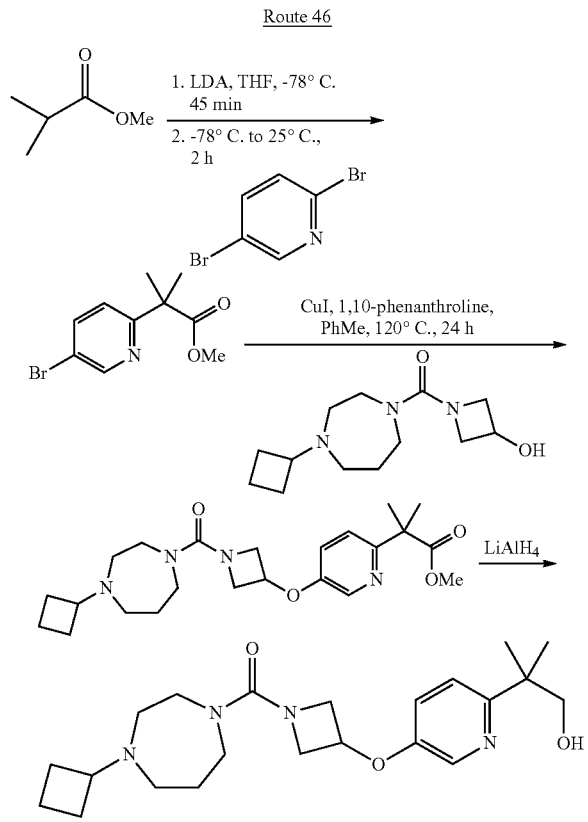

Preparation of methyl 2-(5-bromopyridin-2-yl)-2-methylpropanoate

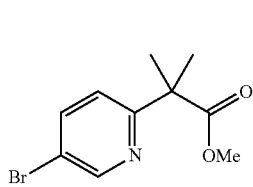

Diisopropylamine (0.45 ml, 3.17 mmol) was dissolved in THF (10 ml) under a nitrogen atmosphere and cooled to −10° C. n-BuLi (2.64 ml, 3.17 mmol, 1.2M solution in THF) was added dropwise over 5 minutes. The reaction mixture was stirred at −10° C. for 30 minutes, after which time the reaction mixture was cooled to −78° C. Methyl isobutyrate (0.36 ml, 3.17 mmol) was added dropwise over 5 minutes. Stirring was continued at −78° C. for 45 minutes. 2,5-Dibromopyridine (0.5 g, 2.11 mmol) in THF (10 ml) was added and the mixture allowed to warm to room temperature and stirred for 2 hours. The reaction was quenched by addition of saturated aqueous ammonium chloride solution, extracted into DCM (3×20 ml), the combined organics dried (MgSO₄), filtered and concentrated in vacuo. The residue was purified by FCC on silica gel [19:1 heptane/EtOAc as eluent] to provide the title compound as colourless oil (195 mg, 36%).

LCMS data: Calculated MH⁺(258/260); Found 97% m/z (258/260), Rt=1.92 min.

NMR data: ¹H NMR (500 MHz, Chloroform-d) δ ppm 8.60 (1 H, s), 7.77 (1 H, dd, J=5 Hz), 7.21 (1 H, d, J=10 Hz), 3.68 (3 H, s), 1.60 (6 H, s).

Example 155a

Preparation of methyl 2-[5-({1-[(4-cyclobutyl-1,4-diazepan-1-yl)carbonyl]azetidin-3-yl}oxy)pyridin-2-yl]-2-methylpropanoate In a similar fashion (Route 21, GP J), 1-[(4-cyclobutyl-1,4-diazepan-1-yl)carbonyl]azetidin-3-ol (383 mg, 1.51 mmol), methyl 2-(5-bromopyridin-2-yl)-2-methylpropanoate (195 mg, 0.755 mmol), CuI (7.2 mg, 0.038 mmol), 1,10-phenanthroline (13.6 mg, 0.0755 mmol) and Cs₂CO₃ (0.49 g, 1.51 mmol) gave the title compound as yellow oil (62% LCMS UV purity) after purification by preparative HPLC (110 mg), which was taken onto the next step without further purification.

LCMS data: Calculated MH⁺(431); Found 62% (MH⁺) m/z 431, Rt=1.22 min.

Example 156

Preparation of 2-[5-({1-[(4-cyclobutyl-1,4-diazepan-1-yl)carbonyl]azetidin-3-yl}oxy)pyridin-2-yl]-2-methylpropan-1-ol. Potency range A To a 0° C. solution of LiAlH₄ (0.56 ml, 0.562 mmol, 1M in THF) in THF (1 ml) under a nitrogen atmosphere was added methyl 2-[5-({1-[(4-cyclobutyl-1,4-diazepan-1-yl)carbonyl]azetidin-3-yl}oxy)pyridin-2-yl]-2-methylpropanoate (110 mg, 62% UV purity) in THF (1 ml). TLC analysis of the reaction mixture after 30 minutes indicated complete consumption of starting material. Water (1 ml), 2M NaOH (1 ml), and water (1 ml) were cautiously added to the reaction mixture. The mixture was diluted with EtOAc (20 ml), dried over MgSO₄, filtered and concentrated in vacuo. The residue was purified by FCC on silica gel [eluting with 5% methanolic ammonia (7N) in DCM] to provide the title compound as colourless oil (34.5 mg).

LCMS data: Calculated MH⁺ (403); Found 97% m/z (403), Rt=2.14 min.

NMR data: $^1$H NMR (500 MHz, Chloroform-d) δ ppm 8.04 (1 H, d, J=5 Hz), 7.28 (1 H, d, J=10 Hz), 7.10 (1 H, dd, J=510 Hz), 4.92-4.97 (1 H, m), 4.73 (1 H, br s), 4.37 (2 H, dd, J=510 Hz), 4.07 (2 H, dd, J=510 Hz), 3.74 (2 H, s), 3.42-3.51 (4 H, m), 2.84-2.90 (1 H, m), 2.44-2.50 (4 H, m), 2.04-2.09 (2 H, m), 1.81-1.92 (4 H, m), 1.62-1.73 (2 H, m) 1.33 (6 H, s).

The following compounds were made as described in Route 20, General Procedure I above.

Example 157

Preparation of 2-[5-({1-[(4-ethyl-1,4-diazepan-1-yl)carbonyl]azetidin-3-yl}oxy)pyridin-2-yl]propan-2-ol. Potency range A

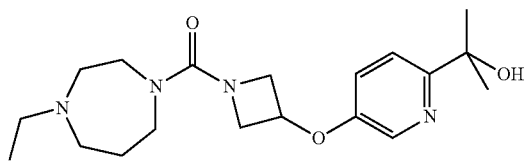 [SMILES: CCN1CCCN(C(=O)N2CC(Oc3ccc(C(C)(C)O)nc3)C2)CC1]

In a similar fashion (Route 20, GP I), 1-[(4-ethyl-1,4-diazepan-1-yl)carbonyl]azetidin-3-ol (90 mg, 0.40 mmol) and 2-(5-fluoropyridin-2-yl)propan-2-ol (95 mg, 0.44 mmol) were used to give the title compound. Crude material (53 mg) after workup gave the title compound as colourless oil (35.6 mg) after purification by preparative HPLC.

LCMS data: Calculated MH⁺(363); Found 100% (MH⁺) m/z 363, Rt=3.48 min.

NMR data: $^1$H NMR (500 MHz, CDCl₃) δ 8.04 (1 H, d, J=2.7 Hz), 7.32 (1 H, d, J=8.7 Hz), 7.08-7.14 (1 H, m), 4.91-4.98 (1 H, m), 4.62 (1 H, br. s.), 4.36 (2 H, dd, J=9.5, 6.6 Hz), 4.06 (2 H, dd, J=9.5, 4.1 Hz), 3.46-3.52 (2 H, m), 3.42 (2 H, m), 2.68-2.75 (2 H, m), 2.60-2.67 (2 H, m), 2.56 (2 H, q), 1.86-1.96 (2 H, m), 1.53 (6 H, s), 1.07 (3 H, t, J=7.1 Hz).

Example 158

Preparation of 2-{5-[(1-{[4-(1-methylethyl)-1,4-diazepan-1-yl]carbonyl}azetidin-3-yl)oxy]pyridin-2-yl}propan-2-ol. Potency range A

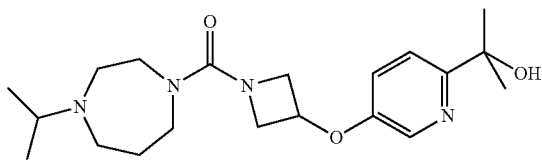 [SMILES: CC(C)N1CCCN(C(=O)N2CC(Oc3ccc(C(C)(C)O)nc3)C2)CC1]

In a similar fashion (Route 20, GP I), 1-{[4-(1-methylethyl)-1,4-diazepan-1-yl]carbonyl}azetidin-3-ol (100 mg, 0.41 mmol) and 2-(5-fluoropyridin-2-yl)propan-2-ol (90 mg, 0.41 mmol) were used to give the title compound. Crude material (50 mg) after workup gave the title compound as colourless oil (17.7 mg) after purification by preparative HPLC.

LCMS data: Calculated MH⁺(377); Found 100% (MH⁺) m/z 377, Rt=3.86 min.

NMR data: $^1$H NMR (500 MHz, CDCl₃) δ 8.04 (1 H, d, J=2.6 Hz), 7.32 (1 H, d, J=8.7 Hz), 7.12 (1 H, d, J=2.7 Hz), 4.89-5.00 (1 H, m), 4.63 (1 H, s), 4.32-4.42 (2 H, m), 4.06 (2 H, dd, J=9.4, 4.0 Hz), 3.37-3.50 (4 H, m), 2.85-2.99 (1 H, m), 2.54-2.76 (4 H, m), 1.77-1.92 (2 H, m), 1.53 (6 H, s), 1.01 (6 H, d, J=6.4 Hz).

Example 159

Preparation of 2-[5-({1-[(4-cyclopentyl-1,4-diazepan-1-yl)carbonyl]azetidin-3-yl}oxy)pyridin-2-yl]propan-2-ol. Potency range C

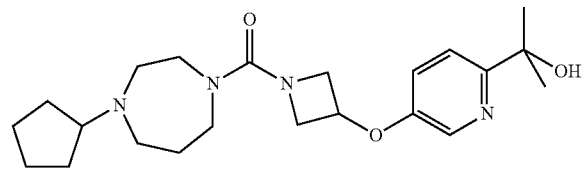 [SMILES: CC(C)(O)c1ccc(OC2CN(C(=O)N3CCCN(C4CCCC4)CC3)C2)cn1]

In a similar fashion (Route 20, GP I), 1-[(4-cyclopentyl-1,4-diazepan-1-yl)carbonyl]azetidin-3-ol (100 mg, 0.41 mmol) and 2-(5-fluoropyridin-2-yl)propan-2-ol (90 mg, 0.41 mmol) were used to give the title compound. Crude material (38 mg) after workup gave the title compound as colourless oil (19.3 mg) after purification by preparative HPLC.

LCMS data: Calculated MH⁺(403); Found 99% (MH⁺) m/z 403, Rt=4.08 min.

NMR data: $^1$H NMR (500 MHz, CDCl₃) δ 8.04 (1 H, d, J=2.7 Hz), 7.32 (1 H, d, J=8.7 Hz), 7.09-7.14 (1 H, m), 4.91-4.98 (1 H, m), 4.63 (1 H, s), 4.31-4.42 (2 H, m), 4.02-4.11 (2 H, m), 3.46-3.54 (2 H, m), 3.43 (2 H, t), 2.63-2.79 (5 H, m), 1.77-1.95 (4 H, m), 1.63-1.72 (2 H, m), 1.58 (2 H, br. s.), 1.53 (6 H, s), 1.33-1.45 (2 H, m).

Example 160

Preparation of 1-cyclobutyl-4-({3-[(5-fluoropyrimidin-2-yl)oxy]azetidin-1-yl}carbonyl)-1,4-diazepane. Potency range A

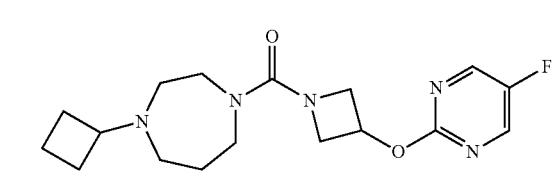 [SMILES: O=C(N1CCCN(C2CCC2)CC1)N1CC(Oc2ncc(F)cn2)C1]

In a similar fashion (Route 20, GP I), 1-[(4-cyclobutyl-1,4-diazepan-1-yl)carbonyl]azetidin-3-ol (1.49 g, 5.9 mmol) and 2-chloro-5-fluoropyrimidine (856 mg, 6.48 mmol) gave the title compound as orange solid after purification by FCC (1.10 g, 54%).

LCMS data: Calculated MH⁺ (350); Found 100% (MH⁺) m/z 350, Rt=2.23 min.

$^1$H NMR (500 MHz, MeOD) δ ppm 8.54 (2 H, s), 5.27-5.39 (1 H, m), 4.42 (2 H, dd, J=9.8, 6.7 Hz), 4.04 (2 H, dd, J=9.8, 4.2 Hz), 3.38-3.53 (4 H, m), 2.86-2.99 (1 H, m), 2.39-2.63 (4 H, m), 2.02-2.15 (2 H, m), 1.79-1.96 (4 H, m), 1.61-1.75 (2 H, m).

(1 H, m), 2.44-2.60 (6 H, m), 2.04-2.16 (2 H, m), 1.81-1.94 (4 H, m), 1.62-1.77 (2 H, m), 1.23 (3 H, t, J=7.6 Hz).

Example 161

Preparation of 1-cyclobutyl-4-({3-[(5-methoxypyridin-2-yl)oxy]azetidin-1-yl}carbonyl)-1,4-diazepane. Potency range A

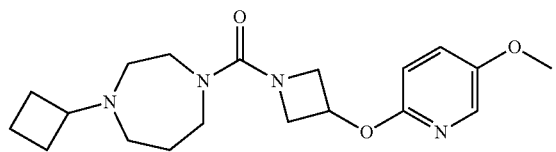 [SMILES: COc1ccc(OC2CN(C(=O)N3CCCN(C4CCC4)CC3)C2)nc1]

In a similar fashion (Route 20, GP I), 1-[(4-cyclobutyl-1,4-diazepan-1-yl)carbonyl]azetidin-3-ol (100 mg, 0.40 mmol) and 2-bromo-5-methoxypyridine (82 mg, 0.43 mmol) gave the title compound as pale yellow oil after purification by FCC (17 mg, 12%).

LCMS data: Calculated MH$^+$(361); Found 83% (MH$^+$) m/z 361, Rt=2.54 min.

$^1$H NMR (250 MHz, CDCl$_3$) δ ppm 7.73 (1 H, d, J=2.6 Hz), 7.22 (1 H, dd, J=8.9, 3.1 Hz), 6.70 (1 H, d, J=9.0 Hz), 5.17-5.34 (1 H, m), 4.23-4.43 (2 H, m), 3.98 (2 H, m), 3.80 (3 H, s), 3.33-3.51 (4 H, m), 2.73-2.93 (1 H, m), 2.34-2.59 (4 H, m), 1.94-2.12 (2 H, m), 1.70-1.94 (4 H, m), 1.52-1.70 (2 H, m).

Example 162

Preparation of 1-cyclobutyl-4-({3-[(5-ethylpyrimidin-2-yl)oxy]azetidin-1-yl}carbonyl)-1,4-diazepane. Potency range C

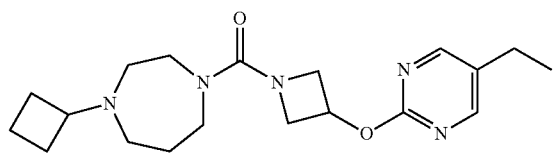 [SMILES: CCc1cnc(OC2CN(C(=O)N3CCCN(C4CCC4)CC3)C2)nc1]

In a similar fashion (Route 20, GP I), 1-[(4-cyclobutyl-1,4-diazepan-1-yl)carbonyl]azetidin-3-ol (70 mg, 0.28 mmol) and 2-chloro-5-ethylpyrimidine (43 mg, 0.30 mmol) gave the title compound as colourless oil after purification by FCC (54 mg, 55%).

LCMS data: Calculated MH$^+$(360); Found 96% (MH$^+$) m/z 360, Rt=3.40 min.

$^1$H NMR (500 MHz, MeOD) δ 8.58 (1 H, d, J=3.2 Hz), 8.06 (1 H, d, J=3.1 Hz), 5.05 (1 H, m), 4.29 (1 H, dd, J=13.7, 2.9 Hz), 4.04 (1 H, dd, J=13.9, 8.9 Hz), 3.93 (1 H, dd, J=12.4, 9.0 Hz), 3.57 (1 H, dd, J=12.4, 5.6 Hz), 3.44-3.52 (4 H, m), 2.96

Example 163

Preparation of 1-cyclobutyl-4-({3-[4-(methylsulfonyl)phenoxy]azetidin-1-yl}carbonyl)-1,4-diazepane. Potency range A

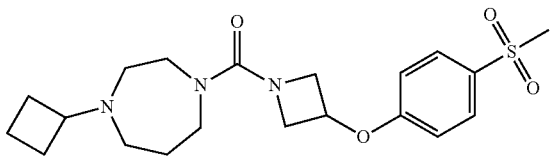 [SMILES: CS(=O)(=O)c1ccc(OC2CN(C(=O)N3CCCN(C4CCC4)CC3)C2)cc1]

In a similar fashion (Route 20, GP I), 1-[(4-cyclobutyl-1,4-diazepan-1-yl)carbonyl]azetidin-3-ol (100 mg, 0.40 mmol) and 4-fluorophenyl methyl sulfone (78 mg, 0.43 mmol) gave the title compound as colourless oil after purification by preparative HLPC (16 mg, 10%).

LCMS data: Calculated MH$^+$(408); Found 100% (MH$^+$) m/z 408, Rt=3.94 min.

$^1$H NMR (500 MHz, MeOD) δ 8.12 (2 H, d, J=8.9 Hz), 7.27 (2 H, d, J=8.8 Hz), 5.27-5.39 (1 H, m), 4.68 (2 H, dd, J=9.3, 6.6 Hz), 4.25 (2 H, dd, J=9.5, 3.8 Hz), 3.63-3.78 (4 H, m), 3.24-3.35 (4 H, m), 2.72-3.04 (4 H, m), 2.29-2.41 (2 H, m), 2.07-2.22 (4 H, m), 1.82-2.03 (2 H, m).

Route 47

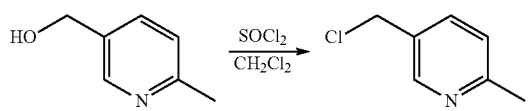

Preparation of 5-(chloromethyl)-2-methylpyridine

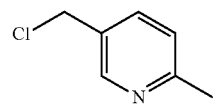

To a stirred solution of (6-methyl-3-pyridinyl)methanol (166 mg, 1.35 mmol) in dichloromethane (10 ml) was added thionyl chloride (108 μl, 1.48 mmol) giving a colourless solution. After 30 minutes the mixture was concentrated giving a brown solid (240 mg, quant. yield) that was used directly in the next step without purification.

¹H NMR (500 MHz, CDCl₃) δ 8.79 (1 H, br. s.), 8.55 (1 H, dd, J=8.3, 1.6 Hz), 7.93 (1 H, d, J=8.4 Hz), 4.89 (2 H, s), 2.77 (3 H, s).

Example 164

Preparation of 1-cyclobutyl-4-({3-[(6-methylpyridin-3-yl)methoxy]azetidin-1-yl}carbonyl)-1,4-diazepane. Potency range A

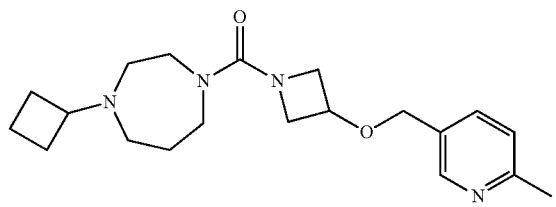 [SMILES: Cc1ccc(COC2CN(C(=O)N3CCCN(C4CCC4)CC3)C2)cn1]

In a similar fashion (Route 20, GP I), 1-[(4-cyclobutyl-1,4-diazepan-1-yl)carbonyl]azetidin-3-ol (317 mg, 1.35 mmol) and 5-(chloromethyl)-2-methylpyridine (240 mg, 1.35 mmol) gave the title compound as colourless oil after purification by FCC (22 mg, 5%).

LCMS data: Calculated MH⁺(359); Found 99% (MH⁺) m/z 359, Rt=3.79 min.

¹H NMR (500 MHz, CDCl₃) δ 8.44 (1 H, d, J=1.4 Hz), 7.58 (1 H, dd, J=7.9, 2.0 Hz), 7.16 (1 H, d, J=7.9 Hz), 4.44 (2 H, s), 4.27-4.36 (1 H, m), 4.03-4.16 (2 H, m), 3.83-3.96 (2 H, m), 3.32-3.48 (4 H, m), 2.75-2.89 (1 H, m), 2.56 (3 H, s), 2.36-2.52 (4 H, m), 1.97-2.09 (2 H, m), 1.75-1.89 (4 H, m), 1.55-1.75 (2 H, m).

Route 48

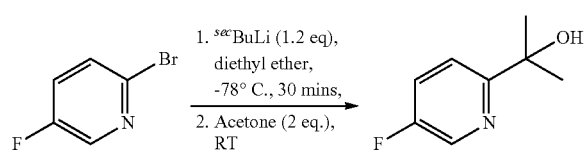

Preparation of 2-(5-fluoropyridin-2-yl)propan-2-ol

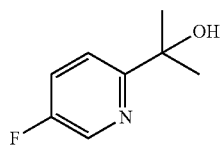

To a stirred solution of 2-bromo-5-fluoropyridine (1.0 g, 5.7 mmol) in diethyl ether (20 ml) under a nitrogen atmosphere at −78° C. was added ˢᵉᶜBuLi (4.87 ml of a 1.4 M solution in heptanes, 6.8 mmol). The resulting dark orange solution was stirred for 30 minutes at −78° C. and acetone (0.84 ml, 11.4 mmol) was then added dropwise. After a further 1 hour the reaction temperature was raised to room temperature giving a clear yellow solution. This was quenched with water (2 ml), diluted with EtOAc (30 ml) and washed with water (2×20 ml), dried (MgSO₄), filtered and concentrated. The residue was purified via silica FCC (using a gradient of eluents; 9:1 to 4:6 hexane/diethyl ether) to give the title product as colourless oil (395 mg, 45%).

LCMS data: Calculated MH⁺(156); Found 78% (MH⁺) m/z 156, Rt=0.91 min.

¹H NMR (500 MHz, CDCl₃) δ 8.37 (1 H, d, J=2.0 Hz), 7.36-7.48 (2 H, m), 4.48 (1 H, br. s.), 1.55 (6 H, s).

The following compound was made as described in Route 20, General Procedure I above.

Example 165

Preparation of 2-[5-({cis-3-[(4-cyclobutyl-1,4-diazepan-1-yl)carbonyl]cyclobutyl}oxy)pyridin-2-yl]propan-2-ol. Potency range A

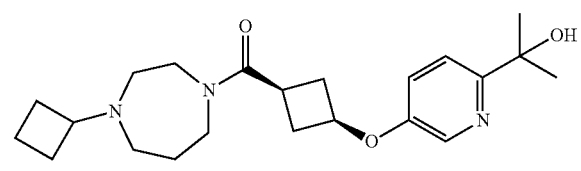 [SMILES: CC(C)(O)c1ccc(O[C@H]2C[C@@H](C(=O)N3CCCN(C4CCC4)CC3)C2)cn1]

In a similar fashion (Route 20, GP I), cis-3-[(4-cyclobutyl-1,4-diazepan-1-yl)carbonyl]cyclobutanol (50 mg, 0.20 mmol) and 2-(5-fluoropyridin-2-yl)propan-2-ol (31 mg, 0.20 mmol) gave the title compound as colourless oil after purification by silica FCC (4 mg, 5%).

LCMS data: Calculated MH⁺(388); Found 100% (MH⁺) m/z 388, Rt=1.87 min.

¹H NMR (500 MHz, MeOD) δ 8.07 (1 H, d, J=2.8 Hz), 7.57 (1 H, d, J=8.8 Hz), 7.29 (1H, dd, J=8.8, 2.8 Hz), 4.68-4.76 (1 H, m), 3.54-3.63 (4 H, m), 3.09-3.18 (1 H, m), 2.88-2.97 (1 H, m), 2.71-2.78 (2 H, m), 2.51-2.59 (2 H, m), 2.44-2.49 (2 H, m), 2.32-2.39 (2 H, m), 2.04-2.12 (2 H, m), 1.81-1.93 (4 H, m), 1.63-1.72 (2 H, m), 1.51 (6 H, s).

Route 49

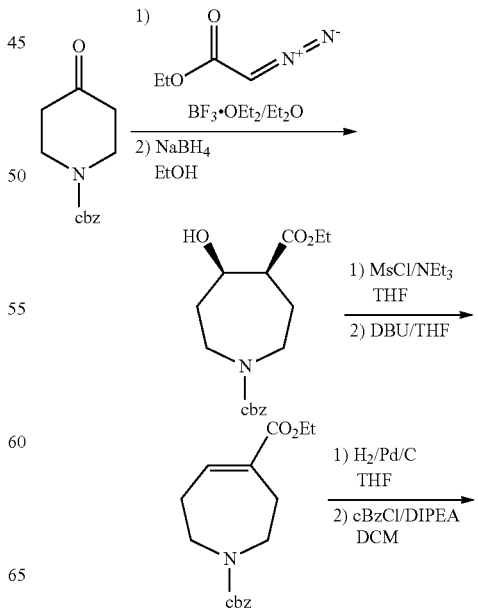

3.84 (2 H, m), 3.34-3.57 (2 H, m), 2.62-2.93 (2 H, m), 1.98-2.14 (2 H, m), 1.18-1.34 (3 H, m).

Preparation of 1-benzyl 4-ethyl-5-hydroxyazepane-1,4-dicarboxylate

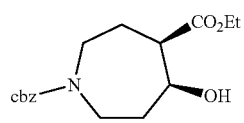

NaBH₄ (1.96 g, 51.7 mmol) was added portionwise to a stirred solution of 1-benzyl 4-ethyl 5-oxoazepane-1,4-dicarboxylate (16.5 g, 51.7 mmol) in EtOH (150 ml) at 0° C. After 10 minutes the reaction was raised to room temperature and stirred for a further 30 minutes. The reaction was quenched by dropwise addition of a saturated solution of aqueous potassium sodium tartrate (10 ml). The resulting solids were separated and the filtrate concentrated. The resulting residue was diluted with dichloromethane (150 ml) and washed with saturated aqueous potassium sodium tartrate (50 ml), water (2×50 ml), dried (MgSO₄), filtered and concentrated at reduced pressure. NMR analysis of the crude material showed a 3:1 mixture of diastereoisomers. The residue was purified by silica FCC (using a gradient of eluents; 4:1 to 1:1 Hexane/EtOAc) to give the major syn diastereoisomer of the title product as colourless oil (5.3 g, 32%).

LCMS data: Calculated MH⁺(322); Found 97% (MH⁺) m/z 322, Rt=1.83 min.

¹H NMR (500 MHz, MeOD) δ 7.27-7.40 (5 H, m), 5.05-5.19 (2 H, m), 4.13-4.30 (2 H, m), 3.84-3.98 (1 H, m), 3.67-3.84 (2 H, m), 3.34-3.57 (2 H, m), 2.62-2.93 (2 H, m), 1.98-2.14 (2 H, m), 1.18-1.34 (3 H, m).

Preparation of 1-benzyl 4-ethyl 2,3,6,7-tetrahydro-1H-azepine-1,4-dicarboxylate

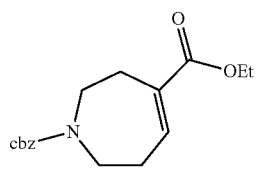

To a stirred solution 1-benzyl 4-ethyl-5-hydroxyazepane-1,4-dicarboxylate (4.4 g, 13.7 mmol) in THF (100 ml) was added MsCl (2.58 ml, 33.6 mmol) and TEA (5.69 ml, 40.5 mmol) in three portions over 16 hours. The mixture was then concentrated, diluted with dichloromethane (100 ml), washed with saturated aqueous NaHCO₃ (2×50 ml), dried (MgSO₄), filtered and reconcentrated. The residue was dissolved in THF (100 ml) and DBU (3.1 ml, 20.6 mmol) was added and the resulting mixture was heated at 80° C. for 1 hour. The reaction was then diluted with dichloromethane (100 ml), washed with saturated aqueous NaHCO₃ (3×30 ml), dried (MgSO₄), filtered and reconcentrated. The residue was purified via silica FCC (using a gradient of eluents; 9:1 to 7:3 Hexane/EtOAc) to give the title product as colourless oil (2.1 g, 51%).

LCMS data: Calculated MH⁺ (304); Found 82% (M+Na⁺) m/z 326, Rt=2.14 min.

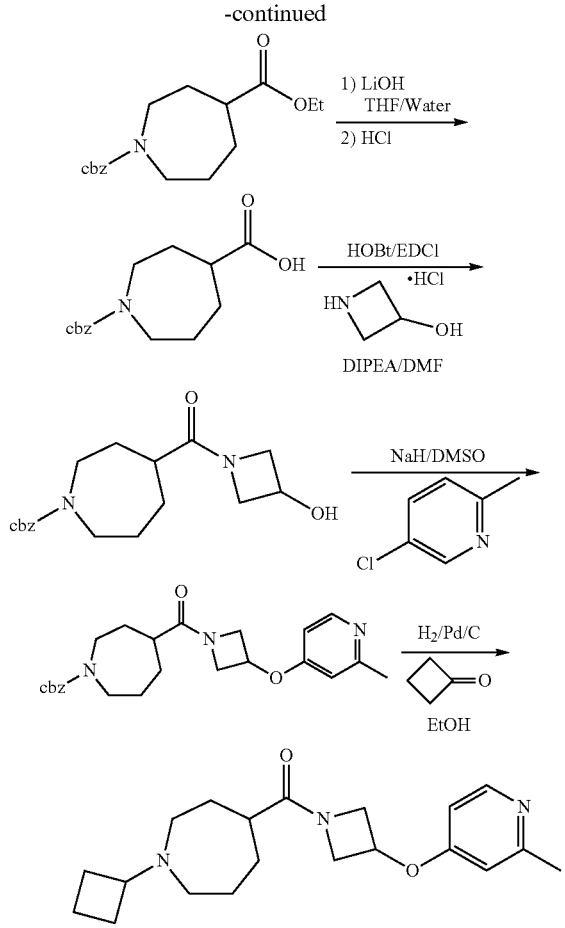

Preparation of 1-benzyl 4-ethyl 5-oxoazepane-1,4-dicarboxylate

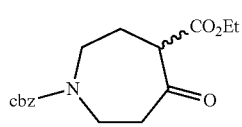

To a suspension of benzyl 4-oxo-1-piperazinecarboxylate (11.7 g, 50.3 mmol) in diethyl ether (100 ml) at −78° C. was added ethyl diazoacetate (6.84 ml, 65.3 mmol) followed by BF₃.OEt₂ (6.30 ml, 50.3 mmol). After 1 hour the reaction was raised to room temperature giving a clear yellow solution. A saturated aqueous solution of K₂CO₃ was added dropwise until no further gas evolution was observed. The organic layer was separated and washed with saturated aqueous K₂CO₃ (2×50 ml), dried (MgSO₄), filtered and concentrated giving the title product as yellow oil (16.5 g, quant. yield). The product was used without further purification.

LCMS data: Calculated MH⁺(320); Found 85% (MH⁺) m/z 320, Rt=1.92 min.

¹H NMR (500 MHz, CDCl₃) δ 7.27-7.40 (5 H, m), 5.05-5.19 (2 H, m), 4.13-4.30 (2 H, m), 3.84-3.98 (1 H, m), 3.67-

¹H NMR (500 MHz, MeOD) δ 7.24-7.43 (5 H, m), 7.12 (1 H, br. s.), 5.14 (2 H, s), 4.16 (2 H, q, J=7.0 Hz), 3.49-3.66 (4 H, m), 2.63-2.75 (2 H, m), 2.40-2.57 (2 H, m), 1.27 (3 H, t, J=7.0 Hz).

Preparation of 1-benzyl 4-ethyl azepane-1,4-dicarboxylate

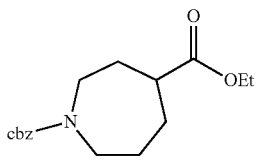

A solution of 1-benzyl 4-ethyl 2,3,6,7-tetrahydro-1H-azepine-1,4-dicarboxylate (890 mg, 2.93 mmol) and 5% Pd/C (90 mg) in THF (70 ml) were stirred under a hydrogen atmosphere for 12 hours. The mixture was then filtered over celite and concentrated giving colourless oil. This was dissolved in dichloromethane (10 ml), cooled to 0° C. and DIPEA (1.02 ml, 5.86 mmol) followed by benzyl chloroformate (0.45 ml, 3.22 mmol) were added. On complete addition the reaction was raised to room temperature and stirred for a further 1 hour. The mixture was then diluted with dichloromethane (40 ml) and washed with water (2×20 ml), dried (MgSO₄), filtered and concentrated. The residue was purified by silica FCC (using a gradient of eluents; 99:1 to 90:10 dichloromethane/MeOH) to give the title product as colourless oil (521 mg, 59%).

LCMS data: Calculated MH⁺(306); Found 86% (M+Na⁺) m/z 328, Rt=2.09 min.

¹H NMR (500 MHz, MeOD) δ 7.28-7.42 (5 H, m), 5.07-5.20 (2 H, m), 4.02-4.17 (2 H, m), 3.59-3.68 (1 H, m), 3.47-3.57 (1 H, m), 3.34-3.47 (2 H, m), 2.42-2.54 (1 H, m), 1.76-2.10 (4 H, m), 1.57-1.73 (2 H, m), 1.23 (3 H, d, J=7.1 Hz).

1-[(benzyloxy)carbonyl]azepane-4-carboxylic acid

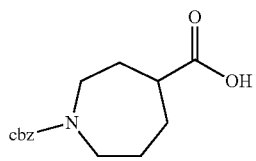

To a stirred solution of 1-benzyl 4-ethyl azepane-1,4-dicarboxylate (500 mg, 1.64 mmol) in THF (3 ml) was added LiOH (96 mmol, 2.30 mmol) dissolved in water (3 ml). After 16 hours the mixture was concentrated, diluted with dichloromethane (30 ml), washed with 1M aq. HCl (15 ml), water (15 ml), dried (MgSO₄), filtered and concentrated giving the title product as colourless oil (372 mg, 82%) that was used without and further purification.

LCMS data: Calculated MH⁺ (278); Found 86% (M+Na⁺) m/z 300, Rt=1.77 min

¹H NMR (500 MHz, MeOD) δ 7.25-7.43 (5 H, m), 5.06-5.18 (2 H, m), 3.49-3.68 (2 H, m), 3.35-3.48 (2 H, m), 2.38-2.51 (1 H, m), 1.74-2.12 (4 H, m), 1.55-1.72 (2 H, m).

Preparation of benzyl 4-[(3-hydroxyazetidin-1-yl) carbonyl]azepane-1-carboxylate

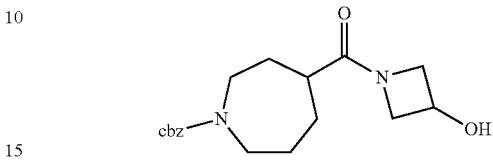

To a stirred solution of 1-[(benzyloxy)carbonyl]azepane-4-carboxylic acid (317 mg, 1.14 mmol) in DMF (5 ml) was added HOBt (154 mg, 1.14 mmol) followed by EDCI (218 mg, 1.14 mmol). After 5 minutes, a solution of 3-hydroxyazetidine hydrochloride (138 mg, 1.26 mmol) and DIPEA (0.44 ml, 2.51 mmol) in DMF (1 ml) was added and the resulting solution was stirred for 12 hours at room temperature. The mixture was diluted with EtOAc (30 ml) and washed with saturated aqueous NaHCO₃ (3×15 ml), dried (MgSO₄), filtered and concentrated. The residue was purified by silica FCC (using a gradient of eluents; 99:1 to 92:8 DCM/MeOH) to give the title product as colourless oil (265 mg, 70%).

LCMS data: Calculated MH⁺(333); Found 100% (M+Na⁺) m/z 355, Rt=1.56 min

¹H NMR (500 MHz, MeOD) δ 7.26-7.42 (5 H, m), 5.05-5.22 (2 H, m), 4.48-4.60 (1 H, m), 4.23-4.41 (1 H, m), 4.09-4.20 (1 H, m), 3.84-3.98 (1 H, m), 3.54-3.76 (3 H, m), 3.33-3.48 (2 H, m), 2.33 (1 H, m), 1.69-1.99 (4 H, m), 1.46-1.69 (2 H, m).

Preparation of benzyl 4-({3-[(6-methylpyridin-3-yl) oxy]azetidin-1-yl}carbonyl)azepane-1-carboxylate

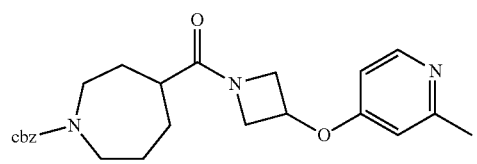

To a solution of benzyl 4-[(3-hydroxyazetidin-1-yl)carbonyl]azepane-1-carboxylate (97 mg, 0.29 mmol) and 4-chloro-2-methylpyridine (52 μl, 0.46 mmol) in DMSO (2 ml) was added NaH (37 mg of a 60% dispersion in mineral oil, 0.93 mmol). The mixture was stirred at room temperature for 12 hours, 50° C. for 3 hours and a further 12 hours at room temperature. The reaction was then diluted with EtOAc (20 ml) and washed with water (3×10 ml), dried (MgSO₄), filtered and concentrated. The residue was purified by silica FCC (using a gradient of eluents; 99:1:1 to 95:5:1 DCM/MeOH/2M NH₃ in MeOH) to give the title product as colourless oil (35 mg, 29%).

LCMS data: Calculated MH⁺(424); Found 96% (MH⁺) m/z 424, Rt=1.44 min

¹H NMR (500 MHz, MeOD) δ 8.21-8.29 (1 H, m), 7.16-7.42 (5 H, m), 6.69-6.82 (2 H, m), 5.04-5.21 (3 H, m), 4.51-4.68 (1 H, m), 4.32-4.44 (1 H, m), 4.05-4.23 (1 H, m), 3.86-

3.99 (1 H, m), 3.53-3.71 (2 H, m), 3.33-3.50 (2 H, m), 2.49 (3 H, s), 2.30-2.41 (1 H, m), 1.69-2.00 (4 H, m), 1.48-1.69 (2 H, m).

Example 166

Preparation of 1-cyclobutyl-4-({3-[(6-methylpyridin-3-yl)oxy]azetidin-1-yl}carbonyl)azepane. Potency range A

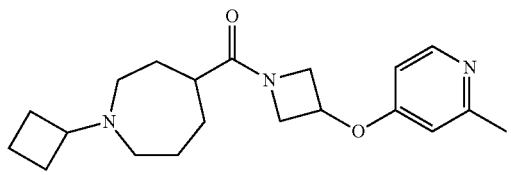 [SMILES: Cc1cc(OC2CN(C(=O)C3CCCN(C4CCC4)CC3)C2)ccn1]

A mixture of benzyl 4-({3-[(6-methylpyridin-3-yl)oxy]azetidin-1-yl}carbonyl)azepane-1-carboxylate (37 mg, 87 μmol), cyclobutanone (13 μl, 0.18 mmol) and 5% Pd/C (5 mg) in EtOH (4 ml) were stirred under a hydrogen atmosphere for 12 hours. The reaction was then filtered over celite and concentrated. The residue was dissolved in EtOAc (30 ml) and washed with water (3×15 ml), dried (MgSO$_4$), filtered and concentrated. The residue was purified by silica FCC (using a gradient of eluents; 98:2:1 to 90:10:1 DCM/MeOH/2M NH$_3$ in MeOH) to give the title product as colourless oil (12 mg, 40%).

LCMS data: Calculated MH$^+$(344); Found 87% (MH$^+$) m/z 344, Rt=4.20 min.

$^1$H NMR (500 MHz, MeOD) δ 8.24 (1 H, d, J=5.8 Hz), 6.70-6.84 (2 H, m), 5.10-5.19 (1 H, m), 4.62-4.75 (1 H, m), 4.36-4.45 (1 H, m), 4.19-4.28 (1 H, m), 3.90-3.99 (1 H, m), 2.95-3.07 (1 H, m), 2.58-2.78 (3 H, m), 2.42-2.58 (5 H, m), 2.02-2.13 (2 H, m), 1.79-1.96 (6 H, m), 1.60-1.79 (4 H, m).

The invention claimed is:

1. A compound of formula (I)

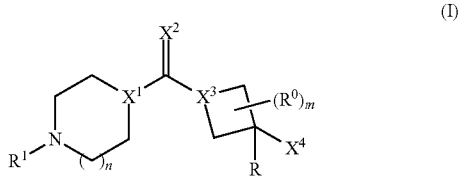

or a pharmaceutically acceptable salt, prodrug or metabolite thereof, wherein

R$^1$ is C$_{3-5}$ cycloalkyl; CH$_2$-cyclopropyl; CHF-cyclopropyl; CF$_2$-cyclopropyl; CH$_2$-cyclobutyl; CHF-cyclobutyl; or CF$_2$-cyclobutyl, wherein C$_{3-5}$ cycloalkyl; CH$_2$-cyclopropyl; CHF-cyclopropyl; CF$_2$-cyclopropyl; CH$_2$-cyclobutyl; CHF-cyclobutyl; and CF$_2$-cyclobutyl are optionally substituted with one or more substituents, which are the same or different and selected from the group consisting of halogen; OH; OCH$_3$; OCH$_2$F; OCHF$_2$; OCF$_3$; CN; CH$_3$; CH$_2$F; CHF2; and CF$_3$;

n is 1 or 2;

X$^1$ is N;

X$^2$ is O; S; N—CN; N—OH; or N—OC$_{1-4}$ alkyl;

X$^3$ is N;

X$^4$ is (CH$_2$)$_{n1}$X$^5$(CH$_2$)$_{n2}$R$^2$;

R$^0$ is F;

m is 0, 1, 2, 3, or 4;

R is H; or F;

Optionally, R, X$^4$ are joined to form oxo (=O);

n1; n2 are independently selected from the group consisting of 0; 1; and 2;

X$^5$ is C(O); C(O)O; OC(O); O; C(O)N(R$^{1a}$); N(R$^{1a}$)C(O); S(O)$_2$N(R$^{1a}$); N(R$^{1a}$)S(O)$_2$; S(O)N(R$^{1a}$); N(R$^{1a}$)S(O); S(O)$_2$; S(O); N(R$^{1a}$)S(O)$_2$N(R$^{1b}$); S; N(R$^{1a}$); N(R$^{1a}$)C(O)N(R$^{1b}$); N(R$^{1a}$)C(O)O; or OC(O)N(R$^{1a}$);

R$^{1a}$, R$^{1b}$ are independently selected from the group consisting of H; C$_{1-4}$ alkyl; C$_{2-4}$ alkenyl; and C$_{2-4}$ alkynyl, wherein C$_{1-4}$ alkyl; C$_{2-4}$ alkenyl; and C$_{2-4}$ alkynyl are optionally substituted with one or more halogen, which are the same or different;

R$^2$ is H; T; C$_{1-6}$ alkyl; C$_{2-6}$ alkenyl; or C$_{2-6}$ alkynyl, wherein C$_{1-6}$ alkyl; C$_{2-6}$ alkenyl; and C$_{2-6}$ alkynyl are optionally substituted with one or more R$^3$, which are the same or different;

R$^3$ is halogen; CN; C(O)R$^4$; C(O)OR$^4$; OR$^4$; C(O)N(R$^4$R$^{4a}$); S(O)$_2$N(R$^4$R$^{4a}$); S(O)N(R$^4$R$^{4a}$); S(O)$_2$R$^4$; S(O)R$^4$; N(R$^4$)S(O)$_2$N(R$^{4a}$R$^{4b}$); SR$^4$; N(R$^4$R$^{4a}$); NO$_2$; OC(O)R$^4$; N(R$^4$)C(O)R$^{4a}$; N(R$^4$)SO$_2$R$^{4a}$; N(R$^4$)S(O)R$^{4a}$; N(R$^4$)C(O)N(R$^{4a}$R$^{4b}$); N(R$^4$)C(O)OR$^{4a}$; OC(O)N(R$^4$R$^{4a}$); or T;

R$^4$, R$^{4a}$, R$^{4b}$ are independently selected from the group consisting of H; T; C$_{1-6}$ alkyl; C$_{2-6}$ alkenyl; and C$_{2-6}$ alkynyl, wherein C$_{1-6}$ alkyl; C$_{2-6}$ alkenyl; and C$_{2-6}$ alkynyl are optionally substituted with one or more R$^5$, which are the same or different;

R$^5$ is halogen; CN; C(O)R$^6$; C(O)OR$^6$; OR$^6$; C(O)N(R$^6$R$^{6a}$); S(O)$_2$N(R$^6$R$^{6a}$); S(O)N(R$^6$R$^{6a}$); S(O)$_2$R$^6$; S(O)R$^6$; N(R$^6$)S(O)$_2$N(R$^{6a}$R$^{6b}$); SR$^6$; N(R$^6$R$^{6a}$); NO$_2$; OC(O)R$^6$; N(R$^6$)C(O)R$^{6a}$; N(R$^6$)SO$_2$R$^{6a}$; N(R$^6$)S(O)R$^{6a}$; N(R$^6$)C(O)N(R$^{6a}$R$^{6b}$); N(R$^6$)C(O)OR$^6$a; OC(O)N(R$^6$R$^{6a}$); or T;

R$^6$, R$^{6a}$, R$^{6b}$ are independently selected from the group consisting of H; T; C$_{1-6}$ alkyl; C$_{2-6}$ alkenyl; and C$_{2-6}$ alkynyl, wherein C$_{1-6}$ alkyl; C$_{2-6}$ alkenyl; and C$_{2-6}$ alkynyl are optionally substituted with one or more halogen, which are the same or different;

T is phenyl; naphthyl; azulenyl; indenyl; indanyl; C$_{3-7}$ cycloalkyl; 3 to 7 membered heterocyclyl; or 7 to 11 membered heterobicyclyl, wherein T is optionally substituted with one or more R$^7$, which are the same or different;

R$^7$ is halogen; CN; C(O)OR$^8$; OR$^8$; C(O)R$^8$; C(O)N(R$^8$R$^{8a}$); S(O)$_2$N(R$^8$R$^{8a}$); S(O)N(R$^8$R$^{8a}$); S(O)$_2$R$^8$; S(O)R$^8$; N(R$^8$)S(O)$_2$N(R$^{8a}$R$^{8b}$); SR$^8$; N(R$^8$R$^{8a}$); NO$_2$; OC(O)R$^8$; NR$^8$)C(O)R$^{8a}$; N(R$^8$)S(O)$_2$R$^{8a}$; N(R$^8$)S(O)R$^{8a}$; N(R$^8$)C(O)OR$^{8a}$; N(R$^8$)C(O)N(R$^{8a}$R$^{8b}$); OC(O)N(R$^8$R$^{8a}$); oxo (=O), where the ring is at least partially saturated; T$^1$; C$_{1-6}$ alkyl; C$_{2-6}$ alkenyl; or C$_{2-6}$ alkynyl, wherein C$_{1-6}$ alkyl; C$_{2-6}$ alkenyl; and C$_{2-6}$ alkynyl are optionally substituted with one or more R$^9$, which are the same or different;

R$^8$, R$^{8a}$, R$^{8b}$ are independently selected from the group consisting of H; T$^1$; C$_{1-6}$ alkyl; C$_{2-6}$ alkenyl; and C$_{2-6}$ alkynyl, wherein C$_{1-6}$ alkyl; C$_{2-6}$ alkenyl; and C$_{2-6}$ alkynyl are optionally substituted with one or more R$^{10}$, which are the same or different;

R$^9$, R$^{10}$ are independently selected from the group consisting of halogen; CN; C(O)R$^{11}$; C(O)OR$^{11}$; OR$^{11}$; C(O)N(R$^{11}$R$^{11a}$); S(O)$_2$N(R$^{11}$R$^{11a}$); S(O)N(R$^{11}$R$^{11a}$); S(O)$_2$R$^{11}$; S(O)R$^{11}$; N(R$^{11}$)S(O)$_2$N(R$^{11a}$R$^{11b}$); SR$^{11}$; N(R$^{11}$R$^{11a}$); NO$_2$; OC(O)R$^{11}$; N(R$^{11}$)C(O)R$^{11a}$; N(R$^{11}$)SO$_2$R$^{11a}$; N(R$^{11}$)S(O)R$^{11a}$; N(R$^{11}$)C(O)N(R$^{11a}$R$^{11b}$); N(R$^{11}$)C(O)OR$^{11a}$; OC(O)N(R$^{11}$R$^{11a}$); and T$^1$;

$R^{11}$, $R^{11a}$; $R^{11b}$ are independently selected from the group consisting of H; $T^1$; $C_{1-6}$ alkyl; $C_{2-6}$ alkenyl; and $C_{2-6}$ alkynyl, wherein $C_{1-6}$ alkyl; $C_{2-6}$ alkenyl; and $C_{2-6}$ alkynyl are optionally substituted with one or more halogen, which are the same or different;

$T^1$ is phenyl; $C_{3-7}$ cycloalkyl; or 3 to 7 membered heterocyclyl, wherein $T^1$ is optionally substituted with one or more $R^{12}$, which are the same or different;

$R^{12}$ is halogen; CN; C(O)OR$^{13}$; OR$^{13}$; C(O)R$^{13}$; C(O)N(R$^{13}$R$^{13a}$); S(O)$_2$N(R$^{13}$R$^{13a}$); S(O)N(R$^{13}$R$^{13a}$); S(O)$_2$R$^{13}$; S(O)R$^{13}$; N(R$^{13}$)S(O)$_2$N(R$^{13a}$R$^{13b}$); SR$^{13}$; N(R$^{13}$R$^{13a}$); NO$_2$; OC(O)R$^{13}$; N(R$^{13}$)C(O)R$^{13a}$; N(R$^{13}$)S(O)$_2$R$^{13a}$; N(R$^{13}$)S(O)R$^{13a}$; N(R$^{13}$)C(O)OR$^{13a}$; N(R$^{13}$)C(O)N(R$^{13a}$R$^{13b}$); OC(O)N(R$^{13}$R$^{13a}$); oxo (=O), where the ring is at least partially saturated; $C_{1-6}$ alkyl; $C_{2-6}$ alkenyl; or $C_{2-6}$ alkynyl, wherein $C_{1-6}$ alkyl; $C_{2-6}$ alkenyl; and $C_{2-6}$ alkynyl are optionally substituted with one or more halogen, which are the same or different;

$R^{13}$, $R^{13a}$, $R^{13b}$ are independently selected from the group consisting of H; $C_{1-6}$ alkyl; $C_{2-6}$ alkenyl; and $C_{2-6}$ alkynyl, wherein $C_{1-6}$ alkyl; $C_{2-6}$ alkenyl; and $C_{2-6}$ alkynyl are optionally substituted with one or more halogen, which are the same or different.

2. A compound of claim 1, wherein $R^1$ is substituted or unsubstituted $C_{3-5}$ cycloalkyl; substituted or unsubstituted CH$_2$-cyclopropyl; or substituted or unsubstituted CH$_2$-cyclobutyl.

3. A compound of claim 1, wherein n is 2.
4. A compound of claim 1, wherein $X^2$ is O.
5. A compound of claim 1, wherein m is 0.
6. A compound of claim 1, wherein n1; n2 are independently selected from the group consisting of 0; and 1.
7. A compound of claim 1, wherein $X^5$ is C(O); O; C(O)N(R$^{1a}$); N(R$^{1a}$)C(O); S(O)$_2$N(R$^{1a}$); N(R$^{1a}$)S(O)$_2$; N(R$^{1a}$); or N(R$^{1a}$)C(O)N(R$^{1b}$).
8. A compound of claim 1, wherein $R^2$ is H; or T.
9. A compound of claim 1 selected from the group consisting of 1-[(4-cyclobutyl-1,4-diazepan-1-yl)carbonyl]azetidin-3-ol;
1-[(4-cyclobutylpiperazin-1-yl)carbonyl]azetidin-3-ol;
6-({1-[(4-cyclobutyl-1,4-diazepan-1-yl)carbonyl]azetidin-3-yl}oxy)-N-methylpyridine-3-carboxamide;
5-({1-[(4-cyclobutyl-1,4-diazepan-1-yl)carbonyl]azetidin-3-yl}oxy)pyridine-2-carboxamide;
5-({1-[(4-cyclobutyl-1,4-diazepan-1-yl)carbonyl]azetidin-3-yl}oxy)-N-methylpyridine-2-carboxamide;
5-({1-[(4-cyclobutyl-1,4-diazepan-1-yl)carbonyl]azetidin-3-yl}oxy)-N,N-dimethylpyridine-2-carboxamide;
5-({1-[(4-cyclobutyl-1,4-diazepan-1-yl)carbonyl]azetidin-3-yl}oxy)-N,N-diethylpyridine-2-carboxamide;
4-({1-[(4-cyclobutyl-1,4-diazepan-1-yl)carbonyl]azetidin-3-yl}oxy)-N-methylbenzamide;
4-({1-[(4-cyclobutyl-1,4-diazepan-1-yl)carbonyl]azetidin-3-yl}oxy)-N,N-dimethylbenzamide;
1-cyclobutyl-4-({3-[4-(trifluoromethyl)phenoxy]azetidin-1yl}carbonyl)-1,4-diazepane;
1-cyclobutyl-4-[(3-{[5-(trifluoromethyl)pyridin-2-yl]oxy}azetidin-1yl)carbonyl]-1,4-diazepane;
4-({1-[(4-cyclobutyl-1,4-diazepan-1-yl)carbonyl]azetidin-3-yl}oxy)benzonitrile;
1-cyclobutyl-4-{[3-(4-fluorophenoxy)azetidin-1-yl]carbonyl}-1,4-diazepane;
1-{[3-(4-chlorophenoxy)azetidin-1-yl]carbonyl}-4-cyclobutyl-1,4-diazepane;
1-cyclobutyl-4-[(3-phenoxyazetidin-1-yl)carbonyl]-1,4-diazepane;
1-cyclobutyl-4-({3-[4-(1H-pyrazol-1-ylmethyl)phenoxy]azetidin-1-yl}carbonyl)-1,4-diazepane;
1-cyclobutyl-4-[(3-{[5-(1H-pyrazol-1-ylmethyl)pyridin-2-yl]oxy}azetidin-1-yl)carbonyl]-1,4-diazepane;
1[4({1-[(4-cyclobutyl-1,4-diazepan-1-yl)carbonyl]azetidin-3-yl}oxy)phenyl]pyrrolidin-2-one;
1-cyclobutyl-4-({3[4-(piperidin-1-ylmethyl)phenoxy]azetidin-1-yl}carbonyl)-1,4-diazepane;
1-cyclobutyl-4-[(3-{4-[(4-methylpiperazin-1-yl)methyl]phenoxyl}azetidin-1-yl)carbonyl]-1,4-diazepane;
1-cyclobutyl-4-[(3-{4[(4,4-difluoropiperidin-1-yl)methyl]phenoxyl}azetidin-1-yl)carbonyl]-1,4-diazepane;
1-({3-[(5-bromopyridin-2-yl)oxy]azetidin-1-yl}carbonyl)-4-cyclobutyl-1,4-diazepane;
1-cyclobutyl-4-{[3-(3,4-dichlorophenoxy)azetidin-1-yl]carbonyl}-1,4-diazepane;
1-({3-[(6-bromopyridin-3-yl)oxy]azetidin-1-yl}carbonyl)-4-cyclobutyl-1,4-diazepane;
1-{[3-(4-chloro-2-methylphenoxy)azetidin-1-yl]carbonyl}-4-cyclobutyl-1,4-diazepane;
1-cyclobutyl-4-({3[4-(1H-imidazol-1-yl)phenoxy]azetidin-1-yl}carbonyl)-1,4-diazepane;
1-cyclobutyl-4-({3-[(2-methylpyridin-4-yl)oxy]azetidin-1-yl}carbonyl)-1,4-diazepane;
1-cyclobutyl-4-({3-[3-(trifluoromethyl)phenoxy]azetidin-1-yl}carbonyl)-1,4-diazepane;
1-cyclobutyl-4-({3-[2-(trifluoromethyl)phenoxy]azetidin-1-yl}carbonyl)-1,4-diazepane;
3-({1-[(4-cyclobutyl-1,4-diazepan-1-yl)carbonyl]azetidin-3-yl}oxy)benzonitrile;
2-({1-[(4-cyclobutyl-1,4-diazepan-1-yl)carbonyl]azetidin-3-yl}oxy)benzonitrile;
1-{[3-(3-chlorophenoxy)azetidin-1-yl]carbonyl}-4-cyclobutyl-1,4-diazepane;
1-{[3-(2-chlorophenoxy)azetidin-1-yl]carbonyl}-4-cyclobutyl-1,4-diazepane;
4-({1-[(4-cyclobutyl-1,4-diazepan-1-yl)carbonyl]azetidin-3-yl}oxy)-N,3-dimethylbenzamide;
5-({1-[(4-cyclobutyl-1,4-diazepan-1-yl)carbonyl]azetidin-3-yl}oxy)-N-(cyclopropylmethyl)pyridine-2-carboxamide;
1-cyclobutyl-4-[(3-{[5-(trifluoromethyl)pyridin-3-yl]oxy}azetidin-1-yl)carbonyl]-1,4-diazepane;
5-({1-[(4-cyclobutylpiperazin-1-yl)carbonyl]azetidin-3-yl}oxy)-N-methylpyridine-2-carboxamide;
1-cyclobutyl-4-[(3-phenoxyazetidin-1-yl)carbonyl]piperazine;
1-cyclobutyl-4-({3-[4-(trifluoromethyl)phenoxy]azetidin-1-yl}carbonyl)piperazine;
4-({1-[(4-cyclobutylpiperazin-1-yl)carbonyl]azetidin-3-yl}oxy)benzonitrile;
1-cyclobutyl-4-{[3-(4-fluorophenoxy)azetidin-1-yl]carbonyl}piperazine;
6-cyclobutyl-2-({1-[(4-cyclobutyl-1,4-diazepan-1-yl)carbonyl]azetidin-3-yl}oxy)-5,6,7,8-tetrahydro-1,6-naphthyridine;
4-({1-[(4-cyclobutyl-1,4-diazepan-1-yl)carbonyl]azetidin-3-yl}oxy)-3-fluoro-N-methylbenzamide;
1-cyclobutyl-4-{[3-(4-iodophenoxy)azetidin-1-yl]carbonyl}-1,4-diazepane;
1-cyclobutyl-4-({3-[(5-fluoropyridin-3-yl)oxy]azetidin-1-yl}carbonyl)-1,4-diazepane;
1-({3-[(6-chloropyridin-3-yl)oxy]azetidin-1-yl}carbonyl)-4-cyclobutyl-1,4-diazepane;

4-({1-[(4-cyclobutyl-1,4-diazepan-1-yl)carbonyl]azetidin-3-yl}oxy)-2-fluoro-N-methylbenzamide;
1-({3-[(4-chloropyridin-3-yl)oxy]azetidin-1-yl}carbonyl)-4-cyclobutyl-1,4-diazepane;
1-cyclobutyl-4-({3-[(3-fluoropyridin-4-yl)oxy]azetidin-1-yl}carbonyl)-1,4-diazepane;
1-({3-[(4-chloro-2-methylpyridin-3-yl)oxy]azetidin-1yl}carbonyl)-4-cyclobutyl-1,4-diazepane;
5-({1-[(4-cyclobutyl-1,4-diazepan1yl)carbonyl]azetidin-3-yl}oxy)imidazo[1,5-a]pyridine;
1-cyclobutyl-4-({3-[(2-methoxypyrimidin-4-yl)oxy]azetidin-1-yl}carbonyl)-1,4-diazepane;
2-[4-({1-[(4-cyclobutyl-1,4-diazepan-1-yl)carbonyl]azetidin-3-yl}oxy)pyridin-2-yl]propan-2-ol;
1-cyclobutyl-4-({3-[(2-ethylpyridin-4-yl)oxy]azetidin-1-yl}carbonyl)-1,4-diazepane;
1-cyclobutyl-4-[(3-{[2-(1-methylethyl)pyridin-4-yl]oxy}azetidin-1-yl)carbonyl]-1,4-diazepane;
1-cyclobutyl-4-({3-[(2-methoxypyridin-4-yl)oxy]azetidin-1-yl}carbonyl)-1,4-diazepane;
4-({1-[(4-cyclobutyl-1,4-diazepan-1-yl)carbonyl]azetidin-3-yl}oxy)pyridin-2-amine;
4-({1-[(4-cyclobutyl-1,4-diazepan-1-yl)carbonyl]azetidin-3-yl}oxy)-N,N-dimethylpyridin-2-amine;
1-cyclobutyl-4-({3-[(6-methylpyridazin-3-yl)oxy]azetidin-1-yl}carbonyl)-1,4-diazepane;
2-[4-({1-[(4-cyclobutyl-1,4-diazepan-1-yl)carbonyl]azetidin-3-yl}oxy)-2-fluorophenyl]propan-2-ol;
1-cyclobutyl-4({3-[(3,5-dimethylpyrazin-2-yl)oxy]azetidin-1-yl}carbonye-1,4-diazepane;
1-cyclobutyl-4-({3-[(2-methoxypyrimidin-4-yl)oxy]azetidin-1-yl}carbonyl)-1,4-diazepane;
1-cyclobutyl-4-({3-[(6-methylpyrazin-2-yl)oxy]azetidin-1-yl}carbonyl)-1,4-diazepane;
1-cyclobutyl-4-({3-[(3,6-dimethylpyrazin-2-yl)oxy]azetidin-1-yl}carbonyl)-1,4-diazepane;
1-cyclobutyl-4-({3-[(2-methylpyrimidin-4-yl)oxy]azetidin-1-yl}carbonyl)-1,4-diazepane;
1-cyclobutyl-4-({3-[(6-methoxypyrazin-2-yl)oxy]azetidin-1-yl}carbonyl)-1,4-diazepane;
1-({3-[(3-chloropyridin-2-yl)oxy]azetidin-1-yl}carbonyl)-4-cyclobutyl-1,4-diazepane;
4-({1-[(4-cyclobutyl-1,4-diazepan-1-yl)carbonyl]azetidin-3-yl}oxy)quinoline;
1-cyclobutyl-4-({3-[(2,6-dimethylpyridin-4-yl)oxy]azetidin-1-yl}carbonyl)-1,4-diazepane;
8-({1-[(4-cyclobutyl-1,4-diazepan-1-yl)carbonyl]azetidin-3-yl}oxy)imidazo[1,2-a]pyridine;
7-({1-[(4-cyclobutyl-1,4-diazepan-1-yl)carbonyl]azetidin-3-yl}oxy)imidazo[1,2-a]pyridine;
4-({1-[(4-cyclobutyl-1,4-diazepan-1-yl)carbonyl]azetidin-3-yl}oxy)pyridine-2-carboxamide;
5-({1-[(4-cyclobutyl-1,4-diazepan-1-yl)carbonyl]azetidin-3-yl}oxy)-N-(cyclopropylmethyl)pyridine-2-carboxamide;
1-cyclobutyl-4-[(3-{[6-(piperidin-1-ylcarbonyl)pyridin-3-yl]oxy}azetidin-1-yl)carbonyl]-1,4-diazepane;
3-({1-[(4-cyclobutyl-1,4-diazepan-1-yl)carbonyl]azetidin-3-yl}oxy)-N-methylbenzamide;
1-({3-[(5-chloropyridin-2-yl)oxy]azetidin-1-yl}carbonyl)-4-cyclobutyl-1,4-diazepane;
1-({3-[(5-chloropyridin-2-yl)oxy]azetidin-1-yl}carbonyl)-4-cyclobutyl-1,4-diazepane;
1-cyclobutyl-4-({3-[(3,5-dimethylpyrazin-2-yl)oxy]azetidin-1-yl}carbonyl)-1,4-diazepane;
1-({3-[(3-chloropyridin-4-yl)oxy]azetidin-1-yl}carbonyl)-4-cyclobutyl-1,4-diazepane;
1-({3-[(5-chloropyridin-3-yl)oxy]azetidin-1-yl}carbonyl)-4-cyclobutyl-1,4-diazepane;
1-cyclobutyl-4-{[3-(pyridin-4-yloxy)azetidin-1-yl]carbonyl}-1,4-diazepane;
1-cyclobutyl-4-({3-[(5-methoxypyridin-3-yl)oxy]azetidin-1-yl}carbonyl)-1,4-diazepane;
2-({1-[(4-cyclobutyl-1,4-diazepan-1-yl)carbonyl]azetidin-3-yl}oxy)-6-(cyclopropylcarbonyl)-5,6,7,8-tetrahydro-1,6-naphthyridine;
2-({1-[(4-cyclobutyl-1,4-diazepan-1-yl)carbonyl]azetidin-3-yl}oxy)-6-(cyclopropylacetyl)-5,6,7,8-tetrahydro-1,6-naphthyridine;
4({1-[(4-cyclobutyl-1,4-diazepan-1-yl)carbonyl]azetidin-3-yl}oxy)-N-methylpyridine-3-carboxamide;
1-cyclobutyl-4-{[3-(4-methoxyphenoxy)azetidin-1-yl]carbonyl}-1,4-diazepane;
1-cyclobutyl-4-({3-[4-(1H-pyrazol-1-yl)phenoxy]azetidin-1-yl}carbonyl)-1,4-diazepane;
1-cyclobutyl-4-({3-[4-(trifluoromethoxy)phenoxy]azetidin-1-yl}carbonyl)-1,4-diazepane;
1-cyclobutyl-4-({3-[4-(difluoromethoxy)phenoxy]azetidin-1-yl}carbonyl)-1,4-diazepane;
1-{[3-(4-chloro-2-fluorophenoxy)azetidin-1-yl]carbonyl}-4-cyclobutyl-1,4-diazepane;
1-cyclobutyl-4-{[3-(3-methoxyphenoxy)azetidin-1-yl]carbonyl}-1,4-diazepane;
1-cyclobutyl-4-{[3-(2-methoxyphenoxy)azetidin-1-yl]carbonyl}-1,4-diazepane;
6-({1-[(4-cyclobutyl-1,4-diazepan-1-yl)carbonyl]azetidin-3-yl}oxy)-2-methylquinoline;
1-cyclobutyl-4-[(3-{[6-(trifluoromethyl)pyridin-3-yl]oxy}azetidin-1-yl)carbonyl]-1,4-diazepane;
1-cyclobutyl-4-({3-[(4-fluorobenzyl)oxy]azetidin-1-yl}carbonyl)-1,4-diazepane;
1-cyclobutyl-4-[(3-methoxyazetidin-1-yl)carbonyl]-1,4-diazepane;
1-({3-[(4-chlorobenzyl)oxy]azetidin-1-yl}carbonyl)-4-cyclobutyl-1,4-diazepane;
4-[({1-[(4-cyclobutyl-1,4-diazepan-1-yl)carbonyl]azetidin-3-yl}oxy)methyl]benzonitrile;
1-cyclobutyl-4-{[3-(prop-2-yn-1-yloxy)azetidin-1-yl]carbonyl}-1,4-diazepane;
1-[(4-cyclobutyl-1,4-diazepan-1-yl)carbonyl]azetidin-3-one;
1-[(4-cyclobutyl-1,4-diazepan-1-yl)carbonyl]azetidin-3-amine;
5-({1-[(4-cyclobutyl-1,4-diazepan-1-yl)carbonyl]azetidin-3-yl}amino)-N-methylpyridine-2-carboxamide;
5-[{1-[(4-cyclobutyl-1,4-diazepan-1-yl)carbonyl]azetidin-3-yl}(methypamino]-N-methylpyridine-2-carboxamide;
4-[({1-[(4-cyclobutyl-1,4-diazepan-1-yl)carbonyl]azetidin-3-yl}amino)methyl]benzonitrile;
5-({1-[(4-cyclopentyl-1,4-diazepan-1-yl)carbonyl]azetidin-3-yl}oxy)-N-methylpyridine-2-carboxamide;
6-({1-[(4-cyclobutyl-1,4-diazepan-1-yl)carbonyl]azetidin-3-yl}oxy)-3,4-dihydroisoquinolin-1(2H)-one;
6-({1-[(4-cyclobutyl-1,4-diazepan-1-yl)carbonyl]azetidin-3-yl}oxy)-2-methyl-3,4-dihydroisoquinolin-1(2H)-one;
2-[5-({1-[(4-cyclobutyl-1,4-diazepan-1-yl)carbonyl]azetidin-3-yl}oxy)pyridin-2-yl]propan-2-ol;
1-[5-({1-[(4-cyclobutyl-1,4-diazepan-1-yl)carbonyl]azetidin-3-yl}oxy)pyridin-2-yl]ethanone;
1-cyclobutyl-4-({3-[(5-methoxypyrimidin-2-yl)oxy]azetidin-1yl}carbonyl)-1,4-diazepane;

1-cyclobutyl-4-({3-[(6-methylpyridin-3-yl)oxy]azetidin-1-yl}carbonyl)-1,4-diazepane;
methyl 1-[(4-cyclobutyl-1,4-diazepan-1-yl)carbonyl]azetidine-3-carboxylate;
N-(4-chlorophenyl)-1-[(4-cyclobutyl-1,4-diazepan-1-yl)carbonyl]azetidine-3-carboxamide;
1-cyclobutyl-4-{[3-(piperidin-1-ylcarbonyl)azetidin-1-yl]carbonyl}-1,4-diazepane;
1-cyclobutyl-4-{[3-(morpholin-4-ylcarbonyl)azetidin-1-yl]carbonyl}-1,4-diazepane;
1-{[3-(azetidin-1-ylcarbonyl)azetidin-1-yl]carbonyl}-4-cyclobutyl-1,4-diazepane;
1-cyclobutyl-4-{[3-(pyrrolidin-1-ylcarbonyl)azetidin-1-yl]carbonyl}-1,4-diazepane;
1-{[3-(azepan-1-ylcarbonyl)azetidin-1-yl]carbonyl}-4-cyclobutyl-1,4-diazepane;
1-cyclobutyl-4-({3-[(4-fluoropiperidin-1-yl)carbonyl]azetidin-1-yl}carbonyl)-1,4-diazepane;
1-cyclobutyl-4-({3-[(4,4-difluoropiperidin-1-yl)carbonyl]azetidin-1-yl}carbonyl)-1,4-diazepane;
1-[(4-cyclobutyl-1,4-diazepan-1-yl)carbonyl]-N-cyclohexylazetidine-3-carboxamide;
1-[(4-cyclobutyl-1,4-diazepan-1-yl)carbonyl]-N-(6-methylpyridin-3-yl)azetidine-3-carboxamide;
1-[(4-cyclobutyl-1,4-diazepan-1-yl)carbonyl]-N-methylazetidine-3-carboxamide;
{1-[(4-cyclobutyl-1,4-diazepan-1-yl)carbonyl]azetidin-3-yl}methanol;
1-({3-[(4-chlorophenoxy)methyl]azetidin-1yl}carbonyl)-4-cyclobutyl-1,4-diazepane;
6-({1-[(4-cyclobutyl-1,4-diazepan-1-yl)carbonyl]azetidin-3-yl}methoxy)-3,4-dihydroisoquinolin-1(2H)-one;
6-({1-[(4-cyclobutyl-1,4-diazepan-1-yl)carbonyl]azetidin-3-yl}methoxy)-2-methyl-3,4-dihydroisoquinolin-1(2H)-one;
5-({1-[(4-cyclobutyl-1,4-diazepan-1-yl)carbonyl]azetidin-3-yl}methoxy)-N-methylpyridine-2-carboxamide;
N-{1-[(4-cyclobutyl-1,4-diazepan-1-yl)carbonyl]azetidin-3-yl}-6-methylpyridine-3-carboxamide;
4-chloro-N-{1-[(4-cyclobutyl-1,4-diazepan-1-yl)carbonyl]azetidin-3-yl}benzamide;
N-{1-[(4-cyclobutyl-1,4-diazepan-1-yl)carbonyl]azetidin-3-yl}cyclohexanecarboxamide;
4-chloro-N-{1-[(4-cyclobutyl-1,4-diazepan-1-yl)carbonyl]azetidin-3-yl}-N-methylbenzamide;
N-{1-[(4-cyclobutyl-1,4-diazepan-1-yl)carbonyl]azetidin-3-yl}-N,6-dimethylpyridine-3-carboxamide;
N-{1-[(4-cyclobutyl-1,4-diazepan-1-yl)carbonyl]azetidin-3-yl}-N-methylcyclohexanecarboxamide;
1-[(4-cyclobutyl-1,4-diazepan-1-yl)carbonyl]-N-methyl-N-(6-methylpyridin-3-yl)azetidine-3-carboxamide;
N-(4-chlorophenyl)-1-[(4-cyclobutyl-1,4-diazepan-1-yl)carbonyl]-N-methylazetidine-3-carboxamide;
4-({1-[(4-cyclobutyl-1,4-diazepan-1-yl)carbonyl]azetidin-3-yl}oxy)-N-methylpyridine-2-carboxamide;
1-cyclobutyl-4-{[3-(methoxymethyl)azetidin-1-yl]carbonyl}-1,4-diazepane;
1-cyclobutyl-4-({3-[4-(1-methyl-1H-pyrazol-4-yl)phenoxy]azetidin-1-yl}carbonyl)-1,4-diazepane;
1-cyclobutyl-4-({3-[4-(1,3,5-trimethyl-1H-pyrazol-4-yl)phenoxy]azetidin-1-yl}carbonyl)-1,4-diazepane;
1-cyclobutyl-4-({3-[(3-fluoro-2-methylpyridin-4-yl)oxy]azetidin-1-yl}carbonyl)-1,4-diazepane;
1-cyclobutyl-4-{[3-(naphthalen-2-yloxy)azetidin-1-yl]carbonyl}-1,4-diazepane;
1-cyclobutyl-4-{[3-({[6-(trifluoromethyl)pyridin-3-yl]oxy}methyl)azetidin-1-yl]carbonyl}-1,4-diazepane;
5-({1-[(4-cyclobutyl-1,4-diazepan-1-yl)carbonyl]azetidin-3-yl}oxy)-1H-indole;
5-({1-[(4-cyclobutyl-1,4-diazepan-1-yl)carbonyl]azetidin-3-yl}oxy)-1-methyl-1H-indole;
2-[5-({1-[(4-cyclobutyl-1,4-diazepan-1-yl)carbonyl]azetidin-3-yl}oxy)pyridin-2-yl]-2-methylpropan-1-ol;
2-[5-({1-[(4-cyclopentyl-1,4-diazepan-1-yl)carbonyl]azetidin-3-yl}oxy)pyridin-2-yl]propan-2-ol;
1-cyclobutyl-4-({3-[(5-fluoropyrimidin-2-yl)oxy]azetidin-1-yl}carbonyl)-1,4-diazepane;
1-cyclobutyl-4-({3-[(5-methoxypyridin-2-yl)oxy]azetidin-1-yl}carbonyl)-1,4-diazepane;
1-cyclobutyl-4-({3-[(5-ethylpyrimidin-2-yl)oxy]azetidin-1-yl}carbonyl)-1,4-diazepane;
1-cyclobutyl-4-({3-[4-(methylsulfonyl)phenoxy]azetidin-1yl}carbonyl)-1,4-diazepane;
1-cyclobutyl-4-({3-[(6-methylpyridin-3-yl)methoxy]azetidin-1yl}carbonyl)-1,4-diazepane;
1-[(4-cyclopentyl-1,4-diazepan-1-yl)carbonyl]azetidin-3-ol;
ethyl 5-({1-[(4-cyclobutyl-1,4-diazepan-1-yl)carbonyl]azetidin-3-yl}oxy)pyridine-2-carboxylate;
1-cyclobutyl-4-{[3-(3-methyl-4-nitrophenoxy)azetidin-1-yl]carbonyl}-1,4-diazepane; and
methyl 2-[5-({1-[(4-cyclobutyl-1,4-diazepan-1-yl)carbonyl]azetidin-3-yl}oxy)pyridin-2-yl]-2-methylpropanoate.

10. A pharmaceutical composition comprising at least one compound or a pharmaceutically acceptable salt thereof of claim 1 together with a pharmaceutically acceptable carrier, optionally in combination with one or more other bioactive compounds or pharmaceutical compositions.

11. A method for the preparation of a compound of claim 1, wherein in formula (I) $X^1$ and $X^3$ are N; $X^2$ is O; n1 and n2 are 0 in the definition of $X^4$ and $R^2$ is an aromatic cycle T, comprising the steps of
(a) reacting the amino group of a compound of formula (II) with a suitable chloroformate

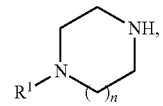

wherein n and $R^1$ have the meaning as indicated in claim 1;
(b) reacting the resulting carbamate compound from step (a) with a compound of formula (III)

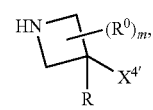

wherein $X^{4'}$ is OH and R has the meaning as indicated in claim 1; and
(c) reacting the resulting compound with a compound of formula Cl-T or F-T to yield a compound of formula (I), wherein $X^1$ and $X^3$ are N; $X^2$ is O; n1 and n2 are 0 in the definition of $X^4$ and $R^2$ is an aromatic cycle T.

12. A method for the preparation of a compound of claim 1, wherein in formula (I) $X^1$ and $X^3$ are N and $X^2$ is O, comprising the steps of (a) reacting the amino group of compound of formula (IIa) with a suitable chloroformate

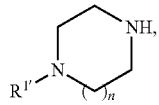
(IIa)

wherein n has the meaning as indicated in claim 1 and R$^{1'}$ is R$^1$ as indicated claim 1 or as suitable N-atom protecting group to yield a compound of formula (I), optionally after removal of the protecting group and reacting the liberated amino group with a compound of formula R$^1$=O, wherein the oxo group is attached to a carbon atom of R$^1$, followed by reduction of the resulting imine; and (b) reacting the resulting carbamate compound from step (a) with a compound of formula (IIIa)

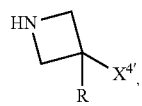
(IIIa)

wherein X$^{4'}$ is H; OH; or C(O)$_2$(alkyl), R has the meaning as indicated claim 1, to yield a compound of formula (I).

13. A method for the preparation of a compound of claim 1, wherein in formula (I) X$^5$ C(O), comprising the steps of
(a) reacting a compound represented by formula (VI) with base or acid;

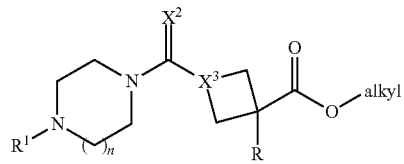
(VI)

(b) reacting the resulting carboxylic acid compound from step (a) with amide coupling reagents and reacting the resulting activated ester with either a primary or secondary amine compound, as defined for R$^2$, to yield a compound of formula (I), wherein X$^4$ is X$^5$(CH$_2$)$_{n2}$R$^2$.

14. A method for the preparation of a compound of claim 1, comprising the further step where compounds of formula (I) represented by formula (XI), wherein the meanings are as indicated in claim 1, are further modified as follows:

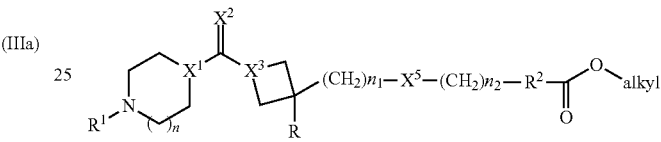
(XI)

reacting the ester group with a Grignard reagent, optionally in the presence of lithium chloride, at a temperature usually between −78° C. and 150° C., to yield a compound of formula (I).

15. A compound of claim 1, wherein R$^1$ is cyclobutyl; or cyclopentyl.

* * * * *